United States Patent
Reynolds et al.

(10) Patent No.: US 10,537,571 B2
(45) Date of Patent: *Jan. 21, 2020

(54) PYRIMIDINE FGFR4 INHIBITORS

(71) Applicant: EISAI R&D MANAGEMENT CO., LTD., Tokyo (JP)

(72) Inventors: Dominic Reynolds, Stoneham, MA (US); Ming-Hong Hao, Quincy, MA (US); John Wang, Andover, MA (US); Sudeep Prajapati, Somerville, MA (US); Takashi Satoh, Andover, MA (US); Anand Selvaraj, Cambridge, MA (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/627,851

(22) Filed: Jun. 20, 2017

(65) Prior Publication Data

US 2017/0360785 A1    Dec. 21, 2017

Related U.S. Application Data

(63) Continuation of application No. 15/221,018, filed on Jul. 27, 2016, now Pat. No. 9,730,931, which is a continuation of application No. 15/000,659, filed on Jan. 19, 2016, now Pat. No. 9,434,697, which is a continuation of application No. PCT/US2014/060857, filed on Oct. 16, 2014.

(60) Provisional application No. 61/892,881, filed on Oct. 18, 2013.

(51) Int. Cl.
*A61K 31/505* (2006.01)
*A61K 31/506* (2006.01)
*A61K 31/5377* (2006.01)

(52) U.S. Cl.
CPC .......... *A61K 31/505* (2013.01); *A61K 31/506* (2013.01); *A61K 31/5377* (2013.01)

(58) Field of Classification Search
CPC ... A61K 31/505; A61K 31/506; C07D 239/48
USPC .......................................... 514/256; 544/326
See application file for complete search history.

(56) References Cited

U.S. PATENT DOCUMENTS

| | | | |
|---|---|---|---|
| 6,844,341 | B2 | 1/2005 | Thomas |
| 7,371,750 | B2 | 5/2008 | Sim et al. |
| 7,501,425 | B1 | 3/2009 | Dobrusin et al. |

(Continued)

FOREIGN PATENT DOCUMENTS

| | | |
|---|---|---|
| RU | 2045520 C1 | 10/1995 |
| WO | WO 2006/000420 A1 | 1/2006 |

(Continued)

OTHER PUBLICATIONS

International Search Report (PCT/ISA/210) dated Feb. 3, 2015, by the European Patent Office as the International Searching Authority for International Application No. PCT/US2014/060857.

(Continued)

*Primary Examiner* — Craig D Ricci
*Assistant Examiner* — Janet L. Coppins
(74) *Attorney, Agent, or Firm* — Buchanan Ingersoll & Rooney PC

(57) ABSTRACT

Provided herein are compounds of Formula I useful as FGFR4 inhibitors, as well as methods of use of the same.

12 Claims, 2 Drawing Sheets

Specification includes a Sequence Listing.

(56) References Cited

U.S. PATENT DOCUMENTS

| | | | | |
|---|---|---|---|---|
| 8,552,002 | B2* | 10/2013 | Ding | C07D 239/48 |
| | | | | 514/256 |
| 9,730,931 | B2* | 8/2017 | Reynolds | A61K 31/505 |
| 2010/0120773 | A1 | 5/2010 | Guagnano et al. | |
| 2010/0143386 | A1 | 6/2010 | Ullrich et al. | |
| 2013/0040949 | A1 | 2/2013 | Gray et al. | |
| 2013/0137708 | A1 | 5/2013 | Garske et al. | |
| 2013/0183294 | A1 | 7/2013 | Pai et al. | |
| 2014/0088100 | A1 | 3/2014 | Bifulco et al. | |
| 2014/0142084 | A1 | 5/2014 | Kameda et al. | |
| 2014/0296216 | A1 | 10/2014 | Ding et al. | |
| 2016/0130237 | A1 | 5/2016 | Reynolds et al. | |
| 2017/0007601 | A1 | 1/2017 | Reynolds et al. | |

FOREIGN PATENT DOCUMENTS

| | | |
|---|---|---|
| WO | WO 2006/038112 A1 | 4/2006 |
| WO | WO 2007/071752 A2 | 6/2007 |
| WO | WO 2009/158571 | 12/2009 |
| WO | WO 2011/071821 A1 | 6/2011 |
| WO | WO 2011/088196 A2 | 7/2011 |
| WO | WO 2012/136732 A1 | 10/2012 |
| WO | WO 2012/167415 A1 | 12/2012 |
| WO | WO 2014/011900 A2 | 1/2014 |
| WO | WO 2014/144737 A1 | 9/2014 |
| WO | WO 2014/149164 A1 | 9/2014 |
| WO | WO 2015/006492 A1 | 1/2015 |
| WO | WO 2015/030021 A1 | 3/2015 |
| WO | WO 2015/057938 A1 | 4/2015 |
| WO | WO 2015/057963 A1 | 4/2015 |
| WO | WO 2015/061572 A1 | 4/2015 |
| WO | WO 2015/108992 A1 | 7/2015 |
| WO | WO 2017/198149 A1 | 11/2017 |
| WO | WO 2017/198221 A1 | 11/2017 |

OTHER PUBLICATIONS

Written Opinion (PCT/ISA/237) dated Feb. 3, 2015, by the European Patent Office as the International Searching Authority for International Application No. PCT/US2014/060857.

Guagnano et al., "Discovery of 3-(2.6-Dichloro-3.5-dimethoxy-phenyl)-1-{6-[-(4-ethyl-piperazin-1-yl)-phenylamino]pyrimidin-4-yl}-1-methyl-urea(NVP-BGJ398). A Potent and Selective Inhibitor of the Fibroblast Growth Factor Receptor Family of Receptor Tyrosine Kinase", Journal of Medicinal Chemistry, Oct. 2011, pp. 7066-7083, vol. 54, No. 2.

Liew et al., "SVM Model for Virtual Screening of Lck Inhibitors", J. Chem. Inf. Model., 2009, pp. 877-885, vol. 49, No. 4.

Maier et al., "Development of N-4,6-pyrimidine-N-alkyl-N0-phenyl ureas as orally active inhibitors of lymphocyte specific tyrosine kinase", Bioorganic & Medicinal Chemistry Letters, 2006, pp. 3646-3650, vol. 16.

Anwer et al., "A QSAR Study on Some Series of Anticancer Tyrosine Kinase Inhibitors", Medicinal Chemistry, 2013, pp. 203-212, vol. 9, No. 2.

Tan et al., "Development of covalent inhibitors that can overcome resistance to first-generation FGFR kinase inhibitors", PNAS, Oct. 2014, pp. E4869-E4877.

Zhang et al., "Targeting cancer with small molecule kinase inhibitors", Nature Reviews/Cancer, Jan. 2009, pp. 28-39, vol. 9 (including one page of Supplementary Information).

Anastassiadis et al., "Comprehensive assay of kinase catalytic activity reveals features of kinase inhibitor selectivity", Nature Biotechnology, Nov. 2011, pp. 1039-1046, vol. 29, No. 11.

Brooks et al., "Molecular Pathways: Fibroblast growth factor signaling: a new therapeutic opportunity in cancer", Clinical Cancer Research, Mar. 2012, pp. 1-25.

Dieci et al., "Fibroblast Growth Factor Receptor Inhibitors as a Cancer Treatment: From a Biologic Rationale to Medical Perspectives", Cancer Discovery, Feb. 2013, pp. OF1-OF16.

French et al., "Targeting FGFR4 Inhibits Hepatocellular Carcinoma Preclinical Mouse Models", PLoS ONE, May 2012, pp. 1-12, vol. 7, issue 5.

Liu et al., "Developing Irreversible Inhibitors of the Protein Kinase Cysteinome", Chemistry & Biology Review, Feb. 2013, pp. 146-159, vol. 20.

Gavine et al., "AZD4547: An Orally Bioavailable, Potent, and Selective Inhibitor of the Fibroblast Growth Factor Receptor Tyrosine Kinase Family", Cancer Research, Feb. 2012, pp. 2045-2056, vol. 72, No. 8.

Olechno et al., "Improving $IC_{50}$ Results with Acoustic Droplet Ejection", Technical Brief JALA, Aug. 2006, pp. 240-246.

Pelaez-Garcia et al., "FGFR4 Role in Epithelial-Mesenchymal Transition and Its Therapeutic Value in Colorectal Cancer", PLOS ONE, May 2013, pp. 1-11, vol. 8, issue 5.

Santos et al., "Michael Acceptors as Cysteine Protease Inhibitors", Mini-Reviews in Medicinal Chemistry, 2007, pp. 1040-1050, vol. 7, No. 10.

Sawey et al., "Identification of a Therapeutic Strategy Targeting Amplified FGF19 in Liver Cancer by Oncogenomic Screening", Cancer Cell, pp. 347-358, Mar. 2011, vol. 19.

Wesche et al., "Fibroblast growth factors and their receptors in cancer", Biochem. Journal, 2011, pp. 199-213.

Yanochko et al., "Pan-FGFR Inhibition Leads to Blockade of FGF23 Signaling, Soft Tissue Mineralization, and Cardiovascular Dysfunction", Toxicological Sciences, Jul. 2013, pp. 1-14.

Zaid et al., "Identification of FGFR4 as a Potential Therapeutic Target for Advanced-Stage, High-Grade Serous Ovarian Cancer", Clinical Cancer Research, Jan. 2013, pp. 809-820, vol. 19, No. 4.

Zhao et al., "A Novel, Selective Inhibitor of Fibroblast Growth Factor Receptors That Shows a Potent Broad Spectrum of Antitumor Activity in Several Tumor Xenograft Models", Molecular Cancer Therapeutics, Sep. 2011, pp. 2200-2210, vol. 10, No. 11.

Hagel et al., "First Selective Small Molecule Inhibitor of FGFR4 for the Treatment of Hepatocellular Carcinomas with an Activated FGFR4 Signaling Pathway", American Association for Cancer Research Journal, Mar. 2015, pp. 1-26.

Xu et al., "FGFR4 $Gly^{388}Arg$ polymorphism contributes to prostate cancer development and progression: A meta-analysis of 2618 cases and 2305 controls", BMC Cancer, 2011, pp. 1-6.

Miura et al., "Fibroblast growth factor 19 expression correlates with tumor progression and poorer prognosis of hepatocellular carcinoma", BMC Cancer, 2012, pp. 1-15.

Boyd et al., "Data Display and Analysis Strategies for the NCI Disease-Oriented in Vitro Antitumor Drug Screen", Cytotoxic Anticancer Drugs: Models and Concepts for Drug Discovery and Development, 1992, pp. 11-34.

Streit et al., "FGFR4 Arg388 allele correlates with tumour thickness and FGFR4 protein expression with survival of melanoma patients", British Journal of Cancer, 1994, pp. 1879-1886, vol. 94, No. 12.

Ye et al., "Fibroblast Growth Factor Receptor 4 Regulates Proliferation and Antiapoptosis During Gastric Cancer Progression", Cancer, Dec. 2011, pp. 5304-5313.

Chiang et al., "Focal Gains of VEGFA and Molecular Classification of Hepatocellular Carcinoma", American Association for Cancer Research Journal, Aug. 2008, pp. 6779-6788.

Sia et al., "Integrative Molecular Analysis of Intrahepatic Cholangiocarcinoma Reveals 2 Classes That Have Different Outcomes", Gastroenterology, 2013, pp. 829-840, vol. 144, No. 4.

Motoda et al., "Overexpression of fibroblast growth factor receptor 4 in high-grade pancreatic intraepithelial neoplasia and pancreatic ductal adenocarcinoma", International Journal of Oncology, 2011, pp. 133-143, vol. 38.

Taylor VI et al., "Identification of FGFR4-activating mutations in human rhabdomyosarcomas that promote metastasis in xenotransplanted models", The Journal of Clinical Investigation, Nov. 2009, pp. 3395-3407, vol. 119, No. 11.

Monks et al., "Feasibility of a High-Flux Anticancer Drug Screen Using a Diverse Panel of Cultured Human Tumor Cell Lines", Articles, Jun. 1991, pp. 757-766, vol. 83, No. 11.

Berge et al., "Pharmaceutical Salts", Journal of Pharmaceutical Sciences, Jan. 1977, pp. 1-19, vol. 66, No. 1.

(56) References Cited

OTHER PUBLICATIONS

Barderas et al., "An optimized predictor panel for colorectal cancer diagnosis based on the combination of tumor-associated antigens obtained from protein and phage microarrays", Journal of Proteomics, 2012, pp. 4647-4655, vol. 75.
Fawdar et al., "Targeted genetic dependency screen facilitates identification of actionable mutations in FGFR4, MAP3K9, and PAK5 in lung cancer", PNAS, Jul. 2013, pp. 12426-12431, vol. 110, No. 30.
Office Action dated Apr. 18, 2017, in Chinese Application No. 201480056358.4.
Office Action dated Sep. 20, 2017, in Colombian Application No. 16097757.
Lima, et al., "Bioisosterism: A Useful Strategy for Molecular Modification and Drug Design", Current Medicinal Chem., 2005, pp. 23-49, vol. 12.
Office Action dated Jun. 25, 2018, in Russian Application No. 2016118981.
Search Report dated Jun. 25, 2018, in Russian Application No. 2016118981.
Office Action for Indian Patent Application No. 201647012800, filed Oct. 16, 2014, dated Jun. 21, 2019.

\* cited by examiner

SEQUENCE LISTING

<160> NUMBER OF SEQ ID NOS: 1

<210> SEQ ID NO 1
<211> LENGTH: 14
<212> TYPE: PRT
<213> ORGANISM: Artificial
<220> FEATURE:
<223> OTHER INFORMATION: FGFR1 substrate

<400> SEQUENCE: 1

Lys Lys Lys Ser Pro Gly Glu Tyr Val Asn Ile Glu Phe Gly
1               5                   10

PYRIMIDINE FGFR4 INHIBITORS

BACKGROUND

Fibroblast growth factors (FGF) are a family of more than 20 structurally related proteins with a variety of biological activities. Their main receptors, the fibroblast growth factor receptors (FGFR1, FGFR2, FGFR3 and FGFR4), are a family of receptor tyrosine kinases that bind FGF and are involved in processes of cell proliferation and differentiation. Deregulation of FGFR signaling networks is implicated in a number of pathophysiological conditions, including many types of human cancers.

"Fibroblast Growth Factor Receptor 4" or "FGFR4" is known to regulate proliferation and antiapoptosis and is expressed or highly expressed in many cancers. See, e.g., Dieci et al. 2013, Cancer Discovery, 0F1-0F16. Studies have shown that expression of FGFR4 is predictive of a more aggressive phenotype of the cancer, and knockdown or reduction of FGFR4 expression serves to reduce proliferation and promote apoptosis. See, e.g., Wesche et al. 2011, Biochem J 437:199-213.

For example, FGFR4 expression or overexpression is associated with cancer aggressiveness in gastric cancer (Ye et al. 2011, Cancer, 5304-5313), prostate cancer (Xu et al. 2011, BMC Cancer, 11; 84), sarcoma such as rhabdomyosarcoma (Taylor V I et al. 2009, J Clin Invest, 119(11):3395-3407), skin cancer such as melanoma (Streit et al. 2006, British J Cancer, 94:1879-1886), liver cancer such as cholangiocarcinoma (Sia et al. 2013, Gastroenterology 144:829-840) and hepatocellular carcinoma (French et al. 2012, PLoS ONE 7(5): e367313; Miura et al. 2012, BMC Cancer 12:56; Chiang et al. 2008, Cancer Res 68(16):6779-6788; Sawey et al. 2011, Cancer Cell 19:347-358), pancreatic cancer such as pancreatic intraepithelial neoplasia and pancreatic ductal adenocarcinoma (Motoda et al. 2011, Int'l J Oncol 38:133-143), lung cancer such as non-small-cell lung cancer (Fawdar et al. 2013, PNAS 110(30):12426-12431), colorectal cancer (Pelaez-Garcia et al. 2013, PLoS ONE 8(5): e63695; Barderas et al. 2012, J Proteomics 75:4647-4655), and ovarian cancer (Zaid et al. 2013, Clin Cancer Res 19:809-820).

Clinical development of several FGFR inhibitors have confirmed their utility as antitumor agents. Dieci et al. 2013, Cancer Discovery, 0F1-0F16. However, new agents are needed that are useful to target FGFR, and FGFR4, in particular.

SUMMARY

A purpose of the present invention is to provide a compound of Formula I:

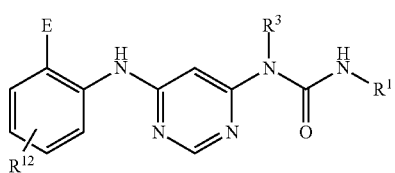

I wherein:
$R^3$ is selected from the group consisting of: $C_{1-6}$alkyl, $C_{1-6}$alkoxyC$_{1-6}$alkyl, NR$^{10}$R$^{11}$C$_{1-6}$alkyl, R$^{10}$heterocyclylC$_{1-6}$alkyl, R$^{10}$arylC$_{1-6}$alkyl, and R$^{10}$heteroarylC$_{1-6}$alkyl, wherein $R^{10}$ and $R^{11}$ are each independently selected from the group consisting of: hydrogen and $C_{1-6}$alkyl;

E is selected from the group consisting of:
—NR$^{13}$C(O)CR$^{14}$=CHR$^{15}$, and
—NR$^{3}$C(O)C≡CR$^{14}$, wherein $R^{13}$ is selected from the group consisting of: hydrogen and methyl, and $R^{14}$ and $R^{15}$ are each independently selected from the group consisting of: hydrogen, methyl, fluoro and chloro;

$R^{12}$ is selected from the group consisting of: hydrogen, halo, $C_{1-6}$alkyl, $C_{1-6}$alkoxy, hydroxyC$_{1-6}$alkyl, hydroxy $C_{1-6}$alkoxy, $C_{1-6}$alkoxyC$_{1-6}$alkoxy, $C_{1-6}$alkoxyC$_{1-6}$alkyl, R$^5$R$^6$heterocyclyl, —C(O)heterocyclylR$^5$R$^6$, R$^5$R$^6$heterocyclylC$_{1-6}$alkyl, NR$^5$R$^6$, NR$^5$R$^6$C$_{1-6}$alkyl, —C(O)NR$^5$R$^6$, and NR$^5$R$^6$C$_{1-6}$alkyoxy, wherein $R^5$ and $R^6$ are each independently selected from the group consisting of hydrogen, $C_{1-6}$alkyl, hydroxyC$_{1-6}$alkyl, aminoC$_{1-6}$alkyl, —C(O)C$_{1-6}$alkyl and $C_{1-6}$alkylsulfonyl; and $R^1$ is phenyl, wherein said phenyl is substituted 2, 3, or 4 times with independently selected halo or $C_{1-6}$alkoxy, or a pharmaceutically acceptable salt thereof.

In some embodiments, $R^3$ is $C_{1-6}$alkyl.

In some embodiments, $R^3$ is selected from the group consisting of: methyl, methoxyethyl, 4-pyridylmethyl, 3-pyridylmethyl, 2-pyridylmethyl, benzyl, N,N-dimethylaminopropyl, 3-methylisoxazol-5-yl-methyl, and 4-methylpiperazin-1-yl-propyl.

In some embodiments, E is —NR$^{13}$C(O)CH=CHR$^{15}$ or —NR$^{13}$C(O)CF=CH$_2$, wherein $R^{13}$ and $R^{15}$ are as defined above. In some embodiments, E is —NHC(O)CH=CH$_2$.

In some embodiments, $R^{12}$ is selected from the group consisting of: hydrogen, fluoro, chloro, methyl, methoxy, N,N-dimethylaminoethyl, piperazin-1-yl, 4-ethylpiperazin-1-yl, 4-ethylpiperazin-1-yl-methyl, 1-methylpiperidine-4-yl, 1-ethylpiperidine-4-yl, N,N-dimethylaminomethyl, N,N-dimethylaminopropyl, piperidine-4-yl, morpholino, 3,5-dimethylpiperazin-1-yl, 4-(methylsulfonyl)piperazin-1-yl, N,N-dimethylaminoethoxy, 4-(2-hydroxyethyl)piperazin-1-yl, hydroxyethoxy, methoxyethoxy, hydroxymethyl, methoxymethyl, 2-methoxypropyl, 2-hydroxypropyl, 2-aminopropyl, 4-methylpiperazin-1-yl-carbonyl, 4-ethylpiperazin-1-yl-carbonyl, 4-[2-propyl]piperazin-1-yl, 4-acetylpiperazin-1-yl, N-methyl-N-hydroxyethyl-amino, N,N-dimethyl amido, and 4-(2-aminoethyl)piperazin-1-yl.

In some embodiments, $R^{12}$ is selected from the group consisting of: hydrogen, $C_{1-6}$alkyl, hydroxyC$_{1-6}$alkyl, R$^5$R$^6$heterocyclyl, R$^5$R$^6$heterocyclylC$_{1-6}$alkyl, —C(O) NR$^5$R$^6$, NR$^5$R$^6$C$_{1-6}$alkyl, NR$^5$R$^6$C$_{1-6}$alkyoxy, $C_{1-6}$alkoxy, and $C_{1-6}$alkoxyC$_{1-6}$alkyl, wherein $R^5$ and $R^6$ are each independently selected from the group consisting of: hydrogen, $C_{1-6}$alkyl, hydroxyC$_{1-6}$alkyl, —C(O)C$_{1-6}$alkyl and $C_{1-6}$alkylsulfonyl.

In some embodiments, $R^{12}$ is R$^5$R$^6$heterocyclyl, wherein $R^5$ and $R^6$ are as defined above.

In some embodiments, R$^5$R$^6$heterocyclyl is R$^5$R$^6$piperazinyl, wherein $R^5$ and $R^6$ are as defined above.

In some embodiments, $R^{12}$ is 4-ethylpiperazin-1-yl.

In some embodiments, $R^{12}$ is not hydrogen.

In some embodiments, $R^1$ is 2,6-dichloro-3,5-dimethoxyphenyl.

In some embodiments, the compound is a compound of Formula I(a):

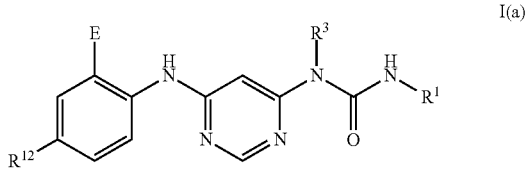

I(a)

wherein $R^3$, E, $R^{12}$ and $R^1$ are as defined above, or a pharmaceutically acceptable salt thereof.

A further purpose is a pharmaceutical composition comprising a compound or salt as described herein and a pharmaceutically acceptable carrier. In some embodiments, the composition is formulated for oral or parenteral administration.

A further purpose is a method of treating hepatocellular carcinoma in a subject in need thereof comprising administering to said subject a treatment effective amount of a compound or salt or composition as described herein. In some embodiments, hepatocellular carcinoma has altered FGFR4 and/or FGF19 status (e.g., increased expression of FGFR4 and/or FGF19).

A further purpose is a method of treating hepatocellular carcinoma in a subject in need thereof, comprising: detecting an altered FGFR4 and/or FGF19 status (e.g., increased expression of FGFR4 and/or FGF19) in a biological sample containing cells of said hepatocellular carcinoma, and if said hepatocellular carcinoma has said altered FGFR4 and/or FGF19 status, administering a compound or composition described herein to said subject in a treatment-effective amount.

A further purpose is the use of a compound or salt or a composition as described herein in a method of treatment of hepatocellular carcinoma.

A further purpose is the use of a compound or salt described herein in the preparation of a medicament for the treatment of hepatocellular carcinoma.

DETAILED DESCRIPTION OF EMBODIMENTS

Figure 1:
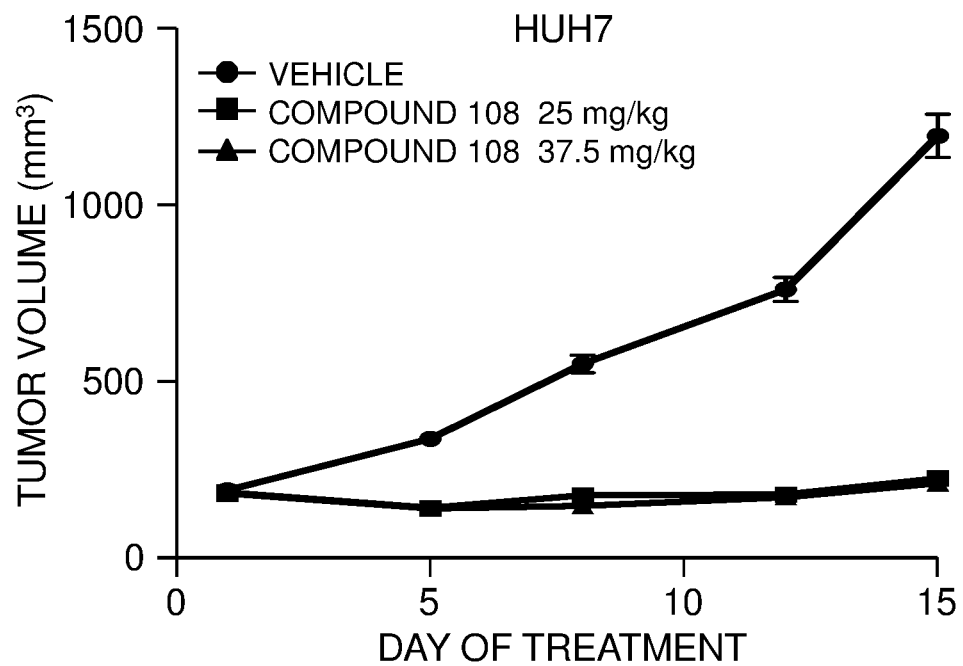
FIG. 1 presents the results of in vivo efficacy testing in hepatocellular carcinoma model using HUH7 cells. Compound 108 (25 mg/kg or 37.5 mg/kg) or Vehicle control was administered via intraperitoneal injection, and tumor volume was measured twice weekly over the course of 15 days.

Provided herein are compounds useful as FGFR4 inhibitors. In some embodiments, the compounds are selective FGFR4 inhibitors in that they have a greater binding affinity and/or inhibitory effect of FGFR4 as compared to that of FGFR1 and/or FGFR2 and/or FGFR3 (e.g., by 10-fold, 100-fold, or 1000-fold greater or more).

A. Definitions

Compounds useful as active agents in accordance with the present disclosure include those described generally above and below, and are further illustrated by the embodiments, sub-embodiments, and species disclosed herein. As used herein, the following definitions shall apply unless otherwise indicated.

As described herein, compounds of the invention may optionally be substituted with one or more substituents, such as those illustrated generally herein, or as exemplified by particular classes, subclasses, and species of the invention. In general, the term "substituted" refers to the replacement of hydrogen in a given structure with a specified substituent. Unless otherwise indicated, a substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable compounds. "Stable" as used herein refers to chemically feasible compound is one that is not substantially altered when kept at a temperature of 40° C. or less, in the absence of moisture or other chemically reactive conditions, for at least a week.

As would be understood by those of skill in the art, as used herein "H" is hydrogen, "C" is carbon, "N" is nitrogen, "S" is sulfur, and "O" is oxygen.

"Alkyl" or "alkyl group," as used herein, means a straight-chain (i.e., unbranched), or branched hydrocarbon chain that is completely saturated. In some embodiments, the alkyl has 1, 2, 3, 4, 5 or 6 carbon atoms. In certain embodiments, alkyl groups contain 1-6 carbon atoms ($C_{1-6}$alkyl). In certain embodiments, alkyl groups contain 1-4 carbon atoms ($C_{1-4}$alkyl). In certain embodiments, alkyl groups contain 1-3 carbon atoms ($C_{1-3}$alkyl). In still other embodiments, alkyl groups contain 2-3 carbon atoms ($C_{2-3}$alkyl), and in yet other embodiments alkyl groups contain 1-2 carbon atoms ($C_{1-2}$alkyl).

"Alkenyl" or "alkenyl group," as used herein, refers to a straight-chain (i.e., unbranched), or branched hydrocarbon chain that has one or more double bonds. In some embodiments, the alkenyl has 2, 3, 4, 5 or 6 carbon atoms. In certain embodiments, alkenyl groups contain 2-8 carbon atoms ($C_{2-8}$alkyl). In certain embodiments, alkenyl groups contain 2-6 carbon atoms ($C_{2-6}$alkyl). In still other embodiments, alkenyl groups contain 3-4 carbon atoms ($C_{3-4}$alkyl), and in yet other embodiments alkenyl groups contain 2-3 carbon atoms ($C_{2-3}$alkyl). According to another aspect, the term alkenyl refers to a straight chain hydrocarbon having two double bonds, also referred to as "diene." Non-limiting examples of exemplary alkenyl groups include —CH═CH$_2$, —CH$_2$CH═CH$_2$, —CH═CHCH$_3$, —CH$_2$CH$_2$CH═CH$_2$, —CH$_2$CH═CHCH$_3$, —CH═CHCH$_2$CH$_3$, and —CH═CHCH═CH$_2$.

"Alkynyl" or "alkynyl group" as used herein refers to a straight-chain (i.e., unbranched), or branched hydrocarbon chain that has one or more triple bonds. In some embodiments, the alkynyl has 2, 3, 4, 5 or 6 carbon atoms. In certain embodiments, alkynyl groups contain 2-8 carbon atoms ($C_{2-8}$alkynyl). In certain embodiments, alkynyl groups contain 2-6 carbon atoms ($C_{2-6}$alkynyl). In still other embodiments, alkynyl groups contain 3-4 carbon atoms ($C_{3-4}$alkynyl), and in yet other embodiments alkynyl groups contain 2-3 carbon atoms (C$_{2-3}$alkynyl).

"Ar" or "aryl" refer to an aromatic carbocyclic moiety having one or more closed rings. Examples include, without limitation, phenyl, naphthyl, anthracenyl, phenanthracenyl, biphenyl, and pyrenyl.

"Halo" refers to chloro (Cl), fluoro (F), bromo (Br) or iodo (I).

"Haloalkyl" refers to one or more halo groups appended to the parent molecular moiety through an alkyl group. Examples include, but are not limited to, chloromethyl, fluoromethyl, trifluoromethyl, etc.

"Heteroaryl" refers to a cyclic moiety having one or more closed rings, with one or more heteroatoms (oxygen, nitrogen or sulfur) in at least one of the rings, wherein at least one of the rings is aromatic, and wherein the ring or rings may independently be fused, and/or bridged. Examples include, without limitation, quinolinyl, isoquinolinyl, indolyl, furyl, thienyl, pyrazolyl, quinoxalinyl, pyrrolyl, indazolyl, thieno[2,3-c]pyrazolyl, benzofuryl, pyrazolo[1,5-a]pyridyl, thiophenylpyrazolyl, benzothienyl, benzothiazolyl, thiazolyl, 2-phenylthiazolyl, and isoxazolyl.

"—OR" or "oxy" refers to an R group appended to the parent molecular moiety through an oxygen atom, wherein R is H, alkyl, alkenyl, alkynyl, and the like.

"Alkoxy" refers to an alkyl group, as herein defined, attached to the principal carbon chain through an oxygen ("alkoxy") atom. Representative examples of "alkoxy" include, but are not limited to, methoxy, ethoxy, propoxy, phenoxy, 2-propoxy, butoxy, tert-butoxy, pentyloxy, hexyloxy and the like.

"Hydroxy" refers to an —OH group.

"Carbonyl" is a group having a carbon atom double-bonded to an oxygen atom (C=O), often depicted in chemical formulae as C(O).

An "acetyl" is a group —C(O)CH$_3$.

An "amine" or "amino" refers to a group —NH$_2$, wherein none, one or two of the hydrogens may replaced by a suitable substituent as described herein, such as alkyl, alkenyl, alkynyl, and the like.

An "amide" or "amido" refers to a group having a carbonyl bonded to a nitrogen atom, such as —C(O)NH$_2$, wherein none, one or two of the hydrogens may replaced by a suitable substituent as described herein, such as alkyl, alkenyl, alkynyl, and the like.

"—SR" refers to an R group appended to the parent molecular moiety through a sulfur atom, wherein R is alkyl, alkenyl, alkynyl, aryl, cycloalkyl, heterocyclo, or heteroaryl. Representative examples of "—SR" include, but are not limited to, ethanethiol, 3-methyl-1-butanethiol, phenylthiol and the like.

"Cycloalkyl" as used herein, refers to a saturated cyclic hydrocarbon group containing from 3 to 8 carbons or more. Representative examples of cycloalkyl include, but are not limited to, cyclopropyl, cyclobutyl, cyclopentyl, cyclohexyl, cycloheptyl, and cyclooctyl.

"Cycloalkenyl" as used herein, refers to an unsaturated cyclic hydrocarbon group containing from 3 to 8 carbons or more and having one or more double bonds.

"Cycloalkynyl" as used herein, refers to an unsaturated cyclic hydrocarbon group containing from 3 to 8 carbons or more and having one or more triple bonds.

"Electrophile" as used herein refers to a group having reduced electron density, typically comprising a carbon atom that is directly bonded to a more electronegative atom, such as an oxygen, nitrogen or halo. Exemplary electrophiles include, but are not limited to, diazomethane, trimethylsilyldiazomethane, alkyl halides, such as for example methyl iodide, benzyl bromide and the like, alkyl triflates, such as for example methyl triflate and the like, alkyl sulfonates, such as for example ethyl toluenesulfonate, butyl methanesulfonate and the like, acyl halides, such as for example acetyl chloride, benzoyl bromide and the like, acid anhydrides, such as for example acetic anhydride, succinic anhydride, maleic anhydride and the like, isocyanates, such as for example methyl isocyanate, phenyl isocyanate and the like, isothiocyanates, such as for example methyl isothiocyanate, phenyl isothiocyanate and the like, chloroformates, such as for example methyl chloroformate, ethyl chloroformate, benzyl chloroformate and the like, sulfonyl halides, such as for example methanesulfonyl chloride, methanesulfonyl fluoride, p-toluenesulfonyl chloride and the like, silyl halides, such as for example trimethylsilyl chloride, tert-butyldimethylsilyl chloride and the like, phosphoryl halides such as for example dimethyl chlorophosphate and the like, epoxides such as for example 2-methyloxirane, aziridines such as for example 2-methylaziridine, alpha-haloketone such as for example 1-chloro-2-propanone, alpha-beta-unsaturated carbonyl compounds such as for example acrolein, methyl vinyl ketone, cinnamaldehyde, N,N-dimethylacrylamide and the like, and gamma-halo-alpha-beta-unsaturated carbonyl compounds such as for example (E)-6-chlorohex-4-en-3-one. In some embodiments, electrophiles are alpha-haloketones, isothiocyanates, epoxides, aziridines, sulfonyl halides, or alpha-beta-unsaturated carbonyls.

In some embodiments, the electrophile is a Michael acceptor. As known in the art, a "Michael acceptor" is an alkene or alkyne of the form

wherein Z comprises an electron withdrawing group, including, but not limited to, CHO, COR, COOR, CONRR', CONROR', CN, NO$_2$, SOR, SO$_2$R. R may be H, alkyl, or aryl; wherein R' is alkyl, alkenyl, alkoxy or aryl. In another embodiment, azodicarboxamides and quinones are Michael acceptors. See, Santos, M. M. M. and Moreira, R., Mini-Reviews in Medicinal Chemistry, 7:1040-1050, 2007.

An example of the Michael Reaction is depicted in the scheme below:

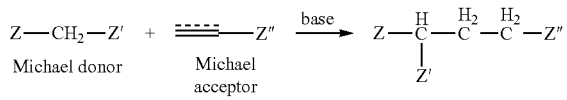

wherein electron withdrawing groups Z, Z' and Z" are as described above. In some embodiments, the Michael acceptors are alpha-beta-unsaturated carbonyl compounds including, but not limited to, alpha-beta-unsaturated amides, alpha-beta-unsaturated ketones, alpha-beta-unsaturated esters, conjugated alkynyl carbonyls and alpha-beta-unsaturated nitriles.

"Alpha-beta-unsaturaturated amide" or "unsaturated amide" as used herein refers to an amide comprising an alkene or alkyne bonded directly to the amide carbonyl group and is represented by the structure

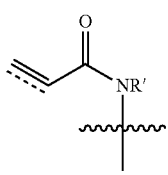

wherein R' is hydrogen or alkyl.

"Heteroatom" refers to O, S or N.

"Heterocycle" or "heterocyclyl" as used herein, means a monocyclic heterocycle, a bicyclic heterocycle, or a tricyclic heterocycle containing at least one heteroatom in the ring.

The monocyclic heterocycle is a 3-, 4-, 5-, 6-, 7, or 8-membered ring containing at least one heteroatom independently selected from the group consisting of O, N, and S. In some embodiments, the heterocycle is a 3- or 4-membered ring containing one heteroatom selected from the group consisting of O, N and S. In some embodiments, the heterocycle is a 5-membered ring containing zero or one double bond and one, two or three heteroatoms selected from the group consisting of O, N and S. In some embodiments, the heterocycle is a 6-, 7-, or 8-membered ring containing zero, one or two double bonds and one, two or three heteroatoms selected from the group consisting of O, N and S. Representative examples of monocyclic heterocycle include, but are not limited to, azetidinyl, azepanyl, aziridinyl, diazepanyl, 1,3-dioxanyl, 1,3-dioxolanyl, dihydropyranyl (including 3,4-dihydro-2H-pyran-6-yl), 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl (including tetrahydro-2H-pyran-4-yl), tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The bicyclic heterocycles of the present invention may be exemplified by a monocyclic heterocycle fused to an aryl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Representative examples of bicyclic heterocycles include, but are not limited to, 3,4-dihydro-2H-pyranyl, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, 3,4-dihydroquinolin-2(1H)-one and 1,2,3,4-tetrahydroquinolinyl.

The tricyclic heterocycle is a bicyclic heterocycle fused to an aryl group, or a bicyclic heterocycle fused to a monocyclic cycloalkyl, or a bicyclic heterocycle fused to a monocyclic cycloalkenyl, or a bicyclic heterocycle fused to a monocyclic heterocycle. Representative examples of tricyclic heterocycles include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

In the above heteroaryl and heterocycles the nitrogen or sulfur atoms can be optionally oxidized to various oxidation states. In a specific example, the group $S(O)_{0-2}$ refers to —S— (sulfide), —S(O)— (sulfoxide), and —SO$_2$— (sulfone) respectively. For convenience, nitrogens, particularly but not exclusively, those defined as annular aromatic nitrogens, are meant to include those corresponding N-oxide forms.

"Pharmaceutically acceptable salt" as used herein refer to acid addition salts or base addition salts of the compounds in the present disclosure. A pharmaceutically acceptable salt is any salt which retains the activity of the parent compound and does not impart any unduly deleterious or undesirable effect on a subject to whom it is administered and in the context in which it is administered. Pharmaceutically acceptable salts include, but are not limited to, metal complexes and salts of both inorganic and carboxylic acids. Pharmaceutically acceptable salts also include metal salts such as aluminum, calcium, iron, magnesium, manganese and complex salts. In addition, pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycolic, glycolylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, and the like. Pharmaceutically acceptable salts may be derived from amino acids including, but not limited to, cysteine. Methods for producing compounds as salts are known to those of skill in the art (see, e.g., Stahl et al., Handbook of Pharmaceutical Salts: Properties, Selection, and Use, Wiley-VCH; Verlag Helvetica Chimica Acta, Zurich, 2002; Berge et al., J. Pharm. Sci. 66: 1, 1977).

Unless indicated otherwise, nomenclature used to describe chemical groups or moieties as used herein follow the convention where, reading the name from left to right, the point of attachment to the rest of the molecule is at the right-hand side of the name. For example, the group "arylC$_{1-6}$alkyl" is attached to the rest of the molecule at the alkyl end.

Unless indicated otherwise, where a chemical group is described by its chemical formula, including a terminal bond moiety indicated by "—," it will be understood that the attachment is read from left to right. For example, —C(O)C$_{1-6}$alkyl is attached to the rest of the molecule at the carbonyl end.

Unless otherwise stated, structures depicted herein are also meant to include all enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. In addition, unless otherwise stated, all rotamer forms of the compounds of the invention are within the scope of the invention. Unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

"Isomers" refer to compounds having the same number and kind of atoms and hence the same molecular weight, but differing with respect to the arrangement or configuration of the atoms. It will be understood, however, that some isomers or racemates or others mixtures of isomers may exhibit more activity than others. "Stereoisomers" refer to isomers that differ only in the arrangement of the atoms in space. "Diastereoisomers" refer to stereoisomers that are not mirror images of each other. "Enantiomers" refers to stereoisomers that are non-superimposable mirror images of one another.

In some embodiments, enantiomeric compounds taught herein may be "enantiomerically pure" isomers that comprise substantially a single enantiomer, for example, greater than or equal to 90%, 92%, 95%, 98%, or 99%, or equal to 100% of a single enantiomer.

In some embodiments, enantiomeric compounds taught herein may be stereomerically pure. "Stereomerically pure" as used herein means a compound or composition thereof that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of diastereomers, and substantially free of the opposite enantiomer, of the compound. A typical stereomerically pure compound comprises greater than about 80% by weight of one stereoisomer of the compound and less than about 20% by weight of the other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. See, e.g., U.S. Pat. No. 7,189,715.

"R" and "S" as terms describing isomers are descriptors of the stereochemical configuration at an asymmetrically substituted carbon atom. The designation of an asymmetrically substituted carbon atom as "R" or "S" is done by application of the Cahn-Ingold-Prelog priority rules, as are well known to those skilled in the art, and described in the International Union of Pure and Applied Chemistry (IUPAC) Rules for the Nomenclature of Organic Chemistry, Section E, Stereochemistry.

"Enantiomeric excess" (ee) of an enantiomer is [(the mole fraction of the major enantiomer) minus (the mole fraction of the minor enantiomer)]×100.

B. Compounds

Provided herein as active agents according to some embodiments is a compound of Formula I:

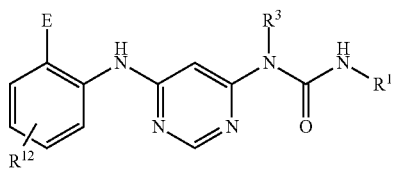

I wherein:
$R^3$ is selected from the group consisting of: $C_{1-6}$alkyl, $C_{1-6}$alkoxyC$_{1-6}$alkyl, $NR^{10}R^{11}C_{1-6}$alkyl, $R^{10}$heterocyclylC$_{1-6}$alkyl, $R^{10}$arylC$_{1-6}$alkyl, and $R^{10}$heteroarylC$_{1-6}$alkyl, wherein $R^{10}$ and $R^{11}$ are each independently selected from the group consisting of: hydrogen and $C_{1-6}$alkyl;

E is selected from the group consisting of:
—NR$^{13}$C(O)CR$^{14}$═CHR$^{15}$, and
—NR$^{13}$C(O)C≡CR$^{14}$,
wherein $R^{13}$ is selected from the group consisting of: hydrogen and methyl, and $R^{14}$ and $R^{15}$ are each independently selected from the group consisting of: hydrogen, methyl, fluoro and chloro;

$R^{12}$ is selected from the group consisting of: hydrogen, halo, $C_{1-6}$alkyl, $C_{1-6}$alkoxy, hydroxyC$_{1-6}$alkyl, hydroxy $C_{1-6}$alkoxy, $C_{1-6}$alkoxyC$_{1-6}$alkoxy, $C_{1-6}$alkoxyC$_{1-6}$alkyl, $R^5R^6$heterocyclyl, —C(O)heterocyclylR$^5R^6$, $R^5R^6$heterocyclylC$_{1-6}$alkyl, $NR^5R^6$, $NR^5R^6C_{1-6}$alkyl, —C(O)NR$^5R^6$, and NR$^5R^6C_{1-6}$alkyoxy, wherein $R^5$ and $R^6$ are each independently selected from the group consisting of hydrogen, $C_{1-6}$alkyl, hydroxyC$_{1-6}$alkyl, aminoC$_{1-6}$alkyl, —C(O)C$_{1-6}$alkyl and $C_{1-6}$alkylsulfonyl; and $R^1$ is phenyl, wherein said phenyl is substituted 2, 3, or 4 times with independently selected halo or $C_{1-6}$alkoxy,
or a pharmaceutically acceptable salt thereof.

In some embodiments, $R^3$ is $C_{1-6}$alkyl.

In some embodiments, $R^3$ is selected from the group consisting of: methyl, methoxyethyl, 4-pyridylmethyl, 3-pyridylmethyl, 2-pyridylmethyl, benzyl, N,N-dimethylaminopropyl, 3-methylisoxazol-5-yl-methyl, and 4-methylpiperazin-1-yl-propyl.

In some embodiments, E is —NR$^{13}$C(O)CH═CHR$^{15}$ or —NR$^{13}$C(O)CF═CH$_2$, wherein $R^{13}$ and $R^{15}$ are as defined above. In some embodiments, E is —NHC(O)CH═CH$_2$.

In some embodiments, $R^{12}$ is selected from the group consisting of: hydrogen, fluoro, chloro, methyl, methoxy, N,N-dimethylaminoethyl, piperazin-1-yl, 4-ethylpiperazin-1-yl, 4-ethylpiperazin-1-yl-methyl, 1-methylpiperidine-4-yl, 1-ethylpiperidine-4-yl, N,N-dimethylaminomethyl, N,N-dimethylaminopropyl, piperidine-4-yl, morpholino, 3,5-dimethylpiperazin-1-yl, 4-(methylsulfonyl)piperazin-1-yl, N,N-dimethylaminoethoxy, 4-(2-hydroxyethyl)piperazin-1-yl, hydroxyethoxy, methoxyethoxy, hydroxymethyl, methoxymethyl, 2-methoxypropyl, 2-hydroxypropyl, 2-aminopropyl, 4-methylpiperazin-1-yl-carbonyl, 4-ethylpiperazin-1-yl-carbonyl, 4-[2-propyl]piperazin-1-yl, 4-acetylpiperazin-1-yl, N-methyl-N-hydroxyethyl-amino, N,N-dimethylamido, and 4-(2-aminoethyl)piperazin-1-yl.

In some embodiments, $R^{12}$ is selected from the group consisting of: hydrogen, $C_{1-6}$alkyl, hydroxyC$_{1-6}$alkyl, $R^5R^6$heterocyclyl, $R^5R^6$heterocyclylC$_{1-6}$alkyl, —C(O)NR$^5R^6$, NR$^5R^6C_{1-6}$alkyl, NR$^5R^6C_{1-6}$alkyoxy, $C_{1-6}$alkoxy, and $C_{1-6}$alkoxyC$_{1-6}$alkyl, wherein $R^5$ and $R^6$ are each independently selected from the group consisting of: hydrogen, $C_{1-6}$alkyl, hydroxyC$_{1-6}$alkyl, —C(O)C$_{1-6}$alkyl and $C_{1-6}$alkylsulfonyl.

In some embodiments, $R^{12}$ is $R^5R^6$heterocyclyl, wherein $R^5$ and $R^6$ are as defined above.

In some embodiments, $R^5R^6$heterocyclyl is $R^5R^6$piperazinyl, wherein $R^5$ and $R^6$ are as defined above.

In some embodiments, $R^{12}$ is 4-ethylpiperazin-1-yl.

In some embodiments, $R^{12}$ is not hydrogen.

In some embodiments, $R^1$ is 2,6-dichloro-3,5-dimethoxyphenyl.

In some embodiments, the compound is a compound of Formula I(a):

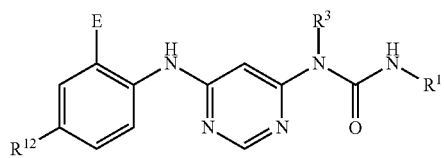

I(a)

wherein $R^3$, E, $R^{12}$ and $R^1$ are as defined above, or a pharmaceutically acceptable salt thereof.

C. Pharmaceutical Formulations

Active agents of the present invention can be combined with a pharmaceutically acceptable carrier to provide pharmaceutical formulations thereof. The particular choice of carrier and formulation will depend upon the particular route of administration for which the composition is intended.

"Pharmaceutically acceptable carrier" as used herein refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, sorbic acid, potassium sorbate, partial glyceride mixtures of saturated vegetable fatty acids, water, salts or electrolytes, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene glycol and wool fat.

The compositions of the present invention may be suitable for parenteral, oral, inhalation spray, topical, rectal, nasal, buccal, vaginal or implanted reservoir administration, etc. In some embodiments, the formulation comprise ingredients that are from natural or non-natural sources. In some embodiments, the formulation or carrier may be provided in a sterile form. Non-limiting examples of a sterile carrier include endotoxin-free water or pyrogen-free water.

The term "parenteral" as used herein includes subcutaneous, intravenous, intramuscular, intra-articular, intra-synovial, intrasternal, intrathecal, intrahepatic, intralesional and intracranial injection or infusion techniques. In particular embodiments, the compounds are administered intravenously, orally, subcutaneously, or via intramuscular administration. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids and their glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents that are commonly used in the manufacture of pharmaceutically acceptable solid, liquid, or other dosage forms may also be used for the purposes of formulation.

For oral administration, a compound or salt may be provided in an acceptable oral dosage form, including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried cornstarch. When aqueous suspensions are required for oral use, the active ingredient may be combined with emulsifying and suspending agents. If desired, certain sweetening, flavoring or coloring agents may also be added. In addition preservatives may also be added. Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

D. Subjects and Methods of Use

Active agents of the present invention may be used to treat hepatocellular carcinoma.

"Treatment," "treat," and "treating" refer to reversing, alleviating, delaying the onset of, inhibiting the progress of, or otherwise ameliorating a disease or disorder as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

"Patient" or "subject", as used herein, means an animal subject, preferably a mammalian subject, and particularly human subjects (including both male and female subjects, and including neonatal, infant, juvenile, adolescent, adult and geriatric subjects). Subjects may also include other mammalian subjects (e.g., dog, cat, horse, cow, sheep, goat, monkey, bird, etc.), for laboratory or veterinary purposes.

In some embodiments, treatment is provided to a subject having hepatocellular carcinoma with altered FGFR4 and/or FGF19 (fibroblast growth factor 19) status.

In some embodiments, treatment may include or be performed in conjunction with analyzing FGFR4 and/or FGF19 status in a biological sample containing cells of said hepatocellular carcinoma, and if said hepatocellular carcinoma exhibits an FGFR4 and/or FGF19 alteration, treating a subject with a treatment effective amount of an active agent as described herein.

"Altered status" as used herein with reference to FGFR4 and/or FGF19 includes an increased expression thereof (e.g., increased levels of the mRNA or increased levels of the protein), increased copy number in the genome, and/or increased activity of the encoded protein as a result of mutation, etc., as compared to a corresponding non-cancerous tissue. In some embodiments, altered status of FGFR4 and/or FGF9 includes gene and/or encoded protein mutations that result in an increase in activity or are otherwise associated with a more aggressive form of hepatocellular carcinoma.

"Expression" of FGFR4 and/or FGF19 means that a gene encoding the same is transcribed, and preferably, translated.

Typically, expression of a coding region will result in production of the encoded polypeptide.

The FGFR4 and FGF19 proteins are known, and their altered status and/or expression may be measured using techniques standard in the art, e.g., genomic analysis of mutations or copy number aberrations such as by nucleic acid amplification, sequencing analysis, and/or hybridization-based techniques, RNA expression analysis such as northern blot or qRT-PCR, western blot or other immunoblot or immunoassay, fluorescent activated cell sorting (FACS), etc.

In order that the invention described herein may be more fully understood, the following examples are set forth. It should be understood that these examples are for illustrative purposes only and are not to be construed as limiting.

EXAMPLES

General:

Microwave heating was done using a Biotage Emrys Liberator or Initiator microwave. Column chromatography was carried out using an Isco Rf200d. Solvent removal was carried out using either a Büchi rotary evaporator or a Genevac centrifugal evaporator. Preparative LC/MS was conducted using a Waters autopurifier and 19×100 mm XTerra 5 micron MS C18 column under acidic mobile phase conditions. NMR spectra were recorded using a Varian 400 MHz spectrometer.

When the term "inerted" is used to describe a reactor (e.g., a reaction vessel, flask, glass reactor, and the like) it is meant that the air in the reactor has been replaced with an essentially moisture-free or dry, inert gas (such as nitrogen, argon, and the like).

General methods and experimentals for preparing compounds of the present invention are set forth below. In certain cases, a particular compound is described by way of example. However, it will be appreciated that in each case a series of compounds of the present invention were prepared in accordance with the schemes and experimentals described below.

Preparative HPLC Conditions for the Purification of Target Compounds

Chromatography Conditions:
  Instrument: Waters 2767-SQD Mass trigger Prep System
  Column: Waters Xbridge C18 150 mm*19 mm*5 μm
  Detector: VWD SQD
  Flow Rate: 15 mL/min
  Gradient Time:

| Time (min) | B % |
|---|---|
| 0 | 5 |
| 7.5 | 70 |
| 8 | 95 |
| 11 | 95 |

Representative Mobile Phase:
1)
  Mobile Phase: A: 0.1% TFA in water
  Mobile Phase: B: ACN
2)
  Mobile Phase: A: 0.1% NH$_4$HCO$_3$ in water
  Mobile Phase: B: ACN
3)
  Mobile Phase: A: 0.1% NH$_4$OAc in water
  Mobile Phase: B: ACN
4)
  Mobile Phase: A: 0.1% NH$_4$OH in water
  Mobile Phase: B: ACN Definitions: The following abbreviations have the indicated meanings:

ACN: Acetonitrile
Boc$_2$O: Di-tert-butyl dicarbonate
Brettphos: 2-(Dicyclohexylphosphino)-3,6-dimethoxy-2',4',6'-triisopropyl-1,1'-biphenyl
tBuONa: Sodium tert-butoxide
CH$_3$I: Iodomethane
Cs$_2$CO$_3$: Cesium carbonate
DCC: N,N'-dicyclohexylcarbodiimide
DCM: Dichloromethane
DIEA: N,N-diisopropylethylamine
DIPEA: N,N-diisopropylethylamine
DMAP: 4-(Dimethylamino)pyridine
DME: Dimethyl ether
DMF: Dimethylformamide
DMSO: Dimethyl sulfoxide
EGTA: Ethylene glycol tetraacetic acid
ESI-MS: Electrospray ionization-mass spectrometry
EtOH: Ethanol
HATU: 1-[Bis(dimethylamino)methylene]-1H-1,2,3-trizolo[4,5-b]pyridinium 3-oxid hexafluorophosphate
H$_2$SO$_4$: Sulfuric acid
iPrOH: Isopropanol
K$_2$CO$_3$: Potassium carbonate
KHMDS: Potassium bis(trimethylsilyl)amide
KOH: Potassium hydroxide
LCMS: Liquid chromatography-mass spectrometry
MeOH: Methanol
MsCl: Methansulfonyl chloride
NaBH$_3$CN: Sodium cyanoborohydride
NaBH(OAc)$_3$: Sodium triacetoxyborohydride
NH$_4$Cl: Ammonium chloride
NH$_4$HCO$_3$: Ammonium bicarbonate
NaI: Sodium iodide
NaNO$_3$: Sodium nitrate
NaOAc: Sodium acetate
nBuOH: n-Butanol
prep-HPLC: Preparative high-performance liquid chromatography
prep-TLC: Preparative thin layer chromatography
TBAF: Tetrabutylammonium fluoride
TBDMS-CL: tert-Butyldimethylsilyl chloride
TBSCl: tert-Butyldimethylsilyl chloride
TBSOTf: tert-Butyldimethylsilyl trifluoromethanesulfonate
TEA: Triethylamine
TESCl: Chlorotriethylsilane
TFA: Trifluoroacetic acid
THF: Tetrahydrofuran
Ti(O$^i$Pr)$_4$: Titanium isopropoxide
TLC: Thin-layer chromatography
PPTS: Pyridinium p-toluenesulfonate
PE: Petroleum ether
PEG: Poly(ethylene glycol)
PtO$_2$: platinum dioxide
EtOAc: Ethyl acetate
Pd/C: Palladium (0) on carbon
Pd$_2$(dba)$_3$: Tris(dibenzylideneacetone) dipalladium(0)
Pd(dppf)$_2$Cl$_2$: [1,1'-Bis(diphenylphosphino)ferrocene]dichloropalladium(II)
Ruphos: 2-Dicyclohexylphosphino-2',6'-diisopropoxybiphenyl Xantphos: 4,5-Bis(diphenylphosphino)-9,9-dimethylxanthene Materials: The following compounds are commercially available and/or can be prepared in a number of ways well known to one skilled in the art of organic synthesis. More specifically, disclosed compounds can be prepared using the reactions and techniques described herein. In the description of the synthetic methods described below, it is to be understood that all proposed reaction conditions, including choice of solvent, reaction atmosphere, reaction temperature, duration of the experiment, and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

Synthesis and Testing of Example Compounds

Compounds of Table 1 were prepared by the Procedures of 2A-2L.

TABLE 1

| Structure | Compound # | FGFR4 IC$_{50}$ (µM) | FGFR1 IC$_{50}$ (µM) |
|---|---|---|---|
| 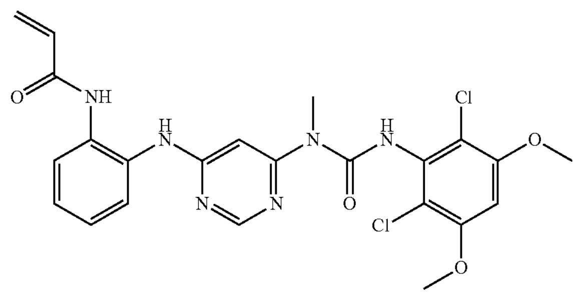 [SMILES: C=CC(=O)Nc1ccccc1Nc1cc(N(C)C(=O)Nc2c(Cl)c(OC)cc(OC)c2Cl)ncn1] | 100 | <0.001 | >10.0 |
| 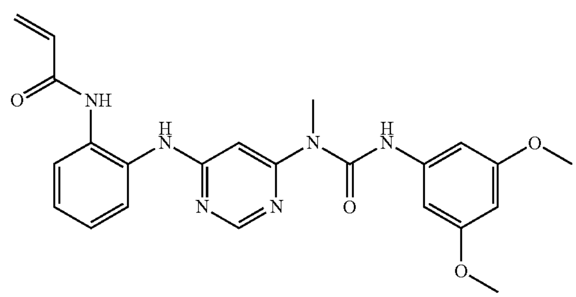 [SMILES: C=CC(=O)Nc1ccccc1Nc1cc(N(C)C(=O)Nc2cc(OC)cc(OC)c2)ncn1] | 102 | 0.853 | >10.0 |
| 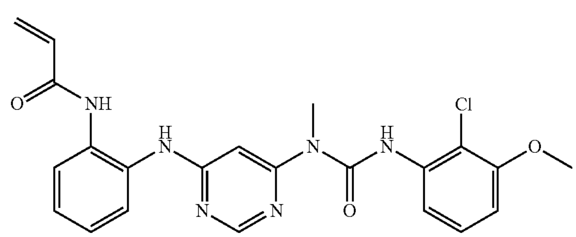 [SMILES: C=CC(=O)Nc1ccccc1Nc1cc(N(C)C(=O)Nc2cccc(OC)c2Cl)ncn1] | 103 | 0.673 | >10.0 |
| 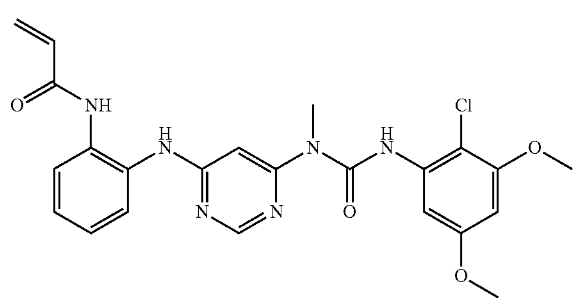 [SMILES: C=CC(=O)Nc1ccccc1Nc1cc(N(C)C(=O)Nc2cc(OC)cc(OC)c2Cl)ncn1] | 105 | 0.201 | >10.0 |

TABLE 1-continued

| Structure | Compound # | FGFR4 IC$_{50}$ (μM) | FGFR1 IC$_{50}$ (μM) |
|---|---|---|---|
| 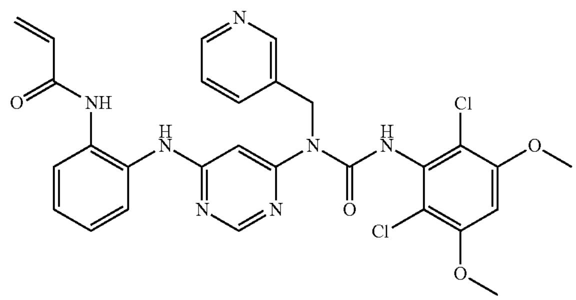 [SMILES: C=CC(=O)Nc1ccccc1Nc1cc(N(Cc2cccnc2)C(=O)Nc2c(Cl)c(OC)cc(OC)c2Cl)ncn1] | 107 | <0.001 | 0.720 |
| 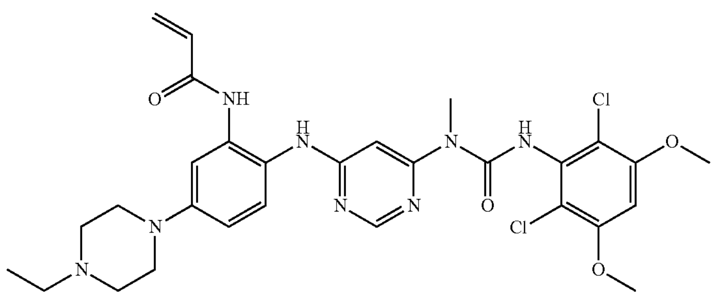 [SMILES: C=CC(=O)Nc1cc(N2CCN(CC)CC2)ccc1Nc1cc(N(C)C(=O)Nc2c(Cl)c(OC)cc(OC)c2Cl)ncn1] | 108 | <0.001 | 0.173 |
| 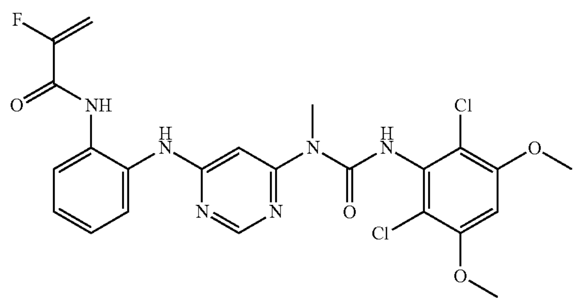 [SMILES: C=C(F)C(=O)Nc1ccccc1Nc1cc(N(C)C(=O)Nc2c(Cl)c(OC)cc(OC)c2Cl)ncn1] | 110 | 0.027 | >50.0 |
| 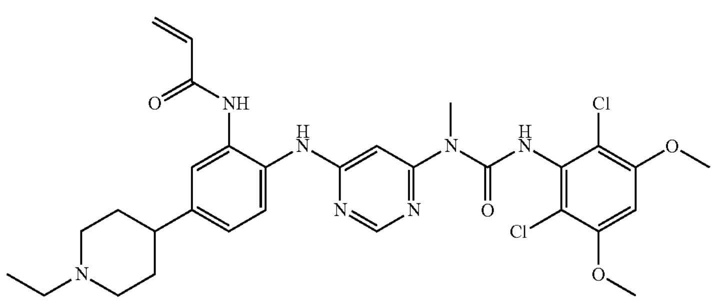 [SMILES: C=CC(=O)Nc1cc(C2CCN(CC)CC2)ccc1Nc1cc(N(C)C(=O)Nc2c(Cl)c(OC)cc(OC)c2Cl)ncn1] | 111 | <0.001 | 1.280 |
| 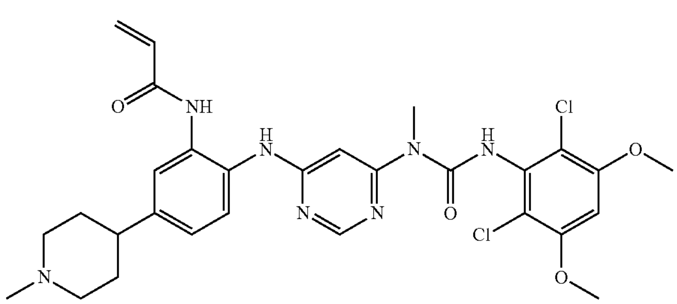 | 112 | <0.001 | 2.600 |

TABLE 1-continued
| Structure | Compound # | FGFR4 IC$_{50}$ (μM) | FGFR1 IC$_{50}$ (μM) |
|---|---|---|---|
| 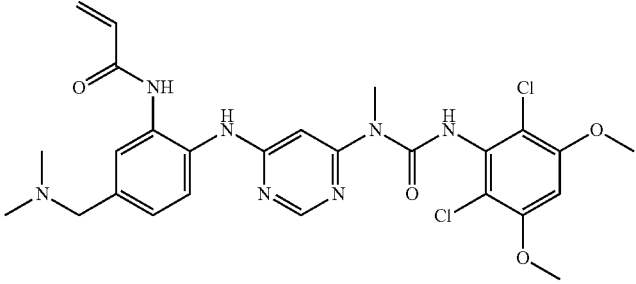 | 113 | <0.001 | 0.621 |
| 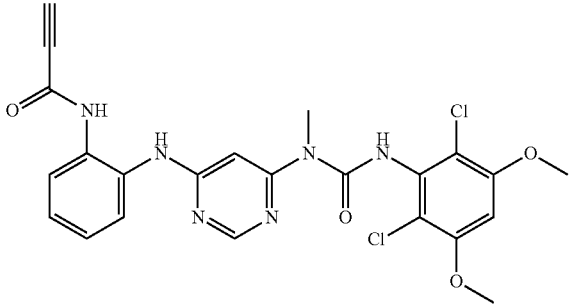 [SMILES: C#CC(=O)Nc1ccccc1Nc1cc(N(C)C(=O)Nc2c(Cl)c(OC)cc(OC)c2Cl)ncn1] | 114 | <0.001 | 0.042 |
| 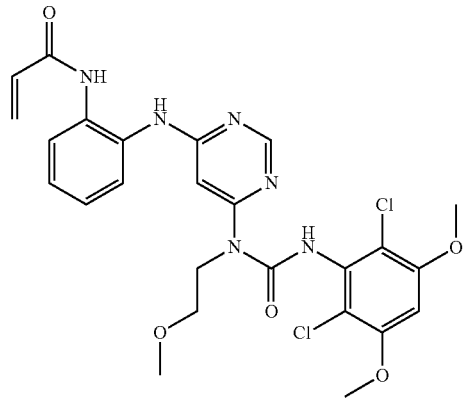 [SMILES: C=CC(=O)Nc1ccccc1Nc1cc(N(CCOC)C(=O)Nc2c(Cl)c(OC)cc(OC)c2Cl)ncn1] | 116 | 0.004 | >20.0 |
| 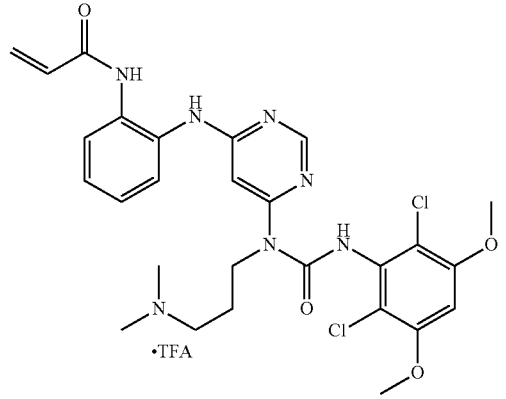 [SMILES: C=CC(=O)Nc1ccccc1Nc1cc(N(CCCN(C)C)C(=O)Nc2c(Cl)c(OC)cc(OC)c2Cl)ncn1] | 120 | <0.001 | 1.190 |

TABLE 1-continued
| Structure | Compound # | FGFR4 IC$_{50}$ (μM) | FGFR1 IC$_{50}$ (μM) |
|---|---|---|---|
| 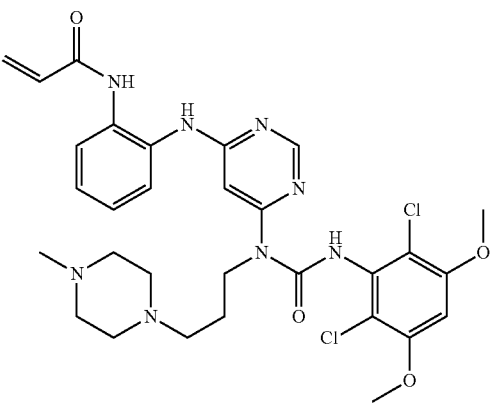 [SMILES: C=CC(=O)Nc1ccccc1Nc1cc(N(CCCN2CCN(C)CC2)C(=O)Nc2c(Cl)c(OC)cc(OC)c2Cl)ncn1] | 121 | <0.001 | 1.020 |
| 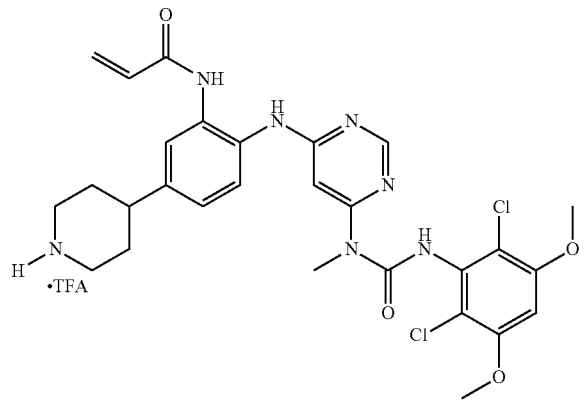 [SMILES: C=CC(=O)Nc1cc(C2CCNCC2)ccc1Nc1cc(N(C)C(=O)Nc2c(Cl)c(OC)cc(OC)c2Cl)ncn1] | 122 | <0.001 | 0.324 |
| 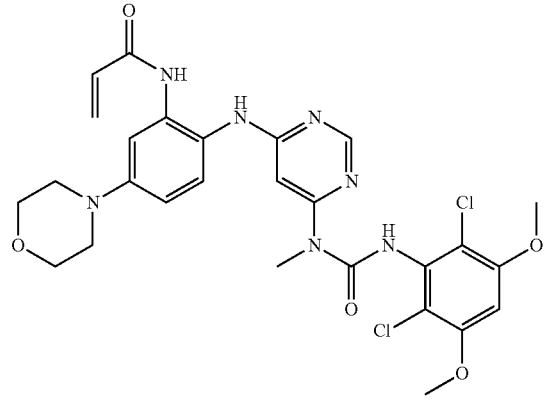 [SMILES: C=CC(=O)Nc1cc(N2CCOCC2)ccc1Nc1cc(N(C)C(=O)Nc2c(Cl)c(OC)cc(OC)c2Cl)ncn1] | 123 | <0.001 | 3.890 |

TABLE 1-continued

| Structure | Compound # | FGFR4 IC$_{50}$ (μM) | FGFR1 IC$_{50}$ (μM) |
|---|---|---|---|
| 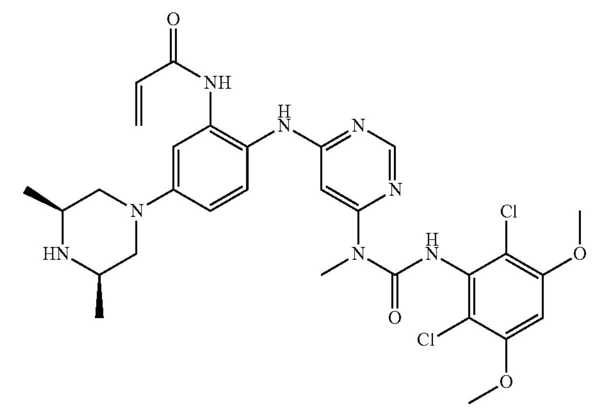 | 124 | <0.001 | 0.164 |
| 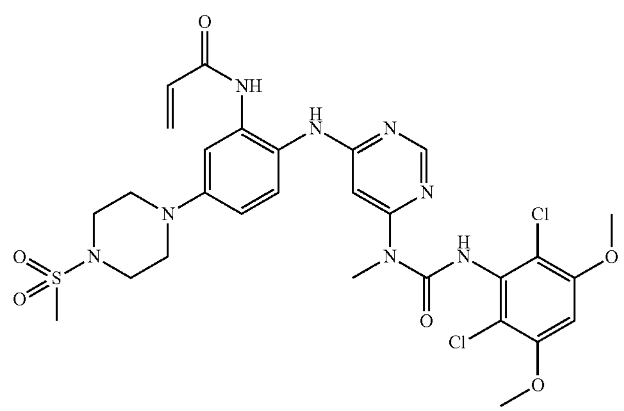 [SMILES: C=CC(=O)Nc1cc(N2CCN(S(C)(=O)=O)CC2)ccc1Nc1cc(N(C)C(=O)Nc2c(Cl)c(OC)cc(OC)c2Cl)ncn1] | 125 | <0.001 | 2.860 |
| 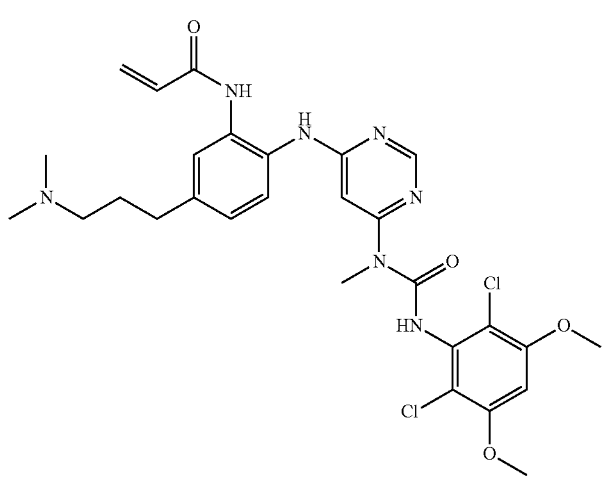 | 126 | <0.001 | 0.601 |

TABLE 1-continued

| Structure | Compound # | FGFR4 IC$_{50}$ (μM) | FGFR1 IC$_{50}$ (μM) |
| --- | --- | --- | --- |
| 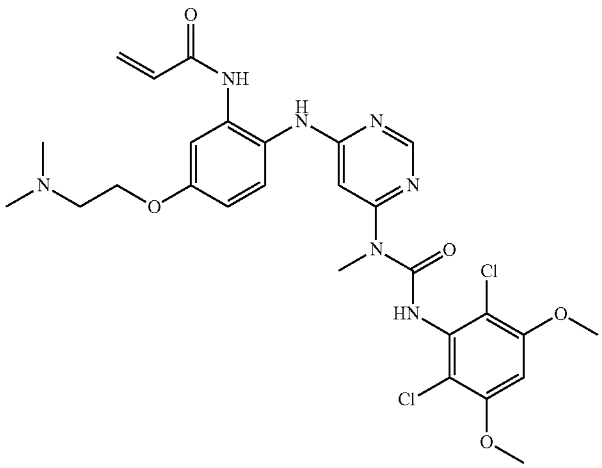 | 127 | <0.001 | 3.200 |
| 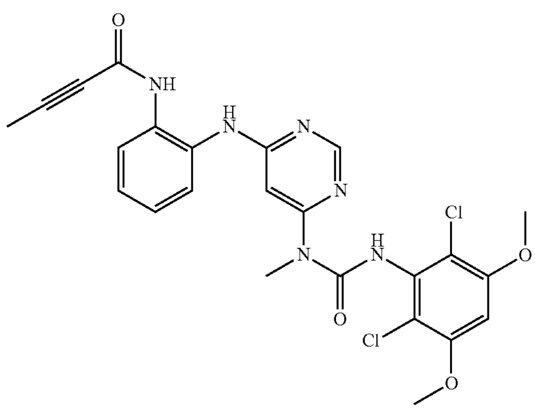 [SMILES: CC#CC(=O)Nc1ccccc1Nc1cc(N(C)C(=O)Nc2c(Cl)c(OC)cc(OC)c2Cl)ncn1] | 128 | 0.033 | 1.680 |
| 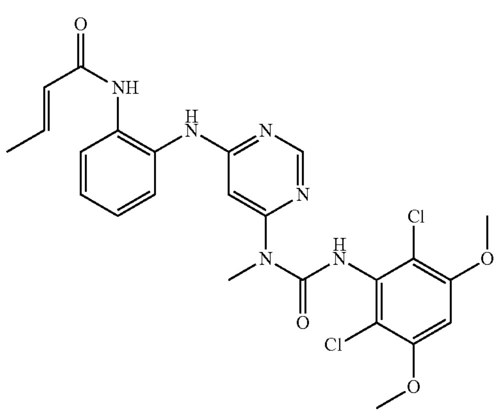 [SMILES: C/C=C/C(=O)Nc1ccccc1Nc1cc(N(C)C(=O)Nc2c(Cl)c(OC)cc(OC)c2Cl)ncn1] | 129 | 0.063 | >10.0 |

TABLE 1-continued
| Structure | Compound # | FGFR4 IC$_{50}$ (μM) | FGFR1 IC$_{50}$ (μM) |
|---|---|---|---|
| 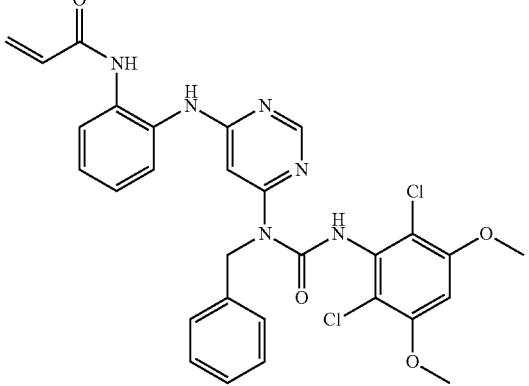 | 130 | 0.002 | >10.0 |
| 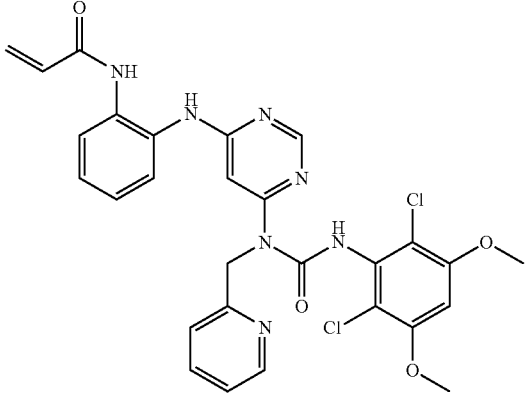 [SMILES: C=CC(=O)Nc1ccccc1Nc1cc(N(Cc2ccccn2)C(=O)Nc2c(Cl)c(OC)cc(OC)c2Cl)ncn1] | 131 | <0.001 | 1.170 |
| 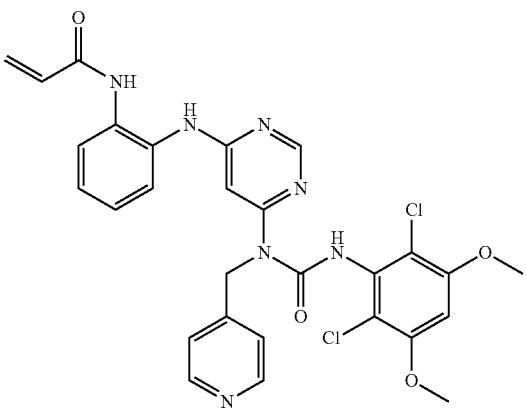 [SMILES: C=CC(=O)Nc1ccccc1Nc1cc(N(Cc2ccncc2)C(=O)Nc2c(Cl)c(OC)cc(OC)c2Cl)ncn1] | 132 | <0.001 | 0.495 |

TABLE 1-continued
| Structure | Compound # | FGFR4 IC$_{50}$ (μM) | FGFR1 IC$_{50}$ (μM) |
|---|---|---|---|
| 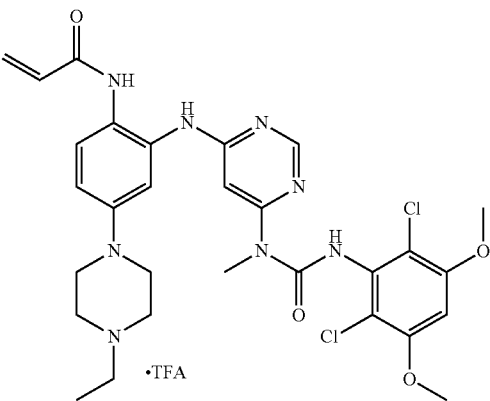 [SMILES: C=CC(=O)Nc1ccc(N2CCN(CC)CC2)cc1Nc1cc(N(C)C(=O)Nc2c(Cl)c(OC)cc(OC)c2Cl)ncn1] | 133 | 0.004 | >10.0 |
| 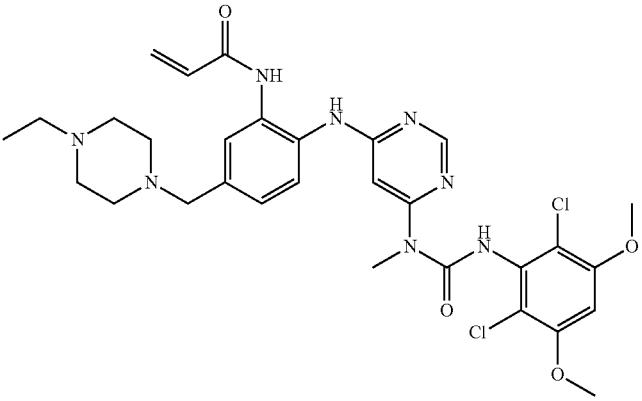 [SMILES: C=CC(=O)Nc1cc(CN2CCN(CC)CC2)ccc1Nc1cc(N(C)C(=O)Nc2c(Cl)c(OC)cc(OC)c2Cl)ncn1] | 135 | <0.001 | 2.027 |
| 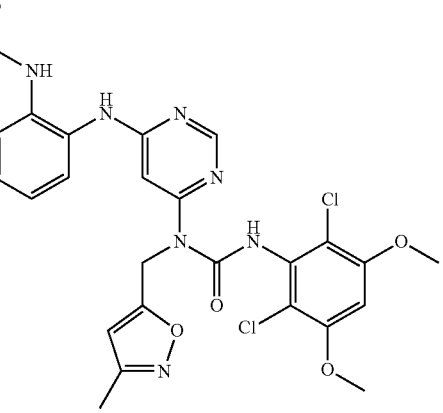 | 136 | <0.001 | 0.112 |

TABLE 1-continued

| Structure | Compound # | FGFR4 IC$_{50}$ (μM) | FGFR1 IC$_{50}$ (μM) |
|---|---|---|---|
| 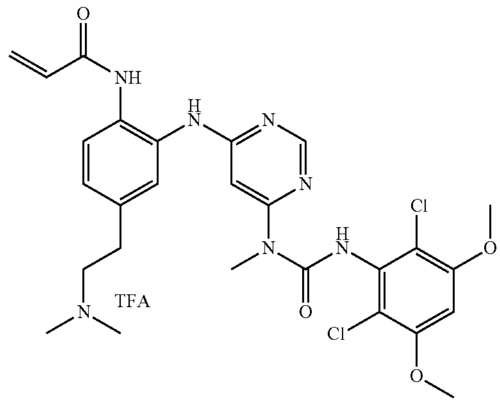 [SMILES: C=CC(=O)Nc1ccc(CCN(C)C)cc1Nc1cc(N(C)C(=O)Nc2c(Cl)c(OC)cc(OC)c2Cl)ncn1] | 137 | <0.001 | >10.0 |
| 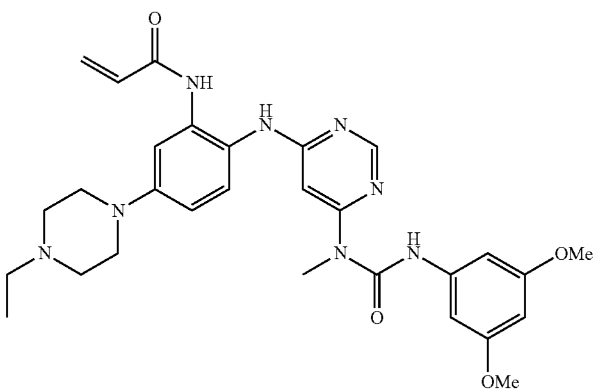 [SMILES: C=CC(=O)Nc1cc(N2CCN(CC)CC2)ccc1Nc1cc(N(C)C(=O)Nc2cc(OC)cc(OC)c2)ncn1] | 139 | 0.006 | >20.0 |
| 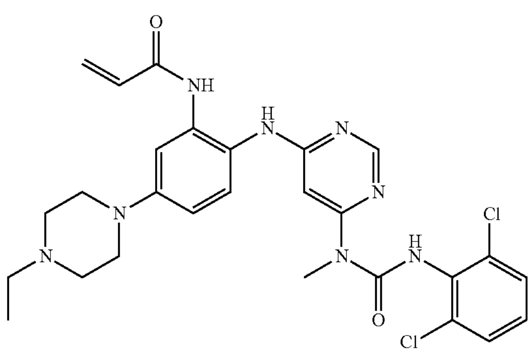 [SMILES: C=CC(=O)Nc1cc(N2CCN(CC)CC2)ccc1Nc1cc(N(C)C(=O)Nc2c(Cl)cccc2Cl)ncn1] | 140 | <0.001 | >20.0 |
| 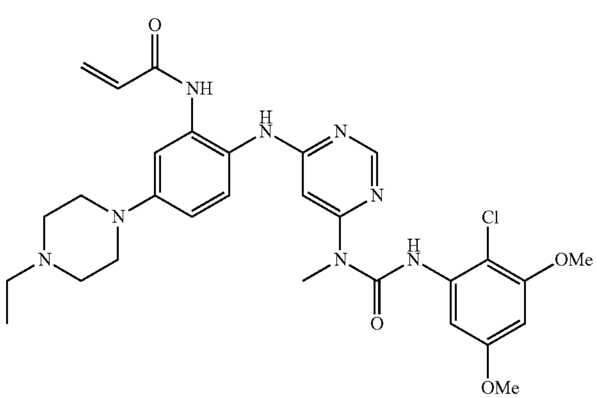 [SMILES: C=CC(=O)Nc1cc(N2CCN(CC)CC2)ccc1Nc1cc(N(C)C(=O)Nc2cc(OC)cc(OC)c2Cl)ncn1] | 141 | 0.002 | >20.0 |

TABLE 1-continued
| Structure | Compound # | FGFR4 IC$_{50}$ (μM) | FGFR1 IC$_{50}$ (μM) |
|---|---|---|---|
| 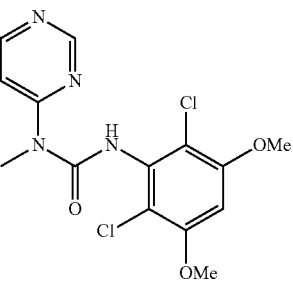 | 142 | <0.001 | >10.0 |
| 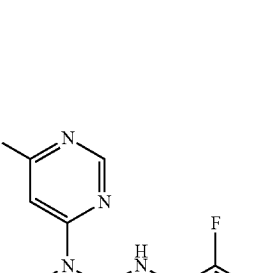 | 143 | 0.010 | 0.155 |
| 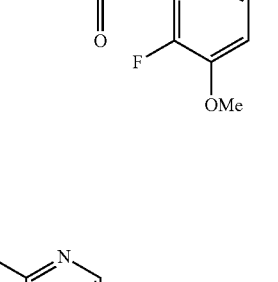 | 144 | <0.001 | 0.105 |
| 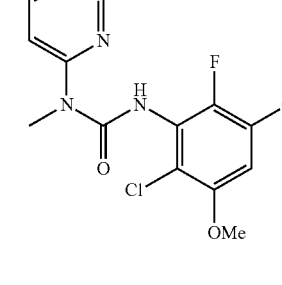 | 145 | <0.001 | 2.190 |

TABLE 1-continued

| Structure | Compound # | FGFR4 IC$_{50}$ (μM) | FGFR1 IC$_{50}$ (μM) |
|---|---|---|---|
| 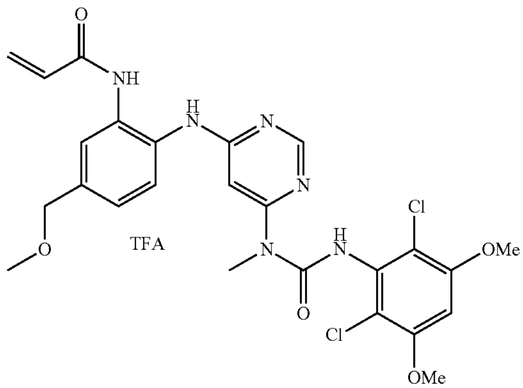 [SMILES: C=CC(=O)Nc1cc(COC)ccc1Nc1cc(N(C)C(=O)Nc2c(Cl)c(OC)cc(OC)c2Cl)ncn1 ; "TFA"] | 147 | <0.001 | 5.940 |
| 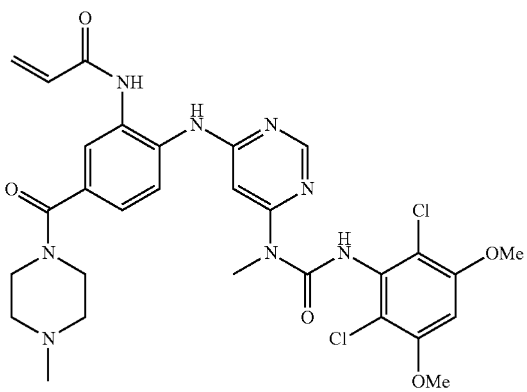 [SMILES: C=CC(=O)Nc1cc(C(=O)N2CCN(C)CC2)ccc1Nc1cc(N(C)C(=O)Nc2c(Cl)c(OC)cc(OC)c2Cl)ncn1] | 148 | <0.001 | 6.440 |
| 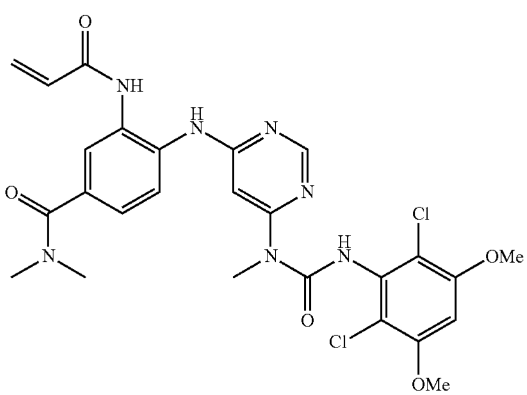 [SMILES: C=CC(=O)Nc1cc(C(=O)N(C)C)ccc1Nc1cc(N(C)C(=O)Nc2c(Cl)c(OC)cc(OC)c2Cl)ncn1] | 149 | <0.001 | 7.700 |
| 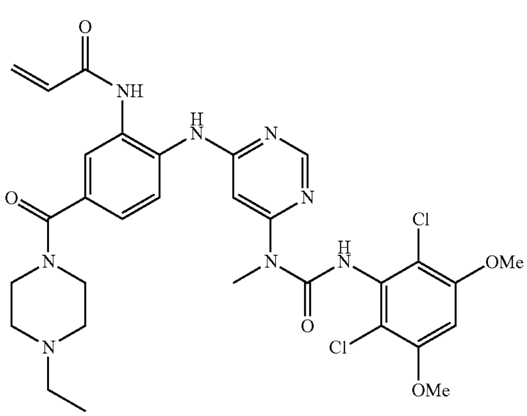 [SMILES: C=CC(=O)Nc1cc(C(=O)N2CCN(CC)CC2)ccc1Nc1cc(N(C)C(=O)Nc2c(Cl)c(OC)cc(OC)c2Cl)ncn1] | 150 | <0.001 | 2.290 |

TABLE 1-continued
| Structure | Compound # | FGFR4 IC$_{50}$ (μM) | FGFR1 IC$_{50}$ (μM) |
|---|---|---|---|
| 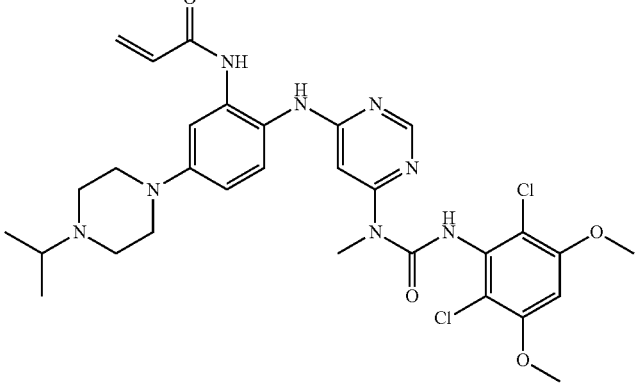 | 151 | <0.001 | 0.197 |
| 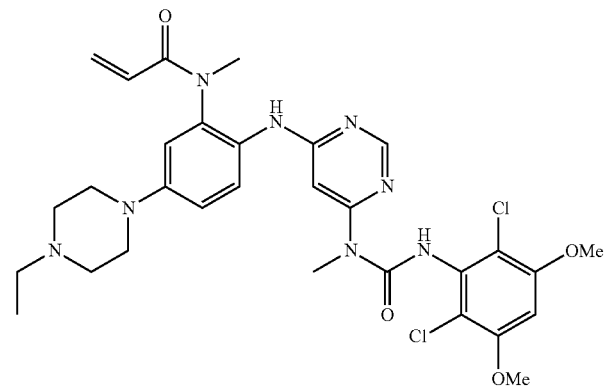 [SMILES: C=CC(=O)N(C)c1cc(N2CCN(CC)CC2)ccc1Nc1cc(N(C)C(=O)Nc2c(Cl)c(OC)cc(OC)c2Cl)ncn1] | 152 | 0.014 | 0.297 |
| 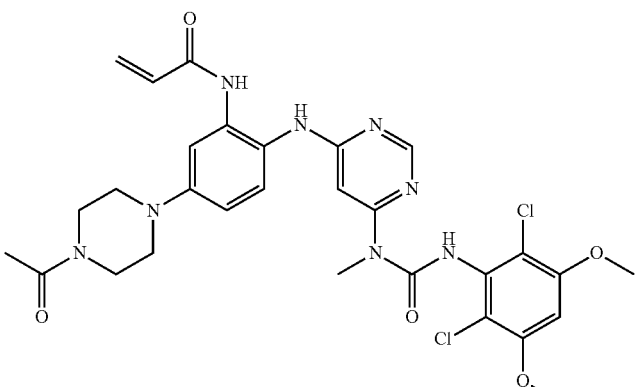 | 154 | <0.001 | 0.777 |
| 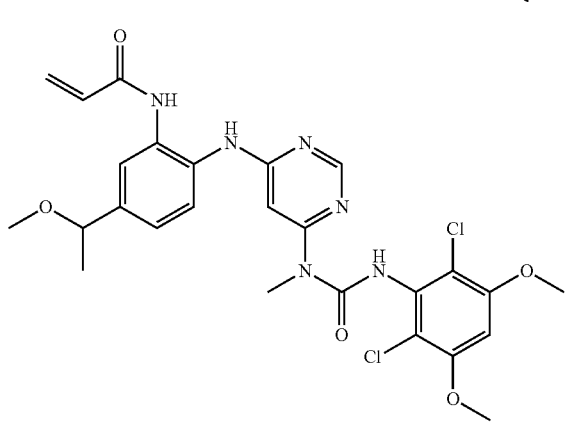 | 155 | <0.001 | 8.030 |

TABLE 1-continued

| Structure | Compound # | FGFR4 IC$_{50}$ (μM) | FGFR1 IC$_{50}$ (μM) |
|---|---|---|---|
| 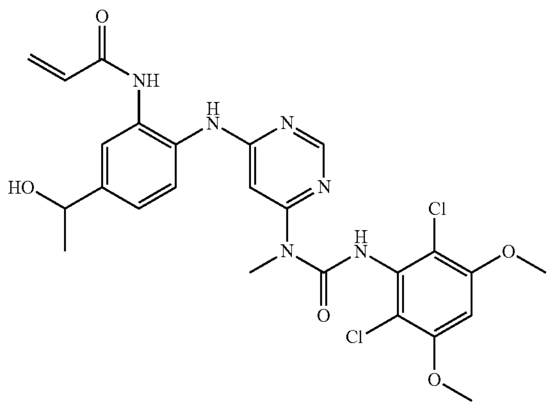 [SMILES: C=CC(=O)Nc1cc(C(C)O)ccc1Nc1cc(N(C)C(=O)Nc2c(Cl)c(OC)cc(OC)c2Cl)ncn1] | 156 | <0.001 | 1.950 |
| 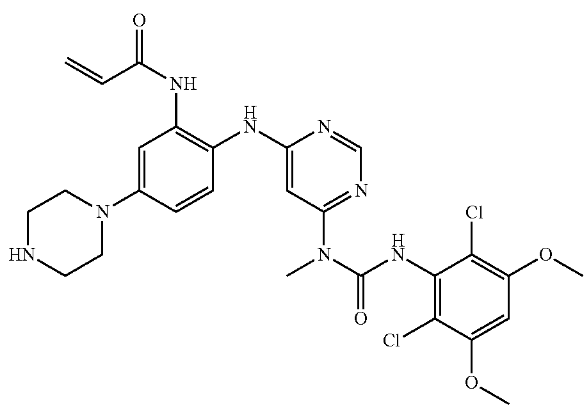 [SMILES: C=CC(=O)Nc1cc(N2CCNCC2)ccc1Nc1cc(N(C)C(=O)Nc2c(Cl)c(OC)cc(OC)c2Cl)ncn1] | 157 | <0.001 | 0.131 |
| 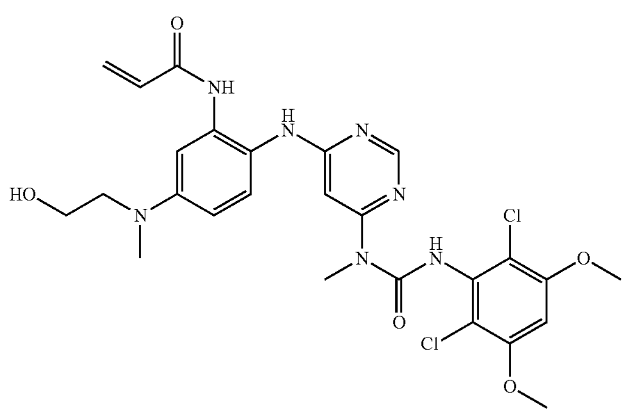 [SMILES: C=CC(=O)Nc1cc(N(C)CCO)ccc1Nc1cc(N(C)C(=O)Nc2c(Cl)c(OC)cc(OC)c2Cl)ncn1] | 158 | <0.001 | 2.152 |

TABLE 1-continued

| Structure | Compound # | FGFR4 IC$_{50}$ (μM) | FGFR1 IC$_{50}$ (μM) |
|---|---|---|---|
| 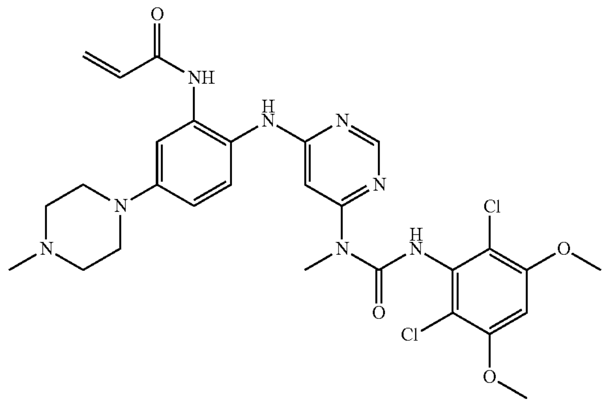 | 159 | <0.001 | 0.115 |
| 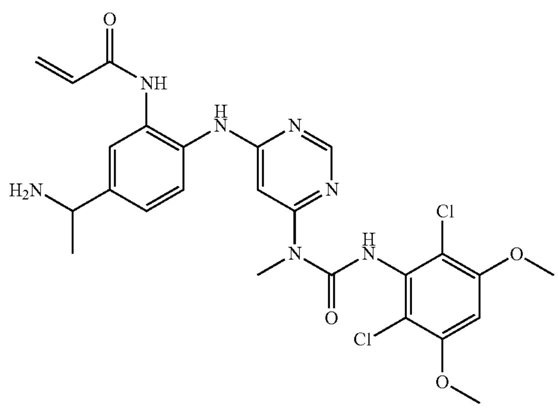 [SMILES: C=CC(=O)Nc1cc(C(C)N)ccc1Nc1cc(N(C)C(=O)Nc2c(Cl)c(OC)cc(OC)c2Cl)ncn1] | 160 | <0.001 | 0.660 |
| 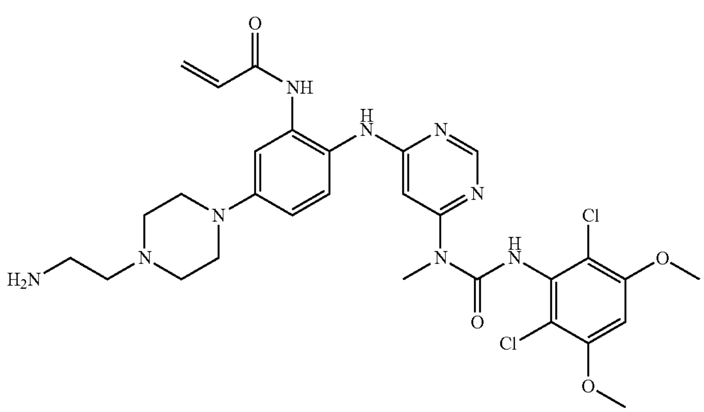 [SMILES: C=CC(=O)Nc1cc(N2CCN(CCN)CC2)ccc1Nc1cc(N(C)C(=O)Nc2c(Cl)c(OC)cc(OC)c2Cl)ncn1] | 161 | <0.001 | 2.694 |

TABLE 1-continued

| Structure | Compound # | FGFR4 IC$_{50}$ (μM) | FGFR1 IC$_{50}$ (μM) |
|---|---|---|---|
| 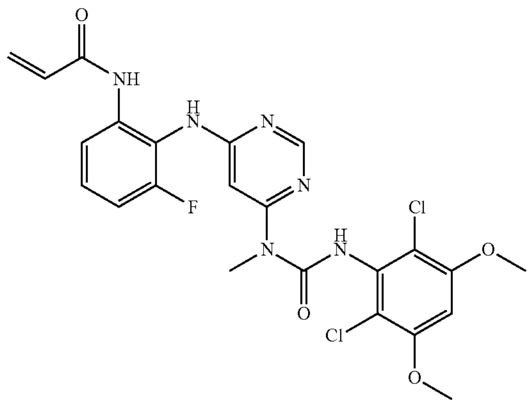 | 162 | <0.001 | >10.0 |
| 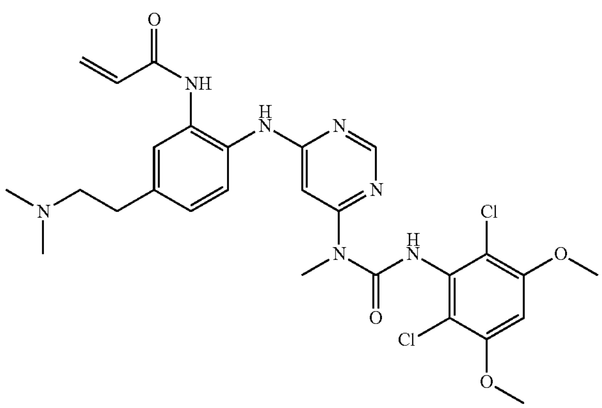 | 163 | <0.001 | 0.519 |
| 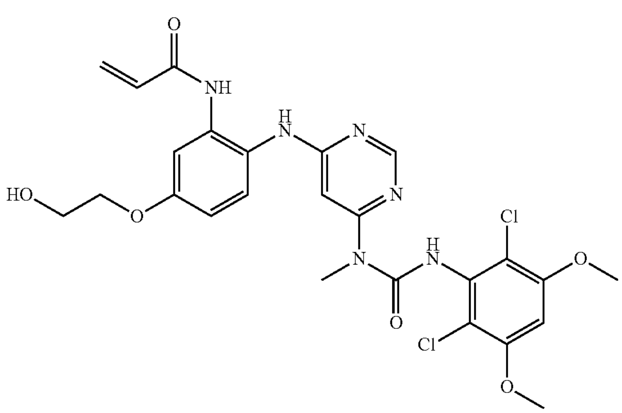 [SMILES: C=CC(=O)Nc1cc(OCCO)ccc1Nc1cc(N(C)C(=O)Nc2c(Cl)c(OC)cc(OC)c2Cl)ncn1] | 164 | <0.001 | 3.510 |

TABLE 1-continued

| Structure | Compound # | FGFR4 IC$_{50}$ (μM) | FGFR1 IC$_{50}$ (μM) |
| --- | --- | --- | --- |
| 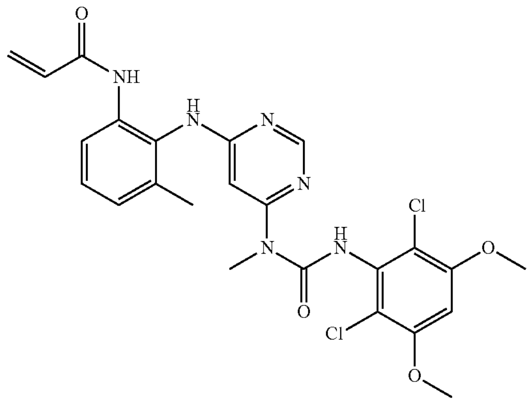 [SMILES: C=CC(=O)Nc1cccc(C)c1Nc1cc(N(C)C(=O)Nc2c(Cl)c(OC)cc(OC)c2Cl)ncn1] | 165 | <0.001 | 7.370 |
| 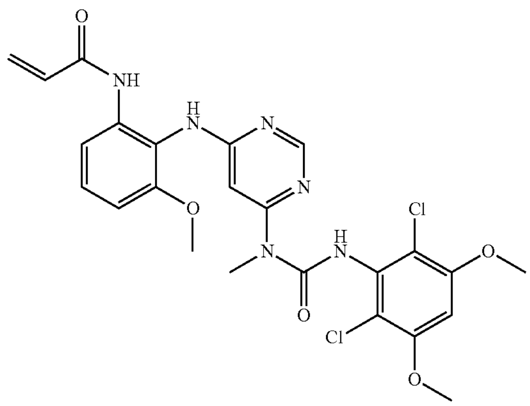 [SMILES: C=CC(=O)Nc1cccc(OC)c1Nc1cc(N(C)C(=O)Nc2c(Cl)c(OC)cc(OC)c2Cl)ncn1] | 166 | <0.001 | 4.920 |
| 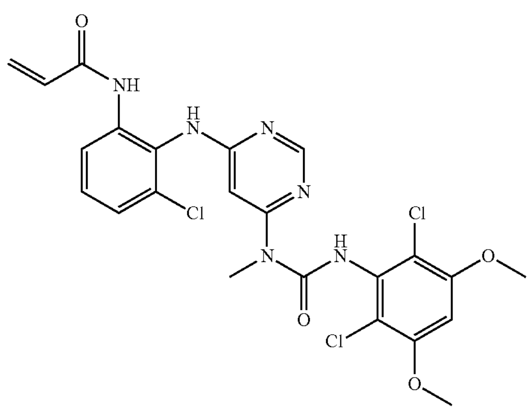 | 167 | <0.001 | >10.0 |
| 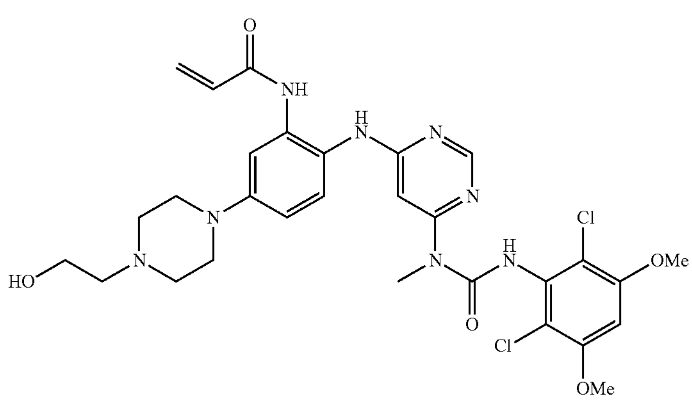 [SMILES: C=CC(=O)Nc1cc(N2CCN(CCO)CC2)ccc1Nc1cc(N(C)C(=O)Nc2c(Cl)c(OC)cc(OC)c2Cl)ncn1] | 168 | <0.001 | 1.030 |

TABLE 1-continued

| Structure | Compound # | FGFR4 IC$_{50}$ (μM) | FGFR1 IC$_{50}$ (μM) |
| --- | --- | --- | --- |
| 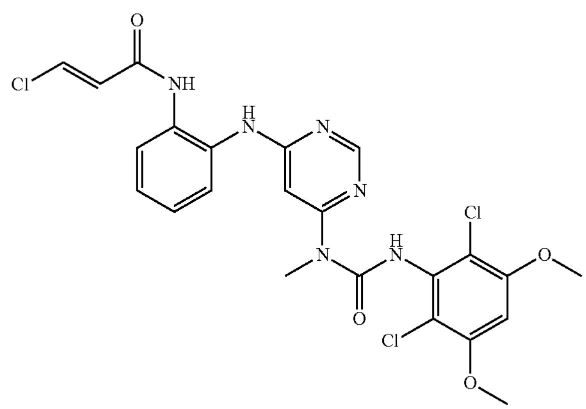 [SMILES: COc1cc(OC)c(Cl)c(NC(=O)N(C)c2cc(Nc3ccccc3NC(=O)/C=C/Cl)ncn2)c1Cl] | 170 | 0.008 | >10.0 |
| 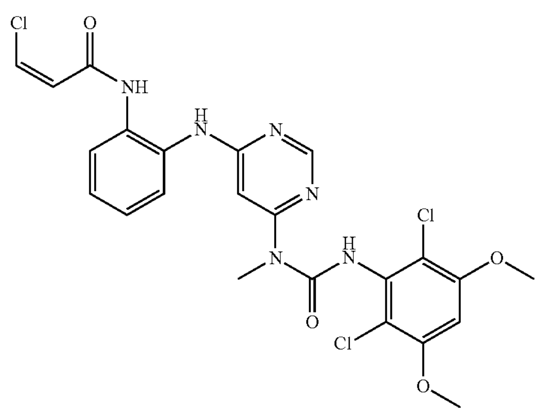 [SMILES: COc1cc(OC)c(Cl)c(NC(=O)N(C)c2cc(Nc3ccccc3NC(=O)/C=C\Cl)ncn2)c1Cl] | 171 | 0.003 | 3.920 |
| 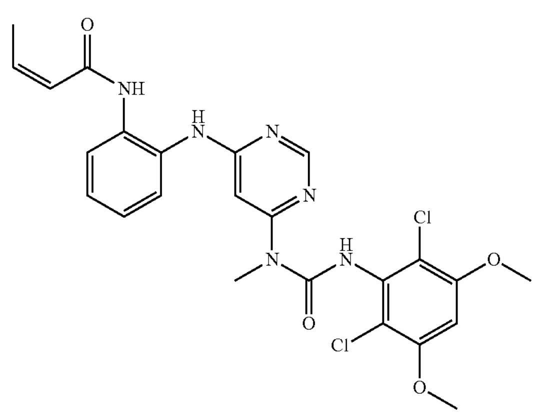 [SMILES: C/C=C\C(=O)Nc1ccccc1Nc1cc(N(C)C(=O)Nc2c(Cl)c(OC)cc(OC)c2Cl)ncn1] | 172 | 0.011 | 7.370 |

TABLE 1-continued

| Structure | Compound # | FGFR4 IC$_{50}$ (µM) | FGFR1 IC$_{50}$ (µM) |
|---|---|---|---|
| 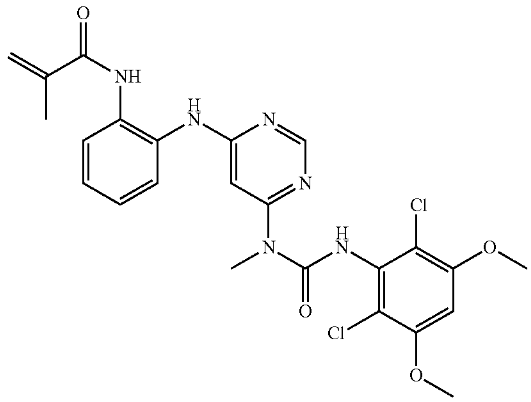 [SMILES: C=C(C)C(=O)Nc1ccccc1Nc1cc(N(C)C(=O)Nc2c(Cl)c(OC)cc(OC)c2Cl)ncn1] | 175 | 0.015 | >10.0 |
| 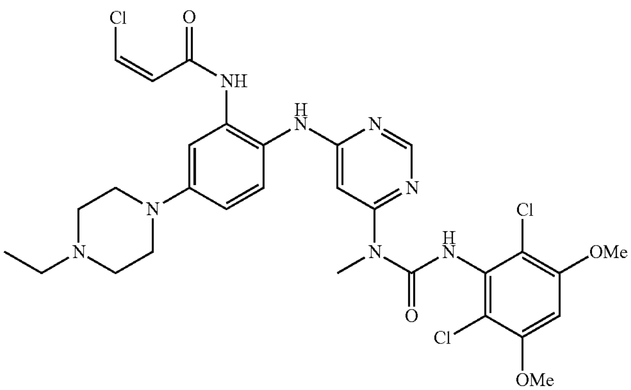 [SMILES: CCN1CCN(c2ccc(Nc3cc(N(C)C(=O)Nc4c(Cl)c(OC)cc(OC)c4Cl)ncn3)c(NC(=O)/C=C\Cl)c2)CC1] | 181 | <0.001 | 0.224 |
| 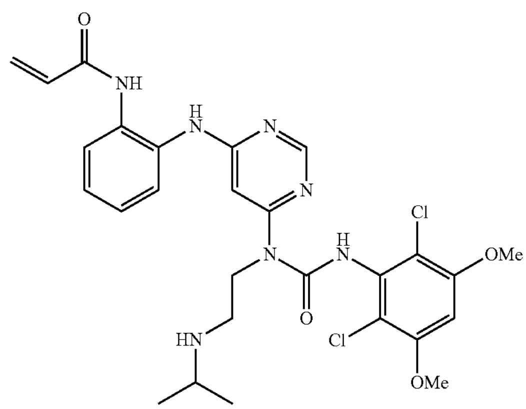 [SMILES: C=CC(=O)Nc1ccccc1Nc1cc(N(CCNC(C)C)C(=O)Nc2c(Cl)c(OC)cc(OC)c2Cl)ncn1] | 183 | 0.180 | 6.210 |
| 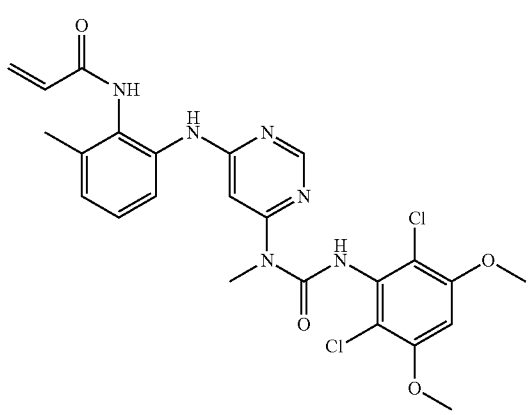 [SMILES: C=CC(=O)Nc1c(C)cccc1Nc1cc(N(C)C(=O)Nc2c(Cl)c(OC)cc(OC)c2Cl)ncn1] | 184 | 0.089 | 6.475 |

TABLE 1-continued
| Structure | Compound # | FGFR4 IC$_{50}$ (μM) | FGFR1 IC$_{50}$ (μM) |
|---|---|---|---|
| 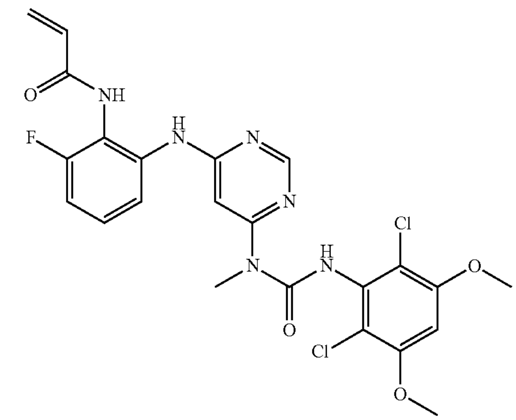 [SMILES: C=CC(=O)Nc1c(F)cccc1Nc1cc(N(C)C(=O)Nc2c(Cl)c(OC)cc(OC)c2Cl)ncn1] | 185 | 0.013 | >10.0 |
| 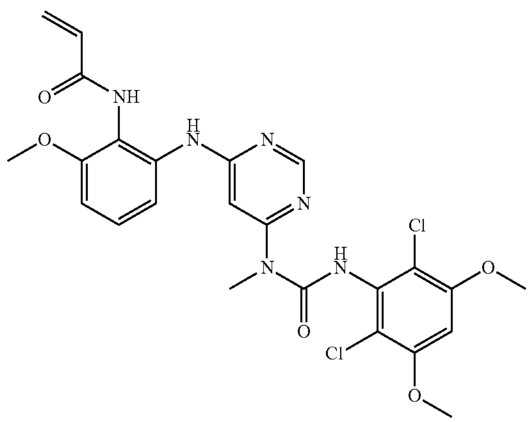 | 186 | 0.345 | >10.0 |
Procedure 2A: Example—100
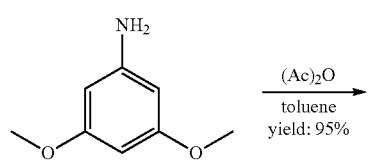
(Ac)$_2$O
toluene
yield: 95%
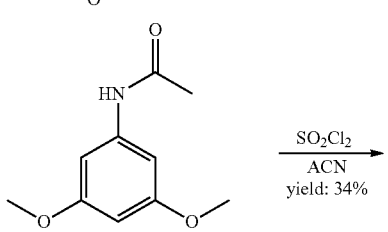
SO$_2$Cl$_2$
ACN
yield: 34%
2M KOH
EtOH
reflux
yield: 76%
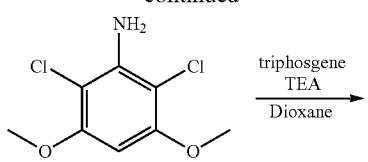
triphosgene
TEA
Dioxane
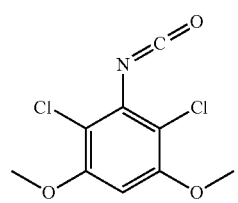
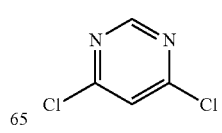
iPrOH
methylamine in THF
rt, overnight
yield: 62%
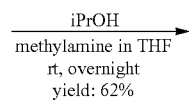

54

N-(2-{6-[3-(2,6-dichloro-3,5-dimethoxy-phenyl)-1-methyl-ureido]-pyrimidin-4-ylamino}-phenyl)-acryl-amide

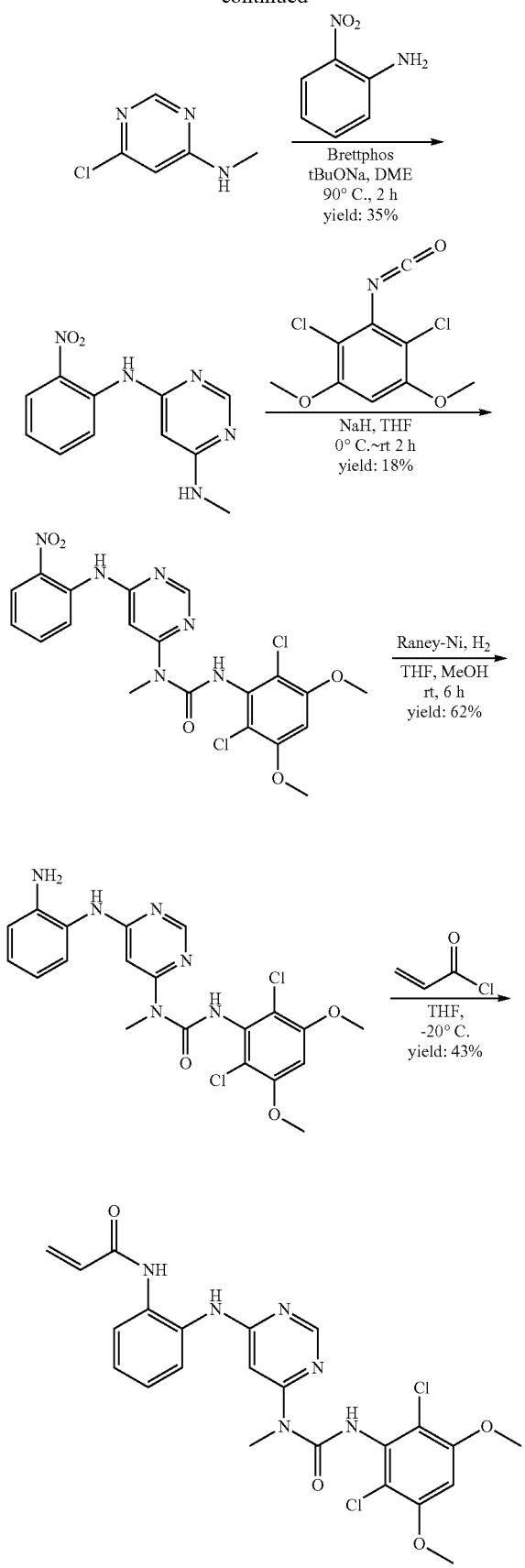

a. N-(3,5-Dimethoxy-phenyl)-acetamide

To a solution of 3,5-dimethoxy-phenylamine (20 g, 0.131 mol) in toluene (110 mL) was added acetic anhydride (14 g, 0.137 mmol) at room temperature. The resulting mixture was stirred for 18 hours at room temperature. PE (55 mL) was added, the precipitate was filtered and washed with PE (100 mL) to obtain the title compound (24.2 g, yield: 95%). $^1$H-NMR (400 MHz, CDCl$_3$) δ 2.16 (s, 3H), 3.77 (s, 6H), 6.23 (s, 1H), 6.75 (s, 2H), 7.20 (s, 1H).

b. N-(2,6-Dichloro-3,5-dimethoxy-phenyl)-acetamide

To a solution of N-(3,5-dimethoxy-phenyl)-acetamide (5 g, 25.6 mmol) in ACN (75 mL) was added sulfuryl chloride (6.9 g, 51.2 mmol) at 0° C. under nitrogen atmosphere. The resulting mixture was stirred for 30 minutes at this temperature and quenched with saturated aqueous NaHCO$_3$ (40 mL). The precipitate was filtered, washed with water and dried to obtain the title compound (2.3 g, yield: 34%). $^1$H-NMR (400 MHz, CDCl$_3$) δ 2.25 (s, 3H), 3.86 (s, 6H), 6.54 (s, 1H), 6.90 (s, 1H).

c. 2,6-Dichloro-3,5-dimethoxy-phenylamine

A solution of N-(2,6-dichloro-3,5-dimethoxy-phenyl)-acetamide (3.6 g, 13.7 mmol) in EtOH (130 mL) and KOH (2M, 75 mL) was heated to reflux for 24 hours. The reaction was cooled to 0° C. and stirred for 1 hour at this temperature. The precipitate was filtered and dried to obtain the title compound (2.3 g, yield: 76%). $^1$H-NMR (400 MHz, CDCl$_3$) δ 3.90 (s, 6H), 4.57 (bs, 2H), 6.05 (s, 1H).

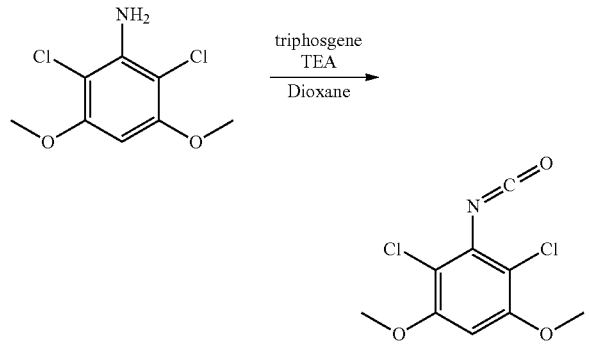

d. 2,4-Dichloro-3-isocyanato-1,5-dimethoxy-benzene

A mixture of 2,6-dichloro-3,5-dimethoxy-phenylamine (500 mg, 2.25 mmol), triphosgene (335 mg, 1.12 mmol) and TEA (342 mg, 3.38 mmol) in dioxane (15 mL) was heated to 130° C. for 2 hours under microwave. The reaction was concentrated and the residue was purified by flash chromatography on silica eluting with DCM to obtain the title compound (450 mg, yield: 80%). $^1$H-NMR (400 MHz, CDCl$_3$) δ 3.92 (s, 6H), 6.42 (s, 1H).

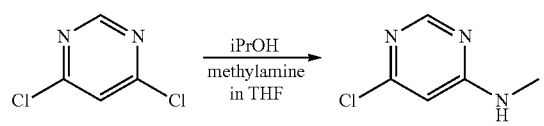

e. (6-Chloro-pyrimidin-4-yl)-methyl-amine

To a solution of 4,6-dichloro-pyrimidine (7.45 g, 50 mmol) in iPrOH (50 mL) was added a solution of methyl amine in THF (2M, 30 mL, 60 mmol) at room temperature. The resulting mixture was stirred for 18 hours. The mixture was concentrated and the residue was purified by flash chromatography on silica eluting with DCM:EtOAc=6:1~1:1 to obtain the title compound (4.4 g, yield: 62%) as a white solid. $^1$H NMR (400 MHz, CDCl$_3$) δ 2.96 (d, 3H), 5.22-5.36 (bs, 1H), 6.35 (s, 1H), 8.35 (s, 1H); MS (ESI): 144 [M+H]$^+$.

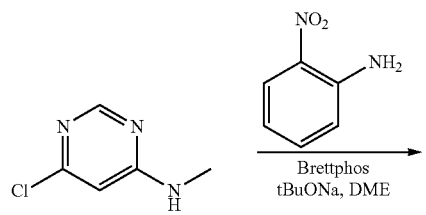

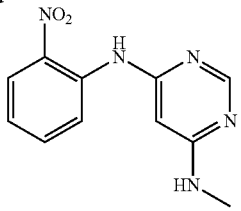

f. N-Methyl-N'-(2-nitro-phenyl)-pyrimidine-4,6-diamine

A mixture of (6-chloro-pyrimidin-4-yl)-methyl-amine (1 g, 7 mmol), 2-nitro-phenylamine (965 mg, 7 mmol), Brettphos (279 mg, 0.35 mmol) and tBuONa (2 g, 21 mmol) in DME (50 mL) was heated to 90° C. for 1 hour under nitrogen atmosphere. The reaction was concentrated, and the residue was purified by flash chromatography on silica eluting with DCM:EtOAc=10:1~1:1 to obtain the title compound (600 mg, yield: 35%) as a yellow solid. $^1$H NMR (400 MHz, CDCl$_3$) δ 2.94 (d, 3H), 4.99 (bs, 1H), 5.82 (s, 1H), 7.04 (t, 1H), 7.60 (t, 1H), 8.21 (d, 1H), 8.33 (s, 1H), 8.75 (d, 1H), 9.91 (s, 1H); MS (ESI): 246 [M+H]$^+$.

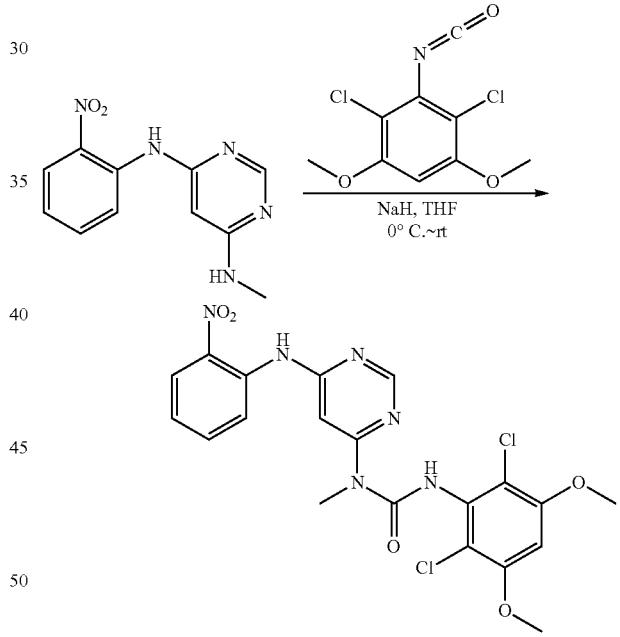

g. 3-(2,6-Dichloro-3,5-dimethoxy-phenyl)-1-methyl-1-[6-(2-nitro-phenylamino)-pyrimidin 4yl]-urea To a solution of N-methyl-N'-(2-nitro-phenyl)-pyrimidine-4,6-diamine (150 mg, 0.61 mmol) in THF (15 mL) was added NaH (60%, 60 mg, 1.5 mmol) at 0° C., and the mixture was stirred for 30 minutes at room temperature. A solution of 2,4-dichloro-3-isocyanato-1,5-dimethoxy-benzene (180 mg, 0.73 mmol) was added dropwise at room temperature. The resulting mixture was stirred for 2 hours. Water (2 mL) was added to quench the reaction. The mixture was concentrated, and the residue was purified by flash chromatography on silica eluting with DCM:EtOAc=6:

1~1:1 to obtain the title compound (54 mg, yield: 18%) as a yellow solid. ¹H NMR (400 MHz, DMSO-d6) δ 3.38 (s, 3H), 3.93 (s, 6H), 6.75 (s, 1H), 6.91 (s, 1H), 7.34 (t, 1H), 7.72 (t, 1H), 7.79 (d, 1H), 8.01 (d, 1H), 8.38 (s, 1H), 9.99 (s, 1H), 11.78 (s, 1H); MS (ESI): 493 [M+H]⁺.

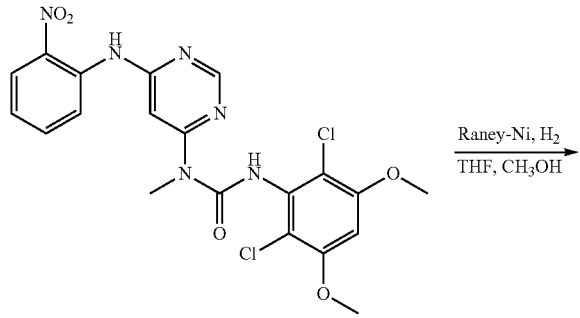

h. 1-[6-(2-Amino-phenylamino)-pyrimidin-4-yl]-3-(2,6-dichloro-3,5-dimethoxy-phenyl)-1-methyl-urea

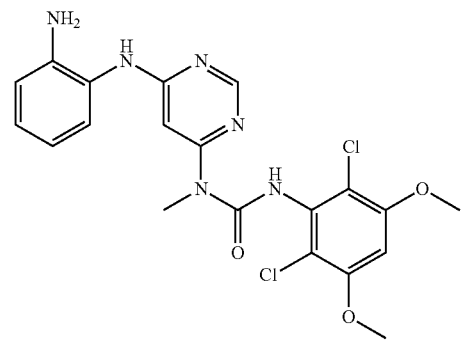

To a solution of 3-(2,6-dichloro-3,5-dimethoxy-phenyl)-1-methyl-1-[6-(2-nitro-phenylamino)-pyrimidin-4-yl]-urea (50 mg, 0.1 mmol) in THF (10 mL) and MeOH (10 mL) was added Raney-Ni (suspension in water) at room temperature, the resulting mixture was stirred for 2 hours under hydrogen atmosphere. The reaction was filtered and concentrated to obtain the title compound (38 mg, yield: 82%), which was used directly in the next step. 1H NMR (400 MHz, CDCl₃) δ 3.28 (s, 3H), 3.85 (s, 2H), 3.94 (s, 6H), 5.86 (s, 1H), 6.52 (s, 1H), 6.78-6.87 (m, 3H), 7.16-7.20 (m, 2H), 8.39 (s, 1H), 12.62 (s, 1H); MS (ESI): 463 [M+H]⁺.

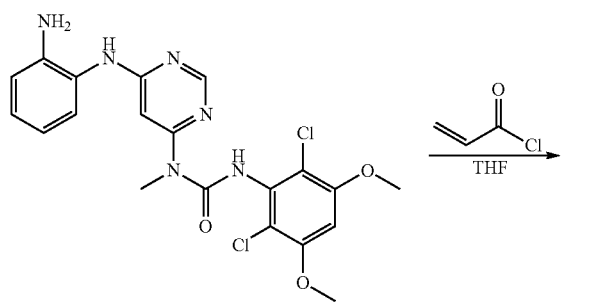

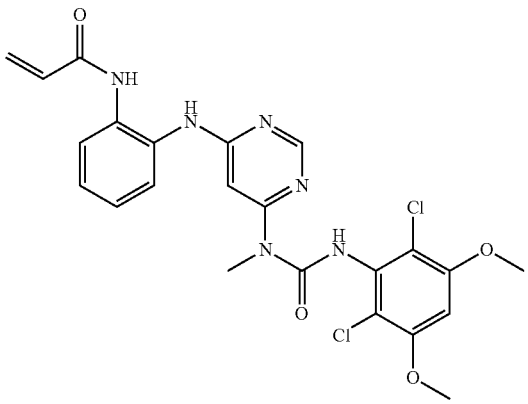

i. N-(2-{6-[3-(2,6-Dichloro-3,5-dimethoxy-phenyl)-1-methyl-ureido]-pyrimidin-4-ylamino}-phenyl)-acrylamide To a solution of 1-[6-(2-amino-phenylamino)-pyrimidin-4-yl]-3-(2,6-dichloro-3,5-dimethoxy-phenyl)-1-methyl-urea (25 mg, 0.05 mmol) in THF (10 mL) was added a solution of acryloyl chloride in THF (20 mg/mL, 0.5 mL, 0.1 mmol) at −10° C., and the resulting mixture was stirred for 1 hour at this temperature. MeOH (1 mL) was added to quench the reaction. The mixture was concentrated and the residue was purified by prep-TLC to obtain the title compound (12 mg, yield: 43%). ¹H NMR (400 MHz, DMSO-d6) δ 3.26 (s, 3H), 3.94 (s, 6H), 5.74 (d, 1H), 6.24 (d, 1H), 6.37 (s, 1H), 6.47-6.54 (m, 1H), 6.90 (s, 2H), 7.20 (d, 2H), 7.56-7.58 (m, 1H), 7.66-7.68 (m, 1H), 8.38 (s, 1H), 9.99 (s, 1H), 9.70 (s, 1H), 11.99 (s, 1H); MS (ESI): 517 [M+H]⁺.

Compounds 102, 103 and 105 were synthesized in a similar manner as compound 100.

Procedure 2B: Example—107

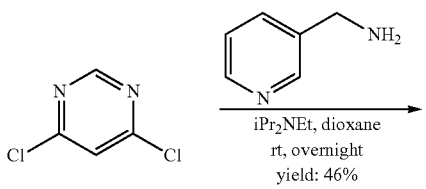

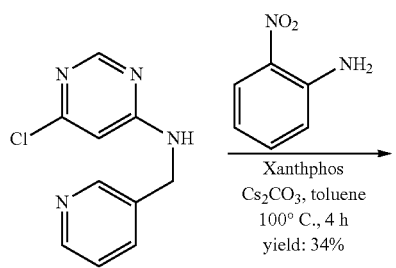

-continued

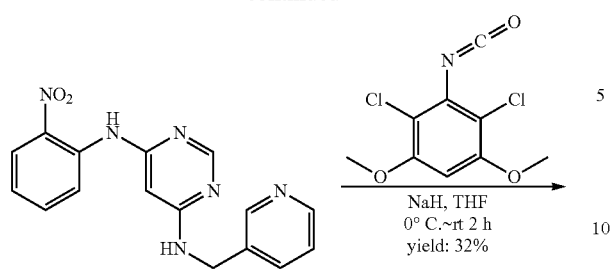

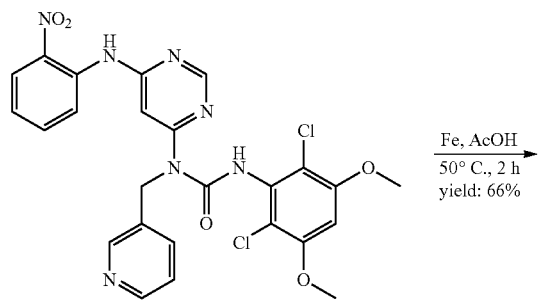

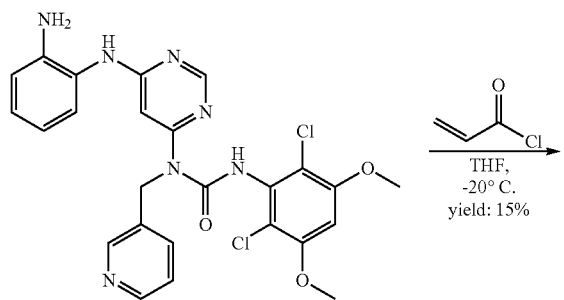

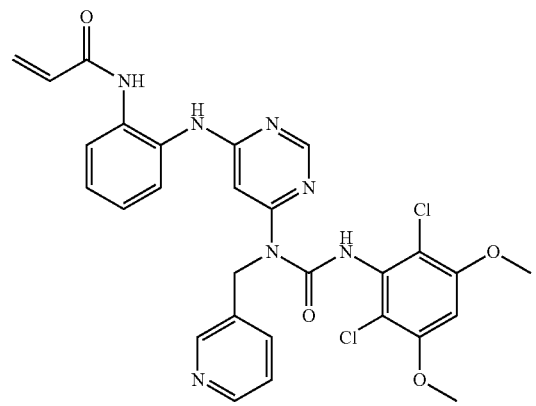

N-(2-{6-[3-(2,6-dichloro-3,5-dimethoxy-phenyl)-1-pyridin-3-ylmethyl-ureido]-pyrimidin-4-ylamino}-phenyl)-acrylamide

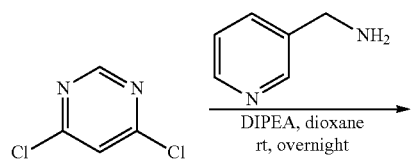

-continued

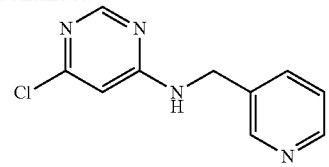

a. (6-Chloro-pyrimidin-4-yl)-pyridin-3-ylmethyl-amine

To a solution of 4,6-dichloro-pyrimidine (1 g, 6.71 mmol) in dioxane (20 mL) was added a solution of pyridin-3-yl-methylamine (745 mg, 6.9 mmol) at room temperature. The resulting mixture was stirred at room temperature overnight. The mixture was concentrated and the residue was purified by flash chromatography on silica to obtain the title compound (680 mg, yield: 46%). MS (ESI): 221 [M+H]+.

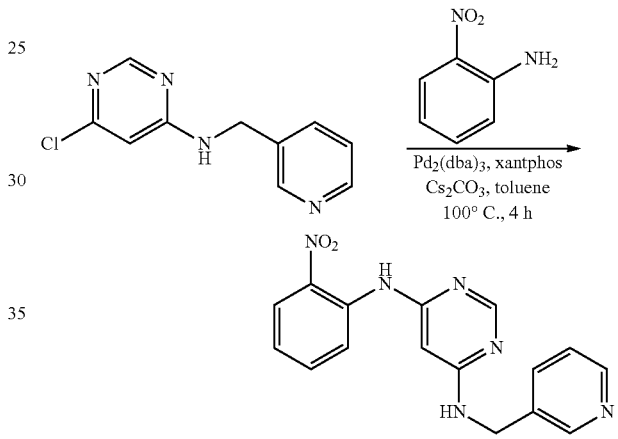

b. N-(2-Nitro-phenyl)-N'-pyridin-3-ylmethyl-pyrimidine-4,6-diamine

A degassed mixture of (6-chloro-pyrimidin-4-yl)-pyridin-3-ylmethyl-amine (300 mg, 1.36 mmol), 2-nitro-phenylamine (188 mg, 1.36 mmol), $Pd_2(dba)_3$ (128 mg, 0.14 mmol), Xantphos (161 mg, 0.28 mmol) and $Cs_2CO_3$ (913 mg, 2.8 mmol) in toluene (10 mL) was heated at 100° C. for 4 hours. The reaction was concentrated, and the residue was purified by flash chromatography on silica to obtain the title compound (150 mg, yield: 34%). MS (ESI): 323 [M+H]+.

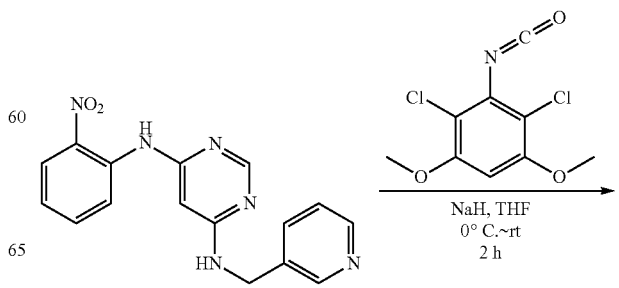

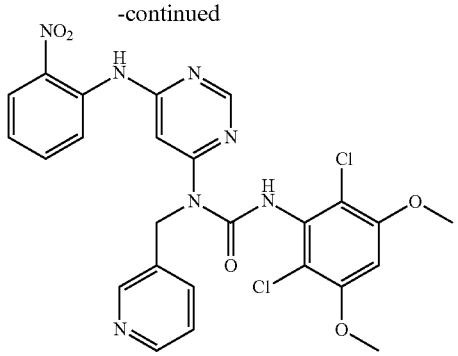

c. 3-(2,6-Dichloro-3,5-dimethoxy-phenyl)-1-[6-(2-nitro-phenylamino)-pyrimidin-4yl]-1-pyridin-3-ylm-ethyl-urea To a solution of N-(2-nitro-phenyl)-N'-pyridin-3-ylm-ethyl-pyrimidine-4,6-diamine (150 mg, 0.467 mmol) in THF (15 mL) was added NaH (60%, 48 mg, 1.2 mmol) at 0° C., and the mixture was stirred for 30 minutes at room temperature. A solution of 2,4-dichloro-3-isocyanato-1,5-dimethoxy-benzene (procedure 2A, steps a-d; 180 mg, 0.73 mmol) was added dropwise at room temperature. The resulting mixture was stirred for 2 hours. Water (2 mL) was added to quench the reaction. The mixture was concentrated, and the residue was purified by flash chromatography on silica to obtain the title compound (85 mg, yield: 32%). MS (ESI): 570 [M+H]⁺.

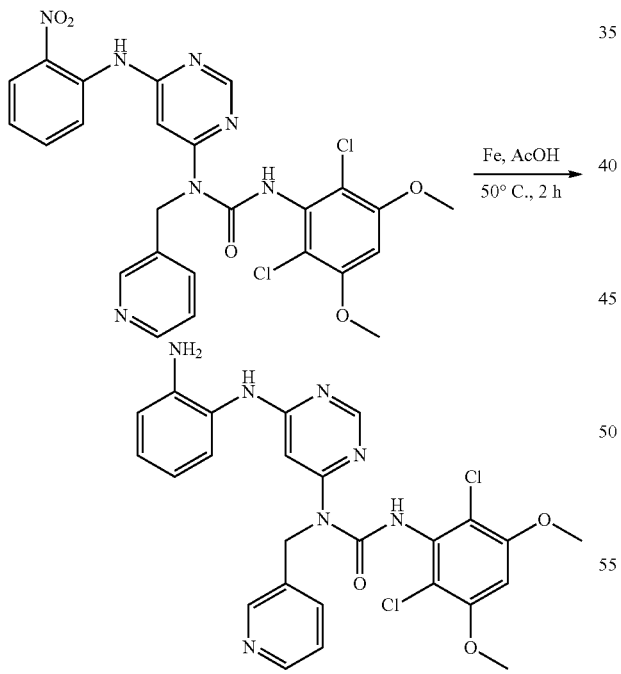

d. 1-[6-(2-Amino-phenylamino)-pyrimidin-4-yl]-3-(2,6-dichloro-3,5-dimethoxy-phenyl)-1-pyridin-3-ylmethyl-urea A mixture of 3-(2,6-dichloro-3,5-dimethoxy-phenyl)-1-[6-(2-nitro-phenylamino)-pyrimidin-4-yl]-1-pyridin-3-ylm-ethyl-urea (85 mg, 0.149 mmol) and Fe (84 mg, 1.5 mmol) in AcOH (5 mL) was heated at 50° C. for 2 hours. The reaction mixture was filtered and the filtrate was concentrated in vacuo to give crude product, which was purified by silica gel column chromatography to afford the title compound (53 mg, yield: 66%). MS (ESI): 540 [M+H]⁺.

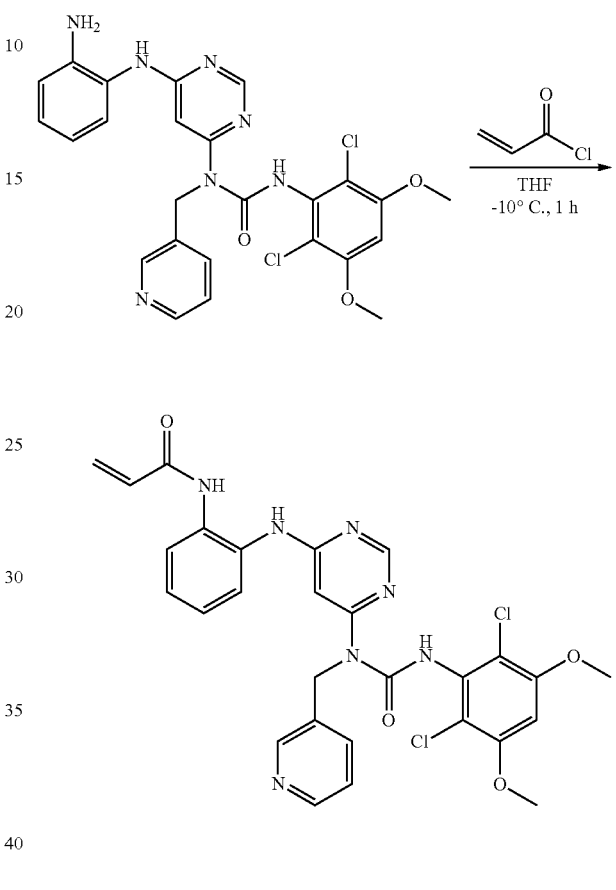

e. N-(2-{6-[3-(2,6-Dichloro-3,5-dimethoxy-phenyl)-1-pyridin-3-ylmethyl-ureido]-pyrimidin-4-ylamino}-phenyl)-acrylamide To a solution of 1-[6-(2-amino-phenylamino)-pyrimidin-4-yl]-3-(2,6-dichloro-3,5-dimethoxy-phenyl)-1-pyridin-3-ylmethyl-urea (53 mg, 0.1 mmol) in THF (10 mL) was added a solution of acryloyl chloride in THF (20 mg/mL, 0.5 mL, 0.1 mmol) at −10° C., and the mixture was stirred for 1 hour at this temperature. MeOH (1 mL) was added to quench the reaction. The mixture was concentrated and the residue was purified by prep-TLC to obtain the title compound (9 mg, yield: 15%). ¹H NMR (400 MHz, CDCl₃) δ 3.84 (s, 6H), 5.01 (s, 2H), 5.69 (d, 1H), 5.75 (s, 1H), 6.10 (dd, 1H), 6.34 (d, 1H), 6.47 (s, 1H), 7.00 (d, 1H), 7.09-7.24 (m, 2H), 7.28 (t, 1H), 7.32 (s, 1H), 7.47 (d, 1H), 7.69-7.71 (m, 2H), 8.31-8.34 (m, 2H), 8.40-8.42 (m, 1H), 12.60 (s, 1H); MS (ESI): 594 [M+H]⁺.

Procedure 2C: Example—108
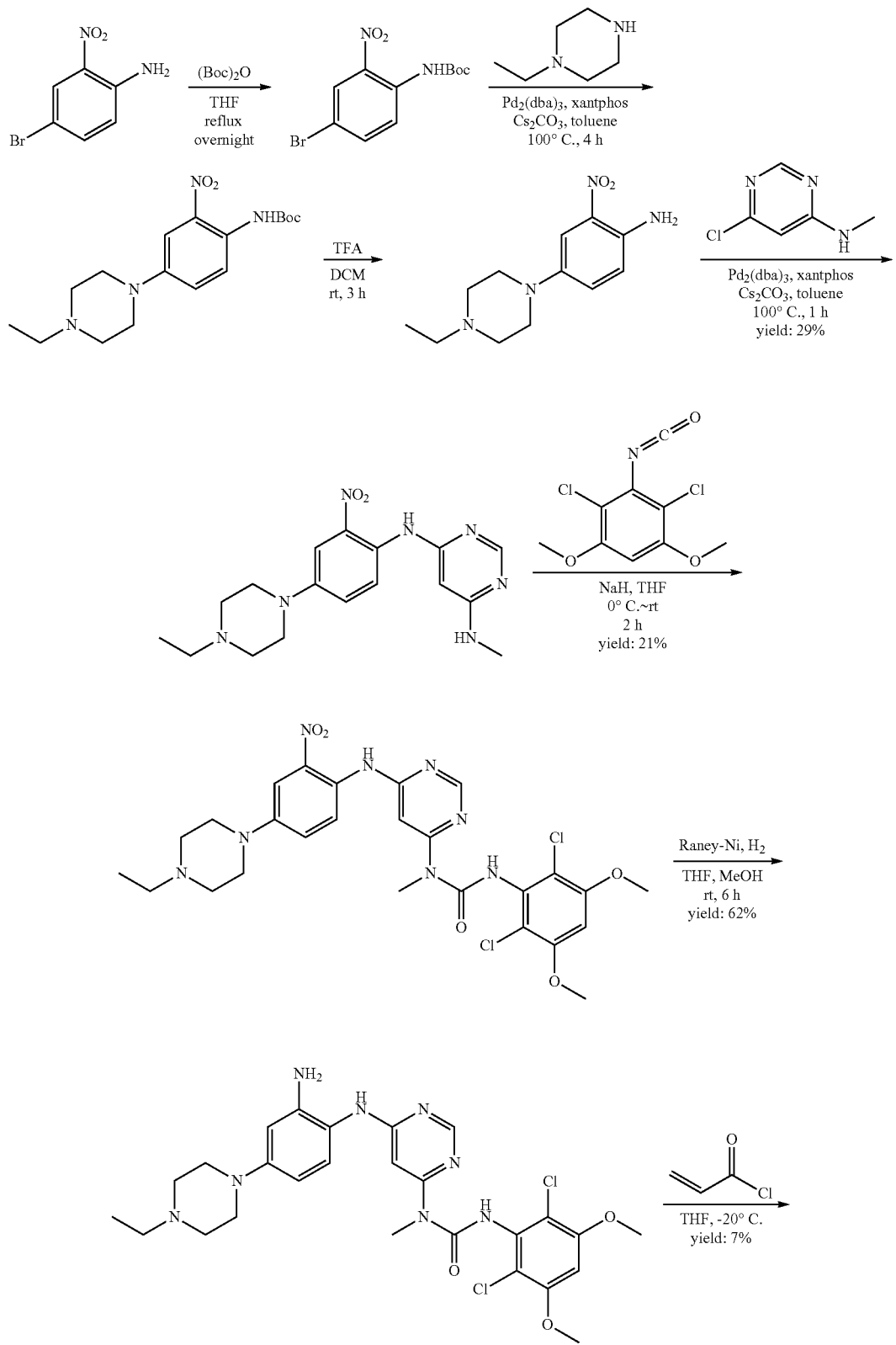

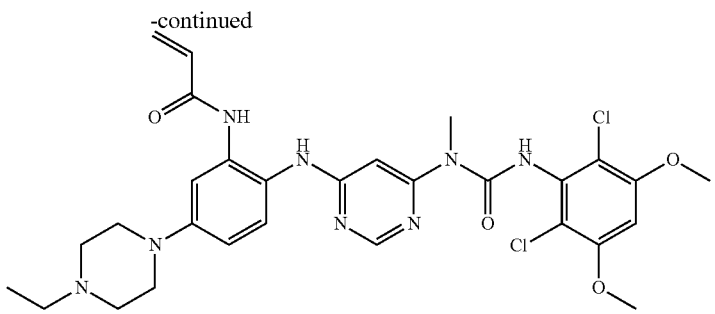

N-(2-(6-(3-(2,6-Dichloro-3,5-dimethoxyphenyl)-1-methylureido)pyrimidin-4-ylamino)-5-(4-ethylpiperazin-1-yl)-phenyl)acrylamide

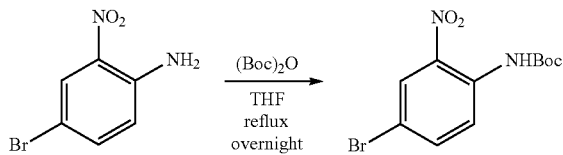

a. tert-Butyl 4-bromo-2-nitrophenylcarbamate

A mixture of 4-bromo-2-nitroaniline (4 g, 18.4 mmol), (Boc)₂O (4.4 g, 20.24 mmol) in THF (50 mL) was heated under reflux overnight. The mixture was concentrated and the residue was purified by flash chromatography on silica eluting with PE:EtOAc=20:1 to obtain the title compound (5.4 g, yield: 93%). MS (ESI): 317, 319 [M+H]⁺.

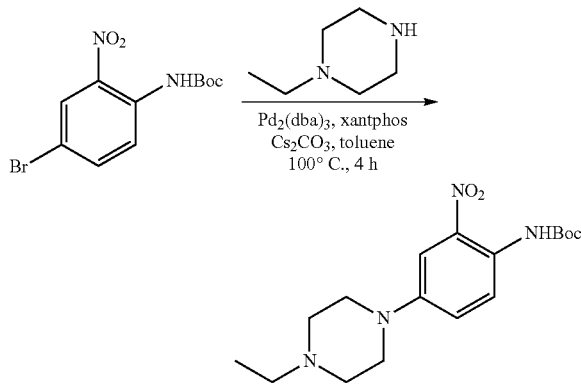

b. tert-Butyl 4-(4-ethylpiperazin-1-yl)-2-nitrophenylcarbamate

A degassed mixture of tert-butyl 4-bromo-2-nitrophenylcarbamate (5.4 g, 17 mmol), 1-ethylpiperazine (2.91 g, 25.5 mmol), Pd₂(dba)₃ (2.1 g, 3.4 mmol), xantphos (3.92 g, 6.8 mmol) and Cs₂CO₃ (11.1 g, 34 mmol) in toluene (85 mL) was heated at 100° C. for 4 hours. The reaction was concentrated, and the residue was purified by flash chromatography on silica eluting with MeOH: DCM=1:50~1:20 to obtain the title compound (3.3 g, yield: 55%). MS (ESI): 351 [M+H]⁺.

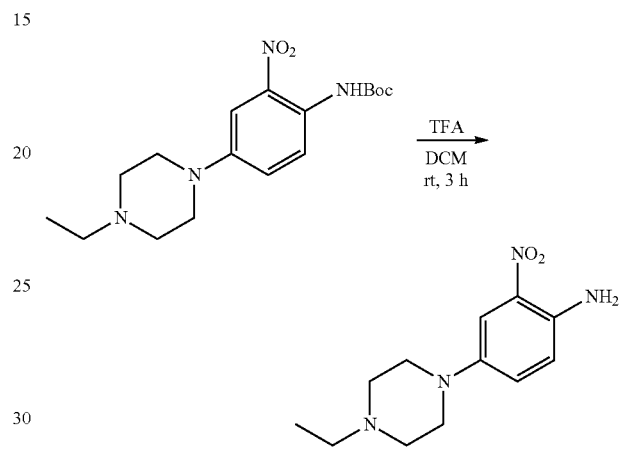

c. 4-(4-Ethylpiperazin-1-yl)-2-nitroaniline

To a solution of tert-butyl 4-(4-ethylpiperazin-1-yl)-2-nitrophenylcarbamate (3.3 g, 9.43 mmol) in DCM (50 mL) was added TFA (20 mL) at 0° C., the resulting mixture was stirred for 3 hours at rt. After removal of all volatiles in vacuo, the residue was re-dissolved in DCM, neutralized with saturated aqueous K₂CO₃ and extracted with DCM. The combined extracts were concentrated to obtain the title compound (2.1 g, yield: 90%), which was used directly in the next step. ¹H NMR (400 MHz, DMSO-d6) δ 1.02 (t, 3H), 2.36 (q, 2H), 2.47-2.49 (m, 4H) 2.97-3.00 (m, 4H), 6.97 (d, 1H), 7.20 (s, 2H), 7.25 (s, 1H), 7.34 (dd, 1H); MS (ESI): 251 [M+H]⁺.

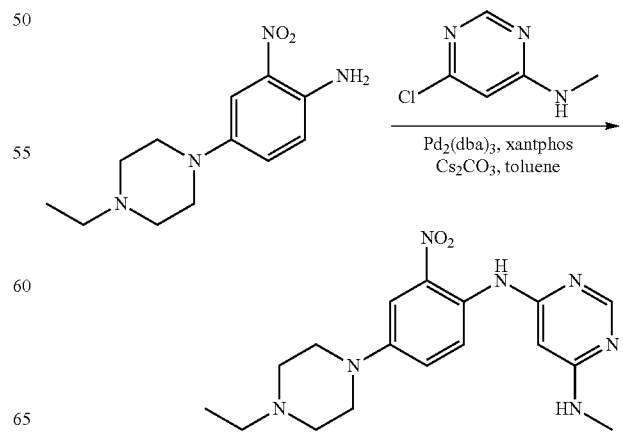

d. N⁴-(4-(4-ethylpiperazin-1-yl)-2-nitrophenyl)-N⁶-methylpyrimidine-4,6-diamine A degassed mixture of 4-(4-ethylpiperazin-1-yl)-2-nitroaniline (2.1 g, 8.4 mmol), 6-chloro-N-methylpyrimidin-4-amine (Procedure 2A, step e; 1.2 g, 8.4 mmol), Pd$_2$(dba)$_3$ (1.54 g, 1.68 mmol), xantphos (1.94 g, 3.36 mmol) and Cs$_2$CO$_3$ (5.48 g, 16.8 mmol) in toluene (45 mL) was heated at 100° C. for 1 hour. The reaction was concentrated, and the residue was purified by flash chromatography on silica eluting with MeOH: DCM=1:40~1:20 to obtain the title compound (870 mg, yield: 29%). MS (ESI): 358 [M+H]⁺.

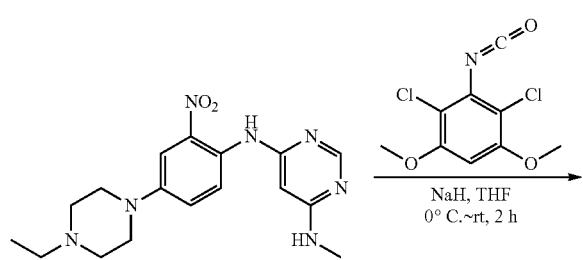

e. 3-(2,6-Dichloro-3,5-dimethoxyphenyl)-1-(6-(4-(4-ethylpiperazin-1-yl)-2-nitrophenylamino)pyrimidin-4yl)-1-methylurea To a solution of N4-(4-(4-ethylpiperazin-1-yl)-2-nitrophenyl)-N6-methylpyrimidine-4,6-diamine (870 mg, 2.44 mmol) in THF (15 mL) was added NaH (60%, 200 mg, 5 mmol) at 0° C., and the mixture was stirred for 30 minutes at room temperature. A solution of 2,4-dichloro-3-isocyanato-1,5-dimethoxy-benzene (Procedure 2A, steps a-d; 908 mg, 3.66 mmol) in THF was added dropwise at 0° C. The resulting mixture was stirred at room temperature for 2 hours. Saturated aqueous NH$_4$Cl solution (2 mL) was added to quench the reaction. The mixture was concentrated and extracted with DCM. The combined extracts were washed with brine, dried over anhydrous Na$_2$SO$_4$, and concentrated to give the crude product, which was purified by flash chromatography on silica to obtain the title compound (330 mg, yield: 21%) as a red oil. ¹H NMR (400 MHz, CDCl$_3$) δ 1.44 (t, 3H), 3.01 (t, 2H), 3.21 (q, 2H), 3.41-3.49 (m, 5H), 3.73-3.80 (m, 4H), 3.92 (s, 6H), 6.27 (s, 1H), 6.55 (s, 1H), 7.25 (d, 1H), 7.69 (s, 1H), 8.32 (d, 1H), 8.52 (s, 1H), 10.28 (br s, 1H), 12.05 (br s, 1H); MS (ESI): 605 [M+H]⁺.

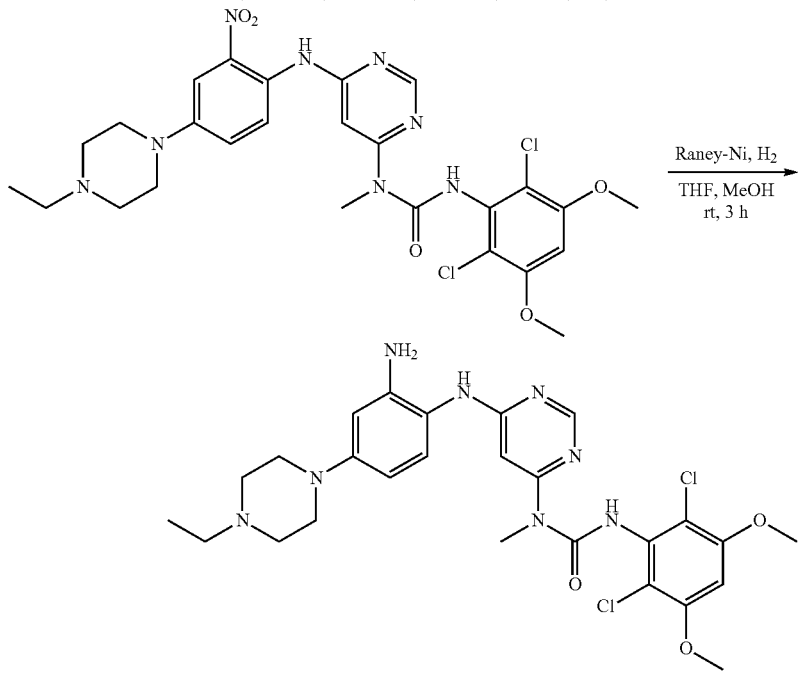

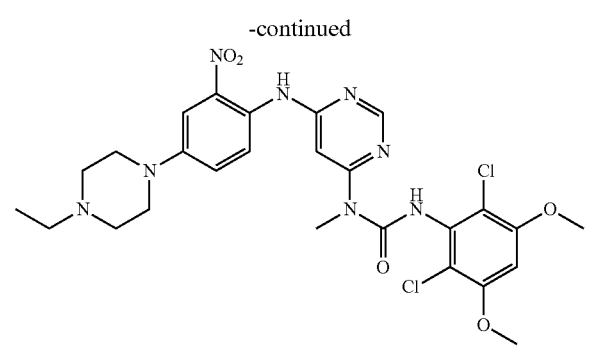

f. 1-(6-(2-Amino-4-(4-ethylpiperazin-1-yl)phenylamino)pyrimidin-4-yl)-3-(2,6-dichloro-3,5-dimethoxyphenyl-1-methylurea To a solution of 3-(2,6-dichloro-3,5-dimethoxyphenyl)-1-(6-(4-(4-ethylpiperazin-1-yl)-2-nitrophenylamino)pyrimidin-4-yl)-1-methylurea (330 mg, 0.546 mmol) in THF (20 mL) and MeOH (20 mL) was added Raney-Ni (suspension in water) at room temperature, the resulting mixture was stirred for 3 hours under hydrogen atmosphere (1 atm). The reaction was filtered and concentrated. The residue was washed twice with MeOH to obtain the title compound (280 mg, purity: 90%), which was used directly in the next step. MS (ESI): 575 [M+H]⁺.

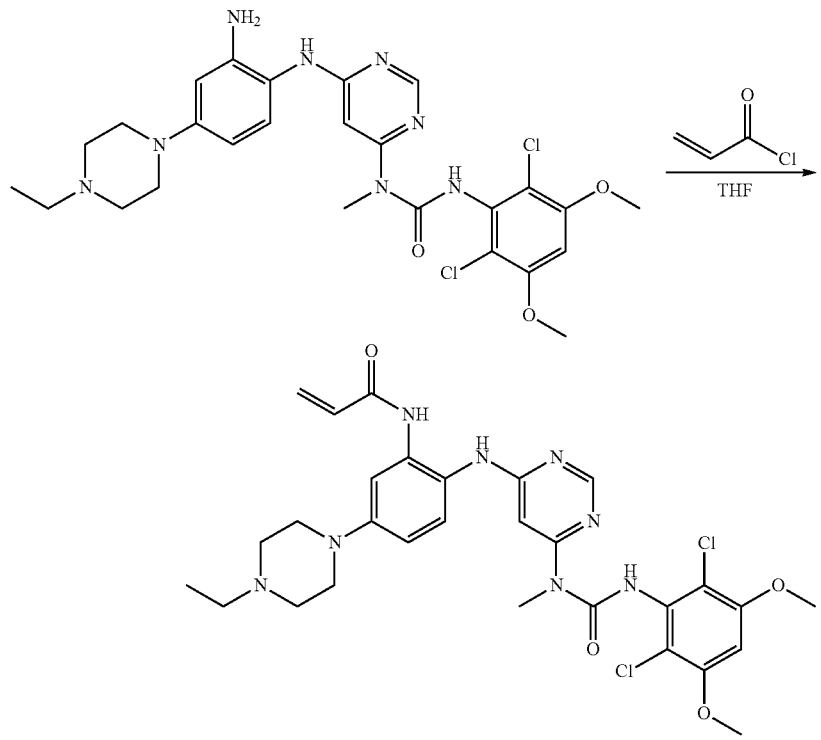

g. N-(2-(6-(3-(2,6-Dichloro-3,5-dimethoxyphenyl)-1-methylureido)pyrimidin-4-ylamino)-5-(4-ethylpiperazin-1-yl)phenyl)acrylamide To a solution of 1-(6-(2-amino-4-(4-ethylpiperazin-1-yl)phenylamino)pyrimidin-4-yl)-3-(2,6-dichloro-3,5-dimethoxyphenyl)-1-methylurea (280 mg, purity: 90%, 0.44 mmol) in THF (30 mL) was added a solution of acryloyl chloride in THF (20 mg/mL, 2 mL, 0.44 mmol) at −10° C., and the resulting mixture was stirred for 1 hour at this temperature. MeOH (1 mL) was added to quench the reaction. The mixture was concentrated and the residue was purified by prep-HPLC and prep-TLC to obtain the title compound (20 mg, yield: 7%). $^1$H NMR (400 MHz, CDCl$_3$) δ 1.31 (t, 3H), 2.65 (q, 2H), 2.62-2.68 (m, 4H), 3.27 (s, 3H), 3.36-3.38 (m, 4H), 3.91 (s, 6H), 5.76 (d, 1H), 5.90 (s, 1H), 6.24 (dd, 1H), 6.41 (d, 1H), 6.52 (s, 1H), 6.74 (dd, 1H), 7.07 (br s, 1H), 7.23 (d, 1H), 7.72 (br s, 1H), 7.98 (br s, 1H), 8.37 (s, 1H), 12.52 (s, 1H); MS (ESI): 629 [M+H]$^+$.

Example—110

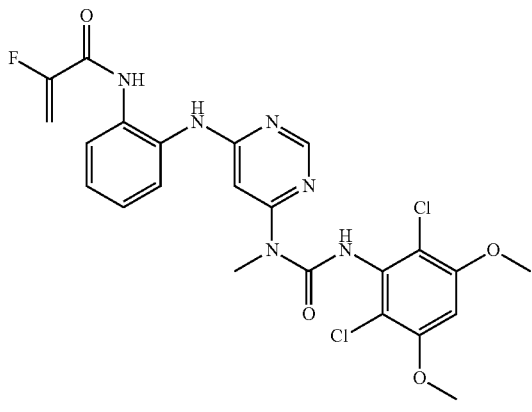 [SMILES: C=C(F)C(=O)Nc1ccccc1Nc1cc(N(C)C(=O)Nc2c(Cl)c(OC)cc(OC)c2Cl)ncn1]

N-(2-(6-(3-(2,6-dichloro-3,5-dimethoxyphenyl)-1-methylureido)pyrimidin-4-ylamino)-phenyl)-2-fluoroacrylamide The compound was synthesized following the approach outlined in Procedure 2A (Example 100), modifying step (i) to the following procedure: To a solution of 1-[6-(2-aminophenylamino)-pyrimidin-4-yl]-3-(2,6-dichloro-3,5-dimethoxy-phenyl)-1-methyl-urea (130 mg, mixed with tetrachloro aniline) and DCC (118 mg, 0.56 mmol) in chloroform (100 mL) was added a solution of 2-fluoroacrylic acid (50 mg, 0.56 mmol) in chloroform (50 mL) at 0° C., and the resulting mixture was stirred at room temperature overnight. Water (1 mL) was added to quench the reaction. The mixture was concentrated and the residue was purified by reverse phase column and prep-TLC to obtain the title compound (4 mg, yield: 5%). $^1$H NMR (400 MHz, CDCl$_3$) δ 12.17 (s, 1H), 8.45 (s, 1H), 8.35 (s, 1H), 7.84 (d, 1H), 7.37 (d, 1H), 7.29 (t, 1H), 7.26 (t, 1H), 6.47 (s, 1H), 5.94 (s, 1H), 5.78 (dd, 1H), 5.21 (dd, 1H), 3.85 (s, 6H), 3.25 (s, 3H); MS (ESI): 535 [M+H]$^+$.

Procedure 2E: Example—111
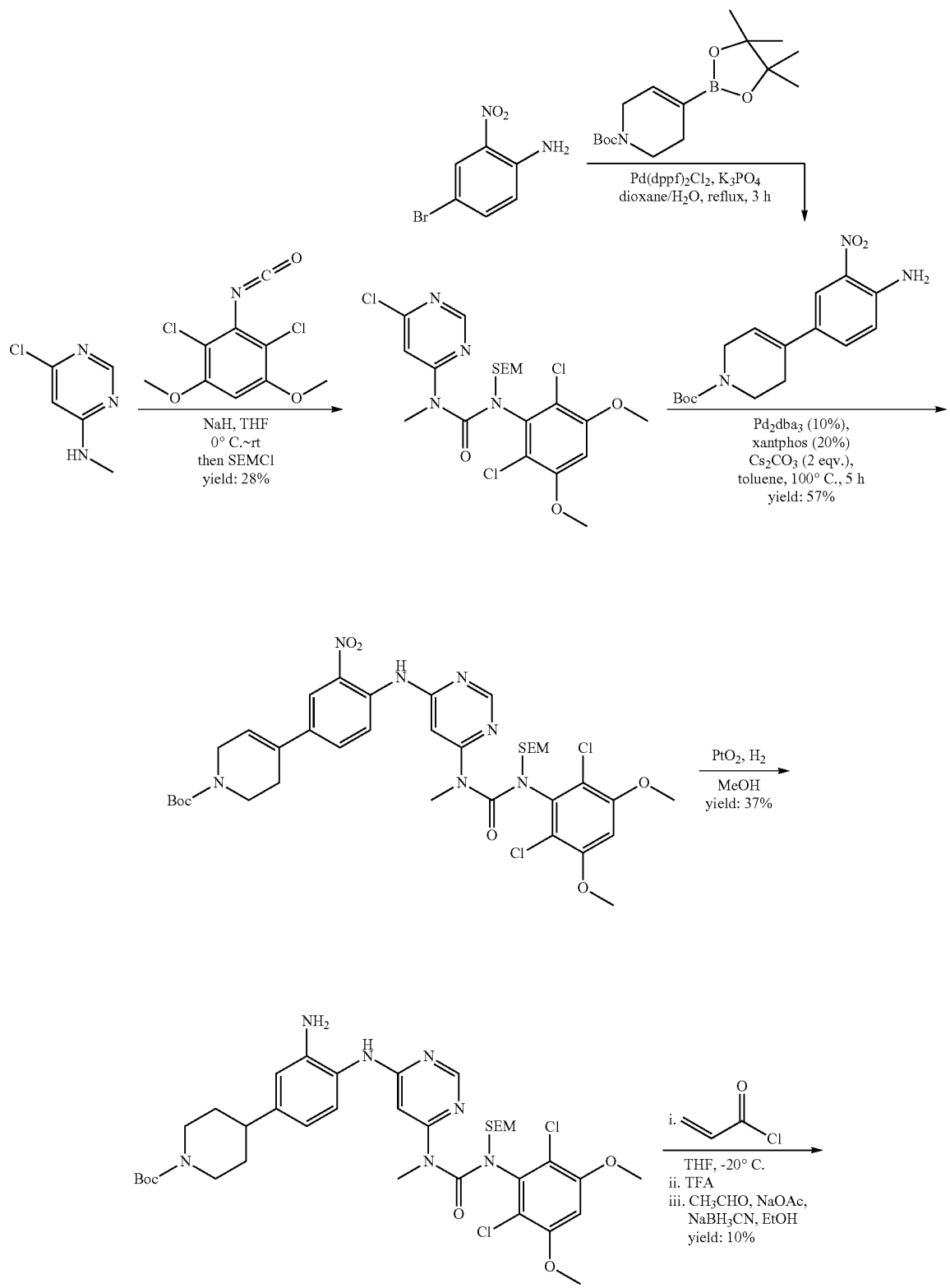

N-(2-(6-(3-(2,6-dichloro-3,5-dimethoxyphenyl)-1-methylureido)pyrimidin-4-ylamino)-5-(1-ethylpiperidin-4-yl)phenyl)acrylamide

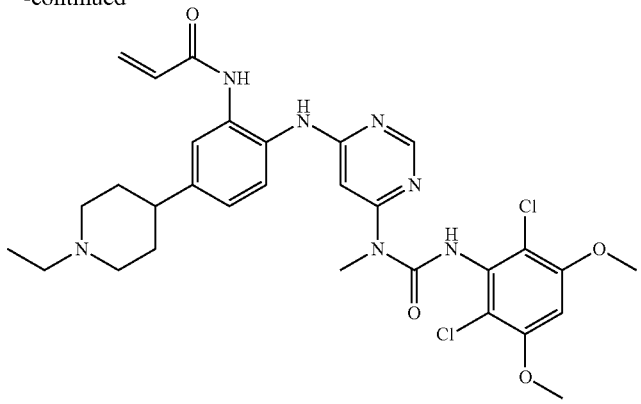

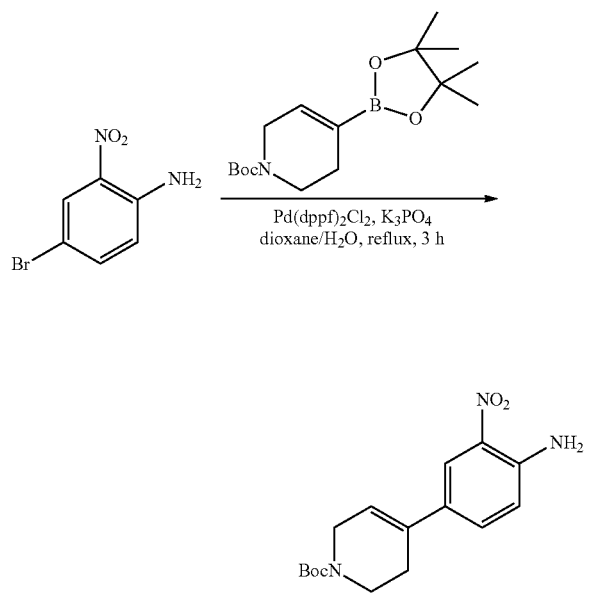

a. tert-butyl 4-(4-amino-3-nitrophenyl)-5,6-dihydropyridine-1(2H)-carboxylate

To a degassed mixture of 4-bromo-2-nitroaniline (1 g, 4.6 mmol), tert-butyl 4-(4,4,5,5-tetramethyl-1,3,2-dioxaborolan-2-yl)-5,6-dihydropyridine-1(2H)-carboxylate (1.42 g, 4.6 mmol), tripotassium phosphate trihydrate (3.9 g, 14.64 mmol) in dioxane and water (30 mL, 8:1) was added Pd(dppf)$_2$Cl$_2$ (337 mg, 0.46 mmol). The mixture was refluxed at 110° C. for 3 hours. Filtration and concentration gave crude product, which was purified by silica gel column chromatography to afford the title compound (1.1 g, yield: 75%). MS (ESI): 320 [M+H]$^+$.

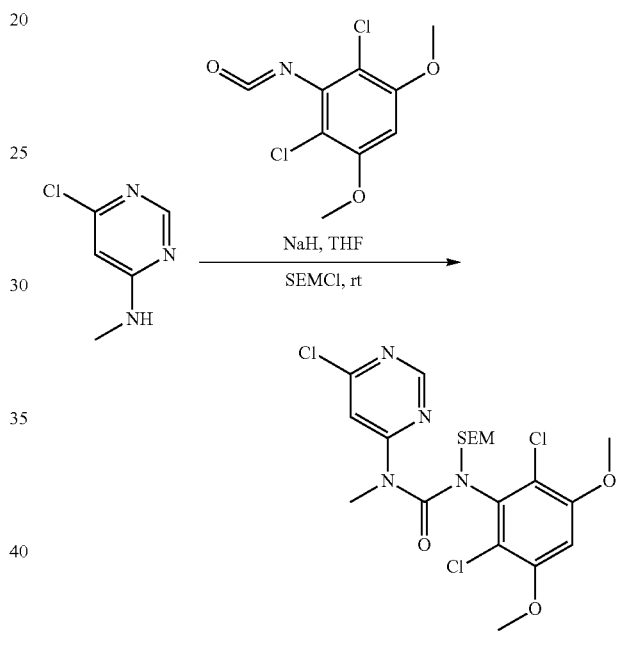

b. 1-(6-chloropyrimidin-4-yl)-3-(2,6-dichloro-3,5-dimethoxyphenyl)-1-methyl-3-((2-(trimethylsilyl)ethoxy)methyl)urea To a solution of 6-chloro-N-methylpyrimidin-4-amine (Procedure 2A, step e; 460 mg, 3.21 mmol) in DMF (15 mL) was added NaH (60%, 193 mg, 4.81 mmol) at 0° C., and the mixture was stirred for 30 minutes at room temperature. A solution of 2,4-dichloro-3-isocyanato-1,5-dimethoxy-benzene (Procedure H, steps a-d; 1.03 g, 4.17 mmol) in DMF (5 mL) was added dropwise at room temperature. The resulting mixture was stirred for 0.5 hour. SEMCl (804 mg, 4.81 mmol) in DMF (2 mL) was added. The reaction mixture was stirred at room temperature for 1 hour. Saturated aqueous NH$_4$Cl was added to quench the reaction. The mixture was diluted with water and extracted with EtOAc. The combined extracts were washed with water and brine, dried over anhydrous Na$_2$SO$_4$ and filtered. The filtrate was evaporated under vacuum to give crude product, which was purified by flash chromatography on silica to obtain the title compound (470 mg, yield: 28%). MS (ESI): 521 [M+H]$^+$.

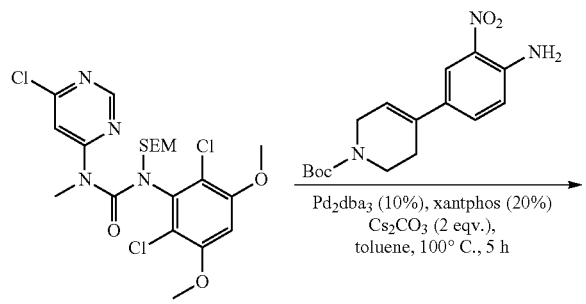
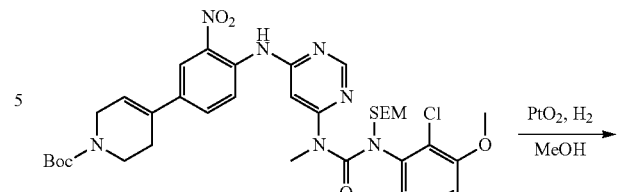

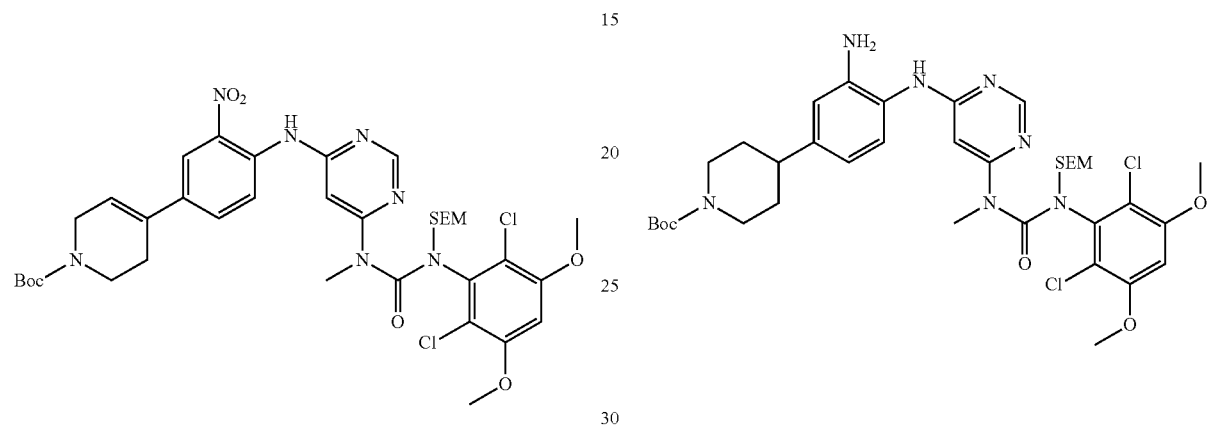

c. tert-butyl-(4-(6-(3-(2,6-dichloro-3,5-dimethoxy-phenyl)-1-methyl-3-((2-(trimethylsilyl)ethoxy)methyl)ureido)pyrimidin-4-ylamino)-3-nitrophenyl)-5,6-dihydropyridine-1(2H)-carboxylate A degassed mixture of 1-(6-chloropyrimidin-4-yl)-3-(2,6-dichloro-3,5-dimethoxyphenyl)-1-methyl-3-((2-(trimethylsilyl)ethoxy)methyl)urea (470 mg, 0.9 mmol), tert-butyl 4-(4-amino-3-nitrophenyl)-5,6-dihydropyridine-1(2H)-carboxylate (320 mg, 1 mmol), Pd$_2$(dba)$_3$ (92 mg, 0.1 mmol), xantphos (115 mg, 0.2 mmol) and Cs$_2$CO$_3$ (652 mg, 2 mmol) in toluene (10 mL) was heated at 100° C. for 5 hours. The reaction was concentrated, and the residue was purified by flash chromatography on silica to obtain the title compound (400 mg, yield: 57%). MS (ESI): 804 [M+H]$^+$.

d. tert-butyl-4-(3-amino-4-(6-(3-(2,6-dichloro-3,5-dimethoxyphenyl)-1-methyl-3-((2-(trimethylsilyl)ethoxy)methy)ureido)pyrimidin-4-ylamino)phenyl)piperidine-1-carboxylate To a solution of tert-butyl-4-(4-(6-(3-(2,6-dichloro-3,5-dimethoxyphenyl)-1-methyl-3-((2-(trimethylsilyl)ethoxy)methyl)ureido)pyrimidin-4-ylamino)-3-nitrophenyl)-5,6-dihydropyridine-1(2H)-carboxylate (380 mg, 0.473 mmol) in MeOH (10 mL) was added PtO$_2$ (38 mg, 10% wt) and one drop of chlorobenzene at room temperature, the resulting mixture was stirred under hydrogen atmosphere (1 atm) overnight. The reaction was filtered and concentrated. The residue was purified by flash chromatography on silica to obtain the title compound (130 mg, yield: 37%). MS (ESI): 776 [M+H]$^+$.

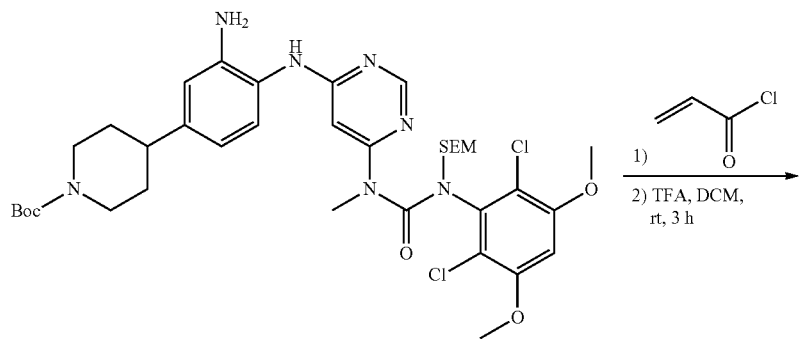

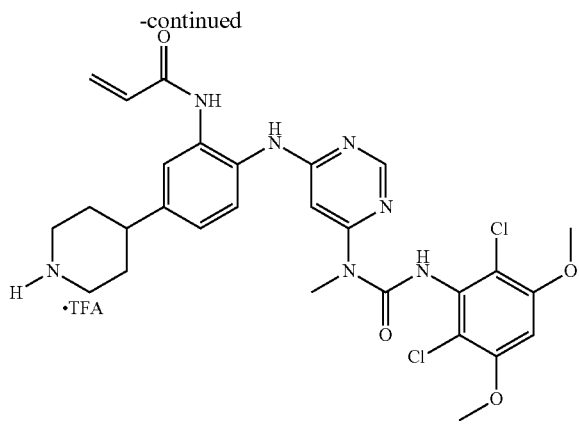

e. N-(2-(6-(3-(2,6-dichloro-3,5-dimethoxyphenyl)-1-methylureido)pyrimidin-4ylamino)-5-(piperidin-4-yl)phenyl)acrylamide TFA Salt To a solution of tert-butyl-4-(3-amino-4-(6-(3-(2,6-dichloro-3,5-dimethoxyphenyl)-1-methyl-3-((2-(trimethylsilyl)ethoxy)methyl)ureido)pyrimidin-4-ylamino)phenyl)piperidine-1-carboxylate (130 mg, 0.168 mmol) in THF (15 mL) was added a solution of acryloyl chloride (10 mg/mL, 1.7 mL, 0.19 mmol) dropwise at −10° C., and the resulting mixture was stirred at 0° C. for 1 hour. LC-MS showed that the reaction was complete. MeOH (5 mL) was added to quench the reaction, and the reaction was concentrated. The residue in DCM (2 mL) was added dropwise to a mixture of DCM/TFA (2/1, v/v, 3 mL). The mixture was stirred at room temperature for 1 hour and then concentrated under vacuum. The residue (50 mg, quant.) was used directly for the next step without further purification. MS (ESI): 600 [M+H]$^+$.

f. N-(2-(6-(3-(2,6-diichloro-3,5-dimethoxyphenyl)-1-methylureido)pyrimidin-4ylamino)-5-(1-ethylpiperidin-4-yl)phenyl)acrylamide To a solution of N-(2-(6-(3-(2,6-dichloro-3,5-dimethoxyphenyl)-1-methylureido)pyrimidin-4-ylamino)-5-(piperidin-4-yl)phenyl)acrylamide TFA salt (35 mg, 0.049 mmol) in EtOH (1 mL), was added NaOAc (4 mg, 0.05 mmol) and aqueous acetaldehyde (1 mL, 0.9 mmol, 40%). After the mixture was stirred at room temperature for 1 hour, NaBH$_3$CN (12 mg, 0.18 mmol) was added, and the solution was stirred at room temperature for another 3 hours. After removal of all volatiles in vacuo, the residue was partitioned between DCM and water. The aqueous layer was extracted with chloroform twice. The combined extracts were washed with brine, dried over anhydrous Na$_2$SO$_4$ and filtered. The filtrate was evaporated under vacuum to give crude product, which was purified by prep-HPLC to afford the title com-

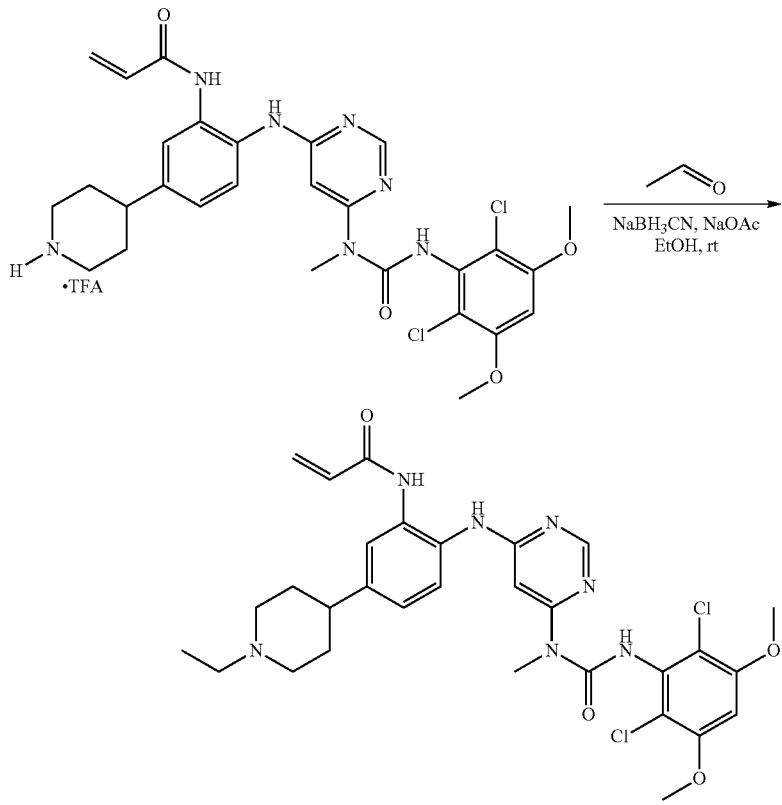

pound (3 mg, yield: 10%). $^1$H NMR (400 MHz, MeOH-d4) δ 8.38 (s, 1H), 7.68 (s, 1H), 7.54 (d, 1H), 7.24 (dd, 1H), 6.83 (s, 1H), 6.46-6.35 (m, 3H), 5.81 (d, 1H), 3.97 (s, 6H), 3.74-3.70 (m, 2H), 3.37 (s, 3H), 3.26 (q, 2H), 3.17-3.11 (m, 2H), 2.99-2.96 (m, 1H), 2.26-2.22 (m, 2H), 2.06-1.99 (m, 2H), 1.43 (t, 3H); MS (ESI): 628 [M+H]$^+$.

Example—112

N-(2-(6-(3-(2,6-dichloro-3,5-dimethoxyphenyl)-1-methylureido)pyrimidin-4-ylamino)-5-(1-methylpiperidin-4-yl)phenyl)acrylamide The compound was synthesized following the approach outlined in Procedure 2E (Example 111), substituting formaldehyde in step (f) to afford the title compound (1.5 mg, yield: 11.6%). $^1$H NMR (400 MHz, MeOH-d4) δ 8.26 (s, 1H), 7.55 (s, 1H), 7.41 (d, 1H), 7.11 (d, 1H), 6.71 (s, 1H), 6.34-6.22 (m, 3H), 5.68 (d, 1H), 3.84 (s, 6H), 3.55-3.52 (m, 2H), 3.25 (s, 3H), 3.21-3.08 (m, 2H), 2.90-2.83 (m, 4H), 2.11-2.08 (m, 2H), 1.89-1.85 (m, 2H); MS (ESI): 614 [M+H]$^+$.

Procedure 2F: Example—113

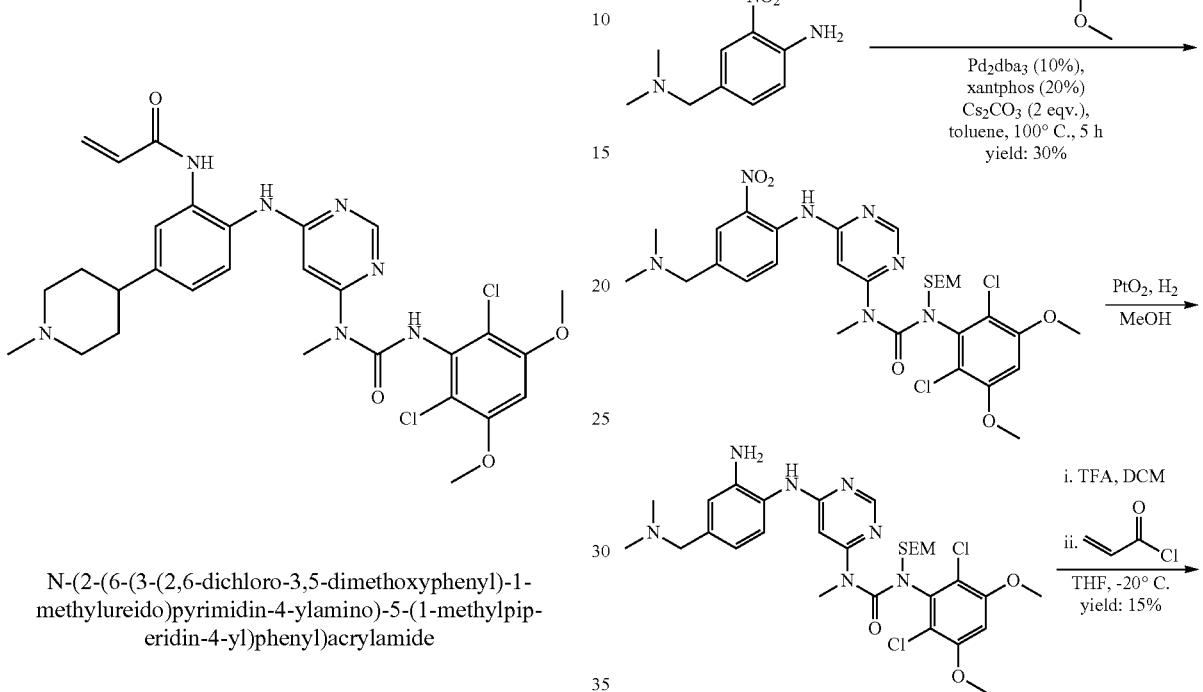

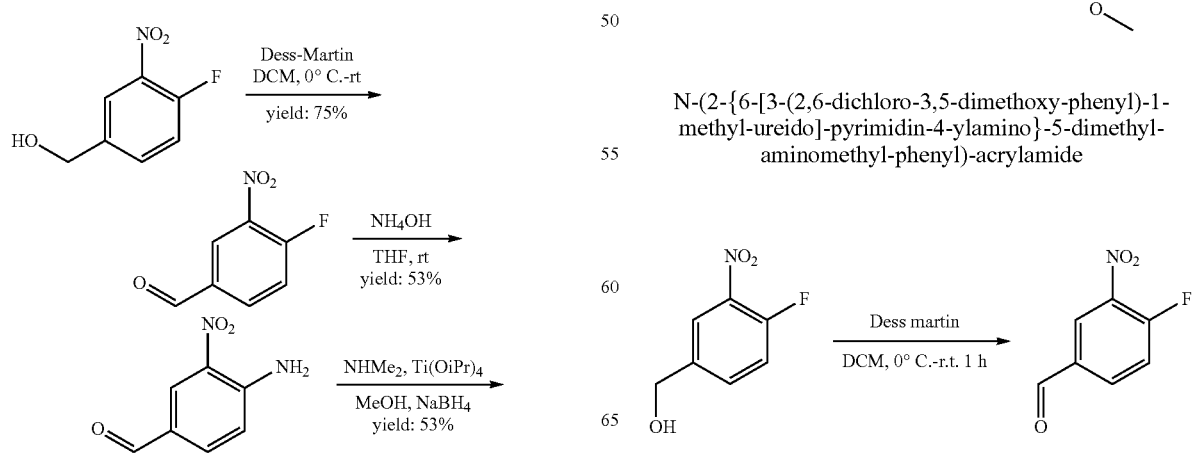

N-(2-{6-[3-(2,6-dichloro-3,5-dimethoxy-phenyl)-1-methyl-ureido]-pyrimidin-4-ylamino}-5-dimethylaminomethyl-phenyl)-acrylamide a. 4-Fluoro-3-nitro-benzaldehyde

To a stirred solution of (4-fluoro-3-nitro-phenyl)-methanol (750 mg, 4.4 mmol) in DCM (40 mL) at 0° C. was added Dess-Martin Reagent (3.0 g, 7 mmol). The solution was stirred at room temperature for 4 hours. TLC showed disappearance of starting material. The reaction was quenched with 10% NaHCO$_3$ and 10% Na$_2$S$_2$O$_3$ aqueous solution and DCM layer separated and washed with water (100 mL) and brine (50 mL). The reaction was concentrated, and the residue was purified by flash chromatography on silica to obtain the title compound (570 mg, yield: 75%). $^1$H-NMR (400 MHz, DMSO-d6) δ 10.09 (d, 1H), 8.36 (t, 1H), 8.06 (dd, 1H), 7.97 (m, 1H).

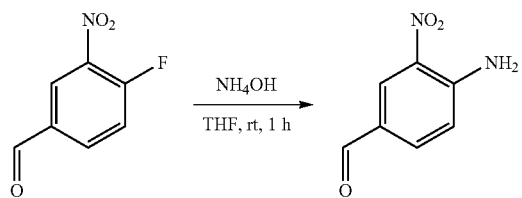 [SMILES: O=Cc1ccc(F)c([N+](=O)[O-])c1 ; "NH4OH" ; Nc1ccc(C=O)cc1[N+](=O)[O-]]

b. 4-Amino-3-nitrobenzaldehyde

To a solution of 4-fluoro-3-nitro-benzaldehyde (570 mg, 3.3 mmol) in THF (20 mL) was added NH$_4$OH (5 mL). The reaction mixture was stirred at room temperature for 1 hour. The resulting yellow solid was collected and washed with water, dried under vacuum to give the title compound (300 mg, yield: 53%). $^1$H-NMR (300 MHz, DMSO-d6) δ 9.76 (s, 1H), 8.57 (d, 1H), 8.18 (br s, 2H), 7.80 (dd, 1H), 7.10 (d, 1H).

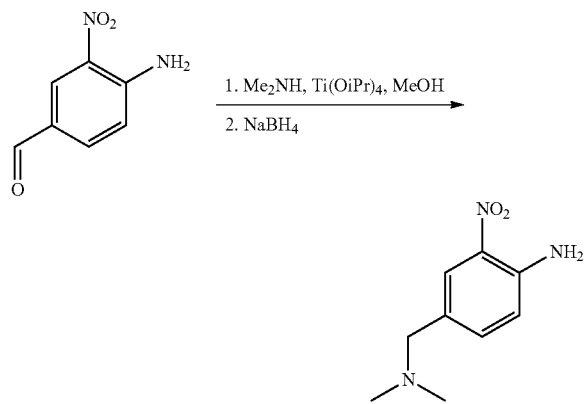

c. 4-Dimethylaminomethyl-2-nitro-phenylamine

To a stirred solution of dimethylamine (4.0 mL, 2 M, 8.0 mmol) in MeOH (4 mL) was added Ti(O$^i$Pr)$_4$ (1.15 g, 4 mmol) and the solution was stirred at room temperature for 15 minutes Then 4-amino-3-nitro-benzaldehyde (160 mg, 1.0 mmol) in MeOH (2 mL) was added and the solution was stirred at room temperature overnight. Then NaBH$_4$ (78 mg, 2 mmol) was added and the solution was stirred at room temperature for 1 hour. LCMS showed major product peak. The solution was diluted with EtOAc (60 mL) and washed with water (2×100 mL) and brine (50 mL), dried over anhydrous Na$_2$SO$_4$. The solution was evaporated to dryness and 130 mg of crude product was collected, which was used for the next step without further purification. $^1$H NMR (400 MHz, DMSO-d6) δ 7.82 (s, 1H), 7.35 (br s, 2H), 7.31 (dd, 1H), 6.97 (d, 1H), 3.26 (s, 2H), 2.12 (s, 6H).

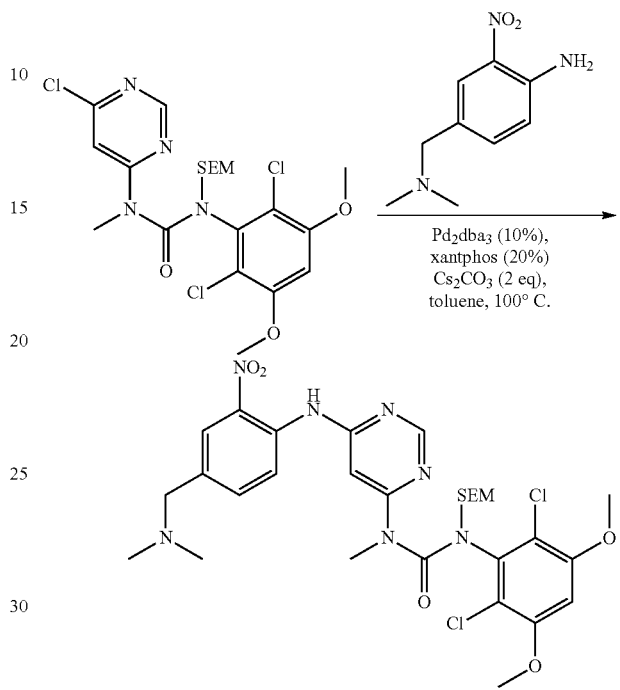

d. 1-(2,6-Dichloro-3,5-dimethoxy-phenyl)-3-[6-(4-dimethylaminomethyl-2-nitro-phenylamino)-pyrimidin-4-yl]-3-methyl-1-(2-trimethylsilanyl-ethoxymethyl)-urea To a stirred solution of 1-(6-chloro-pyrimidin-4-yl)-3-(2,6-dichloro-3,5-dimethoxy-phenyl)-1-methyl-3-(2-trimethylsilanyl-ethoxymethyl)-urea (procedure L, step b; 260 mg, 0.5 mmol) in toluene (5 mL) was added 4-dimethylaminomethyl-2-nitro-phenylamine (100 mg, 0.5 mmol), Cs$_2$CO$_3$ (400 mg, 1.25 mmol), Pd$_2$(dba)$_3$ (46 mg, 0.05 mmol), xantphos (90 mg, 0.15 mmol). The solution was stirred at 100° C. overnight. LCMS showed major product peak. The solution was evaporated with silica gel and purified by flash chromatography on silica eluting with EtOAc (w(/0.5% TEA):MeOH (w/0.5% TEA)=10-10:0.5 to afford the desired product (100 mg, yield: 30%). MS (ESI): 680 [M+H]$^+$.

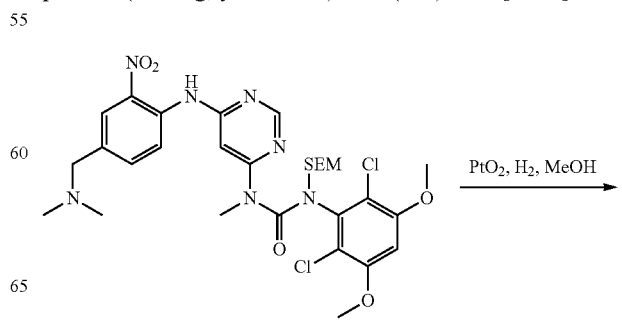

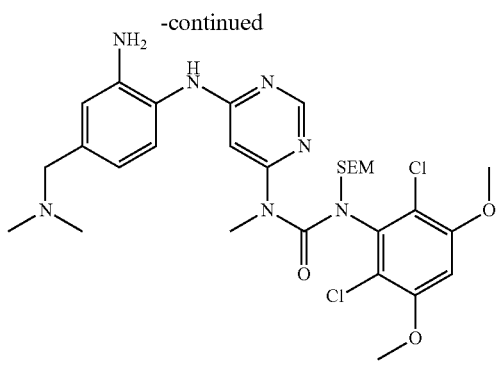

e. [6-(2-Amino-4-dimethylaminomethyl-phenylamino)-pyrimidin-4-yl]-3-(2,6-dichloro-3,5-dimethoxy-phenyl)-1-methyl-3-(2-trimethylsilanyl-ethoxymethyl)-urea To a stirred solution of 1-(2,6-dichloro-3,5-dimethoxy-phenyl)-3-[6-(4-dimethylaminomethyl-2-nitro-phenylamino)-pyrimidin-4-yl]-3-methyl-1-(2-trimethylsilanyl-ethoxymethyl)-urea (100 mg, 0.15 mmol) in MeOH (10 mL) was added 4 drops of chlorobenzene and then $PtO_2$ (30 mg, 30% wt). The solution was stirred under hydrogen atmosphere at room temperature overnight. The reaction was filtered and concentrated. The residue was taken to the next step without further purification. MS (ESI): 650 [M+H]$^+$.

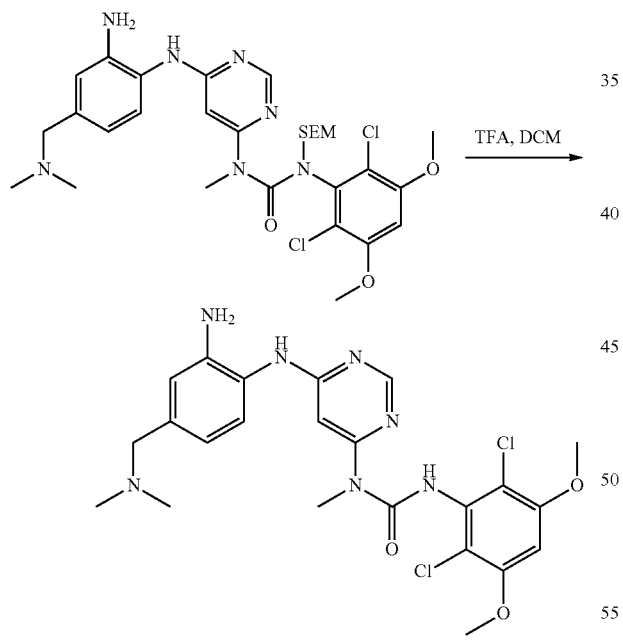

f. 1-[6-(2-Amino-4-dimethylaminomethyl-phenylamino)-pyrimidin-4-yl]-3-(2,6-dichloro-3,5-dimethoxy-phenyl)-1-methyl-urea To a stirred solution of 1-[6-(2-amino-4-dimethylaminomethyl-phenylamino)-pyrimidin-4-yl]-3-(2,6-dichloro-3,5-dimethoxy-phenyl)-1-methyl-3-(2-trimethylsilanyl-ethoxymethyl)-urea in anhydrous DCM (10 mL) was added TFA (10 mL) at room temperature. The solution was stirred at room temperature for 3 hours. LCMS showed major product peak. The solution was evaporated to dryness, diluted with DCM (40 mL) and washed with 10% saturated $Na_2CO_3$ (10 mL). The DCM layer was dried over anhydrous $Na_2SO_4$. Concentration under vacuum gave crude product, which was purified by silica gel column chromatography (10% MeOH/DCM with 0.5% Et$_3$N) to afford the title compound (45 mg, yield: 58% in two steps). MS (ESI): 520 [M+H]$^+$.

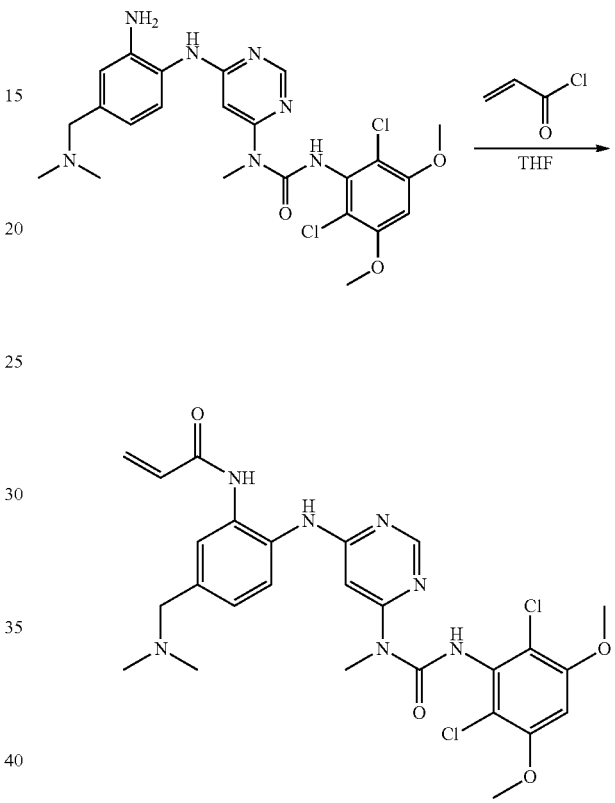

g. N-(2-{6-[3-(2,6-Dichloro-3,5-dimethoxy-phenyl)-1-methyl-ureido]-pyrimidin-4-ylamino}-5-dimethyl-aminomethyl-phenyl)-acrylamide To a stirred solution of 1-[6-(2-amino-4-dimethylaminomethyl-phenylamino)-pyrimidin-4-yl]-3-(2,6-dichloro-3,5-dimethoxy-phenyl)-1-methyl-urea (45 mg, 0.11 mmol) in THF (40 mL) at −10° C. was added acryloyl chloride (30 mg, 0.33 mmol) in THF (3 mL). The solution was stirred at −10° C. for 5 hours. LCMS showed major product peak. The reaction was quenched with MeOH (3 mL) and evaporated. The residue was purified by prep-HPLC (water/ACN in NH$_4$HCO$_3$ condition) to afford the title compound (6 mg, yield: 15%). $^1$H-NMR (400 MHz, MeOH-d$_4$) δ 8.25 (s, 1H), 7.47 (d, 1H), 7.44 (s, 1H), 7.16 (dd, 1H), 6.70 (s, 1H), 6.33-6.20 (m, 3H), 5.67 (dd, 1H), 3.84 (s, 6H), 3.43 (s, 2H) 3.22 (s, 3H), 2.20 (s, 6H); MS (ESI): 574 [M+H]$^+$.

Example—114

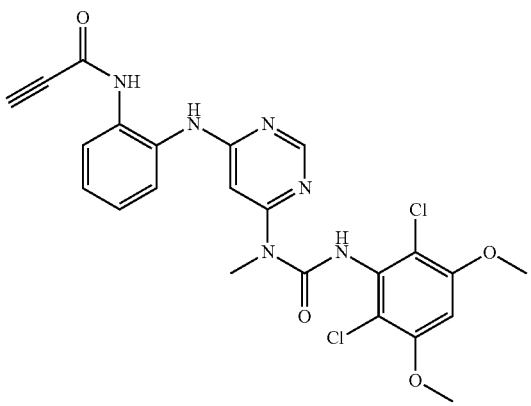 [SMILES: C#CC(=O)Nc1ccccc1Nc1cc(N(C)C(=O)Nc2c(Cl)c(OC)cc(OC)c2Cl)ncn1]

N-(2-(6-(3-(2,6-dichloro-3,5-dimethoxyphenyl)-1-methylureido)pyrimidin-4-ylamino)phenyl)propiolamide The compound was synthesized following the approach outlined in Procedure 2C (Example 108) modifying step (g) to the following procedure: To a solution of 1-[6-(2-aminophenylamino)-pyrimidin-4-yl]-3-(2,6-dichloro-3,5-dimethoxy-phenyl)-1-methyl-urea (50 mg, 0.108 mmol) and DCC (46 mg, 0.22 mmol) in chloroform (50 mL) was added a solution of propiolic acid (16 mg, 0.22 mmol) in chloroform (50 mL) at 0° C., and the resulting mixture was stirred at room temperature overnight. Water (1 mL) was added to quench the reaction. The mixture was concentrated and the residue was purified by reverse phase column and prep-TLC to obtain the title compound (5 mg, yield: 9.1%). $^1$H NMR (400 MHz, DMSO-d6) δ 12.04 (s, 1H), 10.36 (s, 1H), 9.03 (s, 1H), 8.45 (s, 1H), 7.67 (d, 1H), 7.59 (d, 1H), 7.30-7.25 (m, 2H), 6.96 (s, 1H), 6.50 (s, 1H), 4.42 (s, 1H), 4.00 (s, 6H), 3.35 (s, 3H); MS (ESI): 515 [M+H]$^+$

Example—116

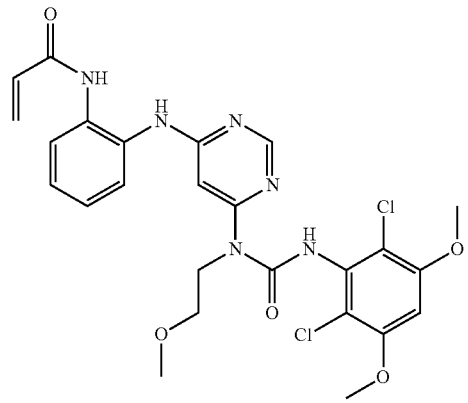 [SMILES: C=CC(=O)Nc1ccccc1Nc1cc(N(CCOC)C(=O)Nc2c(Cl)c(OC)cc(OC)c2Cl)ncn1]

N-(2-{6-[3-(2,6-Dichloro-3,5-dimethoxy-phenyl)-1-(2-methoxy-ethyl)-ureido]-pyrimidin-4-ylamino}-phenyl)-acrylamide The compound was synthesized following the approach outlined in Procedure 2G (Example 123), substituting 1-(6-chloro-pyrimidin-4-yl)-3-(2,6-dichloro-3,5-dimethoxy-phenyl)-1-(2-methoxy-ethyl)-3-(2-trimethylsilanyl-ethoxymethyl)-urea (preparation shown below) in step (d) to afford the title compound (40 mg, yield: 16% over five steps). $^1$H NMR (400 MHz, DMSO-d6) δ 11.28 (s, 1H), 9.71 (s, 1H), 8.85 (s, 1H), 8.38 (s, 1H), 7.70-7.68 (m, 1H), 7.55-7.53 (m, 1H), 7.20-7.18 (m, 2H), 6.89 (s, 1H), 6.69 (s, 1H), 6.50 (dd, 1H), 6.26 (d, 1H), 5.75 (d, 1H), 4.03 (t, 2H), 3.94 (s, 6H), 3.56 (t, 2H), 3.24 (s, 3H); MS (ESI): 437 [M+H]$^+$.

Preparation of 1-(6-Chloro-pyrimidin-4-yl)-3-(2,6-dichloro-3,5-dimethoxy-phenyl)-1-(2-methoxy-ethyl)-3-(2-trimethylsilanyl-ethoxymethyl)-urea

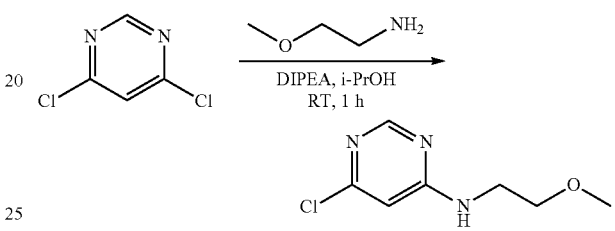

a. (6-Chloro-pyrimidin-4-yl)-(2-methoxy-ethyl)-amine

To a solution of 4,6-dichloro-pyrimidine (2 g, 14 mmol) in iPrOH (70 mL) and DIPEA (1.94 g, 15 mmol) was added a solution of 2-methoxy-ethylamine (1.13 g, 15 mmol) at room temperature. The resulting mixture was stirred at room temperature for 1 hour. Water was added and the mixture was extracted with DCM. The combined extracts were washed with brine, dried over anhydrous Na$_2$SO$_4$, and concentrated to give the crude product, which was purified by flash chromatography on silica to obtain the title compound (1.95 g, yield: 82%). MS (ESI): 188 [M+H]+.

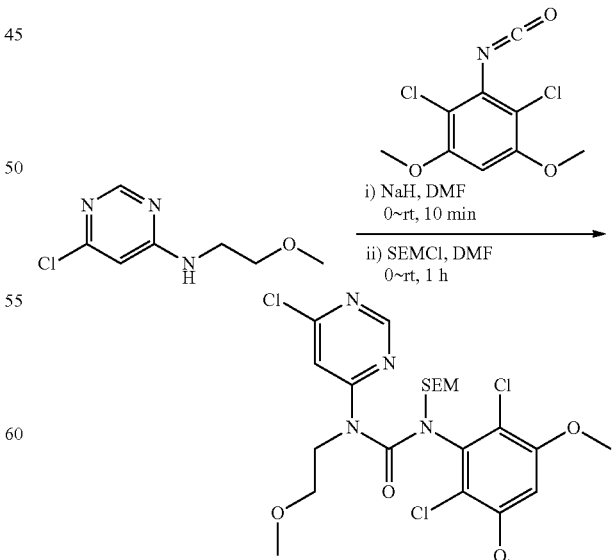

b. 1-(6-Chloro-pyrimidin-4-yl)-3-(2,6-dichloro-3,5-dimethoxy-phenyl)-1-(2-methoxy-ethyl)-3-(2-trimethylsilanyl-ethoxymethyl)-urea To a solution of (6-chloro-pyrimidin-4-yl)-(2-methoxy-ethyl)-amine (300 mg, 1.6 mmol) in DMF (10 mL) was added NaH (60%, 96 mg, 2.4 mmol) at 0° C., and the mixture was stirred for 10 minutes at room temperature. A solution of 1-isocyanato-3,5-dimethoxy-benzene (590 mg, 2.4 mmol) in DMF (5 mL) was added dropwise at 0° C. The resulting mixture was stirred for 30 minutes. SEMCl (400 mg, 2.4 mmol) in DMF (2 mL) was added and the reaction mixture was stirred at room temperature for 1 hour. Saturated aqueous NH$_4$Cl was added to quench the reaction. The mixture was diluted with water and extracted with EtOAc. The combined extracts were washed with water and brine, dried over anhydrous Na$_2$SO$_4$, and concentrated to afford the crude product, which was purified by flash chromatography on silica to obtain the title compound (720 mg, yield: 78%). MS (ESI): 565 [M+H]$^+$.

Example—120

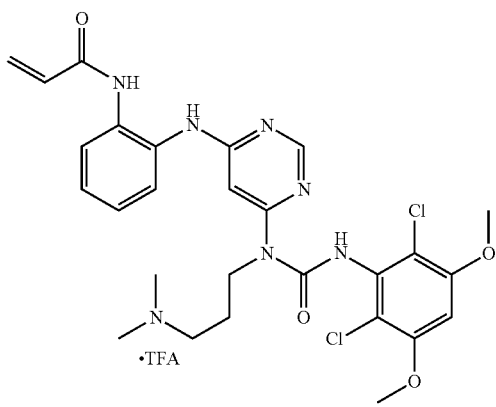 [SMILES: C=CC(=O)Nc1ccccc1Nc1cc(N(CCCN(C)C)C(=O)Nc2c(Cl)c(OC)cc(OC)c2Cl)ncn1]

N-(2-{6-[3-(2,6-Dichloro-3,5-dimethoxy-phenyl)-1-(3-dimethylamino-propyl)-ureido]-pyrimidin-4-ylamino}-phenyl)-acrylamide trifluoroacetic acid The compound was synthesized following the approach outlined in Procedure 2I (Example 142), substituting 2-nitroaniline and N-(3-Dimethylamino-propyl)-N'-(2-nitro-phenyl)-pyrimidine-4,6-diamine (prepared by the method outlined below) in step (c) to afford the title compound (11 mg, yield: 7.5% over six steps). $^1$H NMR (300 MHz, DMSO-d6) δ 11.30 (s, 1H), 9.80 (s, 1H), 9.28 (m, 1H), 8.92 (s, 1H), 8.42 (s, 1H), 7.64 (d, 1H), 7.55 (d, 1H), 7.24-7.16 (m, 2H), 6.90 (s, 1H), 6.53 (s, 1H), 6.49 (dd, 1H), 6.25 (d, 1H), 5.76 (d, 1H), 3.95 (s, 6H), 3.91-3.88 (m, 2H), 3.11-3.05 (m, 2H), 2.74 (d, 6H), 1.97-1.92 (m, 2H); MS (ESI): 588 [M+H]$^+$.

Preparation of N-(3-Dimethylamino-propyl)-N'-(2-nitro-phenyl)-pyrimidine-4,6-diamine

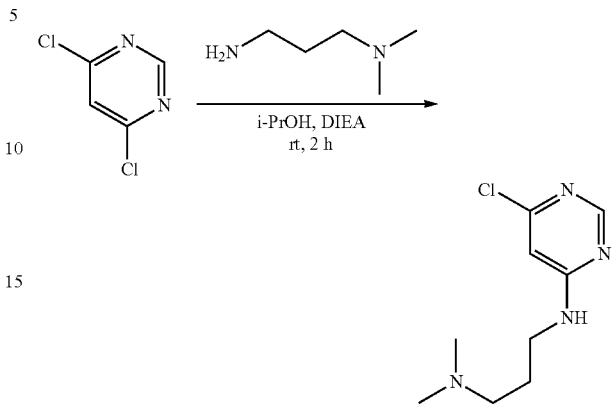

a. N'-(6-Chloro-pyrimidin-4-yl)-N,N-dimethyl-propane-1,3-diamine

To a solution of 4,6-dichloro-pyrimidine (1 g, 6.7 mmol) and DIPEA (1.03 g, 8 mmol) in iPrOH (20 mL) was added N,N-dimethyl-propane-1,3-diamine (714 mg, 7 mmol) at room temperature. The resulting mixture was stirred for 2 hours. Water was added and the mixture was extracted with DCM. The combined extracts were washed with brine, dried over anhydrous Na$_2$SO$_4$, and concentrated to give the crude product, which was purified by flash chromatography on silica to obtain the title compound (1.15 g, yield: 80%). MS (ESI): 215 [M+H]$^+$.

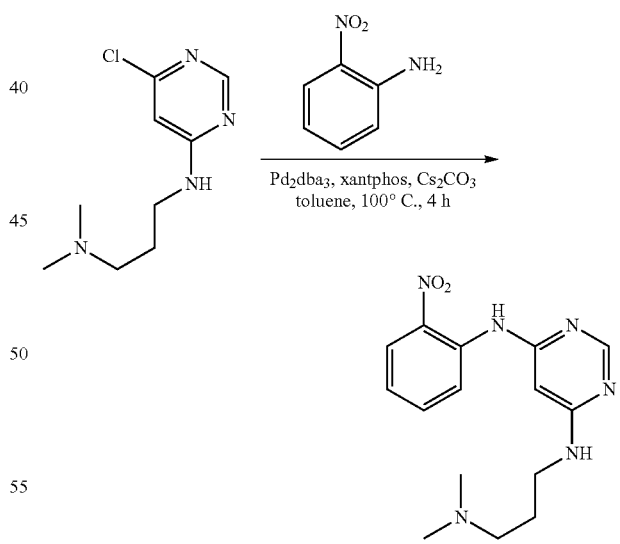

b. N-(3-Dimethylamino-propyl)-N-(2-nitro-phenyl)-pyrimidine-4,6-diamine

A degassed mixture of N'-(6-chloro-pyrimidin-4-yl)-N,N-dimethyl-propane-1,3-diamine (800 mg, 3.74 mmol), nitro aniline (525 mg, 3.8 mmol), Pd$_2$(dba)$_3$ (348 mg, 0.38 mmol), Xantphos (438 mg, 0.76 mmol) and Cs$_2$CO$_3$ (3.05 g, 9.35 mmol) in toluene (15 mL) was heated at 100° C. for 4 hours.

Example—121

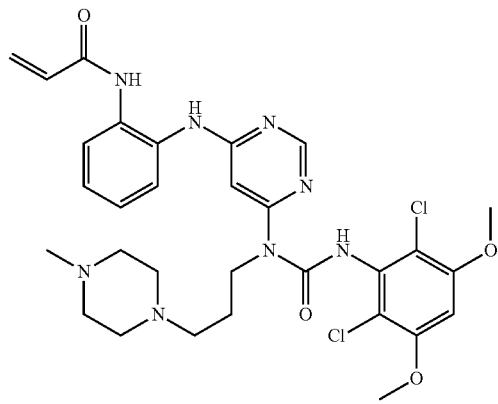 [SMILES: C=CC(=O)Nc1ccccc1Nc1cc(N(CCCN2CCN(C)CC2)C(=O)Nc2c(Cl)c(OC)cc(OC)c2Cl)ncn1]

N-[2-(6-{3-(2,6-Dichloro-3,5-dimethoxy-phenyl)-1-[3-(4-methyl-piperazin-1-yl)-propyl]-ureido}-pyrimidin-4-ylamino)-phenyl]-acrylamide The compound was synthesized following the approach outlined in Procedure 2I (Example 142), substituting 2-nitroaniline and N-[3-(4-Methyl-piperazin-1-yl)-propyl]-N'-(2-nitro-phenyl)-pyrimidine-4,6-diamine (preparation shown below) in step (e) to afford the title compound (8 mg, yield: 1.2% over six steps). $^1$H NMR (300 MHz, Methanol-d4) δ 8.17 (s, 1H), 7.46 (d, 1H), 7.32 (d, 1H), 7.12-7.08 (m, 2H), 6.62 (s, 1H), 6.29-6.14 (m, 3H), 5.58 (d, 1H), 3.82 (t, 2H), 3.75 (s, 6H), 2.27-2.19 (m, 8H), 2.06 (s, 3H), 1.67 (t, 2H); MS (ESI): 643 [M+H]$^+$.

Preparation of N-[3-(4-Methyl-piperazin-1-yl)-propyl]-N'-(2-nitro-phenyl)-pyrimidine-4,6-diamine

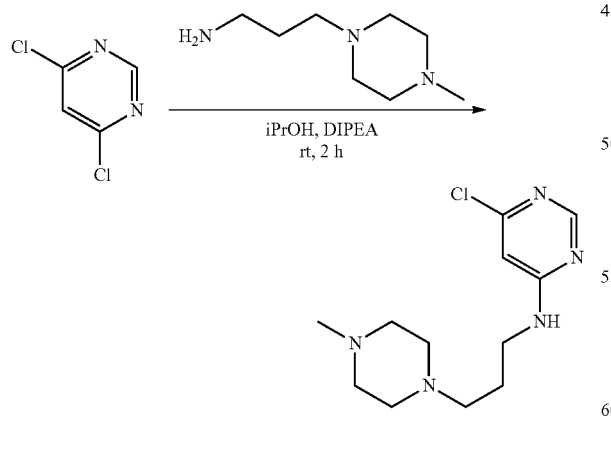

a. (6-Chloro-pyrimidin-4-yl)-[3-(4-methyl-piperazin-1yl)-propyl]-amine

To a solution of 4,6-dichloro-pyrimidine (1.5 g, 10 mmol) and DIPEA (1.55 g, 12 mmol) in iPrOH (50 mL) was added a solution of 3-(4-methyl-piperazin-1-yl)-propylamine (1.73 g, 11 mmol) at room temperature. The resulting mixture was stirred at room temperature for 2 hours. Water was added and the mixture was extracted with DCM. The combined extracts were washed with brine, dried over anhydrous Na$_2$SO$_4$, and concentrated to afford the title compound (1.4 g, 51%), which was used directly in the next step without further purification. MS (ESI): 270 [M+H]$^+$.

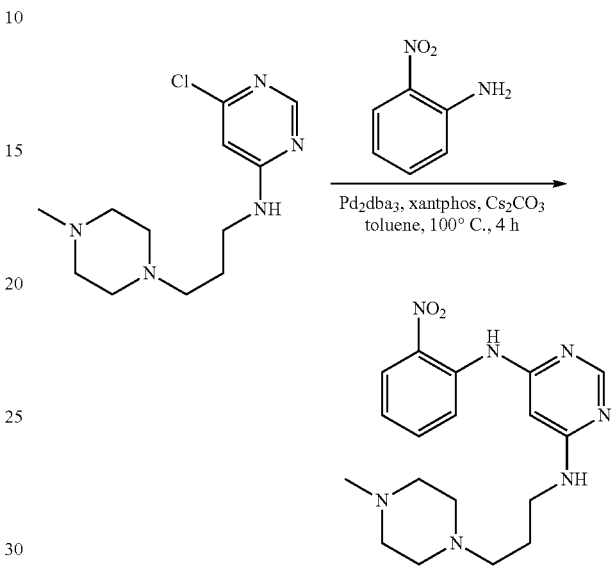

b. N-[3-(4-Methyl-piperazin-1-yl)-propyl]-N'-(2-nitro-phenyl)-pyrimidine-4,6-diamine A degassed mixture of (6-chloro-pyrimidin-4-yl)-[3-(4-methyl-piperazin-1-yl)-propyl]-amine (600 mg, 2.22 mmol), nitroanline (317 mg, 2.3 mmol), Pd$_2$(dba)$_3$ (210 mg, 0.23 mmol), Xantphos (265 mg, 0.46 mmol) and Cs$_2$CO$_3$ (1.81 g, 5.55 mmol) in toluene (15 mL) was heated at 100° C. for 4 hours. The reaction was concentrated, and the residue was purified by reverse phase chromatography to obtain the title compound (400 mg, yield: 48%). MS (ESI): 372 [M+H]$^+$.

Example—122

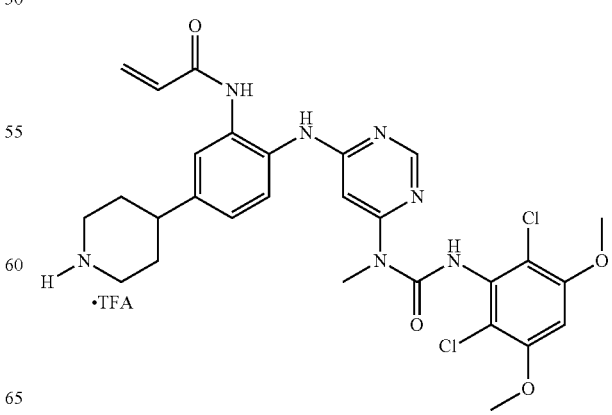

N-(2-{6-[3-(2,6-Dichloro-3,5-dimethoxy-phenyl)-1-methyl-ureido]-pyrimidin-4-ylamino}-5-piperidin-4-yl-phenyl)-acrylamide trifluoroacetic acid The compound was synthesized following the approach outlined in Procedure 2E (Example 111), replacing steps (e) and (f) with the following procedure: To a solution of tert-butyl 4-(3-amino-4-(6-(3-(2,6-dichloro-3,5-dimethoxy-phenyl)-1-methyl-3-((2-(trimethylsilyl)ethoxy) methyl) ureido)pyrimidin-4-ylamino)phenyl)piperidine-1-carboxy-late (Procedure 2E, Example 111, 65 mg, 0.084 mmol) in THF (15 mL) was added a solution of acryloyl chloride (10 mg/mL, 0.9 mL, 0.1 mmol) dropwise at −10° C., and the resulting mixture was stirred at 0° C. for 1 hour. MeOH (5 mL) was added to quench the reaction, and the reaction was concentrated. The residue was dissolved in DCM (2 mL) and added dropwise to a mixture of DCM/TFA (2:1, 3 mL). The mixture was stirred at room temperature for 1 hour and then concentrated. The residue was purified by prep-HPLC to afford the title compound (23 mg, yield: 47%). $^1$H NMR (300 MHz, DMSO-d6) δ 11.92 (s, 1H), 9.64 (s, 1H), 8.98 (s, 1H), 8.60 (m, 1H), 8.36 (s, 1H), 8.25 (m, 1H), 7.66 (s, 1H), 7.51 (d, 1H), 7.05 (d, 1H), 6.90 (s, 1H), 6.52 (dd, 1H), 6.41 (s, 1H), 6.24 (d, 1H), 5.74 (d, 1H), 3.96 (s, 6H), 3.49 (d, 2H), 3.28 (s, 3H), 3.02 (q, 2H), 2.85 (t, 1H), 1.96 (d, 2H), 1.78 (q, 2H); MS (ESI): 600 [M+H]$^+$.

Procedure 2G: Example—123

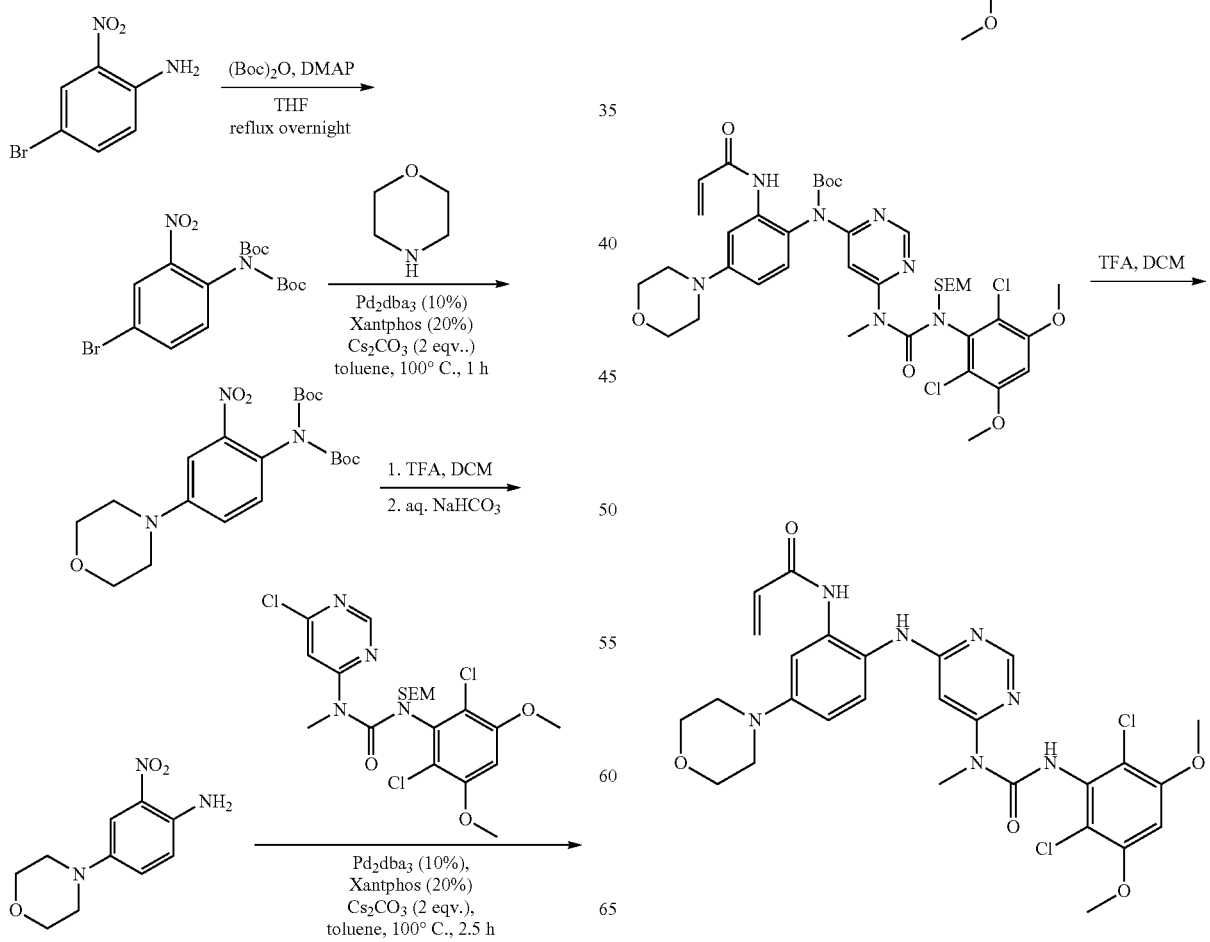

N-(2-{6-[3-(2,6-Dichloro-3,5-dimethoxy-phenyl)-1-methyl-ureido]-pyrimidin-4-ylamino}-5-morpholin-4-yl-phenyl)-acrylamide

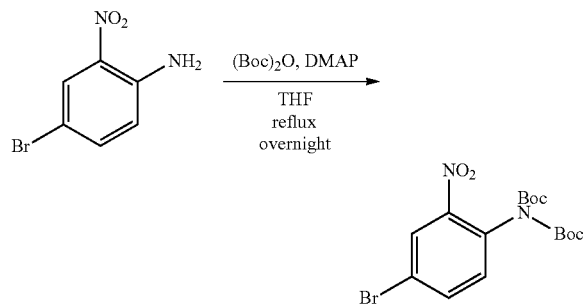

a. di-tert-Butyl 4-bromo-2-nitrophenylcarbamate

A mixture of 4-bromo-2-nitroaniline (10 g, 46 mmol), (Boc)₂O (20.7 g, 95 mmol) in THF (250 mL) was heated under reflux overnight. The mixture was concentrated to afford the title compound (19.2 g, yield: quant.) which was used directly in next step without further purification.

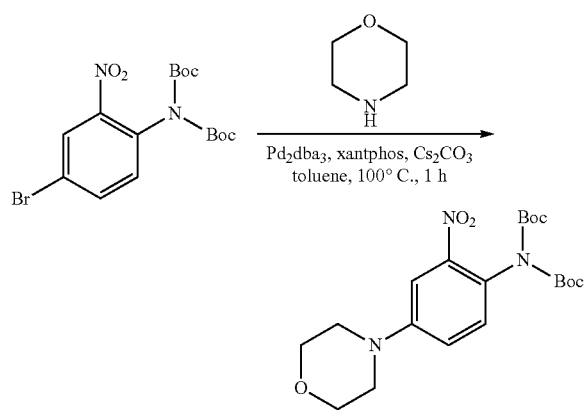

b. (4-Morpholin-4-yl-2-nitro-phenyl)-carbamic acid di-tert-butyl ester

A degassed mixture of tert-butyl 4-bromo-2-nitrophenyl-carbamate (1 g, 2.4 mmol), morpholine (314 mg, 3.6 mmol), Pd₂(dba)₃ (220 mg, 0.24 mmol), Xantphos (278 mg, 0.48 mmol) and Cs₂CO₃ (1.56 g, 4.8 mmol) in toluene (30 mL) was heated at 100° C. for 1 hour. The reaction was concentrated, and the residue was purified by flash chromatography on silica to obtain a crude mixture of the title compound and mono-Boc product (744 mg). The mixture was used directly in the next step without further purification. MS (ESI): 324 [M-Boc+H]⁺.

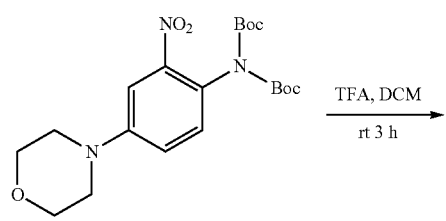

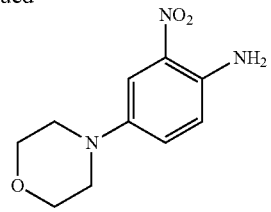

c. 4-Morpholin-4-yl-2-nitro-phenylamine

To a solution of (4-morpholin-4-yl-2-nitro-phenyl)-carbamic acid di-tert-butyl ester and mono-Boc product (744 mg) in DCM (20 mL) was added TFA (10 mL) at 0° C., the resulting mixture was stirred for 3 hours at room temperature. After removal of all volatiles in vacuo, the residue was re-dissolved in DCM, neutralized by saturated aqueous NaHCO₃, and extracted with DCM. The combined extracts were concentrated and the residue was purified by flash chromatography on silica to obtain the title compound (290 mg, yield: 54% over two steps). MS (ESI): 251 [M+H]⁺.

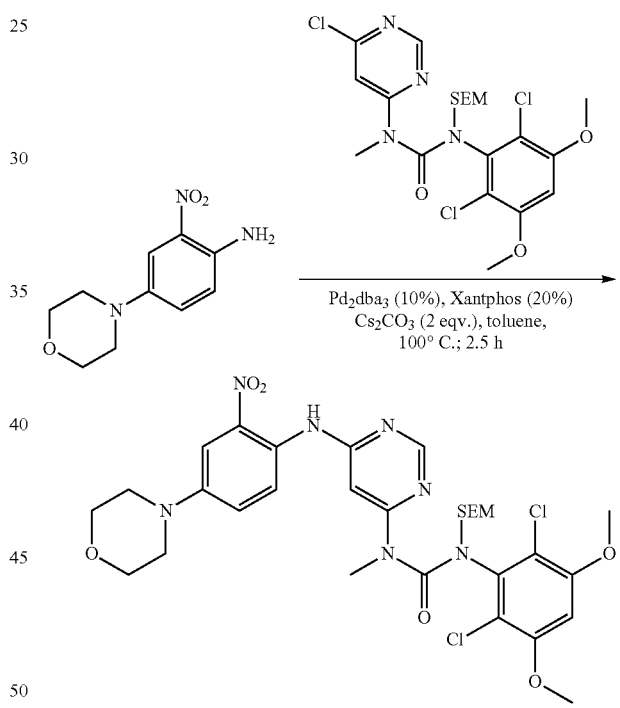

d. 1-(2,6-Dichloro-3,5-dimethoxy-phenyl)-3-methyl-3-[6-(4-morpholin-4-yl-2-nitro-phenylamino)-pyrimidin-4-yl]-1-(2-trimethylsilanyl-ethoxymethyl)-urea A degassed mixture of 4-morpholin-4-yl-2-nitro-phenylamine (290 mg, 1.3 mmol), 1-(6-chloro-pyrimidin-4-yl)-3-(2,6-dichloro-3,5-dimethoxy-phenyl)-1-methyl-3-(2-trimethylsilanyl-ethoxymethyl)-urea (Procedure 2E, step b; 624 mg, 1.2 mmol), Pd₂(dba)₃ (110 mg, 0.12 mmol), Xantphos (139 mg, 0.24 mmol) and Cs₂CO₃ (782 mg, 2.4 mmol) in toluene (15 mL) was heated at 100° C. for 2.5 hours. The reaction was concentrated, and the residue was purified by chromatography flash on silica to obtain the title compound (440 mg, yield: 49%) as a red solid. MS (ESI): 708 [M+H]⁺.

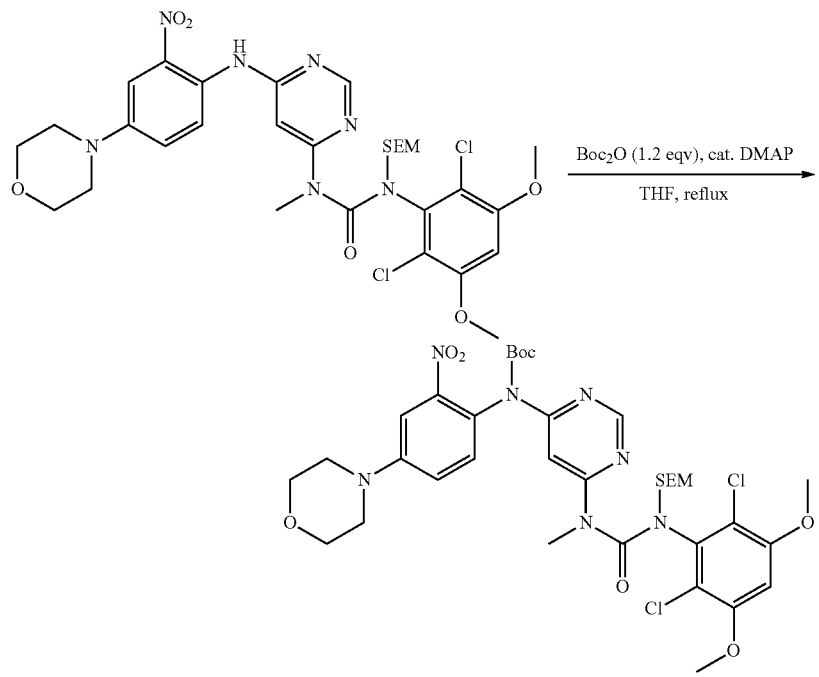

e. {6-[3-(2,6-Dichloro-3,5-dimethoxy-phenyl)-1-methyl-3-(2-trimethylsilanyl-ethoxymethyl)-ureido]-pyrimidin-4-yl}-(4-morpholin-4-yl-2-nitro-phenyl)-carbamic acid tert-butyl ester A mixture of 1-(2,6-dichloro-3,5-dimethoxy-phenyl)-3-methyl-3-[6-(4-morpholin-4-yl-2-nitro-phenylamino)-pyrimidin-4-yl]-1-(2-trimethylsilanyl-ethoxymethyl)-urea (200 mg, 0.28 mmol), (Boc)$_2$O (93 mg, 0.42 mmol) and catalytic amount of DMAP in THF (10 mL) was heated under reflux for 1 hour. The mixture was concentrated and the residue was used for the next step without further purification. MS (ESI): 808 [M+H]$^+$.

f. (2-Amino-4-morpholin-4-yl-phenyl)-{6-[3-(2,6-dichloro-3,5-dimethoxy-phenyl)-1-methyl-3-(2-trimethylsilanyl-ethoxymethyl)-ureido]-pyrimidin-4-yl}-carbamic acid tert-butyl ester To a solution of {6-[3-(2,6-dichloro-3,5-dimethoxy-phenyl)-1-methyl-3-(2-trimethylsilanyl-ethoxymethyl)-ureido]-pyrimidin-4-yl}-(4-morpholin-4-yl-2-nitro-phenyl)-carbamic acid tert-butyl ester (crude, prepared above) in MeOH (20 mL) was added Raney-Ni (suspension in water) at room temperature, the resulting mixture was stirred for 2 hours under hydrogen atmosphere (1 atm). The reaction was filtered and concentrated. The residue was washed twice with MeOH to obtain title product (160 mg, yield: 70%). MS (ESI):778 [M+H]$^+$.

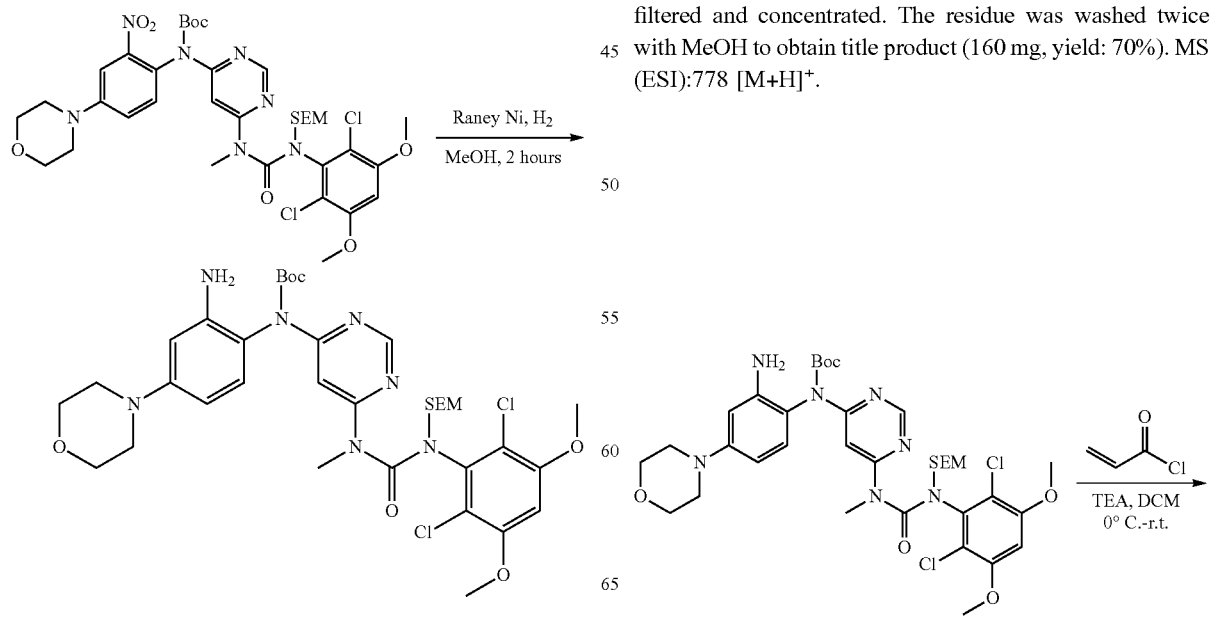

-continued

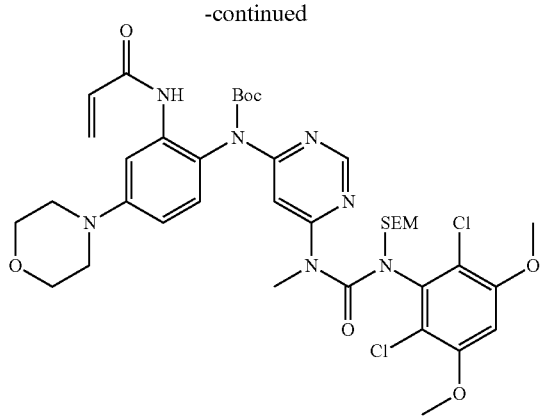

g. (2-Acryloylamino-4-morpholin-4-yl-phenyl)-{6-[3-(2,6-dichloro-3,5-dimethoxy-phenyl)-1methyl-3-(2-trimethylsilanyl-ethoxymethyl)-ureido]-pyrimidin-4-yl}-carbamic acid tert-butyl ester To a solution of (2-amino-4-morpholin-4-yl-phenyl)-{6-[3-(2,6-dichloro-3,5-dimethoxy-phenyl)-1-methyl-3-(2-trimethylsilanyl-ethoxymethyl)-ureido]-pyrimidin-4-yl}-carbamic acid tert-butyl ester (80 mg, 0.103 mmol) in DCM (5 mL) was added a solution of TEA (10 mg/mL, 1.2 mL, 0.12 mmol) and a solution of acryloyl chloride (10 mg/mL, 1 mL, 0.11 mmol) dropwise at 0° C., and the resulting mixture was stirred at room temperature for 1 hour. LC-MS showed that the reaction was complete. Water (5 mL) was added to quench the reaction, and the reaction mixture was extracted with DCM. The combined extracts were washed with brine, dried over anhydrous sodium sulfate and filtered. The filtrate was evaporated under vacuum to give crude product, which was used for the next step without further purification.

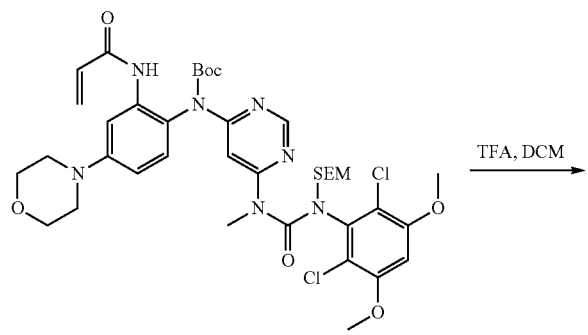

h. N-(2-{6-[3-(2,6-Dichloro-3,5-dimethoxy-phenyl)-1-methyl-ureido]-pyrimidin-4ylamino}-5-morpholin-4-yl-phenyl)-acrylamide To a solution of (2-acryloylamino-4-morpholin-4-yl-phenyl)-{6-[3-(2,6-dichloro-3,5-dimethoxy-phenyl)-1-methyl-3-(2-trimethylsilanyl-ethoxymethyl)-ureido]-pyrimidin-4-yl}-carbamic acid tert-butyl ester (crude, prepared above) in $CH_2Cl_2$ (10 mL) was added TFA (3 mL) at 0° C., the resulting mixture was stirred for 1 hour at room temperature. The reaction mixture was concentrated and neutralized with $NH_3 \cdot H_2O$ to give the crude compound, which was purified by Prep-HPLC to obtain title compound (10 mg, yield: 16% in two steps). $^1$H NMR (300 MHz, DMSO-d6) δ 12.05 (s, 1H), 9.60 (s, 1H), 8.74 (s, 1H), 8.32 (s, 1H), 7.33-7.30 (m, 2H), 6.89 (s, 1H), 6.83 (d, 1H), 6.48 (dd, 1H), 6.25-6.21 (m, 2H), 5.72 (d, 1H), 3.96 (s, 6H), 3.73 (br, 4H), 3.44 (s, 3H), 3.10 (br, 4H); MS (ESI): 602 $[M+H]^+$ Example—124

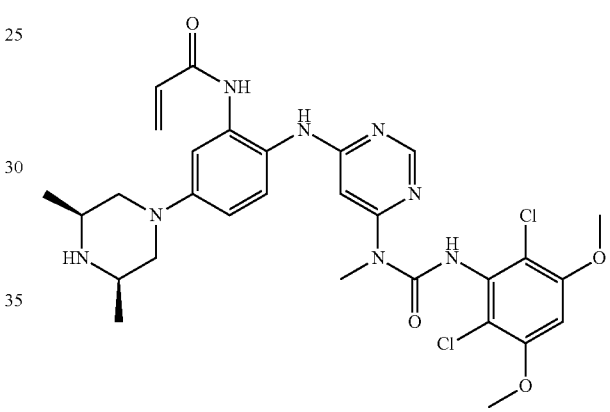

N-[2-{6-[3-(2,6-Dichloro-3,5-dimethoxy-phenyl)-1-methyl-ureido]-pyrimidin-4-ylamino}-5-(3,5-dimethyl-piperazin-1-yl)-phenyl]-acrylamide The compound was synthesized following the approach outlined in Procedure 2G (Example 123), substituting 4-(3,5-dimethyl-piperazin-1-yl)-2-nitro-phenylamine (preparation shown below) in step (d) to afford the title compound (26 mg, yield: 30% over three steps). $^1$H NMR (300 MHz, Methanol-d4) δ 8.32 (s, 1H), 7.36-7.33 (m, 2H), 6.95 (d, 1H), 6.80 (s, 1H), 6.43-6.37 (m, 2H), 6.15 (s, 1H), 5.77 (d, 1H), 3.95 (s, 6H), 3.70 (d, 2H), 3.29 (s, 3H), 3.18-3.13 (m, 2H), 2.45 (t, 2H), 1.24 (d, 6H); MS (ESI): 629 $[M+H]^+$.

Preparation of 4-(3,5-Dimethyl-piperazin-1-yl)-2-nitro-phenylamine

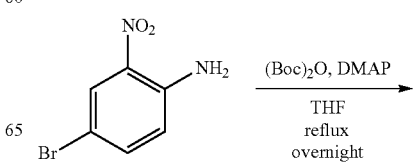

99
-continued

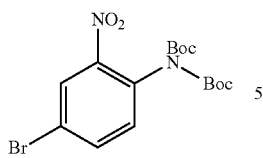

a. di-tert-Butyl 4-bromo-2-nitrophenylcarbamate

A mixture of 4-bromo-2-nitroaniline (10 g, 46 mmol), (Boc)₂O (20.7 g, 95 mmol) in THF (250 mL) was heated under reflux overnight. The mixture was concentrated to afford the title compound (19.2 g, quant) which was used for the next step without further purification.

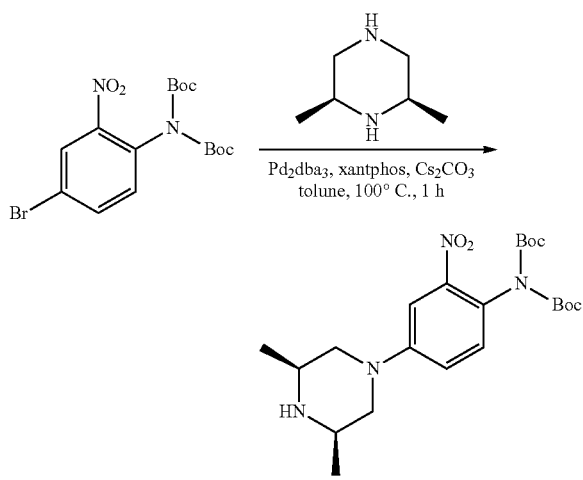

b. [4-(3,5-Dimethyl-piperazin-1-yl)-2-nitro-phenyl]-carbamic acid di-tert-butyl ester A degassed mixture of di-tert-Butyl 4-bromo-2-nitrophenylcarbamate (1 g, 2.4 mmol), 2,6-dimethyl-piperazine (410 mg, 3.6 mmol), Pd₂(dba)₃ (220 mg, 0.24 mmol), Xantphos (278 mg, 0.48 mmol) and Cs₂CO₃ (1.56 g, 4.8 mmol) in toluene (30 mL) was heated at 100° C. for 1 hour. The reaction was concentrated, and the residue was purified by flash chromatography on silica to obtain a mixture of the title compound and mono-Boc product (600 mg). The mixture was used directly in the next step without further purification. MS (ESI): 350 [M-Boc+H]⁺.

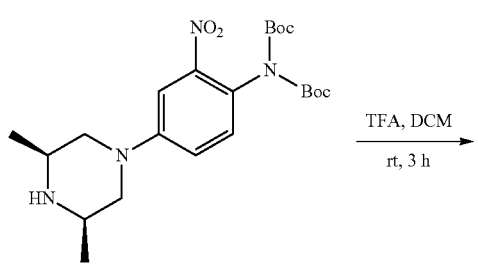

100
-continued

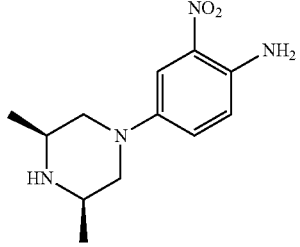

c. 4-(3,5-Dimethyl-piperazin-1-yl)-2-nitro-phenylamine

To a solution of [4-(3,5-dimethyl-piperazin-1-yl)-2-nitro-phenyl]-carbamic acid di-tert-butyl ester and mono-Boc product (600 mg) in DCM (20 mL) was added TFA (10 mL) at 0° C., the resulting mixture was stirred for 3 hours at room temperature. After removal of all volatiles in vacuo, the residue was re-dissolved in DCM, neutralized by saturated aqueous NaHCO₃, and extracted with DCM. The combined extracts were concentrated and the residue was purified by flash chromatography on silica to obtain the title compound (233 mg, yield: 39% over two steps). MS (ESI): 251 [M+H]⁺.

Example—125

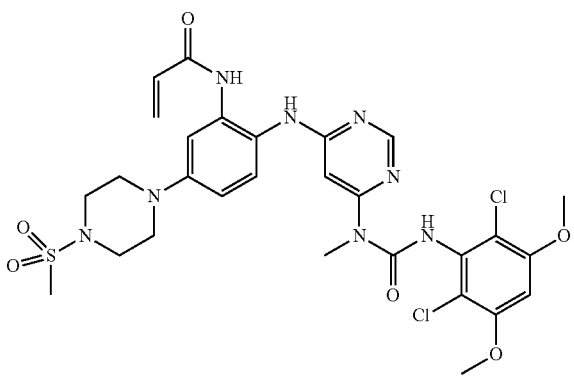 [SMILES: C=CC(=O)Nc1cc(N2CCN(S(C)(=O)=O)CC2)ccc1Nc1cc(N(C)C(=O)Nc2c(Cl)c(OC)cc(OC)c2Cl)ncn1]

N-[2-{6-[3-(2,6-Dichloro-3,5-dimethoxy-phenyl)-1-methyl-ureido]-pyrimidin-4-ylamino}-5-(4-methane-sulfonyl-piperazin-1-yl)-phenyl]-acrylamide The compound was synthesized following the approach outlined in Procedure 2G (Example 123), substituting 4-(4-methanesulfonyl-piperazin-1-yl)-2-nitro-phenylamine (preparation shown below) in step (d) to afford the title compound (15 mg, yield: 9.6% in five steps). $^1$H NMR (300 MHz, DMSO-d6) δ 12.03 (s, 1H), 9.62 (s, 1H), 8.76 (s, 1H), 8.33 (s, 1H), 7.37-7.32 (m, 2H), 6.89-6.83 (m, 2H), 6.46 (dd, 1H), 6.26-6.21 (m, 2H), 5.72 (d, 1H), 3.93 (s, 6H), 3.34-3.16 (m, 11H), 2.93 (s, 3H); MS (ESI): 679 [M+H]⁺.

Preparation of 4-(4-Methanesulfonyl-piperazin-1-yl)-2-nitro-phenylamine

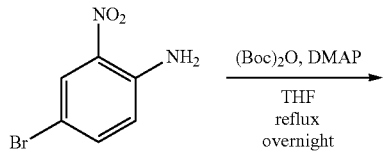

a. di-tert-Butyl 4-bromo-2-nitrophenylcarbamate

A mixture of 4-bromo-2-nitroaniline (10 g, 46 mmol), (Boc)$_2$O (20.7 g, 95 mmol) in THF (250 mL) was heated under reflux overnight. The mixture was concentrated to afford the title compound (19.2 g, quant) which was used directly in next step without further purification.

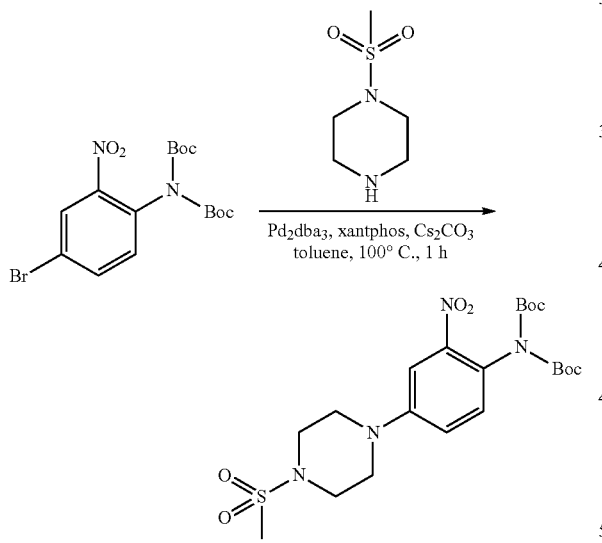

b. [4-(4-Methanesulfonyl-piperazin-1-yl)-2-nitrophenyl]-carbamic acid di-tert-butyl ester A degassed mixture of di-tert-butyl 4-bromo-2-nitrophenylcarbamate (1 g, 2.4 mmol), 1-methanesulfonyl-piperazine (590 mg, 3.6 mmol), Pd$_2$(dba)$_3$ (220 mg, 0.24 mmol), Xantphos (278 mg, 0.48 mmol) and Cs$_2$CO$_3$ (1.56 g, 4.8 mmol) in toluene (30 mL) was heated at 100° C. for 1 hour. The reaction was concentrated, and the residue was purified by flash chromatography on silica to obtain a mixture of the title compound and mono-Boc product (755 mg). The mixture was used directly in next step without further purification. MS (ESI): 400 [M-Boc+H]$^+$.

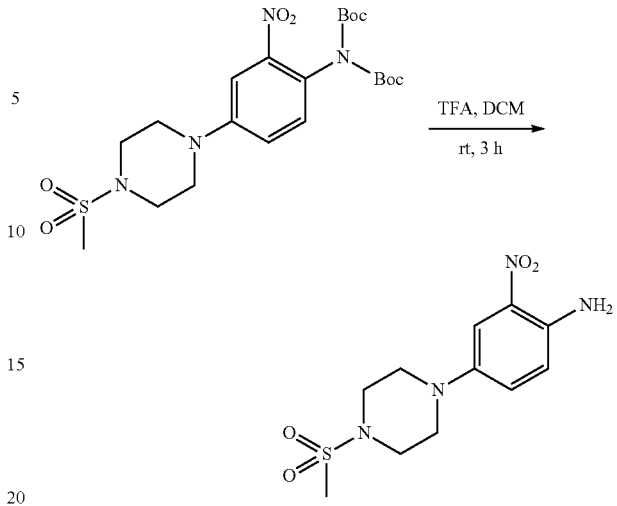

c. 4-(4-Methanesulfonyl-piperazin-1-yl)-2-nitro-phenylamine

To a solution of [4-(4-methanesulfonyl-piperazin-1-yl)-2-nitro-phenyl]-carbamic acid di-tert-butyl ester and mono-Boc product (755 mg) in DCM (20 mL) was added TFA (10 mL) at 0° C., the resulting mixture was stirred for 3 hours at RT. After removal of all volatiles in vacuo, the residue was re-dissolved in DCM, neutralized by saturated aqueous NaHCO$_3$, and extracted with DCM. The combined extracts were concentrated and the residue was purified by flash chromatography on silica to obtain the title compound (290 mg, yield: 40% in two steps). MS (ESI): 301 [M+H]$^+$.

Example—126

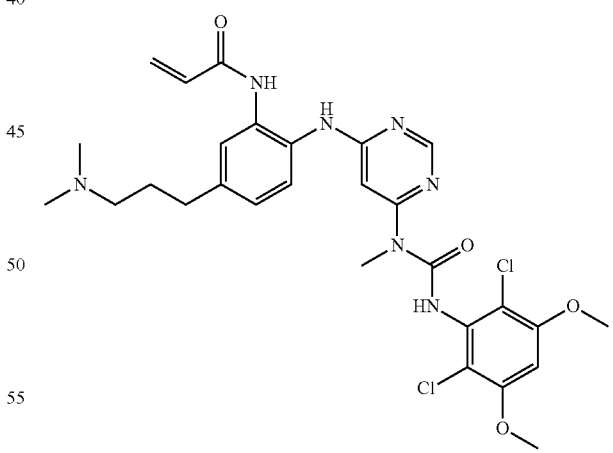

N-[2-{6-[3-(2,6-DICHLORO-3,5-DIMETHOXY-PHENYL)-1-METHYL-UREIDO]-PYRIMIDIN-4-YLAMINO}-5-(3-DIMETHYLAMINO-PROPYL)-PHENYL]-ACRYLAMIDE

The compound was synthesized following the approach outlined in Procedure 2G (Example 123), substituting 4-(3-Dimethylamino-prop-1-ynyl)-2-nitro-phenylamine (preparation shown below) in step (d) and platinum oxide in step (f) to afford the title compound (4 mg, yield: 1.4% in five steps). ¹H-NMR (300 MHz, DMSO-d6) δ 11.98 (s, 1H), 9.66 (d, 1H), 8.88 (s, 1H), 8.36 (s, 1H), 7.52 (d, 1H), 7.44 (d, 1H), 7.04 (dd, 1H), 6.90 (s, 1H), 6.48 (dd, 1H), 6.34 (s, 1H), 6.24 (dd, 1H), 5.72 (dd, 1H), 3.94 (s, 6H), 3.25 (s, 3H), 2.59 (t, 2H), 2.24 (t, 2H), 2.11 (s, 6H), 1.71 (m, 2H); MS (ESI) 602 [M+H]⁺.

Preparation of 4-(3-Dimethylamino-prop-1-ynyl)-2-nitro-phenylamine

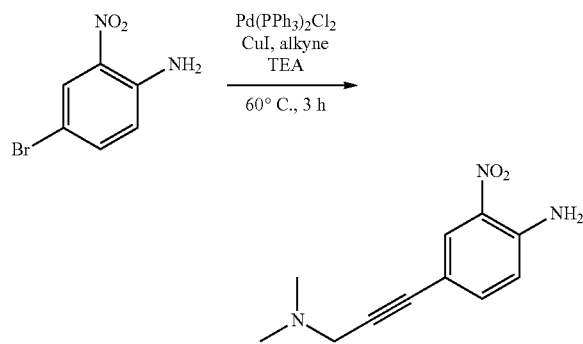

a. 4-(3-Dimethylamino-prop-1-ynyl)-2-nitro-phenylamine

To a stirred solution of 4-bromo-2-nitro-phenylamine (1.08 g, 5 mmol) and dimethyl-prop-2-ynyl-amine (1.0 g, 12 mmol) in TEA (20 mL) was added Pd(PPh₃)₂Cl₂ (0.7 g, 1 mmol) and CuI (360 mg, 2 mmol). The solution was stirred at 60° C. under nitrogen for 3 hours. The solution was evaporated with silica gel and purified by flash chromatography on silica to give the title compound (1.1 g, 70% purity). The title compound was taken directly to the next step without further purification. MS (ESI) 221 [M+H]⁺.

Example—127

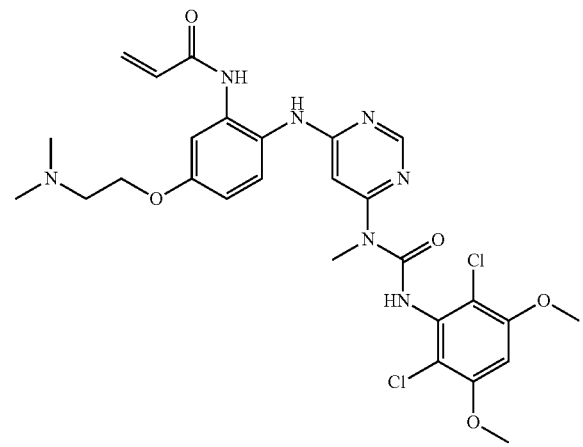

N-[2-{6-[3-(2,6-Dichloro-3,5-dimethoxy-phenyl)-1-methyl-ureido]-pyrimidin-4-ylamino}-5-(2-dimethylamino-ethoxy)-phenyl]-acrylamide The compound was synthesized following the approach outlined in Procedure 2G for compound 123, substituting 4-(2-Dimethylamino-ethoxy)-2-nitro-phenylamine (preparation shown below) in step (d) and platinum oxide in step (f) to afford the title compound (4.3 mg, yield: 8% over five steps). ¹H-NMR (300 MHz, DMSO-d6) δ 12.04 (s, 1H), 9.58 (s, 1H), 8.81 (s, 1H), 8.33 (s, 1H), 7.43 (d, 1H), 7.33 (d, 1H), 6.89 (s, 1H), 6.79 (dd, 1H), 6.51 (dd, 1H), 6.26~6.20 (m, 2H), 5.73 (dd, 1H), 4.04 (t, 2H), 3.96 (s, 6H), 3.27 (s, 3H), 2.67 (t, 2H), 2.24 (s, 6H); MS (ESI) 604 [M+H]⁺.

Preparation of 4-(2-Dimethylamino-ethoxy)-2-nitro-phenylamine

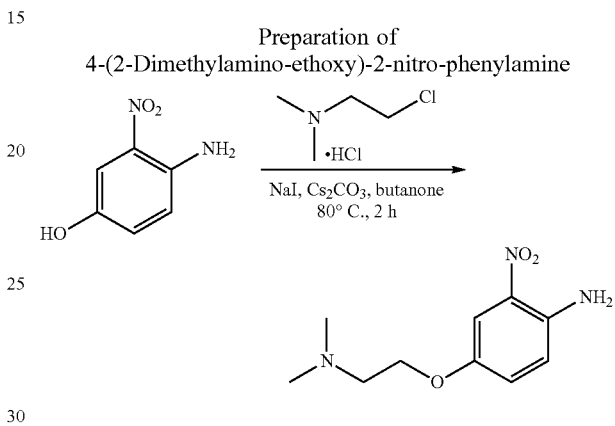

a. 4-(2-Dimethylamino-ethoxy)-2-nitro-phenylamine

To a stirred solution of 4-amino-3-nitro-phenol (1.54 g, 10 mmol) and (2-chloro-ethyl)-dimethyl-amine hydrogen chloride (1.43 g, 10 mmol) in butanone (40 mL) was added Cs₂CO₃ (10 g, 30 mmol) and NaI (150 mg, 1 mmol). The solution was slowly heated to 80° C. over one hour. Then the solution was stirred at 80° C. for 2 hours. The solution was filtered through Celite® and washed with acetone. The solution was evaporated with silica gel and purified by flash chromatography on silica to afford the title compound (1.0 g, yield: 45%) as a brown solid. ¹H-NMR (300 MHz, DMSO-d6) δ 7.38 (d, 1H), 7.24 (s, 2H), 7.16 (dd, 2H), 6.99 (d, 1H), 3.98 (t, 2H), 2.58 (t, 2H), 2.20 (s, 6H); MS (ESI) 226 [M+H]⁺.

Example—128

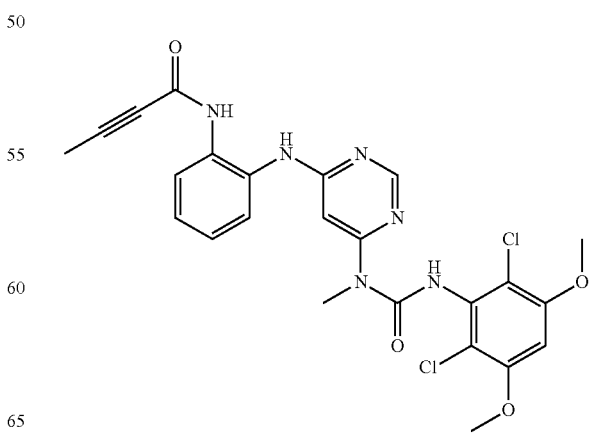

But-2-ynoic acid (2-{6-[3-(2,6-dichloro-3,5-dimethoxy-phenyl)-1-methyl-ureido]-pyrimidin-4-ylamino}-phenyl)-amide The compound was synthesized following the approach outlined in Procedure 2G (Example 123), substituting 2-nitro-phenylamine in step (d), omitting step (e), and replacing step (g) with the following procedure below to afford the title compound (7 mg, yield: 4.8% over five steps). $^1$H NMR (300 MHz, DMSO-d6) δ 11.97 (s, 1H), 10.07 (s, 1H), 8.89 (s, 1H), 8.39 (s, 1H), 7.60 (d, 1H), 7.53 (d, 1H), 7.24-7.15 (m, 2H), 6.90 (s, 1H), 6.44 (s, 1H), 3.93 (s, 6H), 3.29 (s, 3H), 2.22 (s, 3H); MS (ESI): 529 [M+H].

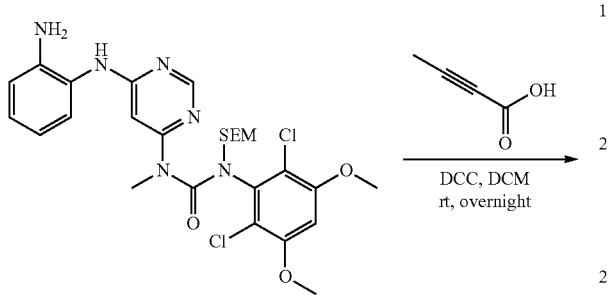

To a solution of (2-amino-phenyl)-{6-[3-(2,6-dichloro-3,5-dimethoxy-phenyl)-1-methyl-3-(2-trimethylsilanyl-ethoxymethyl)-ureido]-pyrimidin-4-yl}-carbamic acid tert-butyl ester (50 mg, 0.075 mmol) and DCC (42 mg, 0.2 mmol) in DCM (50 mL) was added a solution of but-2-ynoic acid (13 mg, 0.15 mmol) in DCM (10 mL) at 0° C., and the resulting mixture was stirred at room temperature overnight. Water (1 mL) was added to quench the reaction. The mixture was concentrated and the residue was purified by reverse phase chromatography to obtain the title compound (20 mg, yield: 34%). MS (ESI): 659 [M+H]$^+$.

Compound 129 was synthesized in a similar manner as compound 100.

Example—130

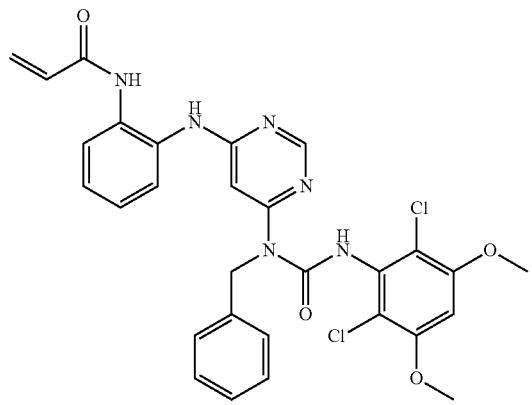

N-(2-{6-[1-Benzyl-3-(2,6-dichloro-3,5-dimethoxy-phenyl)-ureido]-pyrimidin-4-ylamino}-phenyl)-acrylamide The compound was synthesized following the approach outlined in Procedure 2G (Example 123), substituting 2-nitro-phenylamine and 1-benzyl-1-(6-chloro-pyrimidin-4-yl)-3-(2,6-dichloro-3,5-dimethoxy-phenyl)-3-(2-trimethylsilanyl-ethoxymethyl)-urea (preparation shown below) in step (d) to afford the title compound (26 mg, yield: 20% over five steps). $^1$H NMR (300 MHz, DMSO-d6) δ 12.27 (s, 1H), 9.68 (s, 1H), 8.90 (s, 1H), 8.39 (s, 1H), 7.69 (d, 1H), 7.33-7.19 (m, 6H), 6.92 (s, 1H), 6.45 (dd, 1H), 6.24 (d, 1H), 6.18 (s, 1H), 5.74 (d, 1H), 5.07 (s, 2H), 3.95 (s, 6H); MS (ESI): 593 [M+H]$^+$.

Preparation of 1-Benzyl-1-(6-chloro-pyrimidin-4-yl)-3-(2,6-dichloro-3,5-dimethoxy-phenyl)-3-(2-trimethylsilanyl-ethoxymethyl)-urea

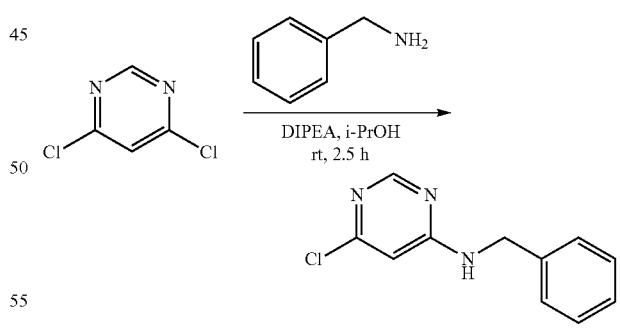

a. Benzyl-(6-chloro-pyrimidin-4-yl)-amine

To a solution of 4,6-dichloro-pyrimidine (1.5 g, 10 mmol) in iPrOH (40 mL) and DIPEA (1.55 g, 12 mmol) was added a solution of benzylamine (1.28 g, 12 mmol) at room temperature. The resulting mixture was stirred at room temperature for 2.5 hours. Water was added and the mixture was extracted with DCM. The combined extracts were washed with brine, dried over anhydrous Na$_2$SO$_4$, and concentrated to give the crude product, which was purified by flash chromatography on silica to obtain the title compound (1.5 g, yield: 68%) as a white solid. $^1$H NMR (300 MHz, CDCl$_3$) δ 8.35 (br s, 1H), 7.20-7.38 (m, 5H), 6.35 (s, 1H), 4.52 (s, 2H); MS (ESI): 220 [M+H]$^+$.

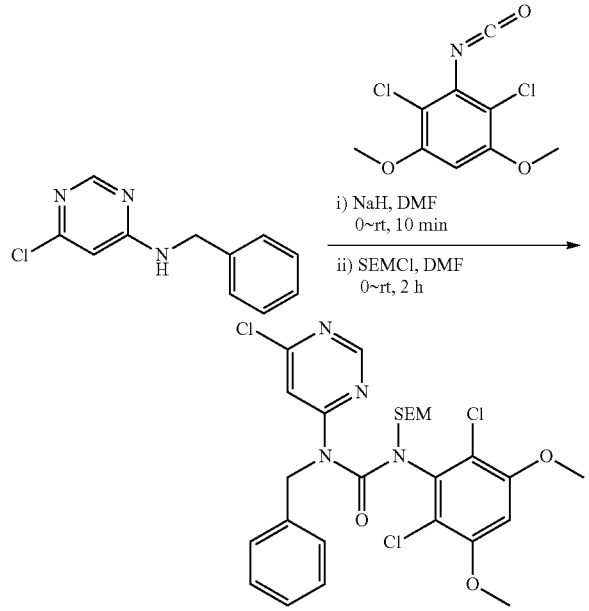

b. 1-Benzyl-1-(6-chloro-pyrimidin-4-yl)-3-(2,6-dichloro-3,5-dimethoxy-phenyl)-3-(2-trimethylsilanyl-ethoxymethyl)-urea To a solution of benzyl-(6-chloro-pyrimidin-4-yl)-amine (800 mg, 3.64 mmol) in DMF (15 mL) was added NaH (60%, 218 mg, 5.45 mmol) at 0° C., and the mixture was stirred for 10 minutes at room temperature. A solution of 1-isocyanato-3,5-dimethoxy-benzene (Procedure 2A, steps a-d; 1.35 g, 5.45 mmol) in DMF (2 mL) was added dropwise at 0° C. The resulting mixture was stirred at room temperature for 2 hours. Saturated aqueous NH$_4$Cl (2 mL) was added to quench the reaction. The mixture was concentrated and extracted with DCM. The combined extracts were washed with brine, dried over anhydrous Na$_2$SO$_4$, and concentrated to give the crude product, which was purified by flash chromatography on silica to obtain the title compound (1.7 g, yield: 77%). MS (ESI): 599 [M+H]$^+$.

Example—131

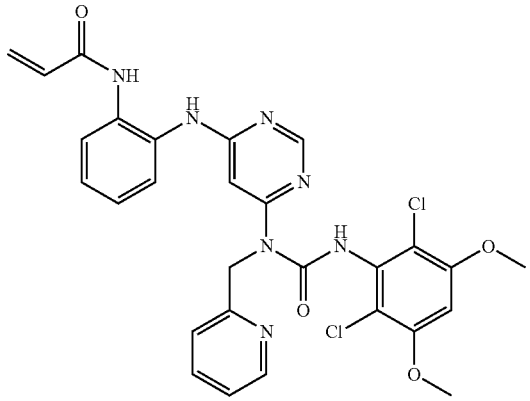

N-(2-{6-[3-(2,6-Dichloro-3,5-dimethoxy-phenyl)-1-pyridin-2-ylmethyl-ureido]-pyrimidin-4-ylamino}-phenyl)-acrylamide The compound was synthesized following the approach outlined in Procedure 2G (Example 123), substituting 2-nitro-phenylamine and 1-(6-chloro-pyrimidin-4-yl)-3-(2,6-dichloro-3,5-dimethoxy-phenyl)-1-pyridin-2-ylmethyl-3-(2-trimethylsilanyl-ethoxymethyl)-urea (preparation shown below) in step (d) to afford the title compound (35 mg, yield: 13% over five steps). $^1$H NMR (300 MHz, DMSO-d6) δ 12.15 (s, 1H), 9.65 (s, 1H), 8.83 (s, 1H), 8.50 (s, 1H), 8.39 (s, 1H), 7.80 (t, 1H), 7.66 (d, 1H), 7.31-7.25 (m, 3H), 7.17 (t, 1H), 7.09 (t, 1H), 6.91 (s, 1H), 6.45 (dd, 1H), 6.39 (s, 1H), 6.23 (d, 1H), 5.74 (d, 1H), 5.17 (s, 2H), 3.94 (s, 6H); MS (ESI): 594 [M+H]$^+$.

Preparation of 1-(6-Chloro-pyrimidin-4-yl)-3-(2,6-dichloro-3,5-dimethoxy-phenyl)-1-pyridin-2-ylmethyl-3-(2-trimethylsilanyl-ethoxymethyl)-urea

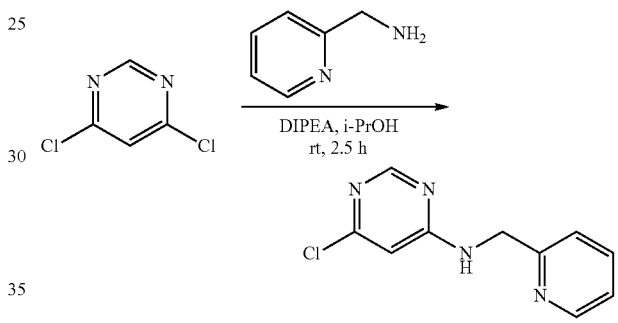

a. (6-Chloro-pyrimidin-4-yl)-pyridin-2-ylmethyl-amine

To a solution of 4,6-dichloro-pyrimidine (1 g, 7 mmol) in iPrOH (40 mL) and DIPEA (1.16 g, 9 mmol) was added a solution of 2-pyridinylmethanamine (970 mg, 9 mmol) at room temperature. The resulting mixture was stirred at room temperature for 2.5 hours. Water was added and the mixture was extracted with DCM. The combined extracts were washed with brine, dried over anhydrous sodium sulfate and concentrated to give a crude product, which was purified by flash chromatography on silica to obtain the title compound (1.2 g, yield: 78%). MS (ESI): 221 [M+H]$^+$.

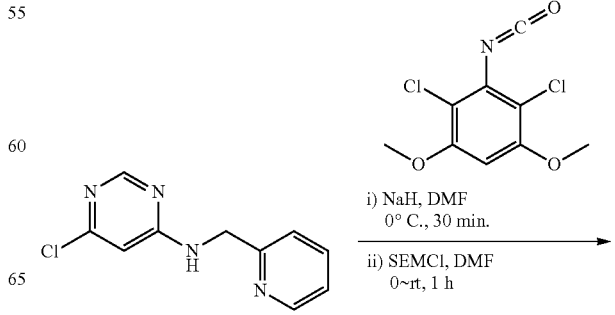

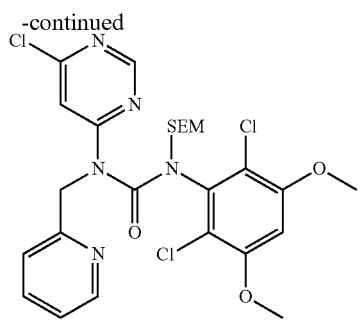

b. 1-(6-Chloro-pyrimidin-4-yl)-3-(2,6-dichloro-3,5-dimethoxy-phenyl)-1-pyridin-2-ylmethyl-3-(2-trimethylsilanyl-ethoxymethyl)-urea To a solution of (6-chloro-pyrimidin-4-yl)-pyridin-2-ylmethyl-amine (200 mg, 0.91 mmol) in DMF (5 mL) was added NaH (60%, 55 mg, 1.37 mmol) at 0° C., and the mixture was stirred for 10 minutes at room temperature. A solution of 1-isocyanato-3,5-dimethoxy-benzene (Procedure 2A, a-d; 337 mg, 1.37 mmol) in DMF (2 mL) was added dropwise at 0° C. The resulting mixture was stirred for 30 minutes. SEMCl (230 mg, 1.37 mmol) in DMF (2 mL) was added and the reaction mixture was stirred at room temperature for 1 hour. Saturated aqueous NH$_4$Cl was added to quench the reaction. The mixture was diluted with water and extracted with EtOAc. The combined extracts were washed with water and brine, dried over anhydrous Na$_2$SO$_4$ and filtered. The filtrate was concentrated to give a crude product, which was purified by flash chromatography on silica to obtain the title product (420 mg, yield: 78%). MS (ESI): 598 [M+H]$^+$.

Example—132

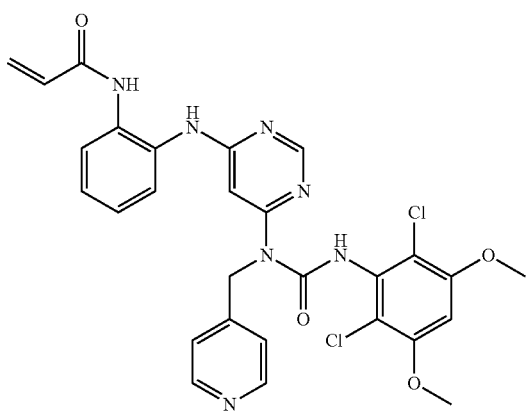 [SMILES: C=CC(=O)Nc1ccccc1Nc1cc(N(Cc2ccncc2)C(=O)Nc2c(Cl)c(OC)cc(OC)c2Cl)ncn1]

N-(2-{6-[3-(2,6-DICHLORO-3,5-DIMETHOXY-PHENYL)-1-PYRIDIN-4-YLMETHYL-UREIDO]-PYRIMIDIN-4-YLAMINO}-PHENYL)-ACRYLAMIDE

The compound was synthesized following the approach outlined in Procedure 2G (Example 123), substituting 3-(2,6-Dichloro-3,5-dimethoxy-phenyl)-1-[6-(2-nitro-phenylamino)-pyrimidin-4-yl]-1-pyridin-4-ylmethyl-urea in step (e) to afford the title compound (14 mg, yield: 8.1%). $^1$H NMR (300 MHz, DMSO-d6) δ 12.03 (s, 1H), 9.68 (s, 1H), 8.92 (s, 1H), 8.49 (d, 2H), 8.39 (s, 1H), 7.67 (d, 1H), 7.27-7.17 (m, 4H), 7.10 (t, 1H), 6.92 (s, 1H), 6.48 (dd, 1H), 6.24 (d, 1H), 6.15 (s, 1H), 5.74 (d, 1H), 5.09 (s, 2H), 3.94 (s, 6H); MS (ESI): 594 [M+H]$^+$.

Preparation of 3-(2,6-Dichloro-3,5-dimethoxy-phenyl)-1-[6-(2-nitro-phenylamino)-pyrimidin-4-yl]-1-pyridin-4-ylmethyl-urea

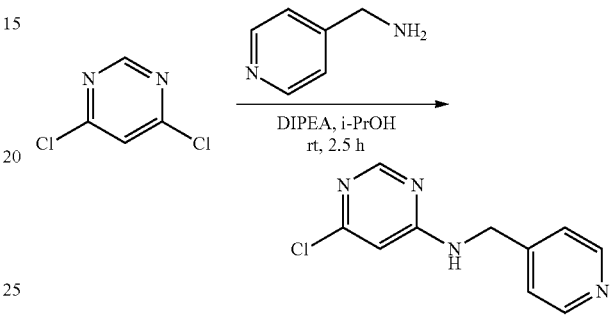

a. (6-Chloro-pyrimidin-4-yl)-pyridin-4-ylmethyl-amine

To a solution of 4,6-dichloro-pyrimidine (1.5 g, 10.5 mmol) and DIPEA (1.62 g, 12.6 mmol) in iPrOH (40 mL) was added 4-pyridinylmethanamine (1.2 g, 11 mmol) at room temperature. The resulting mixture was stirred at room temperature for 2 hours. Water was added and the mixture was extracted with DCM. The combined extracts were washed with brine, dried over anhydrous Na$_2$SO$_4$, and concentrated to give the crude product, which was purified by flash chromatography on silica to obtain the title compound (1.8 g, yield: 80%). MS (ESI): 221 [M+H]$^+$.

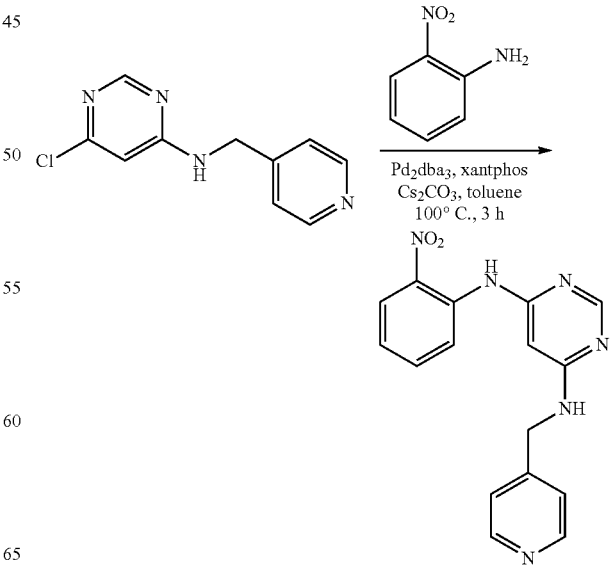

b. N-(2-Nitro-phenyl)-N'-pyridin-4-ylmethyl-pyrimidine-4,6-diamine

A degassed mixture of (6-chloro-pyrimidin-4-yl)-pyridin-4-ylmethyl-amine (500 mg, 2.27 mmol), 2-nitroaniline (317 mg, 2.3 mmol), Pd$_2$(dba)$_3$ (200 mg, 0.22 mmol), Xantphos (253 mg, 0.44 mmol) and Cs$_2$CO$_3$ (1.48 g, 9.35 mmol) in toluene (10 mL) was heated at 100° C. for 3 hours. The reaction was concentrated, and the residue was purified by reverse phase chromatography followed by flash chromatography on silica to obtain the title compound (330 mg, yield: 45%). MS (ESI): 323 [M+H]$^+$.

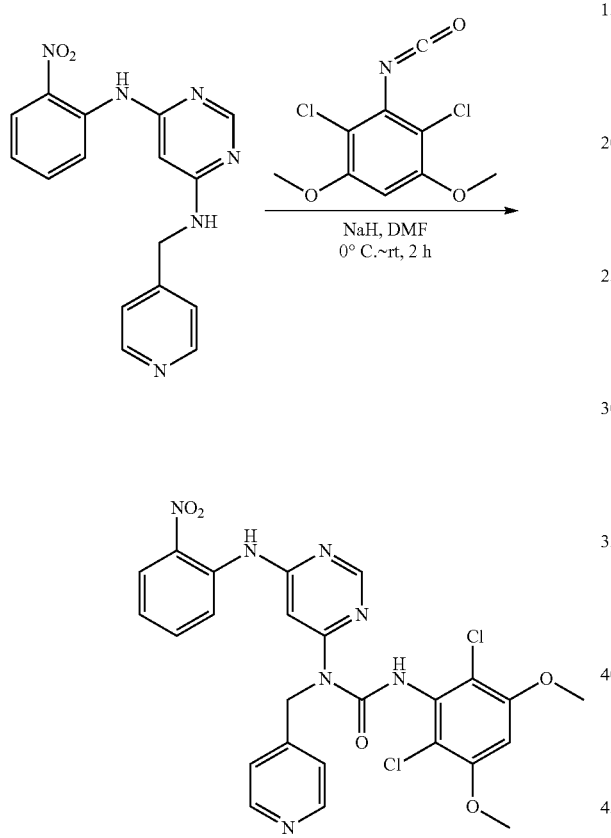

c. 3-(2,6-Dichloro-3,5-dimethoxy-phenyl)-1-[6-(2-nitro-phenylamino)-pyrimidin-4-yl]-1-pyridin-4-ylmethyl-urea To a solution of N-(2-nitro-phenyl)-N'-pyridin-4-ylmethyl-pyrimidine-4,6-diamine (330 mg, 1.02 mmol) in DMF (10 mL) was added NaH (60%, 56 mg, 1.4 mmol) at 0° C., and the mixture was stirred for 30 minutes at room temperature. A solution of 1-isocyanato-3,5-dimethoxy-benzene (Procedure 2A, steps a-d; 345 mg, 1.4 mmol) in DMF (2 mL) was added dropwise at 0° C. The resulting mixture was stirred at room temperature for 2 hours. Saturated aqueous NH$_4$Cl (2 mL) was added to quench the reaction. The mixture was concentrated and extracted with DCM. The combined extracts were washed with brine, dried over anhydrous Na$_2$SO$_4$, and concentrated to give the crude product, which was purified by prep-TLC to obtain the title compound (190 mg, yield: 33%). MS (ESI): 570 [M+H]$^+$.

Example—133

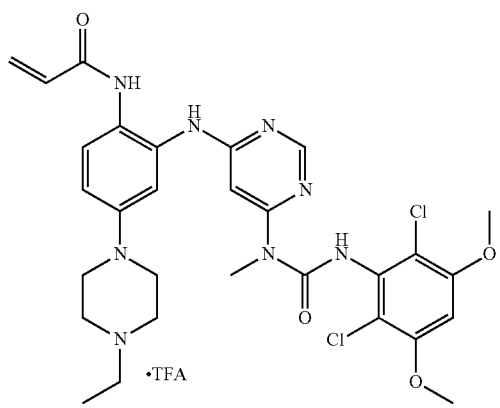 [SMILES: C=CC(=O)Nc1ccc(N2CCN(CC)CC2)cc1Nc1cc(N(C)C(=O)Nc2c(Cl)c(OC)cc(OC)c2Cl)ncn1]

Preparation of 5-(4-ethyl-piperazin-1-yl)-2-nitro-phenylamine

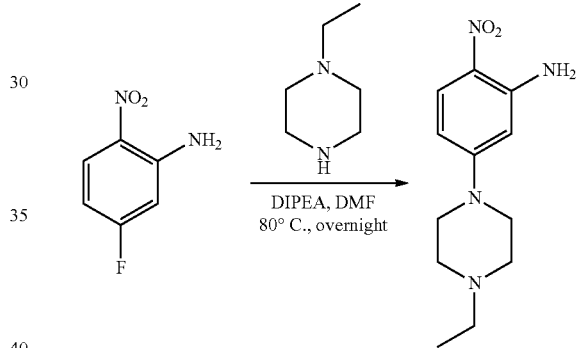

1. 5-(4-Ethyl-piperazin-1-yl)-2-nitro-phenylamine

A mixture of 1-ethyl-piperazine (1.2 mL, 9.6 mmol), 5-fluoro-2-nitro-phenylamine (1 g, 6.4 mmol), DIPEA (1.24 g, 9.6 mmol) in DMF (15 mL) was heated at 80° C. overnight. The reaction mixture was poured into ice water and extracted with EtOAc. The combined extract was washed with brine, dried over anhydrous Na$_2$SO$_4$, and concentrated to obtain a crude product, which was purified by flash chromatography on silica to afford the title compound (1 g, yield: 63%). ESI-MS: 251 [M+H]$^+$.

N-[2-{6-[3-(2,6-Dichloro-3,5-dimethoxy-phenyl)-1-methyl-ureido]-pyrimidin-4-ylamino}-4-(4-ethyl-piperazin-1-yl)-phenyl]-acrylamide trifluoroacetic acid salt The compound was synthesized following the approach outlined in Procedure 2G (Example 123), substituting 5-(4-ethyl-piperazin-1-yl)-2-nitro-phenylamine in step (a) to afford the title compound (20 mg, yield: 39%). $^1$H NMR (300 MHz, Methanol-d4) δ 8.37 (s, 1H), 7.49 (d, 1H), 7.25 (s, 1H), 6.98 (d, 1H), 6.82 (s, 1H), 6.43-6.38 (m, 3H), 5.78 (d, 1H), 3.96-3.88 (m, 8H), 3.68-3.64 (m, 2H), 3.37 (s, 3H), 3.33-3.08 (m, 6H), 1.40 (t, 3H); MS (ESI): 629 [M+H]$^+$.

Example—135

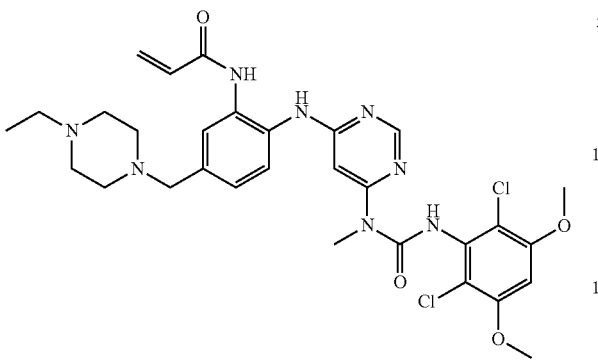

N-[2-{6-[3-(2,6-Dichloro-3,5-dimethoxy-phenyl)-1-methyl-ureido]-pyrimidin-4-ylamino}-5-(4-ethyl-piperazin-1-ylmethyl)-phenyl]-acrylamide The compound was synthesized following the approach outlined in Procedure 2G (Example 123), substituting 4-(4-Ethyl-piperazin-1-ylmethyl)-2-nitro-phenylamine (preparation shown below) in step (d) to afford the title compound (30 mg, yield: 31% over five steps). $^1$H NMR (300 MHz, DMSO-d6) δ 11.97 (s, 1H), 9.71 (s, 1H), 8.95 (s, 1H), 8.37 (s, 1H), 7.60 (s, 1H), 7.50 (d, 1H), 7.12 (d, 1H), 6.90 (s, 1H), 6.50 (dd, 1H), 6.39 (s, 1H), 6.25 (d, 1H), 5.73 (d, 1H), 3.93 (s, 6H), 3.48 (s, 2H), 3.32 (s, 3H), 2.50-2.25 (m, 10H), 0.98 (t, 3H); MS (ESI): 643 [M+H]$^+$.

Preparation of 4-(4-Ethyl-piperazin-1-ylmethyl)-2-nitro-phenylamine

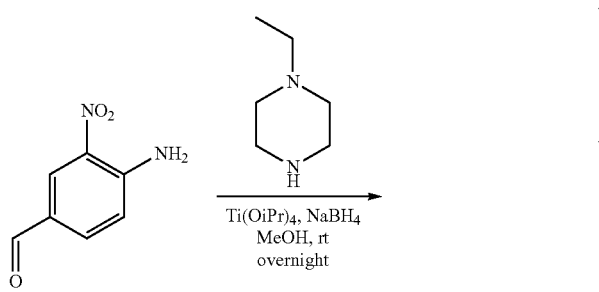

a. 4-(4-Ethyl-piperazin-1-ylmethyl)-2-nitro-phenylamine

To a stirred solution of 1-ethyl-piperazine (1.37 g, 12 mmol) in MeOH (30 mL) was added Ti(O$^i$Pr)$_4$ (1.73 g, 6 mmol). Then the solution was stirred at room temperature for 15 min. Then 4-amino-3-nitro-benzaldehyde (Procedure 2F, steps a-b, 1.5 g, 9 mmol) in MeOH (10 mL) was added and the solution was stirred at room temperature overnight. Then NaBH$_4$ (380 mg, 10 mmol) was added and the solution was stirred at room temperature for 1 hour. The solution was diluted with EtOAc and filtered. The filtrate was washed with water and brine, dried over anhydrous Na$_2$SO$_4$. Concentration gave product, which was purified by flash chromatography on silica to obtain the title compound (800 mg, yield: 34%). MS (ESI): 265 [M+H]$^+$

Example—136

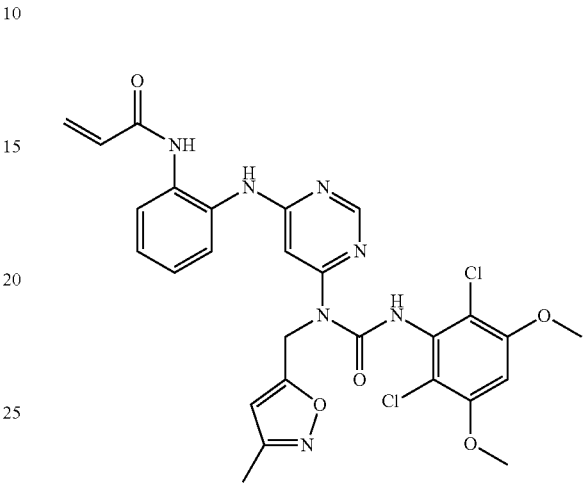

N-(2-{6-[3-(2,6-Dichloro-3,5-dimethoxy-phenyl)-1-(3-methyl-isoxazol-5-ylmethyl)-ureido]-pyrimidin-4-ylamino}-phenyl)-acrylamide The compound was synthesized following the approach outlined in Procedure 2G (Example 123), substituting 1-(6-Chloro-pyrimidin-4-yl)-3-(2,6-dichloro-3,5-dimethoxy-phenyl)-1-(3-methyl-isoxazol-5-ylmethyl)-3-(2-trimethylsilanyl-ethoxymethyl)-urea (preparation shown below) in step (d) and iron/acetic acid at 60° C. in step (f) to afford the title compound (26 mg, yield: 12% in five steps). $^1$H NMR (300 MHz, DMSO-d6) δ 11.78 (s, 1H), 9.72 (s, 1H), 8.97 (s, 1H), 8.40 (s, 1H), 7.66 (d, 1H), 7.45 (d, 1H), 7.21-7.15 (m, 2H), 6.90 (s, 1H), 6.52-6.43 (m, 2H), 6.26 (d, 1H), 6.09 (s, 1H), 5.74 (d, 1H), 5.16 (s, 2H), 3.93 (s, 6H), 2.18 (s, 3H); MS (ESI): 598 [M+H]$^+$ Preparation of 1-(6-Chloro-pyrimidin-4-yl)-3-(2,6-dichloro-3,5-dimethoxy-phenyl)-1-(3-methyl-isoxazol-5-ylmethyl)-3-(2-trimethylsilanyl-ethoxymethyl)-urea

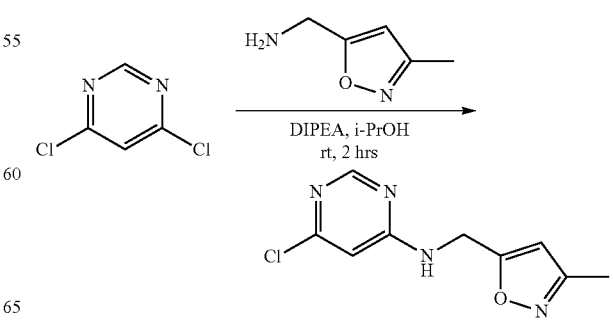

a. (6-Chloro-pyrimidin-4-yl)-(3-methyl-isoxazol-5-ylmethyl)-amine

To a solution of 4,6-dichloro-pyrimidine (660 mg, 4.46 mmol) in iPrOH (40 mL) and DIEA (690 mg, 5.35 mmol) was added a solution of C-pyridin-2-yl-methylamine (560 mg, 5 mmol) at room temperature. The resulting mixture was stirred at room temperature for 2 hours. Water was added and the mixture was extracted with DCM. The combined extracts were washed with brine, dried over anhydrous sodium sulfate, and concentration under vacuum to give the crude product. The crude product was purified by flash chromatography on silica to obtain the title compound (650 mg, yield: 65%). MS (ESI): 225 [M+H]$^+$.

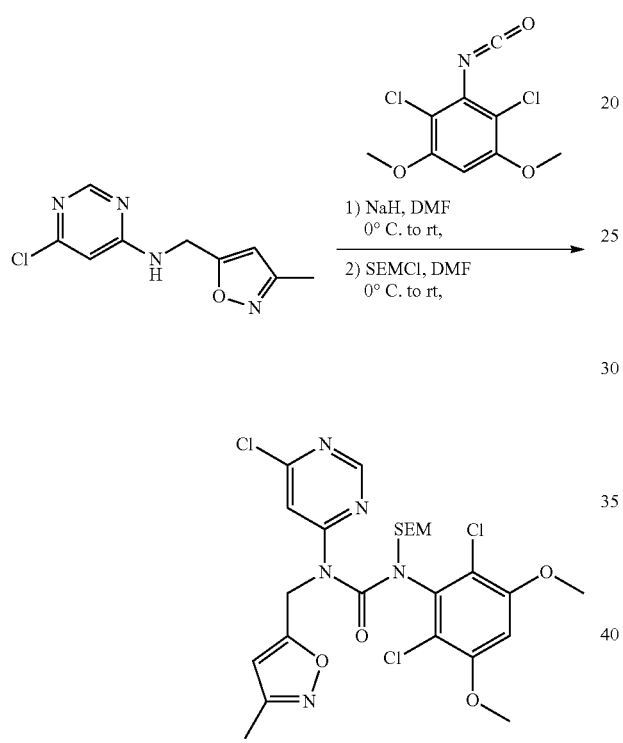

b. 1-(6-Chloro-pyrimidin-4-yl)-3-(2,6-dichloro-3,5-dimethoxy-phenyl)-1-(3-methyl-isoxazol-5-ylmethyl)-3-(2-trimethylsilanyl-ethoxymethyl)-urea To a solution of (6-chloro-pyrimidin-4-yl)-(3-methyl-isoxazol-5-ylmethyl)-amine (300 mg, 1.34 mmol) in DMF (5 mL) was added NaH (60%, 80 mg, 2 mmol) at 0° C., and the mixture was stirred for 10 minutes at room temperature. A solution of 1-isocyanato-3,5-dimethoxy-benzene (Procedure 2A, steps a-d, 337 mg, 1.37 mmol) in DMF (2 mL) was added dropwise at 0° C. The resulting mixture was stirred for 0.5 hour. SEMCl (230 mg, 1.37 mmol) in DMF (2 mL) was added. The reaction mixture was stirred at room temperature for 1 hour. Sat. aqueous NH$_4$Cl was added to quench the reaction. The mixture was diluted with water and extracted with EtOAc. The combined extracts were washed with water and brine, dried over anhydrous sodium sulfate and filtered. The filtrate was evaporated under vacuum to give the crude product, which was purified by flash chromatography on silica to obtain the title product (440 mg, yield: 55%). MS (ESI): 604 [M+H]$^+$

Example—137

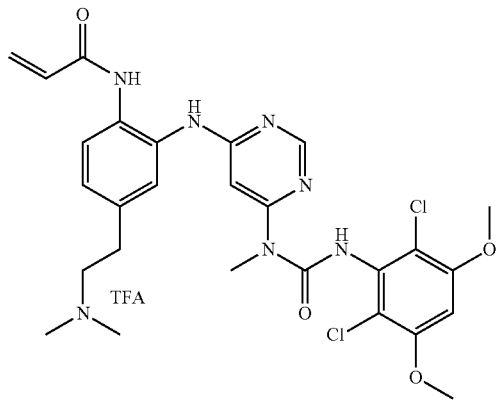 [SMILES: C=CC(=O)Nc1ccc(CCN(C)C)cc1Nc1cc(N(C)C(=O)Nc2c(Cl)c(OC)cc(OC)c2Cl)ncn1]

N-[2-{6-[3-(2,6-Dichloro-3,5-dimethoxy-phenyl)-1-methyl-ureido]-pyrimidin-4-ylamino}-4-(2-dimethylamino-ethyl)-phenyl]-acrylamide TFA Salt The compound was synthesized following the approach outlined in Procedure 2G substituting 5-(2-dimethylamino-ethyl)-2-nitro-phenylamine (prepared by the method outlined below) in step (d) to afford the title compound (39 mg, yield: 29%) as a TFA salt. $^1$H NMR (300 MHz, DMSO-d6) δ 11.86 (s, 1H), 9.76-9.70 (m, 2H), 9.02 (s, 1H), 8.40 (s, 1H), 7.86 (d, 1H), 7.51 (s, 1H), 7.12 (d, 1H), 6.90 (s, 1H), 6.57-6.48 (m, 2H), 6.24 (d, 1H), 5.74 (d, 1H), 3.94 (s, 6H), 3.35-3.28 (m, 5H), 2.98-2.92 (m, 2H), 2.79 (s, 6H); MS (ESI): 588 [M+H]$^+$.

Preparation of 5-(2-Dimethylamino-ethyl)-2-nitro-phenylamine

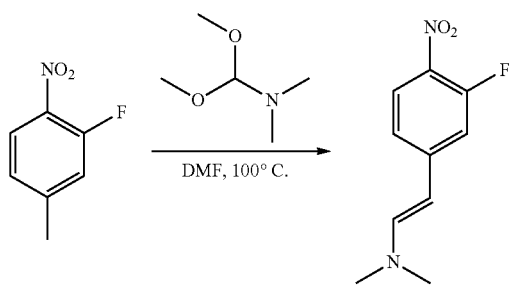

a. [2-(3-Fluoro-4-nitro-phenyl)-vinyl]-dimethylamine

A mixture of 2-fluoro-4-methyl-1-nitro-benzene (3 g, 19.3 mmol), N,N-dimethylformamide dimethylacetal (10 mL) and 3 mL of DMF (30 mL) was heated at 125° C. for 1 hour. The mixture was cooled and concentrated under reduced pressure to give a purple solid. Trituration with hexanes gave the pure title product (2.5 g, yield: 63%). MS (ESI): 211 [M+H]$^+$.

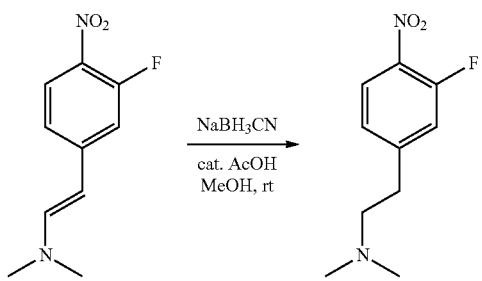
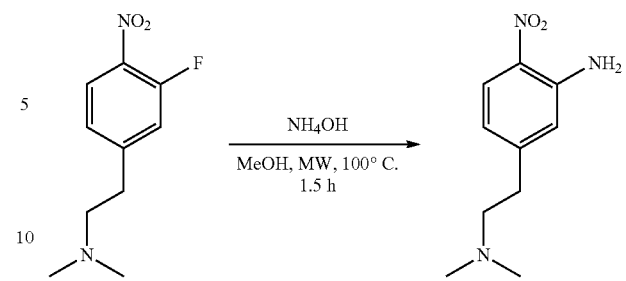

b. [2-(3-Fluoro-4-nitro-phenyl)-ethyl]-dimethyl-amine

To a solution of [2-(3-fluoro-4-nitro-phenyl)-vinyl]-dimethyl-amine (1.7 g, 8 mmol) in MeOH, was added NaBH$_3$CN (770 mg, 12 mmol) and one drop of AcOH. The reaction mixture was stirred at room temperature for 2 hours and quenched with water. After removal of all volatiles in vacuo, the residue was extracted with 10% methanol in DCM twice. The combined extracts were washed with brine, dried over anhydrous sodium sulfate. Concentration under vacuum gave a crude product, which was purified by reverse phase column to afford the title compound (1.08 g, yield: 63%). MS (ESI): 213 [M+H]$^+$ c. 5-(2-Dimethylamino-ethyl)-2-nitro-phenylamine To a solution of [2-(3-fluoro-4-nitro-phenyl)-dimethyl-amine (800 mg, 3.76 mmol) in MeOH (20 mL) was added ammonia hydroxide (5 mL). The reaction mixture was heated at 100° C. under microwave heating for 1.5 hours. The resulting yellow solid was collected and washed with water, dried under vacuum and combined with a previous batch to give the pure title compound (560 mg, yield: 55%). MS (ESI): 210 [M+H]$^+$.

Procedure 2H: Example—139

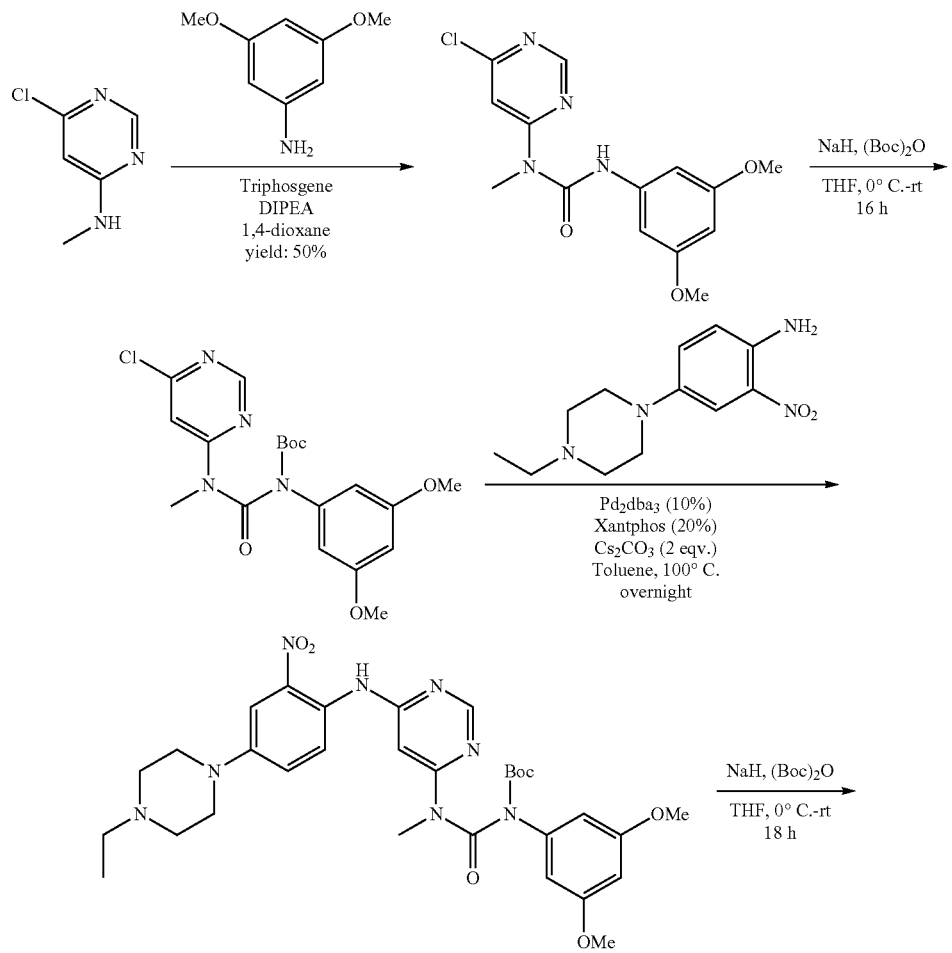

-continued
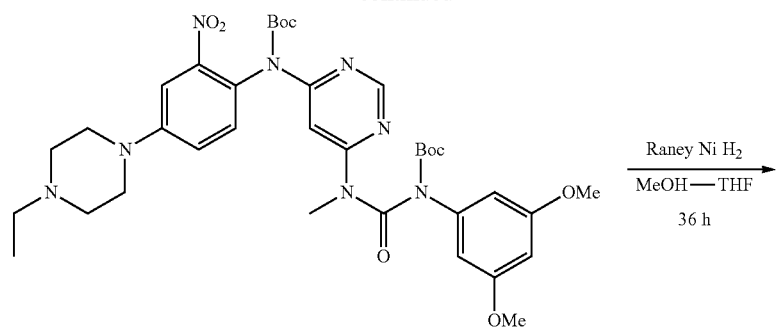
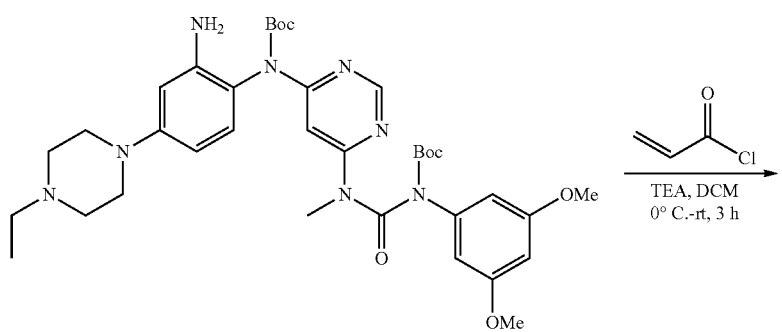
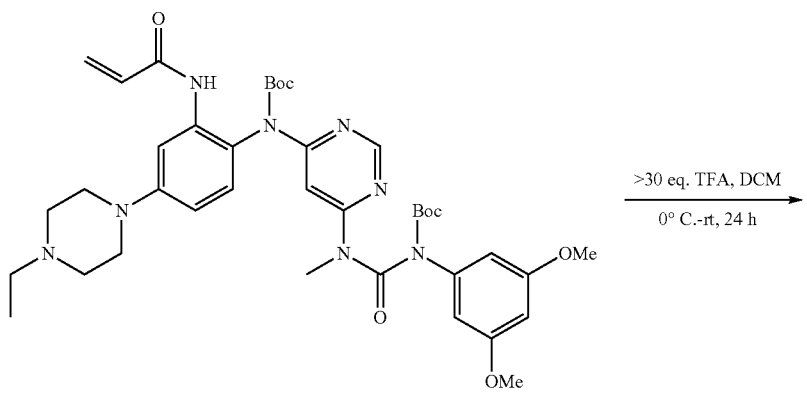
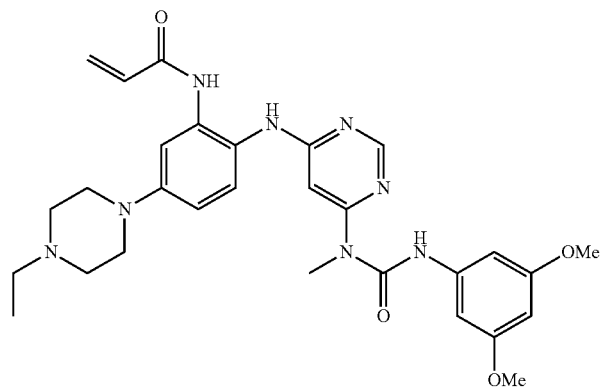

121

N-(2-((6-(3-(3,5-dimethoxyphenyl)-1methylureido)pyrimidin-4-ylamino)-5-(4-ethylpiperazin-1-yl)phenyl)acrylamide

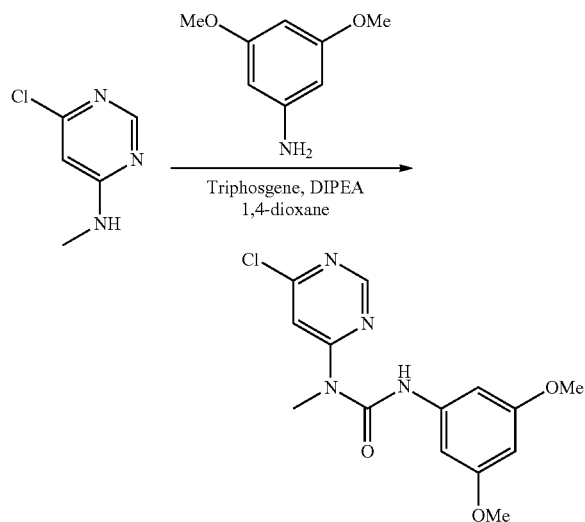

a. 1-(6-chloropyrimidin-4-yl)-3-(3,5-dimethoxyphenyl)-1-methylurea

To a stirred solution of 6-chloro-N-methylpyrimidin-4-amine (1 g, 6.965 mmol) in dioxane (10 mL) was added DIPEA (3.6 mL, 20.895 mmol) and triphosgene (0.81 g, 2.786 mmol) under argon atmosphere at 0° C. The resulting mixture was stirred for 1h at 70° C., and then allowed to cool to room temperature. The resulting mixture was added via cannula to a solution of 3,5-dimethoxyaniline (1.2 g, 8.358 mmol) and DIPEA (1.2 mL, 6.965 mmol) in dioxane (4 mL) under argon atmosphere at 0° C. The reaction mixture was allowed to warm to room temperature and stirred for 12 h. After completion of the reaction by TLC (Hexanes:EtOAc, 7:3), reaction mixture was diluted with ethyl acetate and a saturated aqueous solution of NaHCO$_3$. The aqueous layer was separated and extracted with ethyl acetate (2×50 mL). The combined organic phase washed with brine, dried on Na$_2$SO$_4$, filtered and concentrated under vacuum. The residue was purified by silica gel column chromatography (Hexanes:EtOAc, 70:30) to afford 1-(6-chloropyrimidin-4-yl)-3-(3,5-dimethoxyphenyl)-1-methylurea (1.1 g, yield: 50%) as a white solid. $^1$HNMR (CDCl$_3$, 300 MHz): δ 12.38 (s, 1H), 8.71 (s, 1H), 6.99 (s, 1H), 6.79 (d, 2H), 6.26 (t, 1H), 3.81 (s, 6H), 3.45 (s, 3H); MS (ESI): 323.10 [M+H]$^+$.

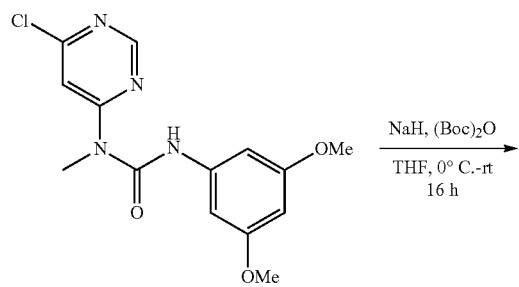

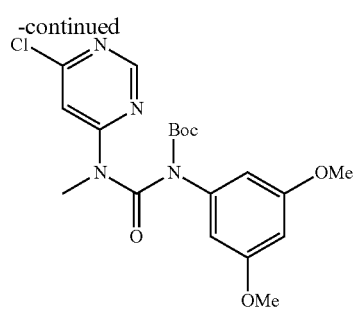

b. 1-(6-chloropyrimidin-1-yl-3-(3,5-dimethoxyphenyl)-1-methyl-3-tert-butyl carbonate urea NaH (0.124 g, 3.098 mmol) was added to a stirred solution of 1-(6-chloropyrimidin-4-yl)-3-(3,5-dimethoxyphenyl)-1-methylurea (0.5 g, 1.549 mmol) in anhydrous DMF (4 mL) under an argon atmosphere at 0° C. The resulting mixture was stirred for 15 min. and added the Di-tert-butyl dicarbonate (0.50 mL, 2.323 mmol) at 0° C. The resulting reaction mixture was allowed to warm to room temperature and stirred for 16h. The reaction mixture was diluted with ethyl acetate and an excess of cold water. The aqueous layer was separated and extracted with ethyl acetate (3×25 mL). The combined organic phase was washed with brine, dried over Na$_2$SO$_4$, filtered, and concentrated under vacuum. The residue was purified by silica gel column chromatography (Hexanes:EtOAc, 80:20) to afford the title compound (0.45 g, 69% of yield) as a white solid. $^1$HNMR (CDCl$_3$, 300 MHz): δ 8.72 (d, 1H), 8.78 (d, 1H), 6.43-6.37 (m, 3H), 3.77 (s, 6H), 3.49 (s, 3H), 1.40 (s, 9H); MS (ESI): 424.10 [M+2]$^+$.

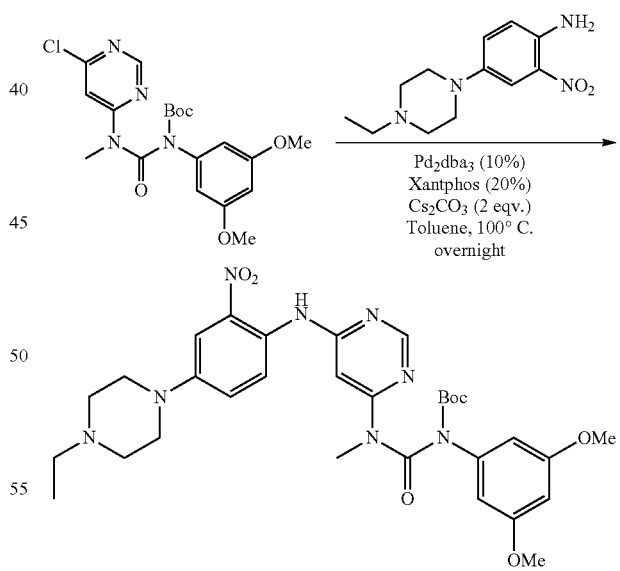

c. 1-(3,5-dimethoxyphenyl)-3-(6-((4(4ethylpiperazin-1-yl)-2-nitrophenyl)amino)pyrimidin-4-yl)-3-methyl-1-tert-butyl carbonate urea Pd$_2$(dba)$_3$ (0.095 g, 0.104 mmol) and Xantphos (0.1202 g, 0.208 mmol) was taken in 10 mL of dry toluene in a seal tube under Argon atmosphere at room temperature. The Argon gas purging was continued for additional 5-10 min. Then 1-(6-chloropyrimidin-4-yl)-3-(3,5-dimethoxyphenyl)-1-dimethyl-3-tert-butyl carbonate urea (0.43 g, 1.042 mmol) and 4-(4-ethylpiperazin-1-yl)-2-nitroaniline (Procedure 2C, Steps a-c; 0.317 g, 1.25 mmol) was added and the resulting reaction mixture was purged with argon gas for 5 min., and then Cs$_2$CO$_3$ (0.676 g, 2.08 mmol) was added. The argon gas purging was continued for additional 5 min. before sealing the reaction vial. Then the reaction mixture was heated at 100° C. for 12 h. After completion of the reaction by TLC (DCM:MeOH, 98:2), reaction mass was partitioned between EtOAc and water. The aqueous layer was extracted with EtOAc (2×25 mL) and the combined organic layer was washed with water, brine, dried over Na$_2$SO$_4$ and evaporated under vacuum. The crude residue was purified by column chromatography on silica gel (DCM:MeOH/97:3) to afford the title compound (0.250 g, 37% of yield). $^1$HNMR (CDCl$_3$, 300 MHz): δ 9.30 (s, 1H), 8.58 (s, 1H), 8.17 (d, 1H), 7.59 (d, 1H), 7.14 (s, 1H), 7.08 (dd, 1H), 6.42 (d, 2H), 6.36 (t, 1H), 3.75 (s, 6H), 3.49 (s, 3H), 3.23 (t, 4H), 2.62 (t, 4H), 2.49 (q, 2H), 1.39 (s, 9H), 1.14 (t, 3H); MS (ESI): 637.4 [M+H]$^+$.

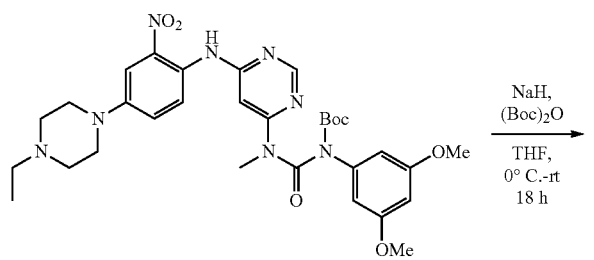

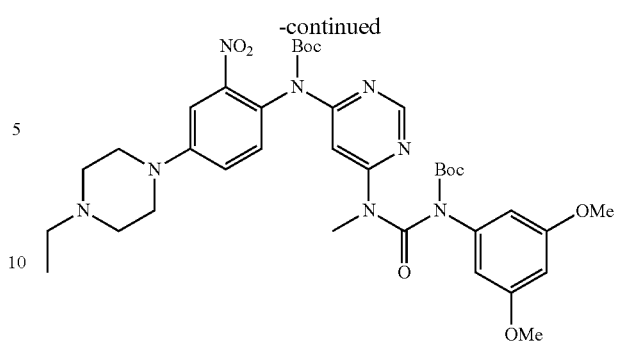

d. tert-butyl (6-(3-(3,5-dimethoxyphenyl)-1-methyl-3-tert-butyl carbonate ureido)pyrimidin-4-yl)(4-(4-ethylpiperazin-1-yl)-2-nitrophenyl)carbamate NaH (0.0314 g, 0.786 mmol) was added to a stirred solution of 1-(3,5-dimethoxyphenyl)-3-(6-((4-(4-ethylpiperazin-1-yl)-2-nitrophenyl)amino)pyrimidin-4-yl)-3-methyl-1-tert-butyl carbonate urea (0.25 g, 0.393 mmol) in anhydrous DMF (4 mL) under an argon atmosphere at 0° C. The resulting mixture was stirred for 15 min. Then Di-tert-butyl dicarbonate (0.12 mL, 0.589 mmol) was added at 0° C. The resulting reaction mixture was allowed to warm to room temperature and stirred for 18 h. The reaction mixture was diluted with ethyl acetate and cold water. The aqueous layer was separated and extracted with ethyl acetate (3×20 mL). The combined organic phase was washed with brine, dried over Na$_2$SO$_4$, filtered and concentrated under vacuum. The residue was purified by silica gel column chromatography (DCM:MeOH, 97:3) to afford the title compound (0.280 g, 96% of yield) as a brown solid. $^1$HNMR (CDCl$_3$, 300 MHz): δ 8.44 (s, 1H), 8.30 (s, 1H), 7.60 (d, 1H), 7.14-7.03 (m, 2H), 6.48 (d, 1H), 6.44-6.21 (m, 2H), 3.75 (s, 6H), 3.49 (s, 3H), 3.49 (t, 4H), 2.62 (t, 4H), 2.49 (q, 2H), 1.38 (d, 18H), 1.14 (t, 3H); MS (ESI):737.5 [M+H]$^+$.

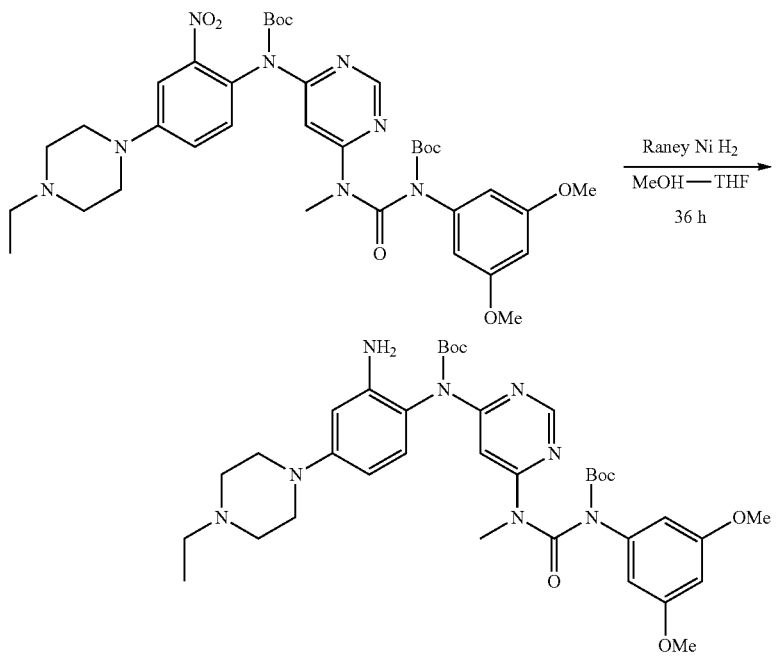

e. tert-butyl (2-amino-4-(4-ethylpiperazin-1-yl)phenyl)(6-(3-(3,5-dimethoxyphenyl)-1-methyl-3-tert-butyl carbonate ureido)pyrimidin-4-yl)carbamate A mixture of tert-butyl (6-(3-(3,5-dimethoxyphenyl)-1-methyl-3-tert-butyl carbonate ureido)pyrimidin-4-yl)(4-(4-ethylpiperazin-1-yl)-2-nitrophenyl)carbamate (0.280 g, 0.380 mmol) and Raney nickel (0.05 g) in mixture of MeOH and THF (1:1)(10 mL) was stirred for 36h at room temperature under a hydrogen atmosphere (balloon). The reaction mixture was filtered through Celite pad. The filtrate was concentrated to afford the title compound (0.14 g, 52% of yield). MS (ESI): 707.7 [M+H]$^+$.

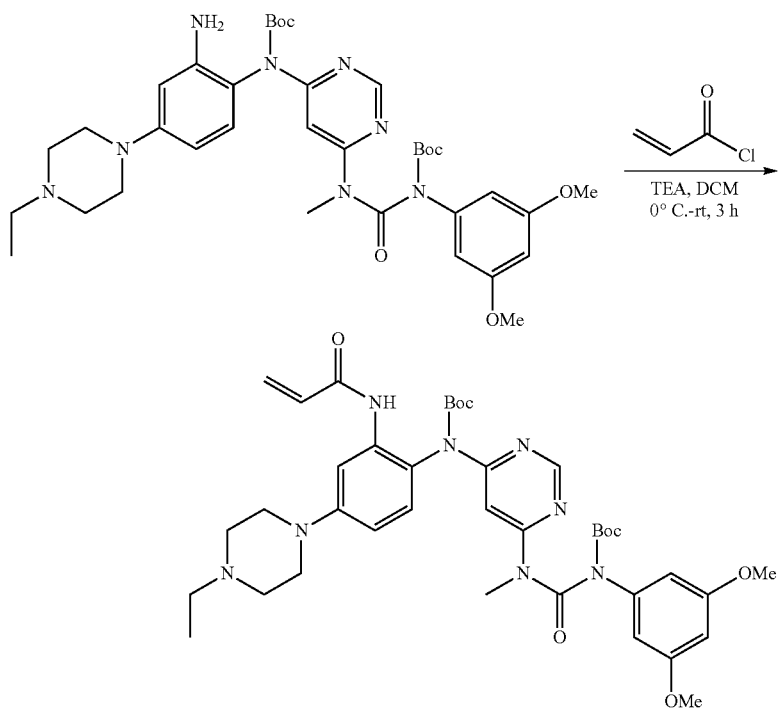

f. tert-butyl (2-acrylamido-4-(4-ethylpiperazin-1-yl)phenyl)(6-(3-(3,5-dimethoxyphenyl)-1-methyl-3-tert-butyl carbonate ureido)pyrimidin-4-yl)carbamate To a stirred solution of tert-butyl (2-amino-4-(4-ethylpiperazin-1-yl)phenyl)(6-(3-(3,5-dimethoxyphenyl)-1-methyl-3-tert-butyl carbonate ureido)pyrimidin-4-yl)carbamate (0.14 g, 0.183 mmol) in anhydrous DCM (5 mL) was added TEA (0.08 mL, 0.594 mmol) under argon atmosphere at 0° C. The resulting mixture was stirred for 15 min. and slowly added the acryloyl chloride (0.03 mL, 0.396 mmol) at 0° C. The resulting reaction mixture was allowed to warm to room temperature stirred for 3h. The reaction mixture was diluted with DCM and water. The aqueous layer was separated and extracted with DCM (3×20 mL). The organic phase was washed with brine, dried over Na$_2$SO$_4$, filtered, and concentrated. The residue was purified by silica gel column chromatography (DCM:MeOH, 97:3) to afford the title compound (0.070 g, 46% of yield) as a brown solid. MS (ESI): 761.4 [M+H]$^+$.

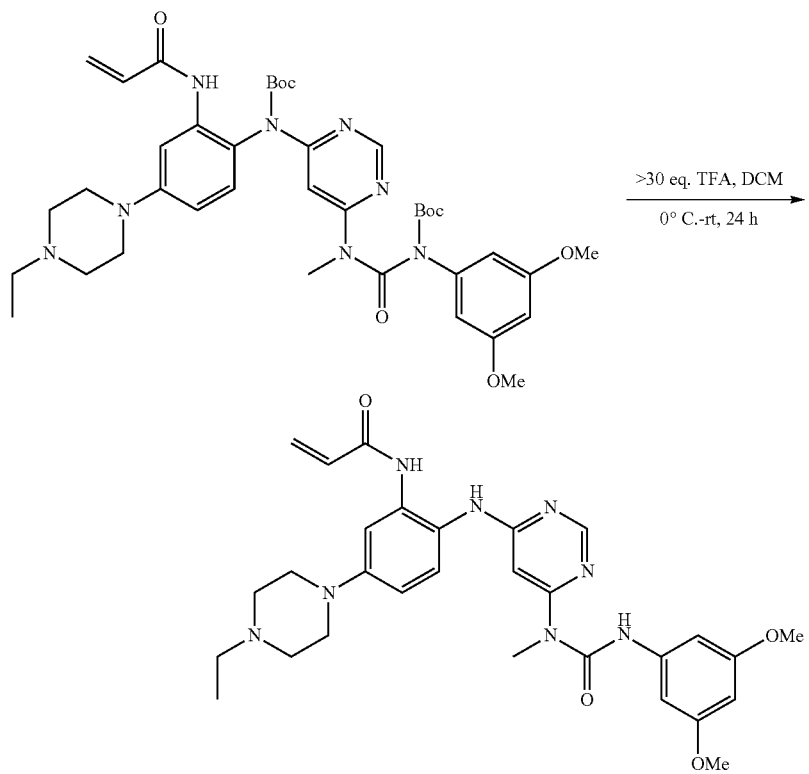

g. N-(2-((6-(3-(3,5-dimethoxyphenyl)-1-methylu-reido)pyrimidin-4-yl)amino)-5-(4-ethylpiperazin-1-yl)phenyl)acrylamide TFA (0.35 mL, 5 vol) was slowly added to a stirred solution of tert-butyl (2-acrylamido-4-(4-ethylpiperazin-1-yl)phenyl)(6-(3-(3,5-dimethoxyphenyl)-1-methyl-3-tert-butyl carbonate ureido)pyrimidin-4-yl)carbamate (0.070 g, 0.124 mmol) in dry DCM (2 mL) under argon atmosphere at 0° C. The resulting reaction mixture was allowed to warm to room temperature and stirred for 24 h. Reaction progress was monitored by LCMS, after completion of the reaction, excess solvents were removed under reduced pressure. The resulting residue was diluted with DCM and a saturated aqueous solution of $NaHCO_3$. The aqueous layer was separated and extracted with DCM (3×10 mL). The organic phase was washed with brine, dried on $Na_2SO_4$, filtered and concentrated under vacuum. The residue was purified by silica gel column chromatography (DCM/MeOH, 97:3) to afford 45 mg of desired product with HPLC purity 80%, which was purified by preparative HPLC (Conditions: Column: XBRIDGE-C18 (19.0×150 mm, 5 micron); (Mobile Phase: A; 0.1% TFA in Water, B; ACN) to afford the title compound (19 mg, 37% of yield) as a off-white solid. $^1$HNMR (CDCl$_3$, 300 MHz): δ 12.85 (s, 1H), 8.39 (s, 1H), 7.72 (s, 1H), 7.55 (s, 1H), 7.19 (d, 1H), 6.79 (s, 2H), 6.75 (d, 1H), 6.64 (s, 1H), 6.39 (d, 1H), 6.22-6.13 (m, 2H), 5.80-5.73 (m, 21H), 3.78 (s, 6H), 3.28 (t, 4H), 3.21 (s, 3H), 2.60 (t, 4H), 2.47 (q, 2H), 1.12 (t, 3H); MS (ESI): 561.60 [M+H]$^+$; HPLC: 96.04%, rt: 6.40 min.

Example—140

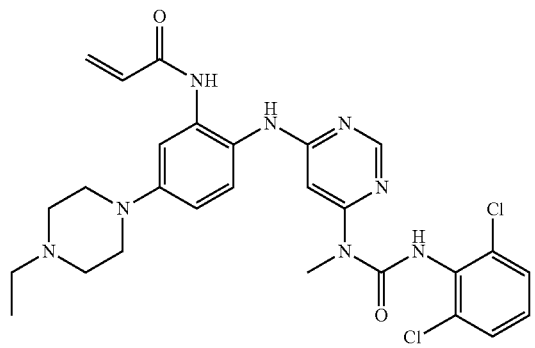 [SMILES: C=CC(=O)Nc1cc(N2CCN(CC)CC2)ccc1Nc1cc(N(C)C(=O)Nc2c(Cl)cccc2Cl)ncn1]

N-(2-((6-(3-(2,6-dichlorophenyl)-1-methylureido)pyrimidin-4-yl)amino)-5-(4-ethylpiperazin-1-yl)phenyl)acrylamide The compound was synthesized following the approach outlined in Procedure 2H (Example 139), substituting 2,6-dichloroaniline in step (a) and (2-(chloromethoxy)ethyl)trimethylsilane in step (b) to afford the title compound (18 mg, 3.2% of yield) as a off-white solid. $^1$HNMR (CDCl$_3$, 300 MHz): δ 12.58 (s, 1H), 8.39 (s, 1H), 7.75 (s, 1H), 7.61 (s, 1H), 7.37 (d, 2H), 7.22 (d, 1H), 7.14 (t, 1H), 6.77 (dd, 1H), 6.67 (s, 1H), 6.42 (d, 1H), 6.25-6.16 (m, 1H), 5.85 (s, 1H), 5.78 (d, 1H), 3.35-3.24 (m, 7H), 2.62 (t, 4H), 2.49 (q, 2H), 1.14 (t, 3H); MS (ESI): 569.10 [M]$^+$; HPLC: 96.98%, rt: 3.49 min.

Example—141

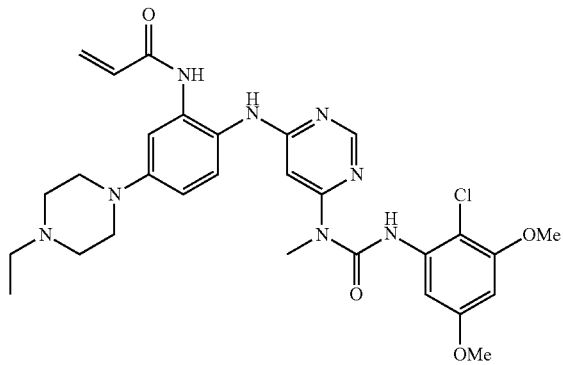 [SMILES: C=CC(=O)Nc1cc(N2CCN(CC)CC2)ccc1Nc1cc(N(C)C(=O)Nc2cc(OC)cc(OC)c2Cl)ncn1]

N-(2-((6-(3-(2-chloro-3,5-dimethoxyphenyl)-1-methylureido)pyrimidin-4-yl)amino)-5-(4-ethylpiperazin-1-yl)phenyl)acrylamide The compound was synthesized following the approach outlined in Procedure 2H (Example 139), substituting 2-chloro-3,5-dimethoxyaniline (procedure shown below) in step (a) to afford the title compound (20 mg, 6.8% of yield) as a off-white solid. 1H-NMR (CDCl$_3$, 400 MHz): δ 13.46 (s, 1H), 8.43 (s, 1H), 7.79-7.71 (m, 2H), 7.56 (s, 1H), 7.18 (d, 1H), 6.74 (dd, 1H), 6.61 (s, 1H), 6.38 (d, 1H), 6.26 (d, 1H), 6.21-6.15 (m, 1H), 5.79-5.74 (m, 2H), 3.86 (s, 3H), 3.81 (s, 3H), 3.28 (t, 4H), 3.23 (s, 3H), 2.59 (t, 4H), 2.47 (q, 2H), 1.12 (t, 3H); MS (ESI): 595.15 [M]$^+$; HPLC: 98.14%, rt: 3.49 min.

Preparation of 2-chloro-3,5-dimethoxyaniline

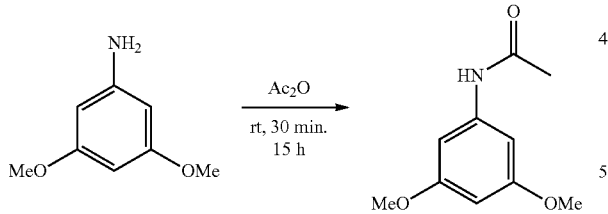

a. N-(3,5-dimethoxyphenyl)acetamide

Acetic anhydride (6.5 mL) was added slowly to a stirred solution of 3,5-dimethoxy aniline (10 g, 65.359 mmol) in toluene (50 mL) under argon atmosphere at room temperature and resulting reaction mixture was stirred for 15 h. After completion of the reaction, reaction was diluted with Hexane and resulted precipitate was collected by filtration and dried under vacuum to afford the title compound (12.5 g, 98% of yield) as a off-white solid. $^1$HNMR (CDCl$_3$, 300 MHz): δ 7.38 (s, 1H), 6.75 (d, 2H), 6.23 (s, 1H), 3.76 (s, 6H), 2.15 (s, 3H); MS (ESI):196.1 [M+H]$^+$.

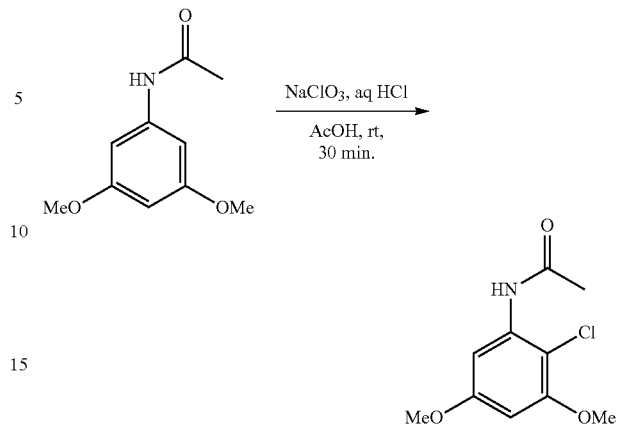

b. N-(2-chloro-3,5-dimethoxyphenyl)acetamide

To a stirred solution of N-(3,5-dimethoxy-phenyl)-acetamide (5 g, 25.64 mmol) in acetic acid (17 mL) was added 32% aqueous hydrochloric acid solution (14 mL), followed by a solution of sodium chlorate (1.16 g, 11 mmol) in water (1.5 mL) at 0° C. The resulting reaction mixture was stirred for 30 min. at 0° C. Thereafter reaction mixture was poured into ice water and made it basic with K$_2$CO$_3$ powder. The precipitate was filtered off and washed with water. The residue was purified by silica gel column chromatography (Hexane/EtOAc, 88:12) to afford the title compound (1.8 g, 31% of yield) as a white solid. $^1$HNMR (DMSO-d$_6$, 300 MHz): δ 9.36 (s, 1H), 7.03 (d, 1H), 6.53 (d, 1H), 3.84 (s, 3H), 3.74 (s, 3H), 2.08 (s, 3H); MS (ESI): 230.2 [M+H]$^+$.

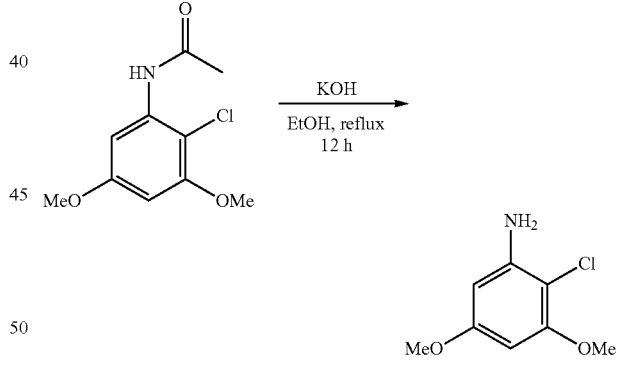

c. 2-chloro-3,5-dimethoxyaniline

Potassium hydroxide (2.19 g, 39.18 mmol) was added to a solution of N-(2-chloro-3,5-dimethoxyphenyl)acetamide (1.8 g, 7.837 mmol) in EtOH (100 mL) and water (10 mL) and the reaction mixture heated to reflux for 12 h. Excess EtOH was removed under reduced pressure to obtain a residue. The residue was then partitioned between water and diethyl ether. The organic layer was separated, dried over sodium sulfate, filtered and concentrated under vacuum to afford the title compound (1.2 g, 82% of yield) as a white solid. $^1$HNMR (CDCl$_3$, 300 MHz): δ 5.97 (s, 2H), 4.08 (brs, 2H), 3.84 (s, 3H), 3.75 (s, 3H); MS (ESI):188.1 [M+H]$^+$.

Procedure 2I: Example—142

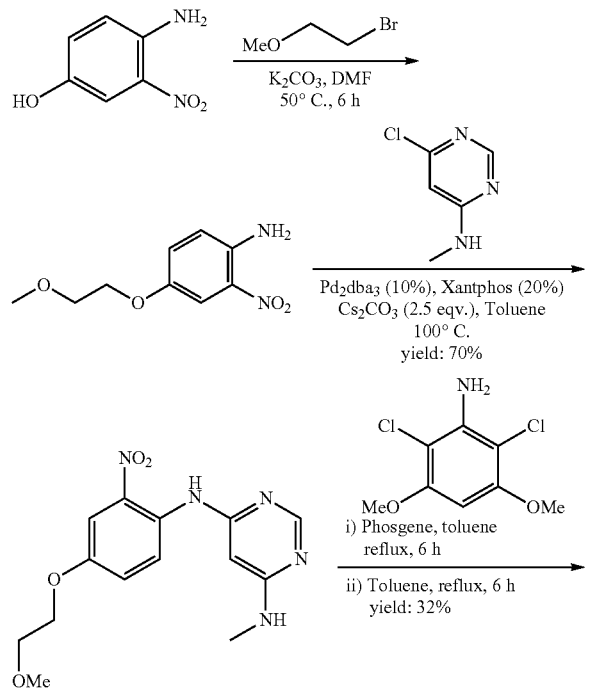

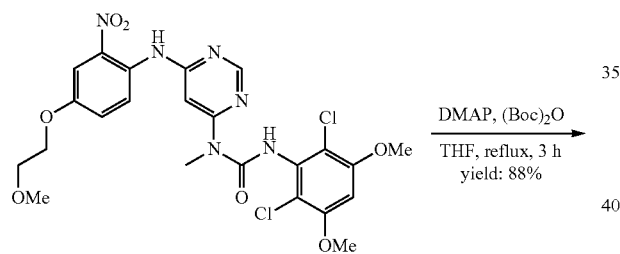

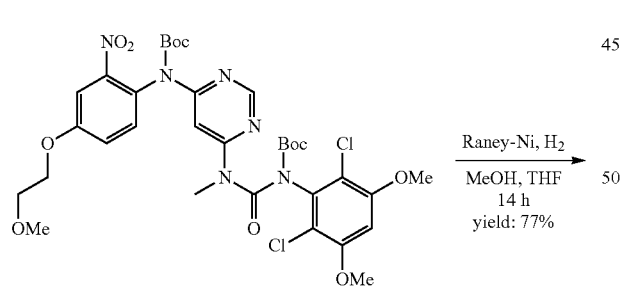

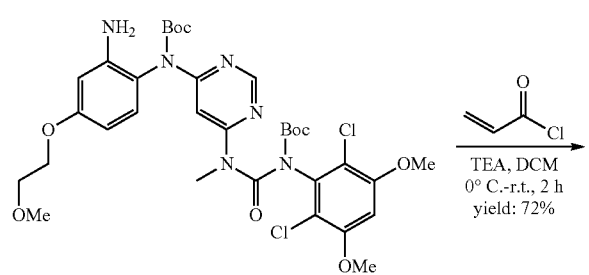

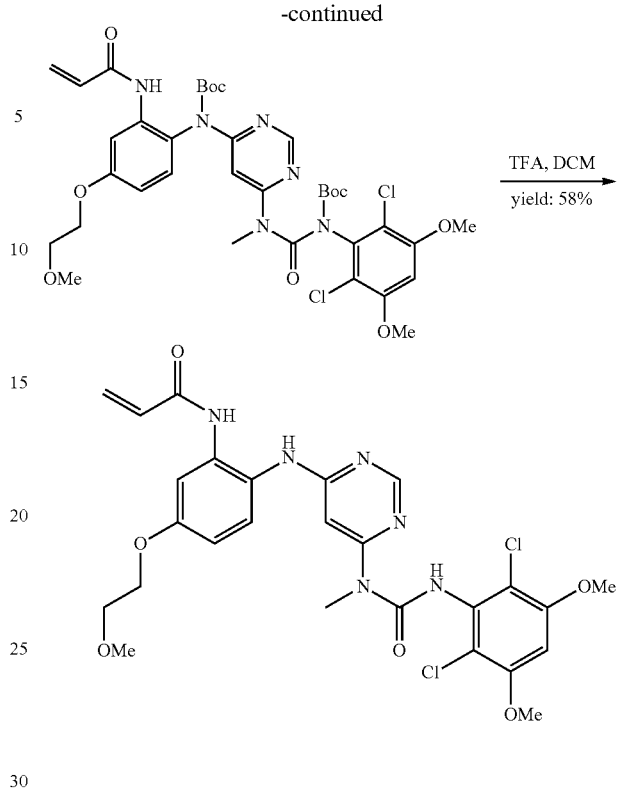

N-(2-((6-(3-(2,6-dichloro-3,5-dimethoxyphenyl)-1-methylureido)pyrimidin-4-yl)amino)-5-(2-methoxyethoxy)phenyl)acrylamide

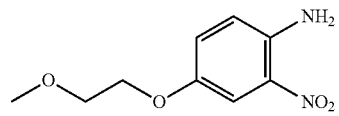

a. 4-(2-methoxyethoxy)-2-nitroaniline

Powdered and dried Potassium carbonate (3.58 g, 0.025 mol) was added to a solution of 4-amino-3-nitrophenol (2 g, 0.012 mol) in DMF (20 mL) at 0° C. under nitrogen atmosphere. To this, 1-bromo-2-methoxyethane (1.34 mL, 0.014 mol) was added dropwise and the resultant reaction mixture was refluxed for overnight. Then, the reaction mixture was filtered through celite. The filterate was concentrated and diluted with ethyl acetate and water. The aqueous layer was separated and extracted with ethyl acetate (3×30 mL). The organic phase was washed with brine, dried on Na₂SO₄, filtered and concentrated under vacuum. The residue was purified by silica gel column chromatography to obtain the title compound (0.6 g, yield: 24%) as a solid. MS (ESI): 213.15 [M+H]$^+$.

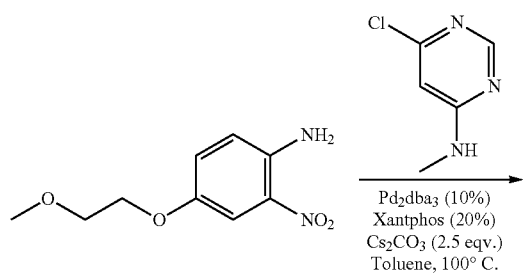

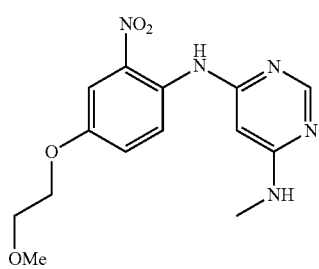

b. N⁴-(4-(2-methoxyethoxy)-2-nitrophenyl)-N⁶-methylpyrimidine-4,6-diamine 4-(2-methoxyethoxy)-2-nitroaniline (0.6 g, 2.830 mmol) and 6-chloro-N-methylpyrimidin-4-amine (0.404 g, 2.830 mmol) were taken in 10 mL of dry toluene in a seal tube under Argon atmosphere at room temperature. The Argon gas purging was continued for additional 5-10 min. Then Cs$_2$CO$_3$ (2.3 g, 7.075 mmol, 2.5eq) and Xantphos (0.490 g, 0.849 mmol) were added and the resulting reaction mixture was purged with argon gas for 5 min, followed by Pd$_2$(dba)$_3$ (0.518 g, 0.566 mmol) was added. The argon gas purging was continued for additional 5 min before sealing the reaction vial. Then the reaction mixture was heated at 100° C. for 7h. After completion of the reaction by TLC (DCM:MeOH, 98:2), reaction mass was filtered through celite and the filtrate was evaporated under vacuum to get a crude residue. The crude residue was purified by column chromatography on silica gel to afford the title compound (0.93 g, yield: 70%); MS (ESI): 320.3 [M+H]⁺.

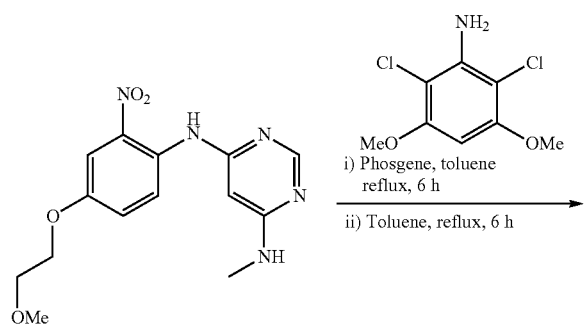

c. 3-(2,6-dichloro-3,5-dimethoxyphenyl)-1-(6-((4-(2methoxyethoxy)-2-nitrophenyl)amino) pyrimidin-4-yl)-1-methylurea To a stirred solution of 2,6-dichloro-3,5-dimethoxyaniline (500 mg, 2.252 mmol) in dioxane (10 mL) was added 20% phosgene in toluene (4.4 mL, 9.0 mmol) under argon atmosphere at 0° C. The resulting mixture was stirred for 6 h at 90° C., and then allowed to cool to room temperature. The solvents were removed and the residue was dissolved in toluene (10 mL). To this, was added N4-(4-(2-methoxyethoxy)-2-nitrophenyl)-N6-methylpyrimidine-4,6-diamine (0.718 g, 8.358 mmol, 1.0 eq). The resultant reaction mixture was then refluxed for 6h. After completion of the reaction by TLC (Hexanes:EtOAc, 7:3), reaction mixture was cooled to room temperature, concentrated under vacuum to obtain a crude reaction mixture. The solid precipitated on addition of ethyl acetate to the crude reaction mixture was filtered, washed with ether and pentane to afford the title compound (0.285, yield: 32%) as a white solid. MS (ESI): 567.0 [M+H]⁺.

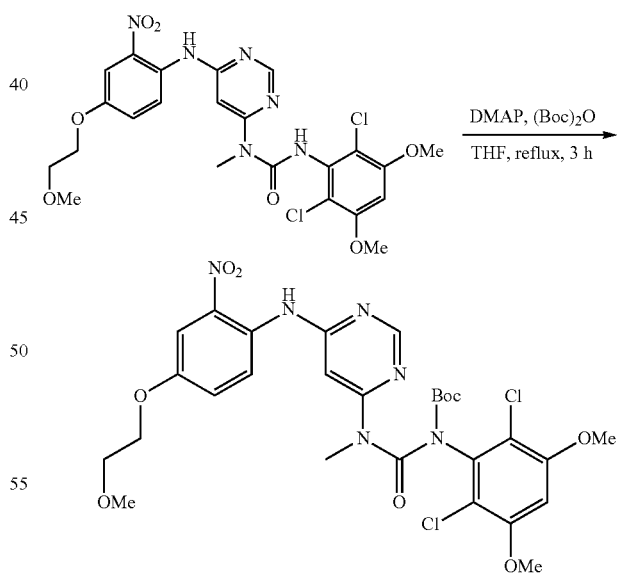

d. tert-butyl (6-(3-(2,6-dichloro-3,5-dimethoxyphenyl)-1-methyl-3-tert-butyl carbonate ureido)pyrimidin-4-yl)(4-(2-methoxyethoxy)-2-nitrophenyl)carbamate DMAP (0.025 g, 0.2 mmol), and Di-tert-butyl dicarbonate (0.438 g, 2.009 mmol) was added to a stirred solution of 3-(2,6-dichloro-3,5-dimethoxyphenyl)-1-(6-((4-(2-methoxyethoxy)-2-nitrophenyl)amino) pyrimidin-4-yl)-1-methylurea (0.285 g, 0.502 mmol) in anhydrous THF (10 mL) under an argon atmosphere at 0° C. The resulting mixture was refluxed for 3-4 h. After completion of the reaction by TLC (Hexanes:EtOAc, 1:1), reaction mixture was cooled to room temperature, concentrated under vacuum to obtain a crude residue. The residue was purified by silica gel column chromatography to afford the title compound (0.35 g, yield: 88%) as an off-white solid. MS (ESI): 767.1 [M+H]⁺.

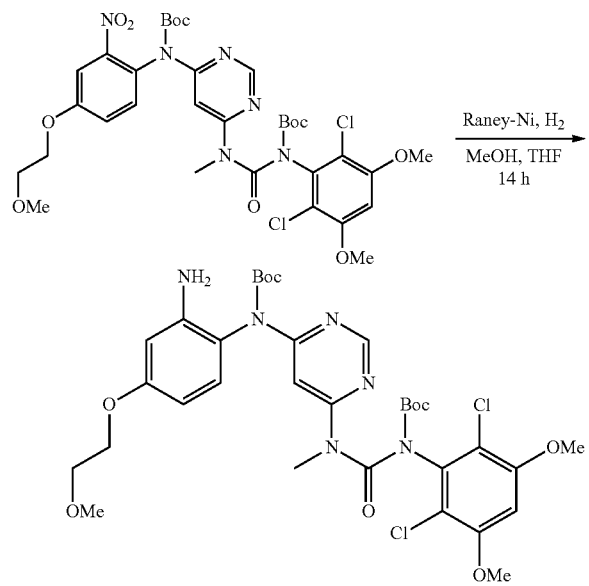

e. tert-butyl (2-amino-4-(2-methoxyethoxy)phenyl) (6-(3-(2,6-dichloro-3,5-dimethoxyphenyl)-1-methyl-3-tert-butyl carbonate ureido)pyrimidin-4-yl) carbamate Raney nickel (0.05 g) was added to a solution of tert-butyl (6-(3-(2,6-dichloro-3,5-dimethoxyphenyl)-1-methyl-3-tert-butyl carbonate ureido)pyrimidin-4-yl)(4-(2-methoxyethoxy)-2-nitrophenyl)carbamate (0.350 g, 0.456 mmol) in mixture of THF and MeOH (10 mL) and the resultant reaction mixture was stirred for 14h at room temperature under a hydrogen atmosphere (balloon). The reaction mixture was filtered through Celite pad. The filtrate was concentrated to afford a crude residue. The residue was purified by silica gel column chromatography (MeOH:DCM, 5:95) to afford the title compound (0.26 g, yield: 77%) as solid. MS (ESI): 737.2 [M+H]⁺.

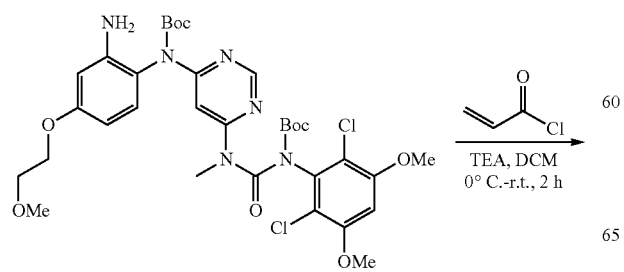

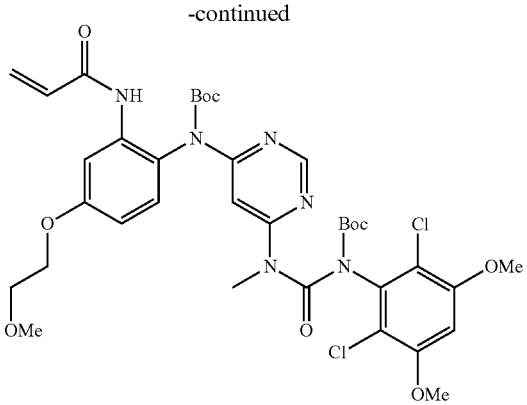

f. tert-butyl (2-acrylamido-4-(2-methoxyethoxy) phenyl)(6-(3-(2,6-dichloro-3,5-dimethoxyphenyl)-1-methyl-3-tert-butyl carbonate ureido)pyrimidin-4-yl) carbamate To a stirred solution of tert-butyl (2-amino-4-(2-methoxyethoxy)phenyl)(6-(3-(2,6-dichloro-3,5-dimethoxyphenyl)-1-methyl-3-tert-butyl carbonate ureido)pyrimidin-4-yl)carbamate (0.26 g, 0.352 mmol) in anhydrous DCM (6 mL) was added TEA (0.09 mL, 0.704 mmol) under argon atmosphere at 0° C. The resulting mixture was stirred for 15 min. and slowly added the acryloyl chloride (0.04 mL, 0.528 mmol) at 0° C. The resulting reaction mixture was allowed to warm to room temperature and stirred for 2 h. The reaction mixture was diluted with DCM and water. The aqueous layer was separated and extracted with DCM (3×30 mL). The organic phase was washed with brine, dried over Na₂SO₄, filtered, and concentrated. The residue was purified by silica gel column chromatography to afford the title compound (0.200 g, yield: 72%) as a solid. MS (ESI): 791.2 [M+H]⁺.

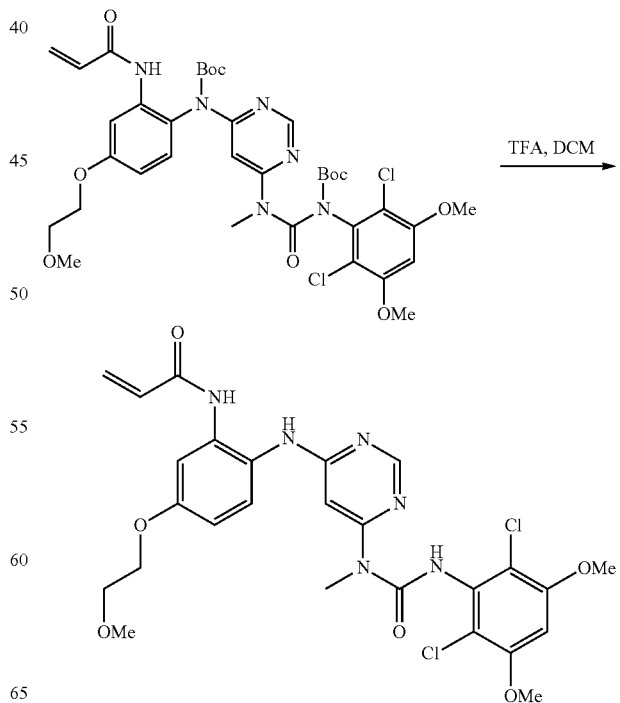

g. N-(2-((6-(3-(2,6-dichloro-3,5-dimethoxyphenyl)-1-methylureido)pyrimidin-4-yl)amino)-5-(2-methoxyethoxy)phenyl)acrylamide TFA (0.38 mL, 5.05 mmol) was slowly added to a stirred solution of tert-butyl (2-acrylamido-4-(2-methoxyethoxy)phenyl)(6-(3-(2,6-dichloro-3,5-dimethoxyphenyl)-1-methyl-3-tert-butyl carbonate ureido)pyrimidin-4-yl)carbamate (0.2 g, 0.252 mmol) in dry DCM (2 mL) under argon atmosphere at 0° C. The resulting reaction mixture was allowed to warm to room temperature and stirred for 12 h. Reaction progress was monitored by LCMS. After completion of the reaction, excess solvents were removed under reduced pressure. The crude solid was washed with ether to afford the title compound (86 mg, yield: 58%) as a white solid. $^1$HNMR (DMSO-d6, 400 MHz): δ12.01 (s, 1H), 9.60 (s, 1H), 8.85 (s, 1H), 8.33 (s, 1H); 7.42 (s, 1H), 7.34 (d, 1H), 6.89 (s, 1H), 6.79 (d, 1H), 6.51 (dd, 1H), 6.23 (d, 2H), 5.72 (d, 1H), 4.08 (m, 2H), 3.93 (s, 6H), 3.66 (m, 2H), 3.31 (s, 3H), 3.23 (s, 3H). MS (ESI): 591.3 [M+H]$^+$; HPLC: 96.04%, rt: 3.72 min.

Example: 144

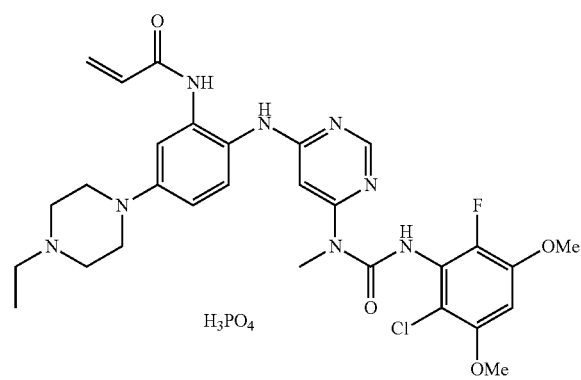

N-(2-((6-(3-(2-chloro-6-fluoro-3,5-dimethoxyphenyl)-1-methylureido) pyrimidin-4-yl)amino)-5-(4-ethylpiperazin-1-yl)phenyl)acrylamide The title compound was synthesized following the approach outlined in Procedure 2I (Example 142), substituting N$^4$-(4-(4-ethylpiperazin-1-yl)-2-nitrophenyl)-N$^6$-methylpyrimidine-4,6-diamine (Procedure 2C, Example 108, Steps a-d) and 2-chloro-6-fluoro-3,5-dimethoxyaniline (Procedure shown below) in step (c) to afford the penultimate title compound (0.46 mg, yield: 2.6% over five steps) as an off-white solid. MS (ESI): 813.1 [M+H]$^+$. The free amine (46 mg, 0.075 mmol) was dissolved in ethyl acetate: DCM: MeOH mixture and treated with phosphoric acid (7 mg, 0.075 mmol). After stirring for 1h, the solid precipitated was filtered and washed with ether and pentane to afford the title compound (34.7 mg, yield: 65%) as an off-white solid. $^1$HNMR (DMSO-d6, 300 MHz): δ 12.15 (s, 1H), 9.60 (s, 1H), 8.76 (s, 1H), 8.32 (s, 1H), 7.29 (d, 2H), 6.9 (d, 2H), 6.81 (dd, 1H), 6.51-6.45 (m, 1H), 6.25-6.20 (m, 2H), 5.72 (d, 1H), 3.91 (s, 3H), 3.89 (s, 3H), 3.23 (t, 4H), 3.14 (t, 4H), 2.54-2.50 (m, 5H), 1.05 (t, 3H); MS (ESI): 613.2 (M–H$_3$PO$_4$)$^+$; HPLC: 98.6%, rt: 6.13 min.

Preparation of 2-chloro-6-fluoro-3,5-dimethoxyaniline

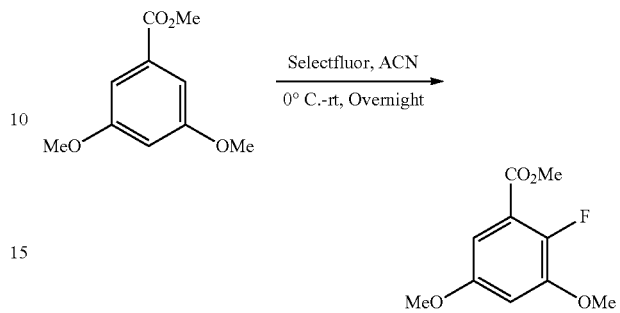

a. methyl 2-fluoro-3,5-dimethoxybenzoate

A suspension of Selectfluor (48.9 g, 0.15 mol) in acetonitrile (1.1 L) was added to a solution of methyl-3,5-dimethoxy benzoate (20 g, 0.10 mol) in acetonitrile at 0° C. under nitrogen atmosphere. The resulting reaction mixture was warmed to room temperature and stirred overnight. The reaction mixture was concentrated under vacuum, diluted with saturated sodium carbonate solution and ethyl acetate. The aqueous layer was separated and extracted with ethyl acetate (3×200 mL). The organic phase was washed with brine, dried over Na$_2$SO$_4$, filtered, and concentrated. The residue was purified by silica gel column chromatography (gradient hexane/ether 30:1 to 4:1) to afford the title compound (4 g, yield: 16.9%).

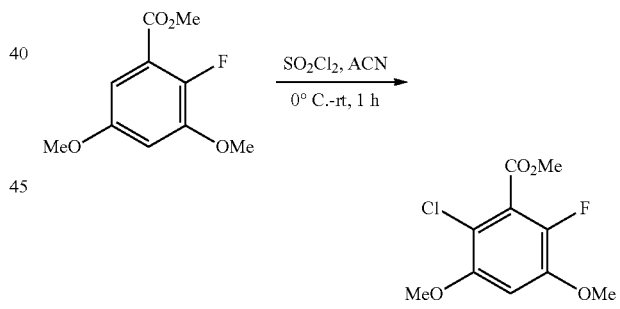

b. methyl 2-chloro-6-fluoro-3,5-dimethoxybenzoate

SO$_2$Cl$_2$ (2.20 g, 0.016 mol) was added dropwise to a solution of methyl-2-fluoro-3,5-dimethoxy benzoate (3.5 g, 0.016 mol) in acetonitrile (40 mL) at 0° C. under nitrogen atmosphere. The resulting reaction mixture was warmed to room temperature slowly and stirred for 1 h. The reaction mixture was quenched with saturated sodium bicarbonate solution, and extracted with ethyl acetate (3×30 mL). The organic phase was washed with brine, dried over Na$_2$SO$_4$, filtered, and concentrated. The residue was purified by silica gel column chromatography using eluent (gradient hexane/ether (20:1) to hexane/ether (5:1) to afford the title compound (2.7 g, yield: 67%) as a solid.

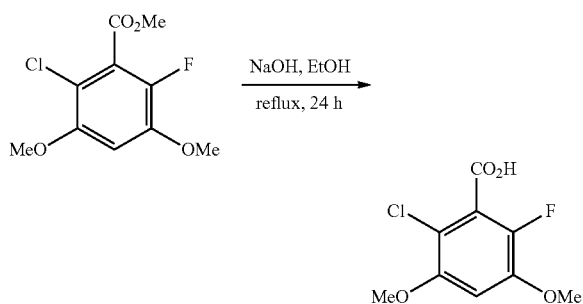

c. 2-chloro-6-fluoro-3,5-dimethoxybenzoic acid

A suspension of methyl 2-chloro-6-fluoro-3,5-dimethoxybenzoate (2.7 g, 0.010 mol) and sodium hydroxide (1.088 g, 0.0272) in anhydrous ethanol (30 mL) was refluxed for 24 h. The resulting reaction mixture was cooled to room temperature and concentrated under vacuum to get a crude residue. The crude residue was dissolved in water and extracted with ether (3×30 mL). The aqueous layer was acidified with conc.HCl and the precipitated solid was filtered, washed with cold water and dried in vacuo to afford the title compound (1.8 g, yield: 71%) as a solid.

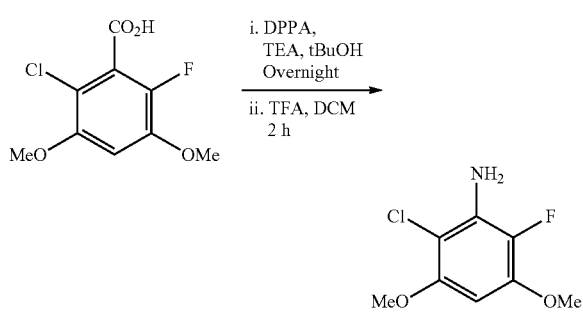

d. 2-chloro-6-fluoro-3,5-dimethoxyaniline

A suspension of 2-chloro-6-fluoro-3,5-dimethoxybenzoic acid (1.8 g, 0.0077 mol) and triethyl amine (0.934 g, 0.0092 mol) in tert-BuOH(50 mL) was stirred for 5 min. To the resulting reaction mixture, Diphenyl phosphoryl azide (2.53 g, 0.0092 mol) was added and heated up to 82° C. and kept at this temperature for overnight. The reaction mixture was then concentrated in vacuo to obtain a crude residue. The crude residue was dissolved in dichloromethane (20 mL) and cooled to 0° C. TFA (4 mL) was added to the reaction mixture and the resultant reaction mixture was then stirred at room temperature for 2 h. The solvents were removed under vacuum and the crude residue was diluted with ethyl acetate and saturated sodium carbonate solution. The aqueous layer was separated and extracted with ethyl acetate (3×30 mL). The organic phase was washed with brine, dried over $Na_2SO_4$, filtered, and concentrated. The residue was purified by silica gel column chromatography using the eluent (gradient hexane to hexane-ether (65:35)) to afford the title compound (0.95 g, yield: 60%) as solid. MS (ESI): 205.7 $[M+H]^+$.

Procedure 2J—Example 145

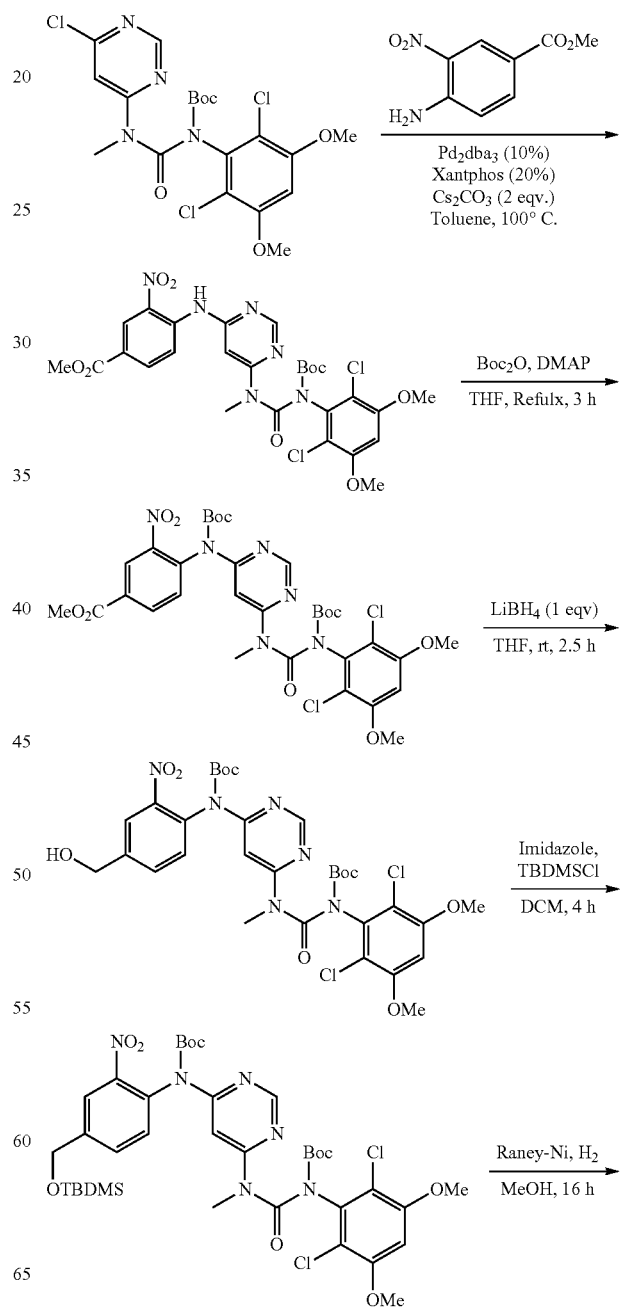

-continued

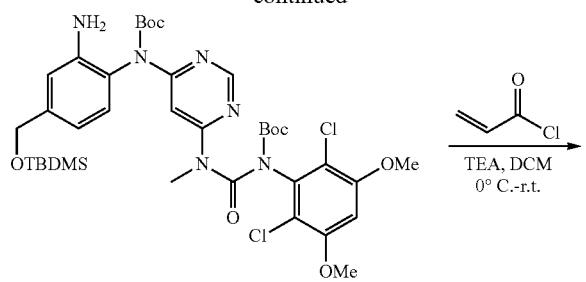

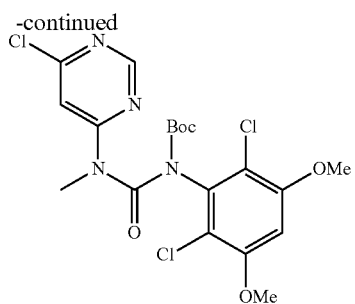

a. 1-(6-chloropyrimidin-4-yl-3-(2,6-dichloro-3,5-dimethoxyphenyl)-1-methyl-3-tert-butyl caronate urea DMAP (0.080 g, 0.655 mmol) and Di-tert-butyl dicarbonate (2.9 mL, 12.6 mmol) was added to a stirred solution of 1-(6-chloropyrimidin-4-yl)-3-(2,6-dichloro-3,5-dimethoxyphenyl)-1-methylurea (Procedure 2E, step b; 2.6 g, 6.632 mmol) in anhydrous THF (20 mL) under an argon atmosphere at 0° C. The resulting mixture was then refluxed for 2 h. After completion of the reaction by TLC (EtOAc: Hexane 3:7), reaction mixture was cooled to room temperature, concentrated under vacuum to obtain a crude residue. The residue was purified by silica gel column chromatography to afford the title compound (2.5 g, yield: 69.4%) as a solid. $^1$H-NMR (CDCl$_3$, 300 MHz): δ 8.73 (d, 1H), 7.95 (d, 1H), 6.61 (s, 1H), 3.95 (s, 6H), 3.63 (s, 3H), 1.35 (s, 9H).

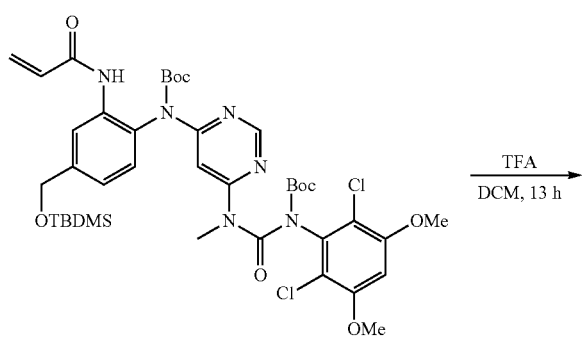

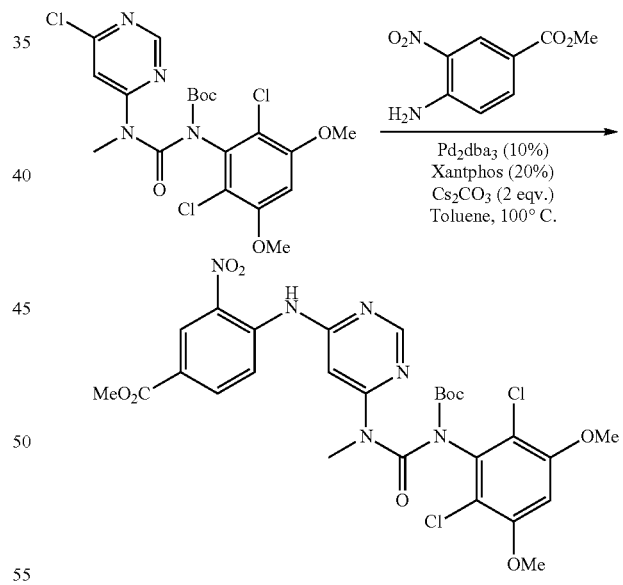

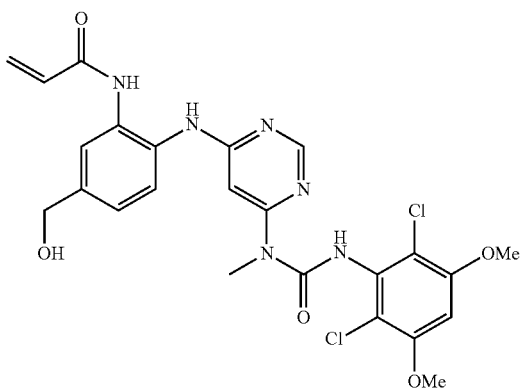

N-(2-((6-(3-(2,6-dichloro-3,5-dimethoxyphenyl)-1-methylureido) pyrimidin-4-yl)amino)-5-(hydroxymethyl)phenyl)acrylamide

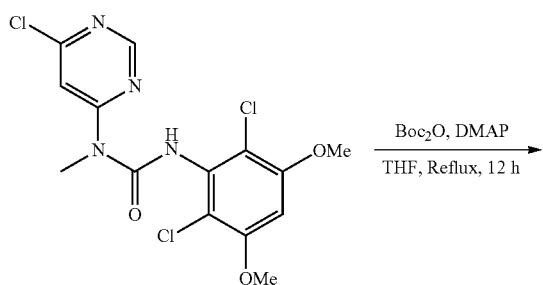

b. methyl 4-((6-(3-(2,6-dichloro-3,5-dimethoxyphenyl)-1-methyl-3-tert-butyl carbonate ureido)pyrimidin-4-yl)amino)-3-nitrobenzoate Methyl 4-amino-3-nitrobenzoate (0.956 g, 0.004 mol) and 1-(6-chloropyrimidin-4-yl)-3-(2,6-dichloro-3,5-dimethoxyphenyl)-1-methyl-3-tert-butyl caronate urea (2 g, 0.004 mol) were taken in 10 mL of dry toluene in a seal tube at room temperature and Argon gas was purged for 5-10 min. Then Cs$_2$CO$_3$ (3.25 g, 0.01 mol) and Xantphos (0.46 g, 0.0008 mol) were added and the resulting reaction mixture was purged with argon gas for 5 min, followed by Pd₂(dba)₃ (0.36 g, 0.0004 mol) was added. The argon gas purging was continued for additional 5 min before sealing the reaction vial. Then the reaction mixture was heated at 100° C. for 12 h. After completion of the reaction by TLC, reaction mass was filtered through celite and the filterate was evaporated under vacuum to get a crude residue. The crude residue was purified by column chromatography on silica gel to afford the title compound (2.10 g, yield: 79%); ¹H-NMR (CDCl₃, 300 MHz): δ 10.3 (s, 1H), 9.00-8.95 (m, 2H), 8.75 (s, 1H), 8.22 (dd, 1H), 7.63 (s, 1H), 6.61 (s, 1H), 3.95 (s, 6H), 3.94 (s, 3H), 3.67 (s, 3H), 1.39 (s, 9H).

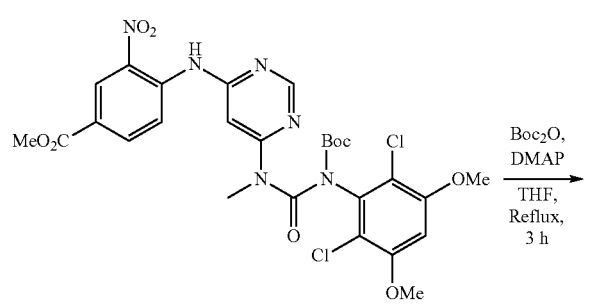

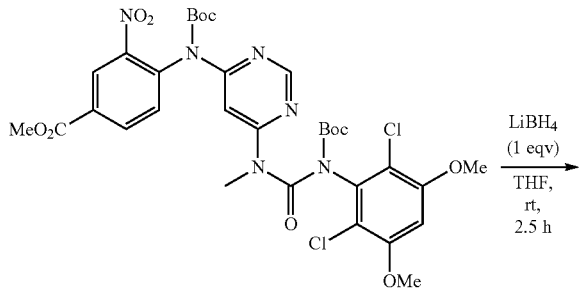

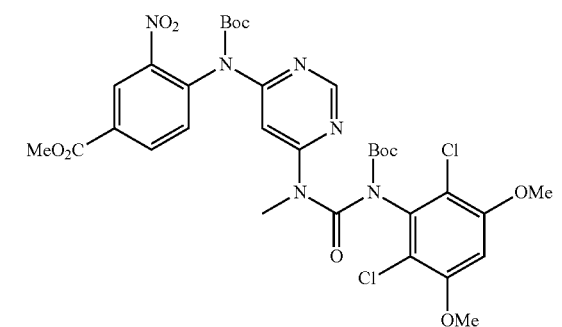

c. methyl 4-((tert-butoxycarbonyl)(6-(3-(2,6-di-chloro-3,5-dimethoxyphenyl)-1-methyl-3-tert-butyl ureido)pyrimidin-4-yl)amino)-3-nitrobenzoate DMAP (0.039 g, 0.322 mmol) and Di-tert-butyl dicarbonate (1.48 mL, 6.45 mmol) was added to a stirred solution of methyl 4-((6-(3-(2,6-dichloro-3,5-dimethoxyphenyl)-1-methyl-3-tert-butyl carbonate ureido)pyrimidin-4-yl)amino)-3-nitrobenzoate (2.1 g, 3.22 mmol) in anhydrous THF (5 mL) under an argon atmosphere at 0° C. The resulting mixture was refluxed for 12 h. After completion of the reaction by TLC (EtOAc:Hexane 40:60), reaction mixture was cooled to room temperature, concentrated under vacuum to obtain a crude residue. The residue was purified by silica gel column chromatography to afford the title compound (2.1 g, yield: 87%) as a solid. MS (ESI): 751.0 [M]⁺.

d. tert-butyl (6-(3-(2,6-dichloro-3,5-dimethoxyphenyl)-1-methyl-3-tert-butyl carbonate ureido)pyrimidin-4-yl)(4-(hydroxymethyl)-2-nitrophenyl)carbamate Lithium borohydride (0.049 g, 2.26 mmol) was added to a solution of methyl 4-((tert-butoxycarbonyl)(6-(3-(2,6-dichloro-3,5-dimethoxyphenyl)-1-methyl-3-tert-butyl ureido)pyrimidin-4-yl)amino)-3-nitrobenzoate (1.7 g, 2.26 mmol) in anhydrous THF (18 mL) under argon atmosphere at 0° C. The resulting reaction mixture was then allowed to warm to room temperature by 2.5 h. The reaction mixture was then quenched with ice-water and diluted with ethylacetate. The aqueous layer was separated and extracted with ethyl acetate (3×20 mL). The organic phase was washed with brine, dried over Na₂SO₄, filtered and concentrated under vacuum. The residue was purified by silica gel column chromatography to afford the title compound (0.480 g, yield: 29%) as a solid. MS (ESI): 723.2 [M]⁺.

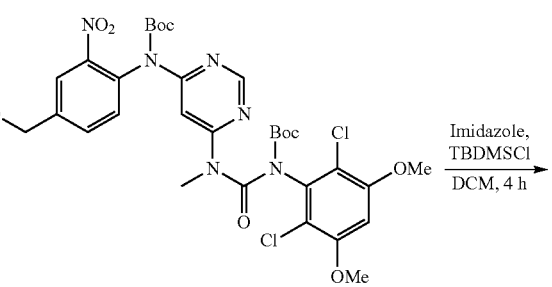

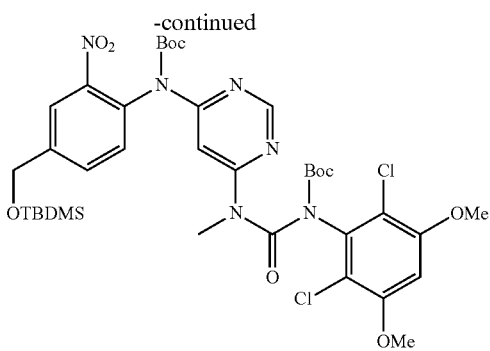

e. tert-butyl (4-(((tert-butyldimethylsilyl)oxy)
methyl)-2-nitrophenyl)(6-(3-(2,6-dichloro-3,5-dime-
thoxyphenyl)-1-methyl-3-tert-butyl carbonate
ureido)pyrimidin-4-yl)carbamate Imidazole (0.071 g, 1.051 mmol) and TBDMS-Cl (0.118 g, 0.787 mmol) were added to a stirred solution of tert-butyl (6-(3-(2,6-dichloro-3,5-dimethoxyphenyl)-1-methyl-3-tert-butyl carbonate ureido)pyrimidin-4-yl)(4-(hydroxymethyl)-2-nitrophenyl)carbamate (0.380 g, 0.525 mmol) in anhydrous dichloromethane (5 mL) under an argon atmosphere at 0° C. The resultant reaction mixture was stirred for 4h at room temperature. The reaction mixture was then diluted with DCM and water. The aqueous layer was separated and extracted with DCM (3×10 mL). The organic phase was washed with brine, dried over Na$_2$SO$_4$, filtered and concentrated under vacuum. The residue was purified by silica gel column chromatography to afford the title compound (0.330 g, yield: 75%) as a solid. MS (ESI): 837.4 [M]$^+$.

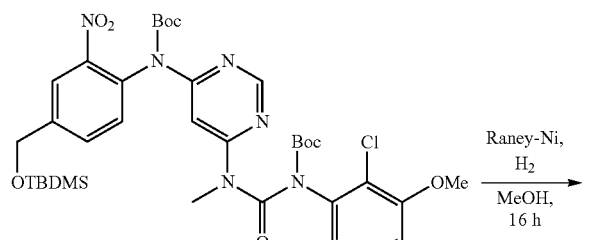

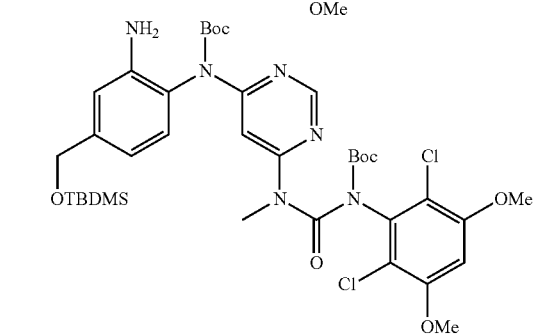

f. tert-butyl (2-amino-4-(((tert-butyldimethylsilyl)
oxy)methyl)phenyl)(6-(3-(2,6-dichloro-3,5-dime-
thoxyphenyl)-1-methyl-3-tert-butyl carbonate
ureido)pyrimidin-4-yl)carbamate Raney nickel (0.06 g) was added to a solution of tert-butyl (4-(((tert-butyldimethylsilyl) oxy)methyl)-2-nitrophenyl)(6-(3-(2,6-dichloro-3,5-dimethoxyphenyl)-1-methyl-3-tert-butyl carbonate ureido)pyrimidin-4-yl)carbamate (0.3 g, 0.358 mmol) in MeOH (5 mL) and the resultant reaction mixture was stirred for 12 h at room temperature under a hydrogen atmosphere (balloon). The reaction mixture was filtered through Celite pad. The filtrate was concentrated to afford a crude residue which was then purified by column chromatography to afford the title compound (0.180 g, yield: 64%) as a solid. MS (ESI): 807.2 [M]$^+$.

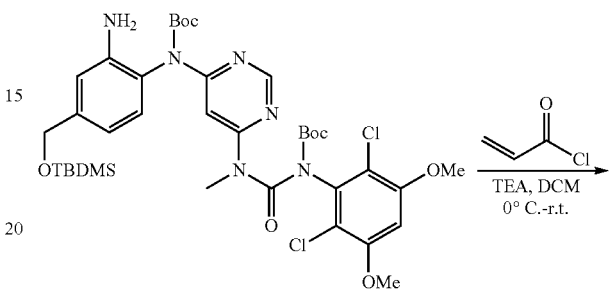

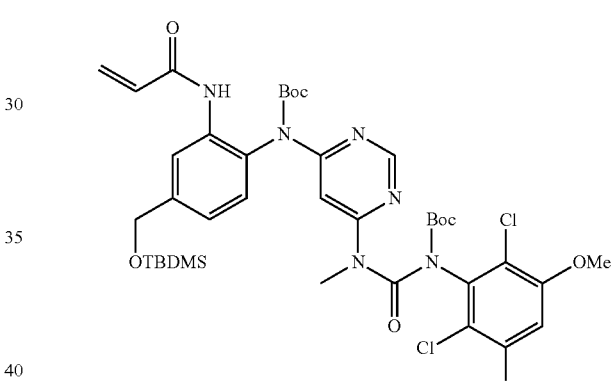

g. tert-butyl (2-acrylamido-4-(((tert-butyidimethylsi-
lyl)oxy)methy)phenyl)(6-(3-(2,6-dichloro-3,5-dime-
thoxyphenyl)-1-methyl-3-tert-butyl carbonate
ureido)pyrimidin-4-yl)carbamate To a stirred solution of tert-butyl (2-amino-4-(((tert-butyldimethylsilyl)oxy)methyl)phenyl)(6-(3-(2,6-dichloro-3,5-dimethoxyphenyl)-1-methyl-3-tert-butyl carbonate ureido)pyrimidin-4-yl)carbamate (0.180 g, 0.223 mmol) in anhydrous DCM (5 mL) was added TEA (0.08 mL, 0.557 mmol) under argon atmosphere at 0° C. The resulting mixture was stirred for 15 min. and slowly added the acryloyl chloride (0.03 mL, 0.334 mmol) at 0° C. The resulting reaction mixture was allowed to warm to room temperature and stirred for 4 h. The reaction mixture was then concentrated and the residue was purified by silica gel column chromatography to afford desired the title compound (0.130 g, yield: 68%) as a solid. MS (ESI): 861.3 [M]$^+$.

147

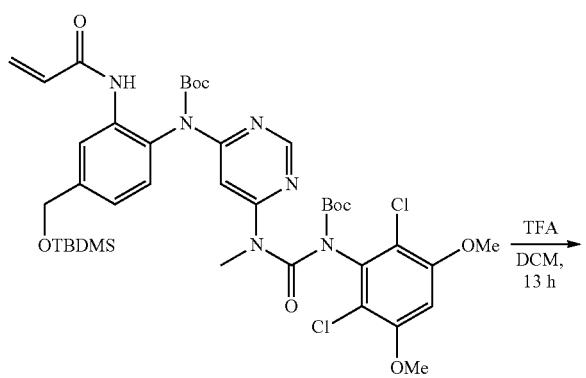

h. N-(2-((6-(3-(2,6-dichloro-3,5-dimethoxyphenyl)-1-methylureido)pyrimidin-4-yl)amino)-5-(hydroxymethyl)phenyl)acrylamide TFA (1.0 mL) was slowly added to a stirred solution of tert-butyl (2-acrylamido-4-(((tert-butyldimethylsilyl)oxy)methyl)phenyl)(6-(3-(2,6-dichloro-3,5-dimethoxyphenyl)-1-methyl-3-tert-butyl carbonate ureido)pyrimidin-4-yl)carbamate (0.130 g, 0.150 mmol) in dry DCM (3 mL) under argon atmosphere at 0° C. The resulting reaction mixture was allowed to warm to room temperature and stirred for 13 h. Reaction progress was monitored by LCMS, after completion of the reaction, excess solvents were removed under reduced pressure. The resulting residue was diluted with DCM and a saturated aqueous solution of NaHCO$_3$. The aqueous layer was separated and extracted with DCM (3×10 mL). The organic phase was washed with brine, dried over Na$_2$SO$_4$, filtered and concentrated under vacuum. The residue was purified by silica gel column chromatography to afford 95 mg of desired product with HPLC purity 84%, which was then purified by preparative HPLC (Conditions: Column: X bridge C18 (19 mm×150 mm, 5 μm); (Mobile Phase: A; 0.01% TFA in Water, B; ACN) to afford the title compound (16 mg, yield: 16%) as a white solid. $^1$H-NMR (DMSO-d6, 400 MHz): δ 12.08 (s, 1H), 9.70 (s, 1H), 8.95 (s, 1H), 8.37 (s, 1H), 7.64 (s, 1H), 7.49 (d, 1H), 7.15 (s, 1H), 6.90 (s, 1H), 6.53-7.46 (q, 1H), 6.32 (s, 1H), 6.25 (d, 1H), 5.74 (d, 1H), 5.42 (s, 1H), 5.35 (s, 1H), 4.49 (s, 2H), 3.94 (s, 6H), 3.25 (s, 3H); MS (ESI): 547.0 [M+H]$^+$; HPLC: 97.4%, rt: 3.83 min.

Example 147

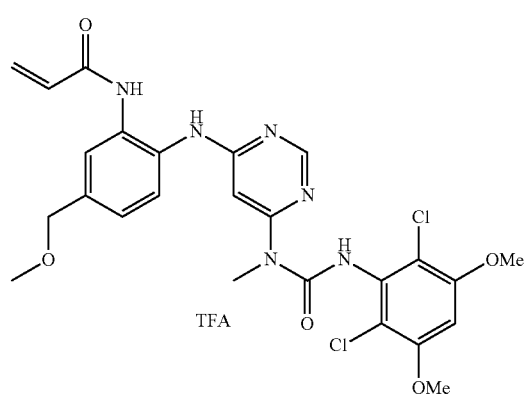 [SMILES: C=CC(=O)Nc1cc(COC)ccc1Nc1cc(N(C)C(=O)Nc2c(Cl)c(OC)cc(OC)c2Cl)ncn1]

N-(2-((6-(3-(2,6-dichloro-3,5-dimethoxyphenyl)-1-methylureido) pyrimidin-4-yl)amino)-5-(methoxymethyl)phenyl)acrylamide The title compound was synthesized following the approach outlined in Procedure 2I (Example 142), substituting N$^4$-(4-(methoxymethyl)-2-nitrophenyl)-N$^6$-methylpyrimidine-4,6-diamine (procedure shown below) in step (c) to afford the title compound (5.0 mg, yield: 1.8%) as an off-white solid. 1H-NMR (CDCl$_3$, 400 MHz): δ 12.30 (s, 1H), 8.41 (s, 1H), 7.86 (s, 1H), 7.81 (s, 1H), 7.52 (d, 1H), 7.49 (s, 1H), 7.30 (d, 1H), 6.54 (s, 1H), 6.46 (d, 1H), 6.26 (dd, 1H), 6.07 (s, 1H), 5.83 (d, 1H), 5.18 (s, 2H), 3.93 (s, 6H), 3.82 (s, 3H), 3.34 (s, 3H); MS (ESI): 561.1 [M+H]$^+$; HPLC: 95.76%, rt: 4.36 min.

Preparation of N$^4$-(4-(methoxymethyl)-2-nitrophenyl)-N$^6$-methylpyrimidine-4,6-diamine

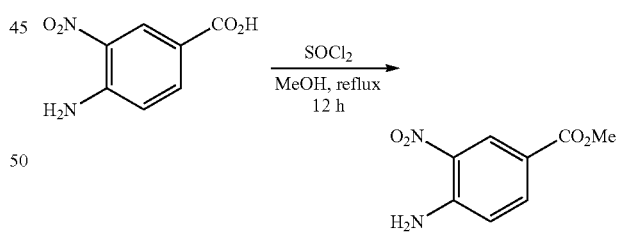

a. methyl 4-amino-3-nitrobenzoate

Thionyl chloride (19.4 g, 164.85 mmol) was added to a solution of 4-amino-3-nitrobenzoic acid (20 g, 109.89 mmol) in methanol (200 mL) at 0° C. The resulting mixture was then refluxed for 12 h. The reaction mixture was allowed to cool to room temperature. The yellow solid precipitated was filtered and dried to afford the title compound (22 g, yield: 100%) as a solid. 1H-NMR (CDCl$_3$, 300 MHz): δ 8.85 (d, 1H), 7.99 (dd, 1H), 6.83 (d, 1H), 6.40 (s, 2H), 3.90 (s, 3H).

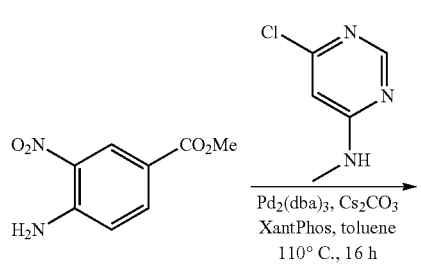

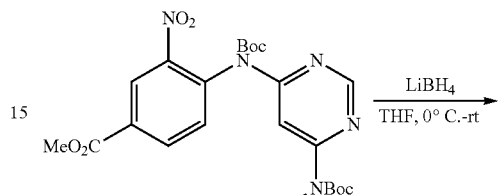

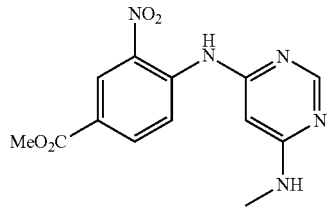

b. methyl 4-((6-(methylamino)pyrimidin-4-yl)amino)-3-nitrobenzoate 6-chloro-N-methylpyrimidin-4-amine, 3 (3 g, 20.97 mmol) and methyl 4-amino-3-nitrobenzoate (3.9 g, 20.97 mmol) were taken in toluene (5 mL) in a seal tube under Argon atmosphere at room temperature. The Argon gas was purged for 5-10 min. Then $Cs_2CO_3$ (17.0 g, 52.4 mmol) and Xantphos (3.6 g, 6.29 mmol) were added and the resulting reaction mixture was purged with argon gas for 5 min, followed by $Pd_2(dba)_3$ (3.8 g, 4.19 mmol) was added. The argon gas purging was continued for additional 5 min before sealing the reaction vial. Then the reaction mixture was heated at 110° C. for 16h. After completion of the reaction by TLC, the reaction mixture was cooled to rt, filtered through celite bed and the filtrate was evaporated under vacuum to get a crude residue. The crude residue was purified by column chromatography on silica gel to afford the title compound (3.2 g, yield: 51%) as a solid; MS (ESI): 304.2 [M+H]$^+$.

of intermediate-4 (3.1 g, 10.197 mmol) in anhydrous THF (35 mL) under an argon atmosphere at room temperature. The resulting mixture was refluxed for 2-3h. After completion of the reaction by TLC, reaction mixture was cooled to room temperature, concentrated under vacuum to obtain a crude residue. The residue was purified by silica gel column chromatography to afford the title compound (1.9 g, yield: 37%) as a solid. MS (ESI): 504.0 [M+H]$^+$.

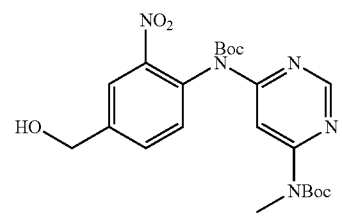

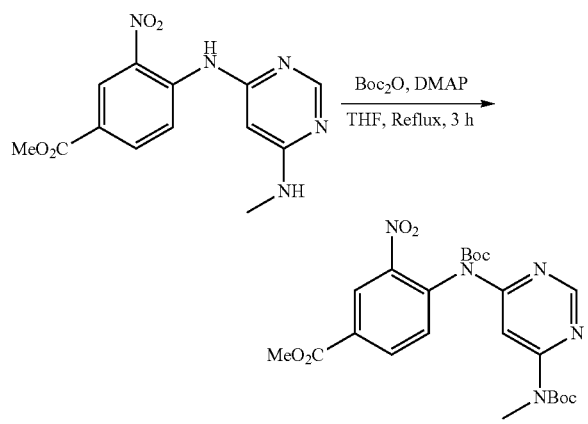

c. methyl 4-((tert-butoxycarbonyl)(6-((tert-butoxycarbonyl)(methyl)amino)pyrimidin-4-yl)amino)-3-nitrobenzoate DMAP (0.497 g, 4.078 mmol) and Di-tert-butyl dicarbonate (8.89 g, 40.78 mmol) were added to a stirred solution d. tert-butyl (6-((tert-butoxycarbonyl)(4-(hydroxymethyl)-2-nitrophenyl)amino)pyrimidin-4-yl)(methy)carbamate Lithium borohydride (0.157 g, 7.14 mmol) was added to a solution of methyl 4-((tert-butoxycarbonyl)(6-((tert-butoxycarbonyl)(methyl)amino)pyrimidin-4-yl)amino)-3-nitrobenzoate (1.8 g, 3.57 mmol) in THF (20 mL) under an argon atmosphere at 0° C. The resulting mixture was then allowed to warm to rt and stirred for 12 h. The reaction mixture was then quenched with ice-water and diluted with ethyl acetate. The aqueous layer was separated and extracted with ethyl acetate (3×40 mL). The organic phase was washed with brine, dried over $Na_2SO_4$, filtered, and concentrated to get a crude residue. The residue was purified by silica gel column chromatography to afford desired intermediate-6 (1.2 g, 75%) as a solid. MS (ESI): 476.1 [M+H]$^+$.

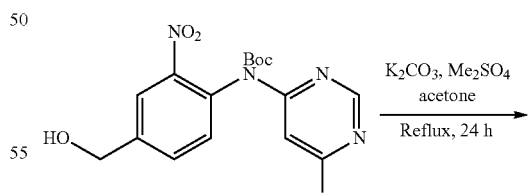

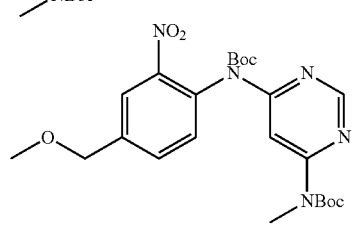

e. tert-butyl (6-(((tert-butoxycarbonyl)(4-(methoxymethyl)-2-nitrophenyl)amino)pyrimidin-4-yl)(methyl)carbamate To a solution of tert-butyl (6-(((tert-butoxycarbonyl)(4-(hydroxymethyl)-2-nitrophenyl)amino) pyrimidin-4-yl)(methyl)carbamate (15 g, 3.488 mmol) in acetone (20 mL) under an argon atmosphere at 0° C., was added potassium carbonate (0.48 g, 6.97 mmol) followed by dimethyl sulfate (0.87 g, 6.97 mmol). The resulting reaction mixture was then refluxed for 24 h and then allowed to cool to rt. The reaction mixture was concentrated under vacuum to obtain a crude residue. The residue was purified by silica gel column chromatography to afford the title compound (0.3 g, yield: 19%) as a solid. MS (ESI): 490.55 [M+H]$^+$.

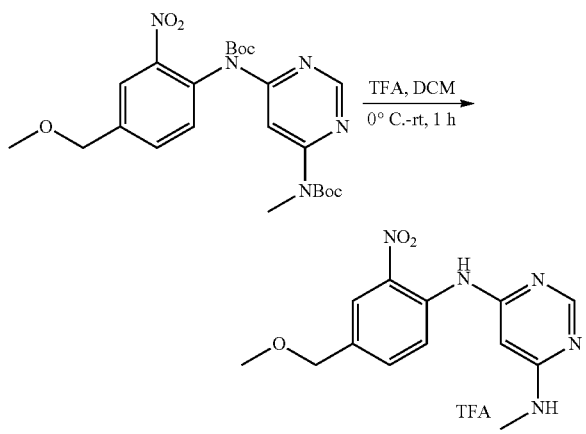

f. N$^4$-(4-(methoxymethyl)-2-nitrophenyl)N$^6$-methyl-pyrimidine-4,6-diamine TFA (5 mL) was slowly added to a stirred solution of tert-butyl (6-(((tert-butoxycarbonyl)(4-(methoxymethyl)-2-nitrophenyl)amino)pyrimidin-4-yl)(methyl)carbamate (0.85 g) in dry DCM (10 mL) under argon atmosphere at 0° C. The resulting reaction mixture was allowed to warm to room temperature and stirred for 1 h. After completion of the reaction, excess solvents were removed under reduced pressure and washed with ether to afford the title compound (0.7 g crude) as a solid. MS (ESI): 290.2 [M+H]$^+$.

Procedure 2K—Example 148

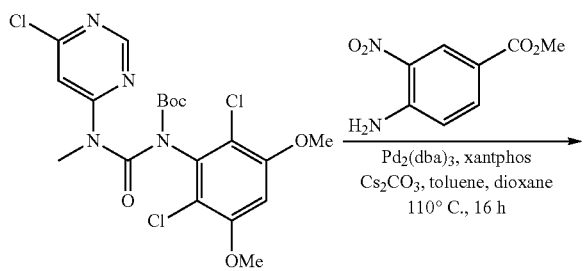

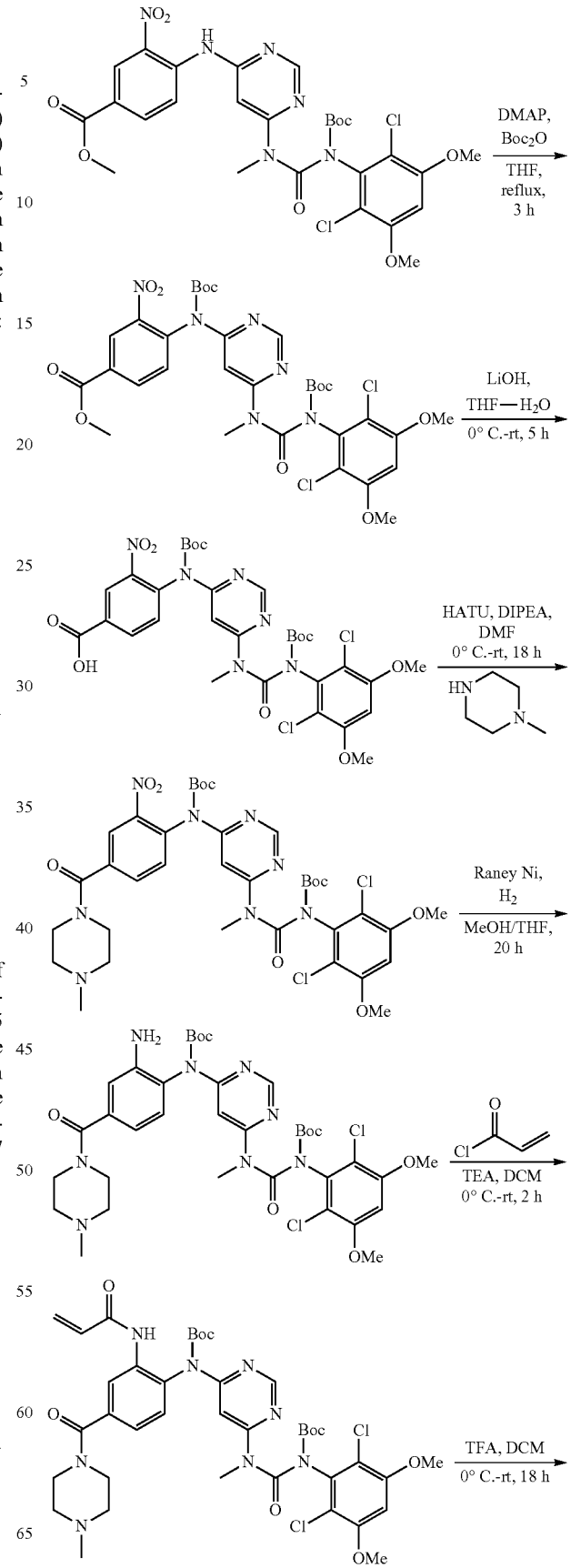

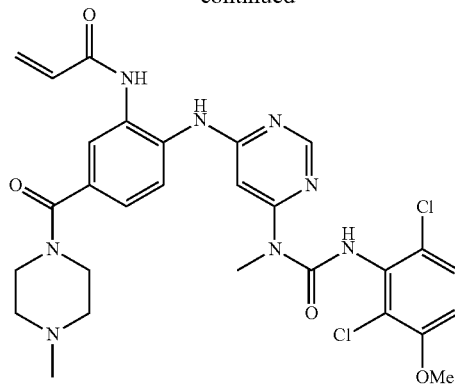

N-(2-(((6-(3-(2,6-dichloro-3,5-dimethoxyphenyl)-1-methylureido)pyrimidin-4-yl)amino)-5-(4-methylpiperazine-1-carbonyl)phenyl)acrylamide

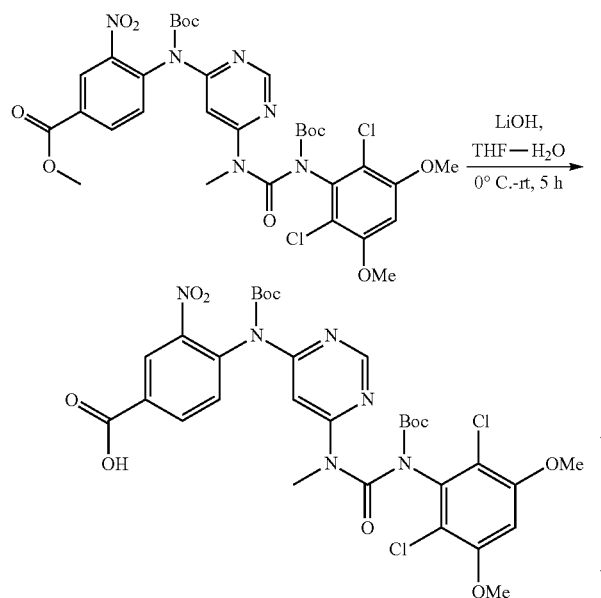

a. 4-((tert-butoxycarbonyl)(6-(3-(tert-butoxycarbonyl)-3-(2,6-dichloro-3,5-dimethoxyphenyl)-1-methylureido)pyrimidin-4-yl)amino)-3-nitrobenzoic acid Lithium hydroxide (0.08 g, 2.99 mmol) was added to a solution of methyl 4-((tert-butoxycarbonyl)(6-(3-(tert-butoxycarbonyl)-3-(2,6-dichloro-3,5-dimethoxyphenyl)-1-methylureido)pyrimidin-4-yl)amino)-3-nitrobenzoate (1.5 g, 1.997 mmol)(Procedure 2J, Step c) in a mixture of THF (10 mL) and water (2 mL) at 0° C. The resulting reaction mixture was allowed to warm to room temperature and stirred for 5 h. After completion of the reaction by TLC (EtOAc:Hexane 3:7), the reaction mixture was concentrated under vacuum to get a crude residue. The crude residue was dissolved in water and extracted with ether (3×30 mL). The aqueous layer was acidified with 10% citric acid solution and the precipitated solid was filtered, washed with cold water and dried in vacuo to afford the title compound (1.3 g, yield: 93%) as a light brown solid. MS (ESI): 737.2 [M+H]+.

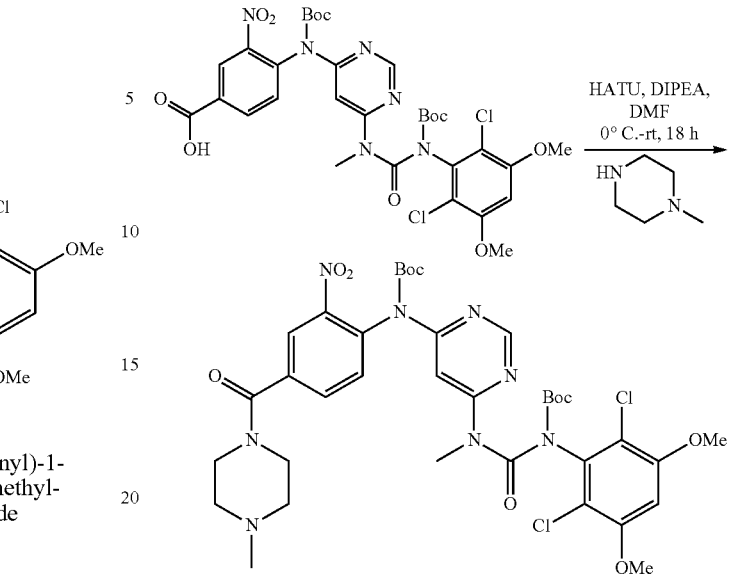

b. tert-butyl (2-nitro-4-(4-methylpiperazine-1-carbonyl)phenyl)(6-(3-(2,6-dichloro-3,5-dimethoxyphenyl)-3-tert-butoxycarbonyl-1-methylureido)pyrimidin-4-yl)carbamate DIPEA (0.3 mL, 1.62 mmol), HATU (0.515 g, 1.355 mmol) and N-methyl piperazine, 6 (0.09 mL, 0.813 mmol) were added to a solution of 4-((tert-butoxycarbonyl)(6-(3-(tert-butoxycarbonyl)-3-(2,6-dichloro-3,5-dimethoxyphenyl)-1-methylureido)pyrimidin-4-yl)amino)-3-nitrobenzoic acid (0.4 g, 0.542 mmol) in DMF (5 mL) at 0° C. under argon atmosphere. The resulting reaction mixture was then allowed to warm to rt and stirred for 18 h. After completion of the reaction by TLC (MeOH:DCM 1:19), water was added to the reaction mixture. The precipitated crude solid was filtered, dried and purified by silica gel column chromatography to obtain the title compound (0.27 g, yield: 61%) as a solid. MS (ESI): 819.1 [M+H]+.

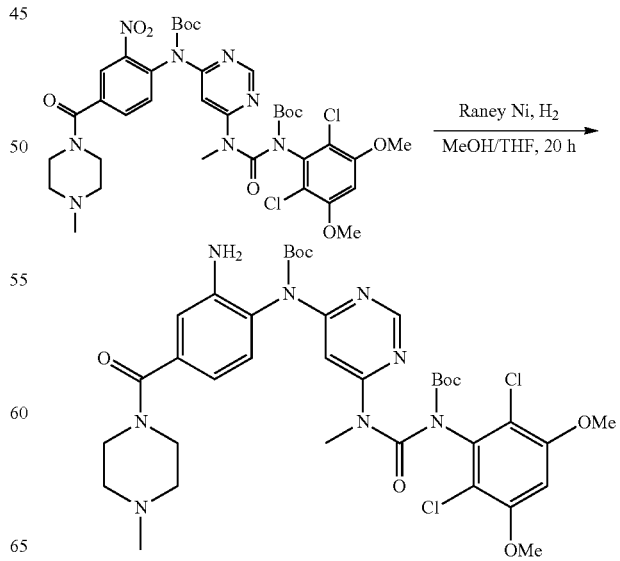

c. tert-butyl (2-amino-4-(4-methylpiperazine-1-carbonyl)phenyl)(6-(3-(2,6-dichloro-3,5-dimethoxyphenyl)-3-tert-butoxycarbonyl-1-methylureido)pyrimidin-4-yl)carbamate Raney nickel (0.06 g) was added to a solution of tert-butyl (2-nitro-4-(4-methylpiperazine-1-carbonyl)phenyl)(6-(3-(2,6-dichloro-3,5-dimethoxyphenyl)-3-tert-butoxycarbonyl-1-methylureido)pyrimidin-4-yl)carbamate (0.27 g, 0.329 mmol) in a mixture of MeOH (4 mL) and THF (4 mL) and the resultant reaction mixture was stirred for 20 h at room temperature under a hydrogen atmosphere. The reaction mixture was filtered through Celite bed. The filtrate was concentrated, to afford crude title compound (0.22 g, yield: 84%) as a solid. MS (ESI): 789.4 [M+H]$^+$.

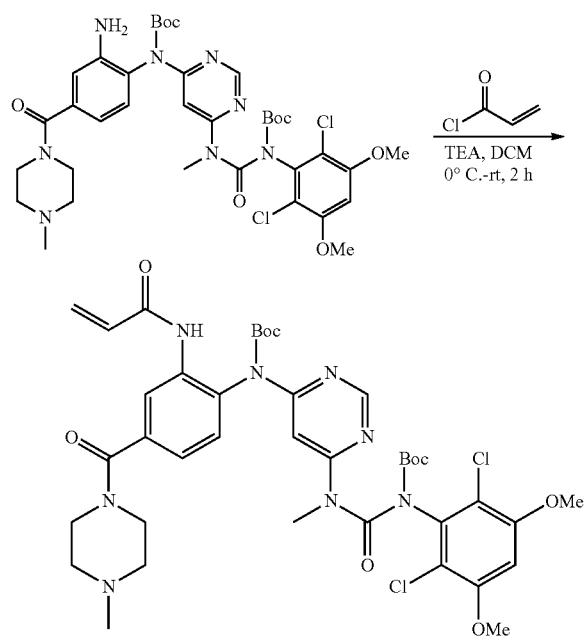

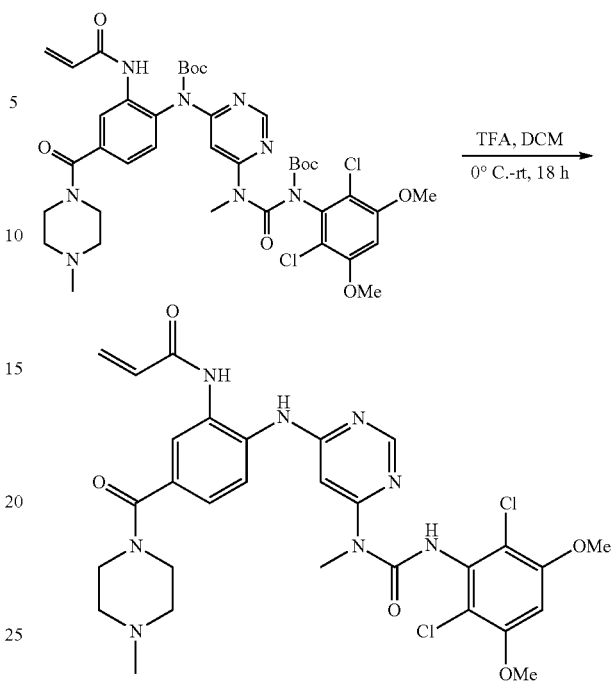

d. tert-butyl (2-acrylamido-4-(4-methylpiperazine-1-carbonyl)phenyl)(6-(3-(2,6-dichloro-3,5-dimethoxyphenyl)-3-tert-butoxycarbonyl-1-methylureido)pyrimidin-4-yl)carbamate To a stirred solution of tert-butyl (2-amino-4-(4-methylpiperazine-1-carbonyl)phenyl)(6-(3-(2,6-dichloro-3,5-dimethoxyphenyl)-3-tert-butoxycarbonyl-1-methylureido)pyrimidin-4-yl)carbamate (0.22 g, 0.278 mmol) in anhydrous DCM (5 mL) was added TEA (0.08 mL, 0.557 mmol) under argon atmosphere at 0° C. The resulting mixture was stirred for 15 min. and slowly added the acryloyl chloride (0.037 g, 0.417 mmol) at 0° C. The resulting reaction mixture was allowed to warm to room temperature and stirred for 2 h. The reaction mixture was quenched with a saturated sodium bicarbonate solution and diluted with DCM. The aqueous layer was separated and extracted with DCM (3×20 mL). The organic phase was washed with brine, dried over Na$_2$SO$_4$, filtered, and concentrated to get a crude residue. The residue was purified by silica gel column chromatography to afford the title compound (0.060 g, yield: 25%) as a solid. MS (ESI): 843.3 [M+H]$^+$.

e. N-(2-((6-(3-(2,6-dichloro-3,5-dimethoxyphenyl)-1-methylureido)pyrimidin-4-yl)amino)-5-(4-methylpiperazine-1-carbonyl)phenyl)acrylamide TFA (0.2 mL) was slowly added to a stirred solution of tert-butyl (2-acrylamido-4-(4-methylpiperazine-1-carbonyl)phenyl)(6-(3-(2,6-dichloro-3,5-dimethoxyphenyl)-3-tert-butylcarbonyl-1-methylureido)pyrimidin-4-yl)carbamate (0.060 g, 0.071 mmol) in dry DCM (2 mL) under argon atmosphere at 0° C. The resulting reaction mixture was allowed to warm to room temperature and stirred for 18 h. Reaction progress was monitored by LCMS, after completion of the reaction, excess solvents were removed under reduced pressure. The resulting residue was diluted with DCM and quenched with a saturated aqueous solution of NaHCO$_3$. The aqueous layer was separated and extracted with DCM (3×10 mL). The organic phase was washed with brine, dried over Na$_2$SO$_4$, filtered and concentrated under vacuum to get a crude residue. The residue was purified by silica gel column chromatography to afford 70 mg of desired product with HPLC purity 35% which was then purified by preparative HPLC (Conditions: Column: Gemini NX C18 (21.2 mm×150 mm particle size 5 μm); (Mobile Phase: A; 0.1% Ammonium bicarbonate in Water, B; ACN) to afford the desired compound. The compound was then diluted with dichloromethane and water. The aqueous layer was separated and extracted with DCM (3×10 mL). The organic phase was washed with brine, dried over Na$_2$SO$_4$, filtered and concentrated under vacuum to afford the title compound (0.005 g, yield: 11%) as a white solid. 1H-NMR (CD$_3$OD, 400 MHz): δ 8.41 (s, 1H), 7.79-7.76 (m, 2H), 7.36 (dd, 1H), 6.82 (s, 1H), 6.47-6.42 (m, 3H), 5.82 (d, 1H), 3.96 (s, 6H), 3.81-3.55 (m, 8H), 2.54 (s, 3H), 2.37 (s, 3H); MS (ESI): 643.1 [M+H]$^+$; HPLC: 97.26%, rt: 6.19 min.

Example 149

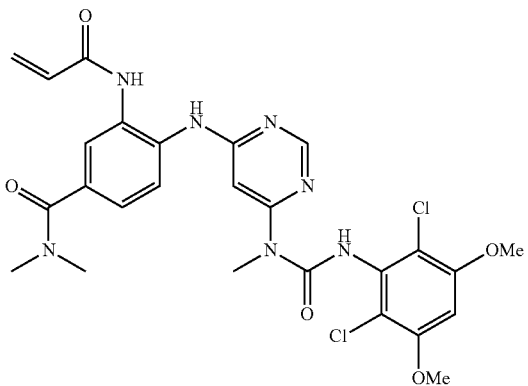 [SMILES: C=CC(=O)Nc1cc(C(=O)N(C)C)ccc1Nc1cc(N(C)C(=O)Nc2c(Cl)c(OC)cc(OC)c2Cl)ncn1]

3-acrylamido-4-((6-(3-(2,6-dichloro-3,5-dimethoxyphenyl)-1-methylureido)pyrimidin-4-yl)amino)-N,N-dimethylbenzamide The title compound was synthesized following the approach outlined in Procedure 2K (Example 148), substituting dimethylamine in step (b) to afford the title compound (12.0 mg, yield: 6.1%) as an off-white solid. 1H-NMR (CD$_3$OD, 400 MHz): δ 8.38 (s, 1H), 7.78-7.72 (m, 2H), 7.34 (dd, 1H), 6.80 (s, 1H), 6.46-6.38 (m, 3H), 5.80 (dd, 1H), 3.94 (s, 6H), 3.36 (s, 3H), 3.10 (s, 6H); MS (ESI): 587.9 [M+H]$^+$; HPLC: 99.04%, rt: 3.98 min.

Example 150

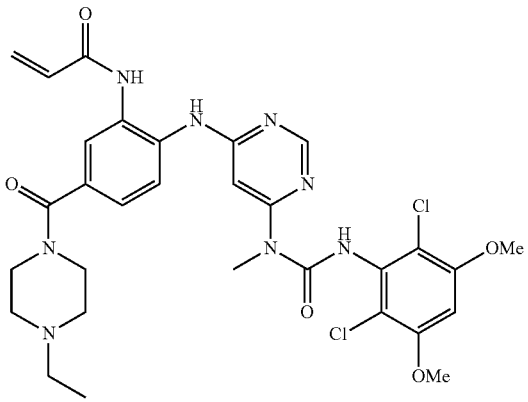 [SMILES: C=CC(=O)Nc1cc(C(=O)N2CCN(CC)CC2)ccc1Nc1cc(N(C)C(=O)Nc2c(Cl)c(OC)cc(OC)c2Cl)ncn1]

N-(2-((6-(3-(2,6-dichloro-3,5-dimethoxyphenyl)-1-methylureido)pyrimidin-4-yl)amino)-5-(4-ethylpiperazine-1-carbonyl)phenyl)acrylamide The title compound was synthesized following the approach outlined in Procedure 2K (Example 148), substituting 1-ethylpiperazine in step (b) to afford the title compound (10.0 mg, yield: 9.7%) as an off-white solid. 1H-NMR (CD$_3$OD, 400 MHz): δ 8.41 (s, 1H), 7.76-7.79 (m, 2H), 7.36 (d, 1H), 6.82 (s, 1H), 6.38-6.47 (m, 3H), 5.82 (d, 1H), 3.96 (s, 6H), 3.72-3.82 (m, 2H), 3.53-3.65 (m, 3H), 3.39 (s, 4H), 2.49-2.54 (m, 6H), 1.15 (t, 3H); MS (ESI): 657.0 [M+H]+; HPLC: 95.98%, rt: 6.25 min.

Example 151

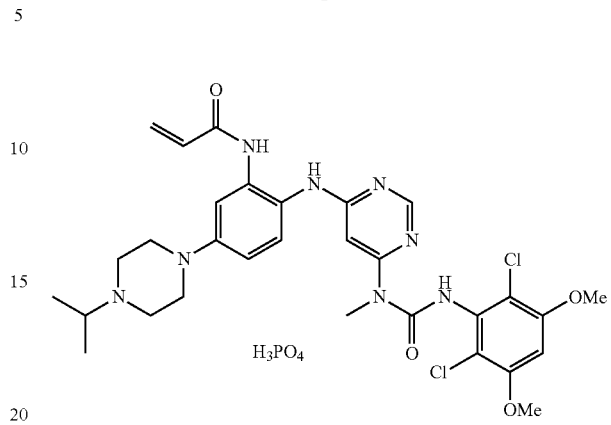

N-(2-((6-(3-(2,6-dichloro-3,5-dimethoxyphenyl)-1-methylureido)pyrimidin-4-yl)amino)-5-(4-isopropylpiperazin-1-yl)phenyl)acrylamide phosphoric acid The title compound was synthesized following the approach outlined in Procedure 2J (Example 145), substituting 4-(4-isopropylpiperazin-1-yl)-2-nitroaniline (procedure shown below) in step (b) and omitting steps (d) and (e) to afford the free base of the title compound (0.1 g, overall yield: 9.7%) as an off-white solid. MS (ESI): 643.1 [M+H]$^+$. 85% H$_3$PO$_4$ was slowly added to a solution of N-(2-((6-(3-(2,6-dichloro-3,5-dimethoxyphenyl)-1-methylureido)pyrimidin-4-yl)amino)-5-(4-isopropylpiperazin-1-yl)phenyl) acrylamide (0.1 g) in 95% THF-MeOH (5 mL). The resulting reaction mixture was then allowed to stir at room temperature for 30 min., evaporated the solvent and triturated with diethyl ether, dried under vacuum to afford the title compound (0.16 g) as a off white solid. $^1$HNMR (DMSO-d$_6$, 400 MHz): δ 12.08 (s, 1H), 9.62 (s, 1H), 8.76 (s, 1H), 8.32 (s, 1H), 7.30 (d, 2H), 6.89 (d, 1H), 6.81 (d, 1H), 6.46-6.49 (m, 1H), 6.21-6.25 (m, 2H), 5.72 (d, 1H), 3.93 (s, 6H), 3.35-3.41 (m, 1H), 3.23 (s, 3H), 3.12-3.17 (m, 4H), 2.67-2.70 (m, 4H), 1.05-1.11 (m, 6H); MS (ESI): 643.3 (M+1); HPLC: 95.41%, rt: 6.48 min.

Preparation of 4-(4-isopropylpiperazin-1-yl)-2-nitroaniline

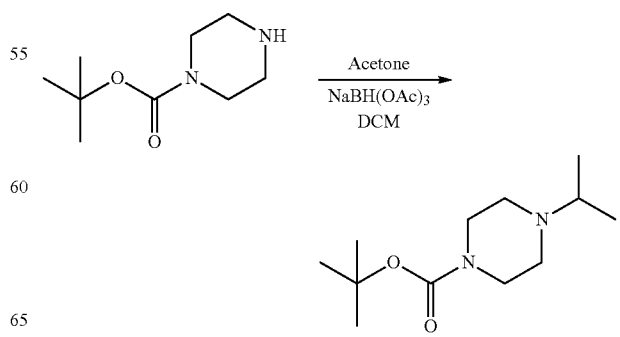

a. tert-butyl 4-isopropylpiperazine-1-carboxylate

Boc piperizine, 1 (10 g, 53.76 mmol) and acetone (4 mL) was taken in a mixture of dry DCM (100 mL) and acetic acid (3.2 mL). Stirred at room temperature for 20 min. Added Na(OAc)$_3$BH (17 g, 80.2 mmol) and stirring continued at room temperature for 12 hr. The reaction mixture was diluted with water, extracted with ethyl acetate (3×25 mL). The organic layer was washed with brine, dried over Na$_2$SO$_4$, filtered and concentrated under vacuum to get crude title compound (13 g, crude). MS (ESI): 229.2 [M+H]$^+$.

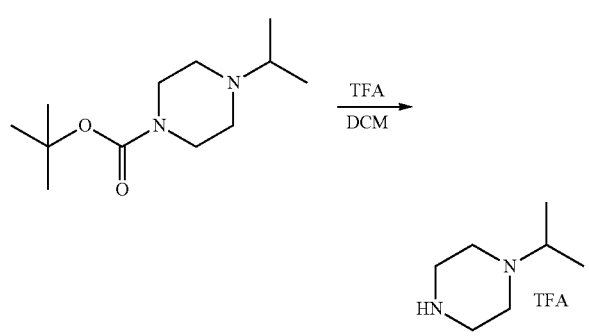

b. 1-isopropylpiperazine

TFA (15 mL) was slowly added to a stirred solution of tert-butyl 4-isopropylpiperazine-1-carboxylate (13 g crude) in dry DCM (20 mL) under argon atmosphere at 0° C. The resulting reaction mixture was allowed to warm to room temperature and stirred for 18 hr. The reaction mass was concentrated under vacuum and triturated the residue with n-hexane and diethyl ether. Dried under vacuum to afford the title compound (7 g, yield: 97%). MS (ESI): 129.1 [M+H]$^+$.

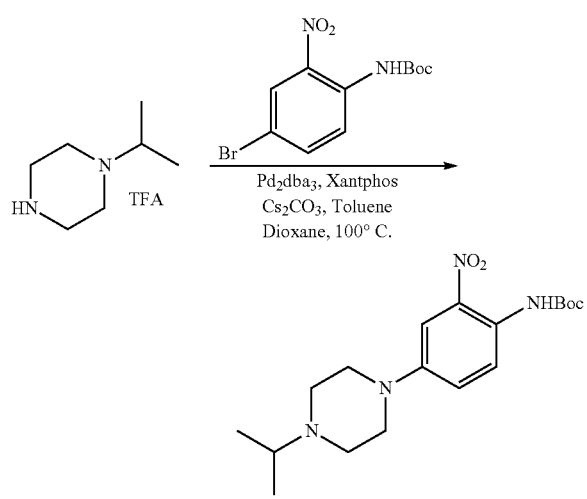

c. tert-butyl (4-(4-isopropylpiperazin-1-yl)-2-nitrophenyl)carbamate 1-isopropylpiperazine (1.29 g, 5.66 mmol) and tert-butyl (4-bromo-2-nitrophenyl)carbamate (1.5 g, 4.71 mmol) were taken in a mixture of dry toluene (15 mL) and dioxane (2 mL) in a seal tube under argon atmosphere at room temperature. The Argon gas was purged for 5-10 min. Then Cs$_2$CO$_3$ (3.06 g, 9.43 mmol) and Xantphos (0.54 g, 0.94 mmol) were added and the resulting reaction mixture was purged with argon gas for 5 min., followed by Pd$_2$(dba)$_3$ (0.43 g, 0.47 mmol). The argon gas purging was continued for additional 5 min. before sealing the reaction vial. Then the reaction mixture was heated at 100° C. for 12 hr. After completion of the reaction by TLC, the reaction mixture was cooled to room temperature, filtered through celite bed and concentrated. The residue was purified by silica gel column chromatography (DCM:MeOH/97:3) to afford the title compound (1.2 g, yield: 70.5%). MS (ESI): 365.5 [M+H]$^+$.

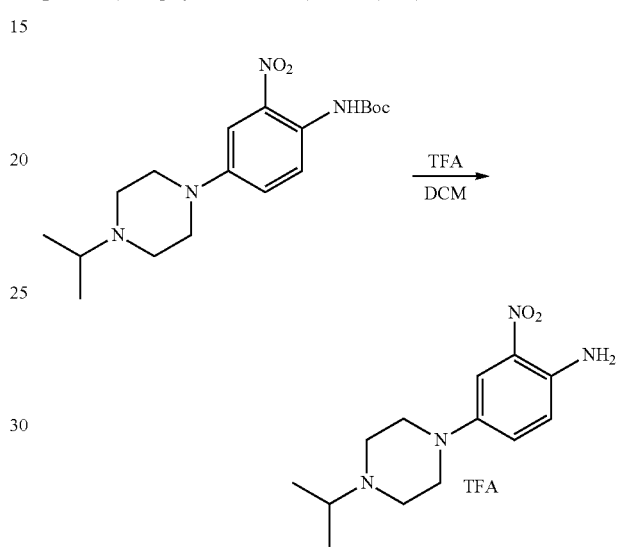

d. 4-(4-isopropylpiperazin-1-yl)-2-nitroaniline

TFA (3 mL) was slowly added to a stirred solution of tert-butyl (4-(4-isopropylpiperazin-1-yl)-2-nitrophenyl)carbamate (1.2 g, 3.29 mmol) in dry DCM (5 mL) under argon atmosphere at 0° C. The resulting reaction mixture was allowed to warm to room temperature and stirred for 12 hr. Reaction progress was monitored by LCMS, after completion of the reaction, excess solvents were removed under reduced pressure to afford a crude residue. The crude residue was repeatedly washed with ether to get the title compound (1 g, yield: 80.6%) as a red solid. MS (ESI): 265.1 [M+H]$^+$.

Example—154

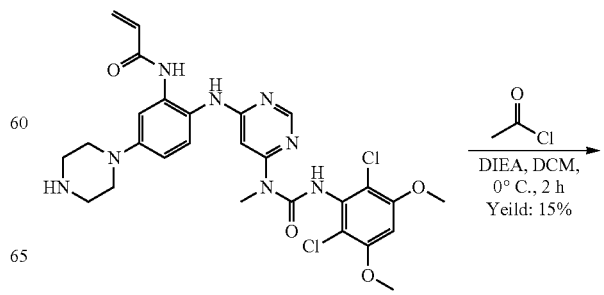

161

-continued

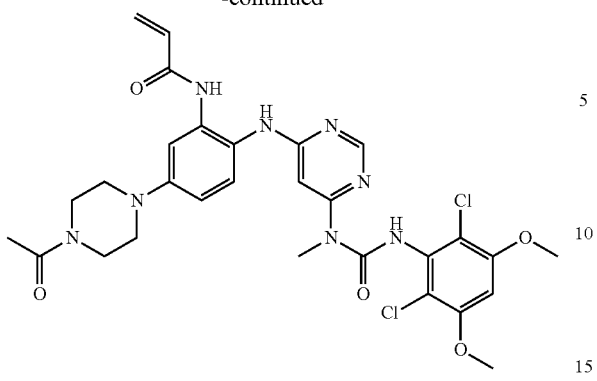

Preparation of N-(5-(4-acetylpiperazin-1-yl)-2-((6-(3-(2,6-dichloro-3,5-dimethoxyphenyl)-1-methylureido)pyrimidin-4-yl)amino)phenyl)acrylamide N-(2-((6-(3-(2,6-dichloro-3,5-dimethoxyphenyl)-1-methylureido)pyrimidin-4-yl)amino)-5-(piperazin-1-yl)phenyl)acrylamide (Procedure 2L, Example 157)(8.6 mg, 0.014 mmol) and DIEA (7.5 μl, 0.043 mmol) were stirred in DCM (1.0 ml) at room temperature under nitrogen atmosphere. A solution of acetyl chloride (1.0 μl, 0.016 mmol) in DCM (11 μl) was added and the reaction mixture was stirred at room temperature for 2 hours. The solvent was evaporated and the resulting material was dissolved in 400 ul of DMSO. The DMSO solution was diluted with 1.0 ml of MeOH and purified by prep-HPLC (water/ACN in formic acid condition) to afford the title compound (1.4 mg, yield: 15%). $^1$H-NMR (400 MHz, MeOH-d$_4$) δ 2.16 (s, 3 H) 3.65-3.80 (m, 4 H) 3.94 (s, 6 H) 5.76 (dd, 1 H) 6.15 (s, 1 H) 6.28-6.49 (m, 2 H) 6.78-6.82 (m, 1 H) 6.95 (dd, 2.89 Hz, 1 H) 7.28-7.38 (m, 2 H) 8.31 (d, 1 H) 8.58 (br. s., 1 H); ESI-MS: 643 [M+H]$^+$.

Example—155 and 156

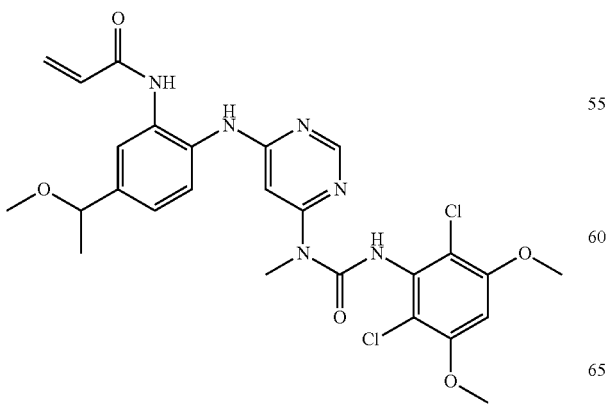

162

-continued

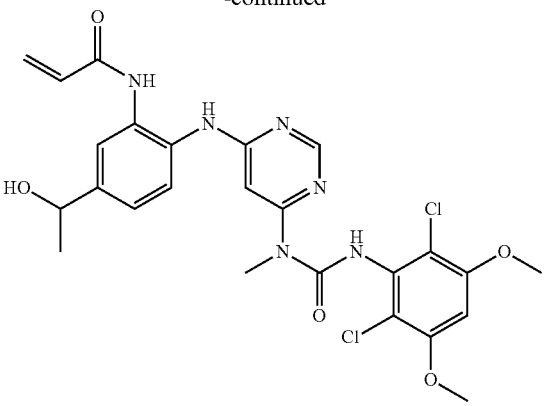

Preparation of N-(2-((6-(3-(2,6-dichloro-3,5-dimethoxyphenyl)-1-methylureido)pyrimidin-4-yl)amino)-5-(1-methoxyethyl)phenyl)acrylamide and N-(2-((6-(3-(2,6-dichloro-3,5-dimethoxyphenyl)-1-methylureido)pyrimidin-4-yl)amino)-5-(1-hydroxyethyl)phenyl)

The compound was synthesized following the approach outlined in Procedure 2G (Example 123), substituting 4-(1-methoxyethyl)-2-nitroaniline (procedure shown below) in step (d) to afford the title compounds after purification using flash chromatography on silica eluting with 90% to 100% EtOAc/Hexane. Non-polar fraction was N-(2-((6-(3-(2,6-dichloro-3,5-dimethoxyphenyl)-1-methylureido)pyrimidin-4-yl)amino)-5-(1-methoxyethyl)phenyl)acrylamide (16 mg, yield: 6% in five steps) $^1$H-NMR (400 MHz, MeOH-d$_4$) δ 1.46 (d, 3 H) 3.29 (s, 3 H) 3.96 (s, 6 H) 4.12 (d, 1 H) 4.40 (q, 1 H) 5.78-5.82 (m, 1 H) 6.33-6.50 (m, 3 H) 6.82 (s, 1 H) 7.27 (dd, 1 H) 7.55-7.64 (m, 2 H) 8.37 (d, 1 H); ESI-MS: 575 [M+H]$^+$. Polar fraction was N-(2-((6-(3-(2,6-dichloro-3,5-dimethoxyphenyl)-1-methylureido)pyrimidin-4-yl)amino)-5-(1-hydroxyethyl)phenyl) acrylamide (22 mg, yield: 8% in five steps). $^1$H-NMR (400 MHz, MeOH-d$_4$) δ 1.53 (d, 3 H) 4.00 (s, 6 H) 5.83 (dd, 1 H) 6.29-6.56 (m, 3 H) 6.86 (s, 1 H) 7.38 (dd, 1 H) 7.57 (d, 1 H) 7.69 (s, 1 H) 8.40 (d, 1 H); ESI-MS: 661 [M+H]$^+$.

Preparation of 4-(1-methoxyethyl)-2-nitroaniline

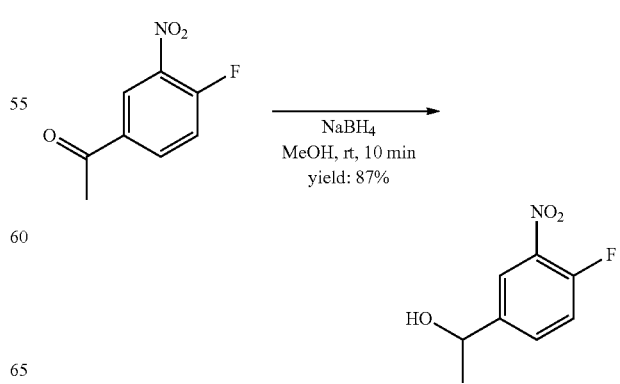

a. 1-(4-fluoro-3-nitrophenyl)ethanol 1-(4-fluoro-3-nitrophenyl)ethanone (1.0 g, 5.46 mmol) was dissolved in MeOH (15.0 ml) and stirred over ice bath. NaBH₄ (0.62 g, 16.0 mmol) was added portionwise. Upon completion of the addition, the reaction mixture was stirred at rt for 10 minutes. The reaction mixture was poured into EtOAc and brine. The organic layer was separated, dried over MgSO₄ and evaporated. The resulting material was purified by flash chromatography on silica eluting with 20% to 70% EtOAc/Hexane to afford the title compound (881 mg, yield: 87%). %). ¹H-NMR (400 MHz, CDCl₃) δ 1.53 (d, 4 H) 4.99 (dd, 1 H) 7.22-7.33 (m, 1 H) 7.66 (ddd, 1 H) 8.09 (dd, 1 H)

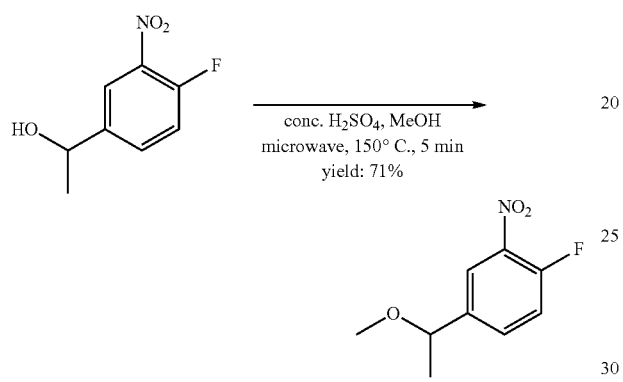

b. 1-fluoro-4-(1-methoxyethyl)-2-nitrobenzene 1-(4-fluoro-3-nitrophenyl)ethanol (870 mg, 4.7 mmol) was dissolved in MeOH (10 ml) and concentrated sulfuric acid (2.5 ml, 47 mmol) was added carefully. The reaction mixture was heated at 150° C. using microwave (Biotage Initiator) for 5 minutes. After cooling to room temperature, the reaction mixture was poured into EtOAc/water. The organic layer was washed with brine, dried over MgSO₄ and evaporated. The resulting material was purified by flash chromatography on silica eluting with 0% to 50% EtOAc/Hexane to afford the title compound (664 mg, yield: 71%). ¹H-NMR (400 MHz, CDCl₃) δ 1.45 (d, 3 H) 3.27 (s, 3 H) 4.36 (q, 1 H) 7.28-7.32 (m, 1 H) 7.56-7.63 (m, 1 H) 7.98-8.04 (m, 1 H)

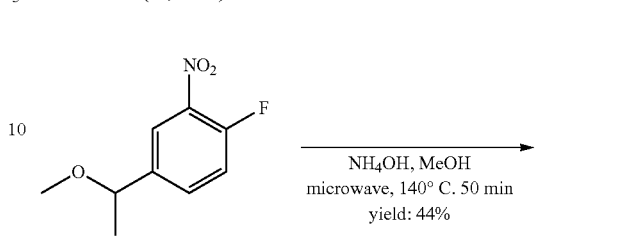

c. 4-(1-methoxyethyl)-2-nitroaniline 1-fluoro-4-(1-methoxyethyl)-2-nitrobenzene (664 mg, 3.33 mmol) was stirred in THF (10 ml). NH₄OH (0.39 ml, 10.0 mmol) was added and the reaction mixture was stirred at room temperature for 2 hours. Further 780 ul of NH₄OH was added and the reaction mixture was heated at 120° C. for 10 minutes using microwave (Biotage Initiator) and then at 140° C. for 50 minutes. After cooling to room temperature, the reaction mixture was poured into EtOAc/water. The organic layer was washed with brine, dried over MgSO₄ and evaporated. The resulting material was purified by flash chromatography on silica eluting with 0% to 50% EtOAc/Hexane to afford the title compound (290 mg, yield: 44%). ¹H-NMR (400 MHz, CDCl₃) δ 1.42 (d, 3 H) 3.22 (s, 3 H) 4.24 (q, 1 H) 6.05 (br. s., 2 H) 6.83 (d, 1 H) 7.38 (dd, 2.01 Hz, 1 H) 8.04 (d, 1 H)

Procedure 2L: Example—157

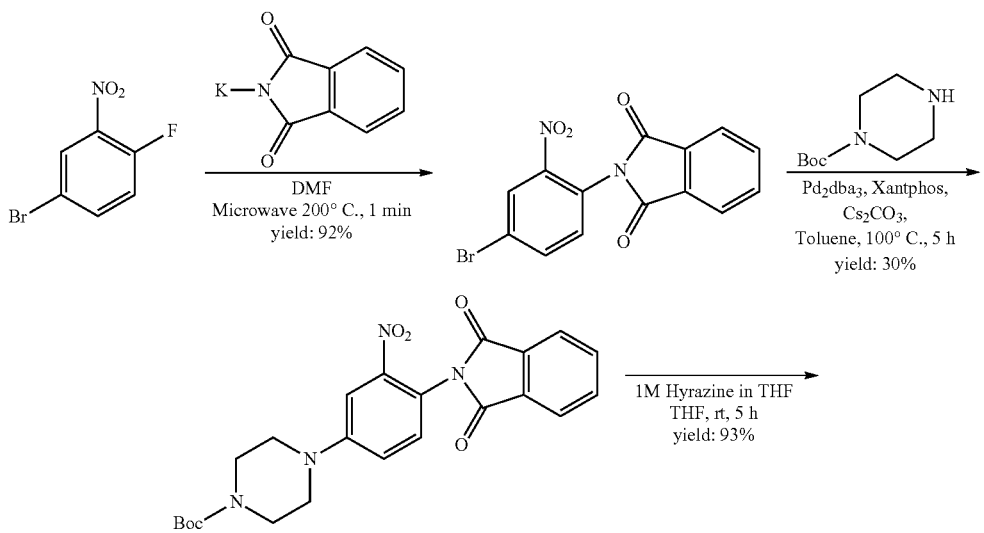

-continued
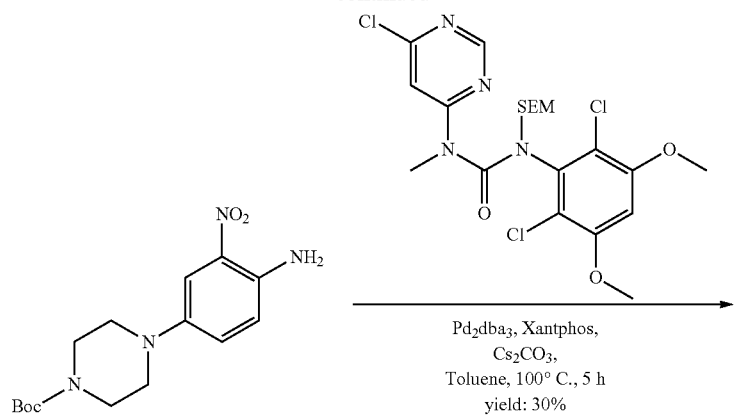
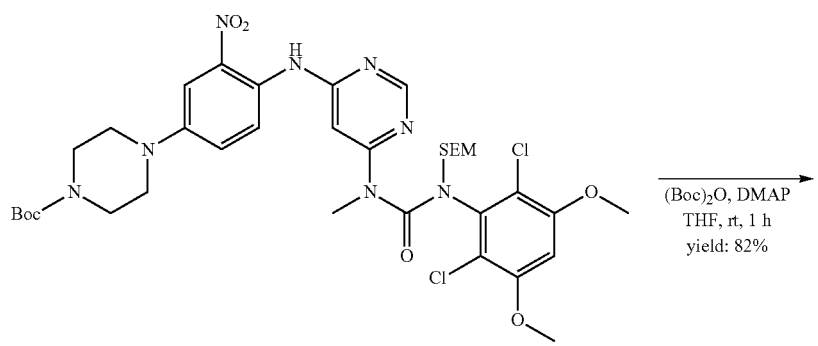
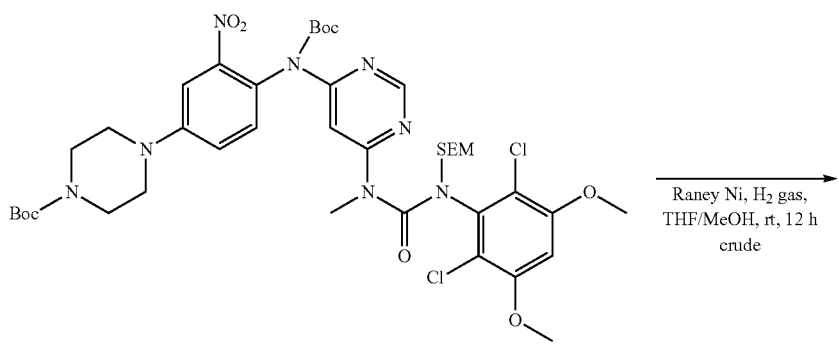
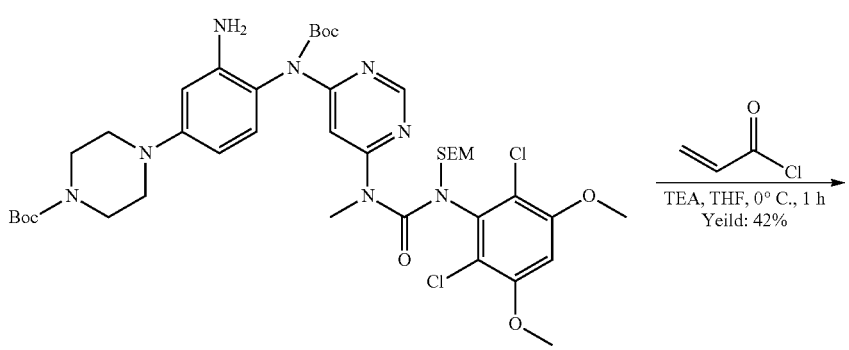

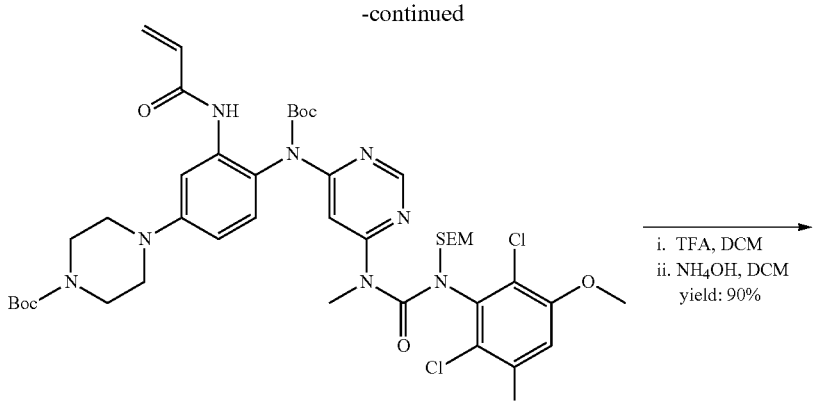

Preparation of N-(2-((6-(3-(2,6-dichloro-3,5-dimethoxyphenyl)-1-methylureido)pyrimidin-4-yl)amino)-5-(piperazin-1-yl)phenyl)acrylamide was collected, washed with water and dried under stream of nitrogen to afford the title compound (2.89 g, yield: 92%). $^1$H-NMR (400 MHz, CDCl$_3$) δ 7.26 (s, 2H) 7.43 (d, 2H) 7.81-7.87 (m, 3H) 7.91 (dd, 2H) 7.95-8.05 (m, 3H) 8.33 (d, 1H)

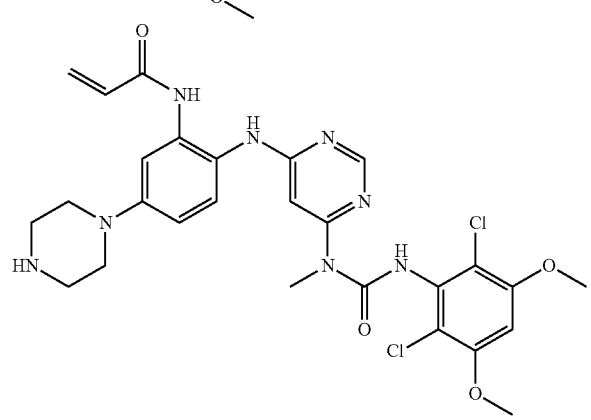

a. 2-(4-bromo-2-nitrophenyl)isoindoline-1,3-dione 4-bromo-1-fluoro-2-nitrobenzene (2.0 g, 9.1 mmol) and potassium 1,3-dioxoisoindolin-2-ide (2.0 g, 10.9 mmol) were placed in microwave vial (0.5-2 ml) and NMP (12.0 ml) was added. The reaction mixture was heated at 200° C. using microwave (Biotage, Initiator) for 1 min. After cooling to rt, the reaction mixture was added dropwise to stirring water which resulted in formation of precipitate. The solid

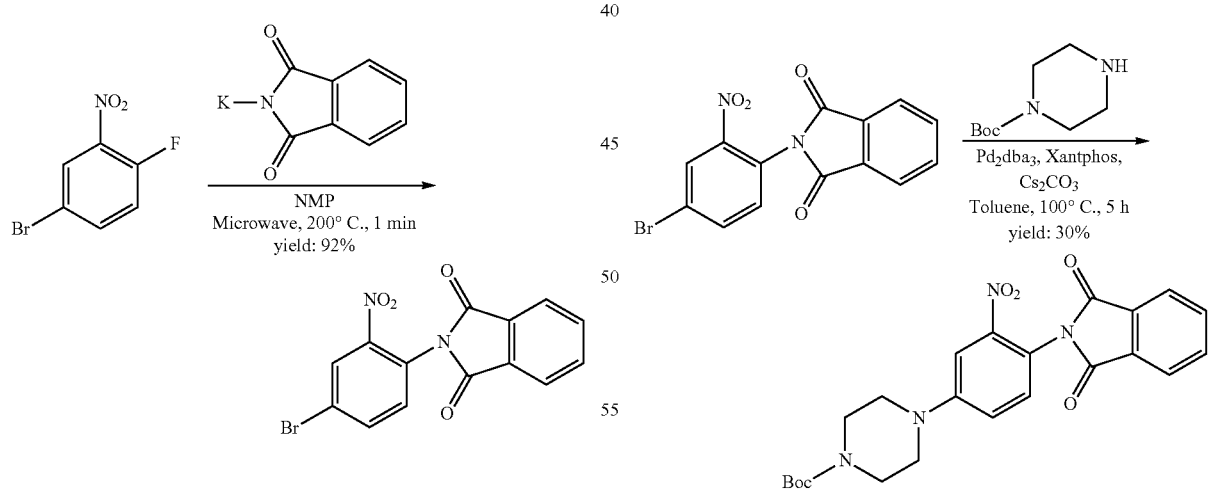

b. tert-butyl 4-(4-(1,3-dioxoisoindolin-2-yl)-3-nitrophenyl)piperazine-1-carboxylate 2-(4-bromo-2-nitrophenyl)isoindoline-1,3-dione (500 mg, 1.4 mmol), tert-butyl piperazine-1-carboxylate (402 mg, 2.2 mmol), Pd$_2$(dba)$_3$ (66.0 mg, 0.07 mmol), Xantphos (83 mg, 0.144 mmol) and Cs$_2$CO$_3$ (939 mg, 2.9 mmol) were placed in reaction vial (microwave reaction vial 10-20 ml) and purged with nitrogen. Toluene (5.0 ml) was added and nitrogen was bubbled for 10 min. The reaction mixture was heated at 100° C. for 5 hours. Heating was stopped and cooled to rt. The reaction mixture was filtered through a pad of celite and filtrate was evaporated. The remaining material was purified by flash chromatography on silica eluting with 20% to 70% EtOAc/Hexane to afford the title compound (275 mg, yield: 42%). ¹H-NMR (400 MHz, CDCl₃) δ 1.51 (s, 6H) 3.28-3.39 (m, 2H) 3.57-3.70 (m, 2H) 7.20-7.24 (m, 1H) 7.35 (d, 1H) 7.66 (d, 1H) 7.75-7.87 (m, 1H) 7.96 (dd, 1H)

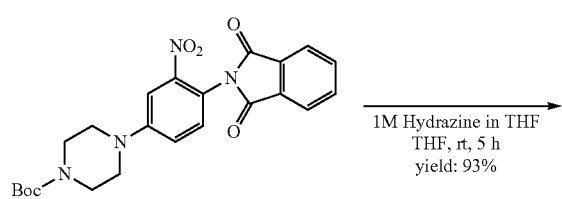

c. tert-butyl 4-(4-amino-3-nitrophenyl)piperazine-1-carboxylate

To a suspension of tert-butyl 4-(4-(1,3-dioxoisoindolin-2-yl)-3-nitrophenyl)piperazine-1-carboxylate 275.4 mg, 0.6 mmol) in THF (5.0 ml) was added 1.0M Hydrazine in THF (1.8 ml, 1.8 mmol) at room temperature. The reaction mixture was stirred at room temperature for 2 hours. The reaction mixture was poured into EtOAc/water and organic layer was washed with brine, dried over MgSO₄ and evaporated. The resulting oil was purified by flash chromatography on silica eluting with 20% to 70% EtOAc/Hexane to afford the title compound (182 mg, 93% yield). ¹H-NMR (400 MHz, DMSO-d₆) δ 1.42 (s, 9H) 2.89-2.99 (m, 4H) 3.44 (d, 4H) 6.98 (d, 1H) 7.22 (s, 2H) 7.26-7.38 (m, 2H)

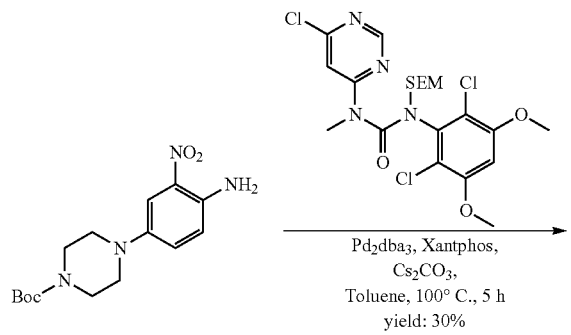

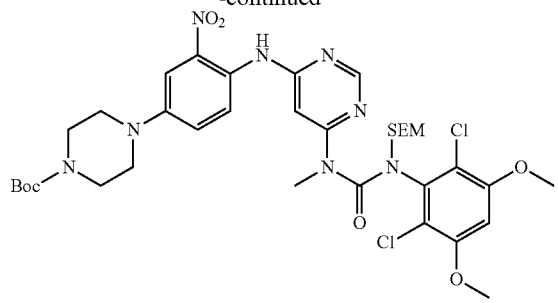

d. tert-butyl 4-(4-((6-(3-(2,6-dichloro-3,5-dimethoxyphenyl)-1-methyl-3-((2-(trimethylsilyl)ethoxy)methy)ureido)pyrimidin-4-yl)amino)-3-nitrophenyl)piperazine-1-carboxylate 1-(6-chloropyrimidin-4-yl)-3-(2,6-dichloro-3,5-dimethoxyphenyl)-1-methyl-3-((2-(trimethylsilyl)ethoxy)methyl)urea (175 mg, 0.34 mmol), tert-butyl 4-(4-amino-3-nitrophenyl)piperazine-1-carboxylate (90 mg, 0.28 mmol), Pd₂(dba)₃ (13 mg, 0.014 mmol), Brettphos (13 mg, 0.028 mmol) and sodium tert-butoxide (54 mg, 0.56 mmol) were placed in a reaction vial (2 to 5 ml) and purged with nitrogen. Toluene (1.0 ml) was added and nitrogen was bubbled for 5 min then the reaction mixture was heated at 100° C. overnight. Heating was stopped and cooled to room temperature. The reaction mixture was filtered through pad of Celite®. The filtrate was evaporated and resulting material was purified by flash chromatography on silica eluting with 20% to 70% EtOAc/Hexane to afford the title compound (102.4 mg, yield: 45%). ¹H-NMR (400 MHz, CDCl₃) δ 0.01 (s, 9 H) 0.85-0.98 (m, 2 H) 1.50 (s, 9 H) 3.03 (s, 3 H) 3.17 (br. s., 4 H) 3.56-3.66 (m, 4 H) 3.75-3.97 (m, 8 H) 5.22 (s, 2 H) 6.50 (s, 1 H) 6.95 (s, 1 H) 7.65 (s, 1 H) 8.46 (s, 1 H)

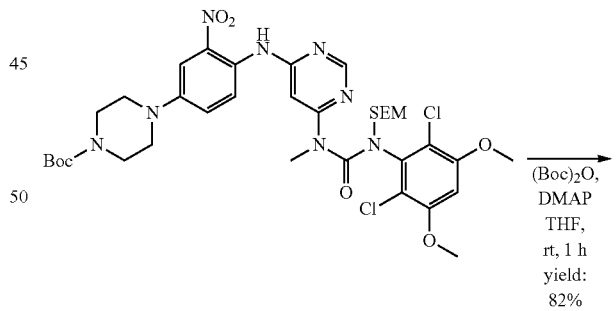

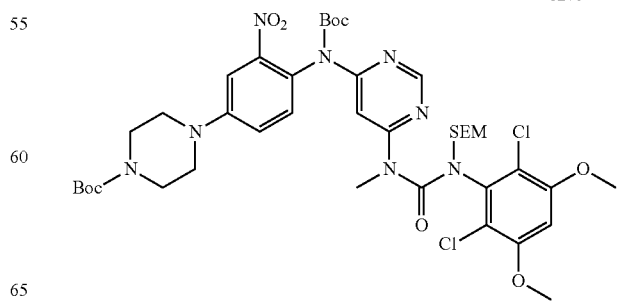

e. tert-butyl 4-(4-((tert-butoxycarbonyl)(6-(3-(2,6-dichloro-3,5-dimethoxyphenyl)-1-methyl-3-((2-(trimethylsilyl)ethoxy)methyl)ureido)pyrimidin-4-yl)amino)-3-nitrophenyl)piperazine-1-carboxylate tert-butyl 4-(4-((6-(3-(2,6-dichloro-3,5-dimethoxyphenyl)-1-methyl-3-((2-(trimethylsilyl)ethoxy)methyl)ureido)pyrimidin-4-yl)amino)-3-nitrophenyl)piperazine-1-carboxylate (162 mg, 0.2 mmol), di-tert-butyl dicarbonate (53 mg, 0.24 mmol) and DMAP (4.9 mg, 0.04 mmol) were stirred in THF (2.0 ml) at room temperature under nitrogen atmosphere for 1 hour. The reaction mixture was poured into EtOAc and water. The organic layer was washed with brine, dried over MgSO$_4$ and evaporated. The resulting material was purified by flash chromatography on silica eluting with 10% to 70% EtOAc/Hexane to afford the title compound (148 mg, yield: 82%). $^1$H-NMR (400 MHz, CDCl$_3$) δ 0.01 (s, 9 H) 0.80-1.04 (m, 2 H) 1.4 (s, 9 H) 1.49 (s, 9 H) 3.12 (s, 3 H) 3.19-3.36 (m, 4 H) 3.50-3.70 (m, 4 H) 3.83-3.92 (m, 9 H) 3.96 (d, 11 H) 5.14 (d, 1 H) 5.42 (d, 1 H) 6.46 (s, 1 H) 7.05-7.19 (m, 2 H) 7.58 (d, 1 H) 8.03 (s, 1 H) 8.29 (s, 1 H)

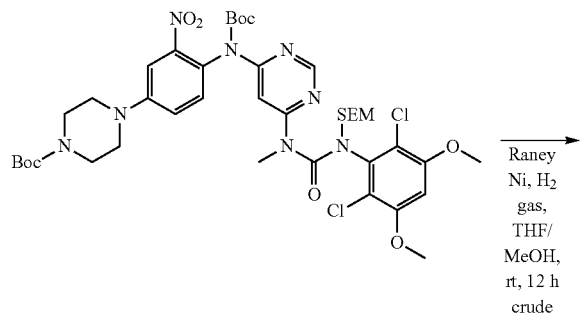

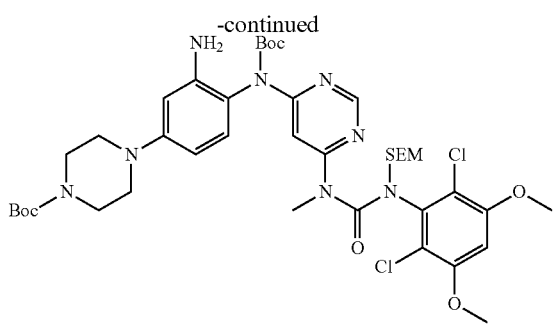

f. tert-butyl 4-(3-amino-4-((tert-butoxycarbonyl)(6-(3-(2,6-dichloro-3,5-dimethoxyphenyl)-1-methyl-3-((2-(trimethylsilyl)ethoxy)methyl)ureido)pyrimidin-4-yl)amino)phenyl)piperazine-1-caroxylate tert-butyl 4-(4-((tert-butoxycarbonyl)(6-(3-(2,6-dichloro-3,5-dimethoxyphenyl)-1-methyl-3-((2-(trimethylsilyl)ethoxy)methyl)ureido)pyrimidin-4-yl)amino)-3-nitrophenyl)piperazine-1-carboxylate (149 mg, 0.164 mmol) was stirred in THF (1.5 ml) and MeOH (1.5 ml). Five drops of Raney Nickel suspension in water was added. The solution was stirred under hydrogen atmosphere at room temperature overnight. The reaction was filtered through a pad of Celite®. and filtrate was concentrated to give crude title compound which was taken to the next step without further purification. ESI-MS: 877 [M+H]$^+$.

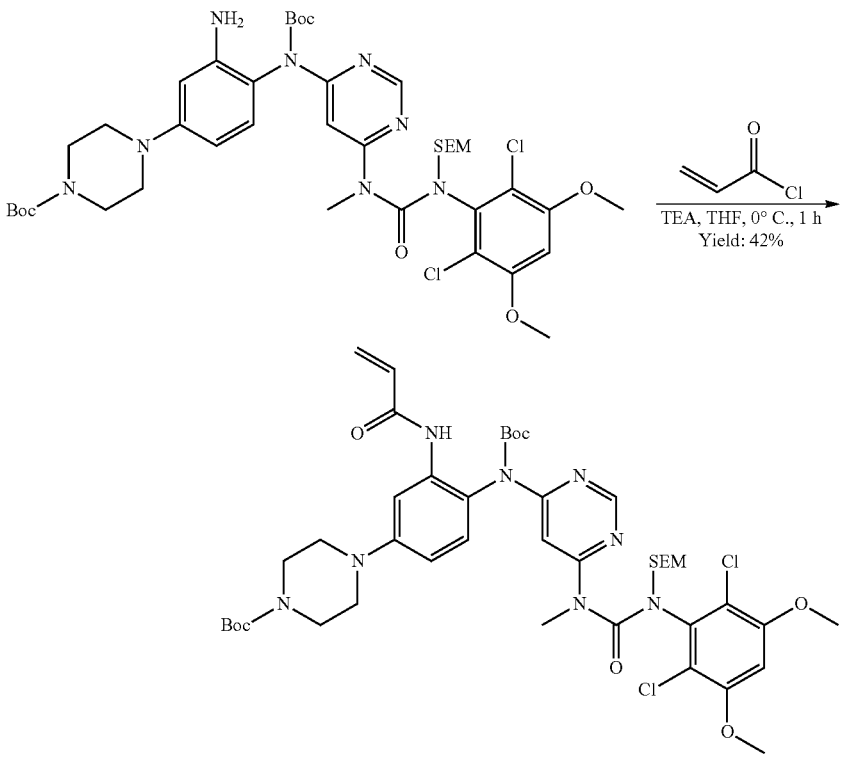

173 g. tert-butyl 4-(3-acrylamido-4-((tert-butoxycarbonyl)(6-(3-(2,6-dichloro-3,5-dimethoxyphenyl)-1-methyl-3-((2-(trimethylsilyl)ethoxy)methyl)ureido)pyrimidin-4-yl)amino)phenyl)piperazine-1-carboxylate Crude tert-butyl 4-(3-amino-4-((tert-butoxycarbonyl)(6-(3-(2,6-dichloro-3,5-dimethoxyphenyl)-1-methyl-3-((2-(trimethylsilyl)ethoxy)methyl)ureido)pyrimidin-4-yl)amino)phenyl)piperazine-1-carboxylate (95 mg, 0.11 mmol) was dissolved in THF (1.5 ml) and stirred over ice bath under nitrogen atmosphere. DIEA (57 µl, 0.30 mmol) followed by acryloyl chloride (13 µl, 0.16 mmol) were added and the reaction mixture was stirred at room temperature for 1 hour. The reaction mixture was poured into EtOAc and brine. The organic. layer was separated, dried over MgSO$_4$ and evaporated. The resulting material was purified by flash chromatography on silica eluting with 30% to 100% EtOAc/Hexane to afford the title compound (47 mg, yield: 47%).
$^1$H-NMR (400 MHz, CDCl$_3$) δ 0.02 (s, 9 H) 0.79-1.04 (m, 2 H) 1.36 (s, 9 H) 1.49 (s, 9 H) 3.08 (s, 4 H) 3.05 (s, 3 H) 3.25 (br. s., 4 H) 3.64 (br. s., 4 H) 3.86 (s, 6 H) 5.27 (s, 1 H) 5.67-5.79 (m, 1 H) 6.15-6.56 (m, 2 H) 6.48 (s, 1 H) 7.03-7.14 (m, 1 H) 7.87-8.09 (m, 2 H) 8.19-8.29 (br. s., 1H) 8.44 (s, 1 H).

174 h. N-(2-((6-(3-(2,6-dichloro-3,5-dimethoxyphenyl)-1-methylureido)pyrimidin-4-yl)amino)-5-(piperazin-1-yl)phenyl)acrylamide tert-butyl 4-(3-acrylamido-4-((tert-butoxycarbonyl)(6-(3-(2,6-dichloro-3,5-dimethoxyphenyl)-1-methyl-3-((2-(trimethylsilyl)ethoxy)methyl)ureido)pyrimidin-4-yl)amino)phenyl)piperazine-1-carboxylate (59 mg, 0.06 mmol) was stirred in DCM (2.0 ml). TFA (97 µl, 1.3 mmol) was added and the mixture was stirred at room temperature for 6 hours. The reaction mixture was evaporated. The remaining residue was dissolved in DCM and washed with saturated NaHCO$_3$, dried over MgSO$_4$ and evaporated. The resulting material was dissolved in THF (2.0 ml) and NH$_4$OH (74 µl, 1.9 mmol) was added. The reaction mixture was stirred at room temperature for 5 minutes. The reaction mixture was evaporated to obtain the title compound (34 mg, yield: 90%) which was taken to the next step without further purification.
$^1$H-NMR (400 MHz, DMSO-d$_6$) δ 2.62 (br. s., 4 H) 3.08-3.27 (m, 7 H) 3.77-4.03 (m, 6 H) 5.72 (d, 1 H) 6.11-6.34 (m, 2 H) 6.40-6.62 (m, 1 H) 6.70-6.98 (m, 2 H) 7.22-7.37 (m, 2 H) 8.32 (s, 1 H) 8.70 (s, 1 H) 9.58 (br. s., 1 H) 12.06 (s, 1 H); ESI-MS: 601 [M+H]$^+$.

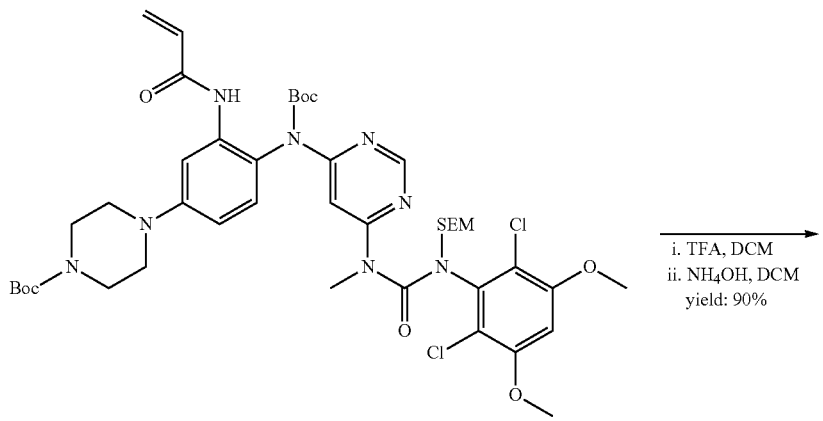

i. TFA, DCM
ii. NH$_4$OH, DCM
yield: 90%

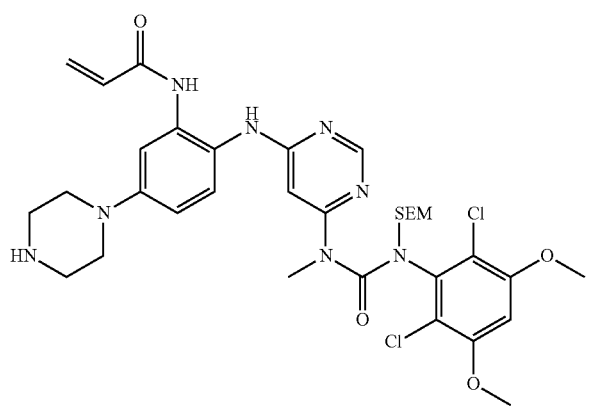

Example—158

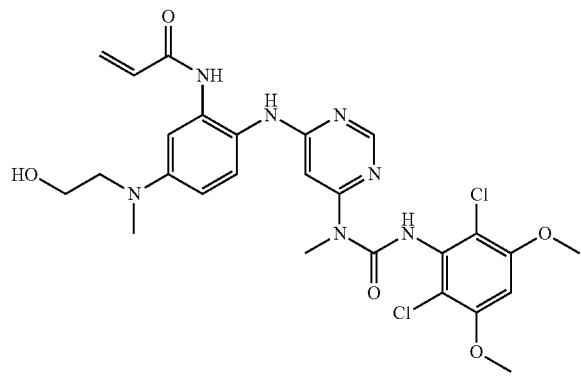

N-(2-((6-(3-(2,6-dichloro-3,5-dimethoxyphenyl)-1-methylureido)pyrimidin-4-yl)amino)-5-((2-hydroxy-ethyl)(methyl)amino)phenyl)acrylamide The compound was synthesized following the approach outlined in Procedure 2L (Example 157), substituting 2-((tert-butyldimethylsilyl)oxy)-N-methylethanamine, Pd(dba)$_2$ and Ruphos in step (b), and Pd(dba)$_2$, Brettphos and sodium tert-butoxide in step (d) to afford the title compound (64 mg, yield: 16% in seven steps) $^1$H-NMR (400 MHz, MeOH-d$_4$) δ 3.04 (s, 3 H) 3.26 (s, 3 H) 3.51 (s, 2 H) 3.69-3.81 (m, 2 H) 3.94 (s, 6 H) 5.71-5.78 (m, 1 H) 6.03-6.10 (m, 1 H) 6.26-6.45 (m, 2 H) 6.72 (d, 1 H) 6.79 (s, 1 H) 7.04-7.10 (m, 1 H) 7.23 (d, 1 H) 8.28 (d, 1 H); ESI-MS: 590 [M+H].

Preparation of 2-((tert-butyldimethylsilyl)oxy)-N-methylethanamine

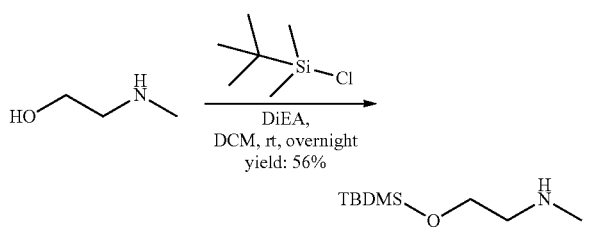

a. 2-((tert-butyldimethylsilyl)oxy)-N-methylethan-amine 2-(methylamino)ethanol (1.0 g, 13.3 mmol) was stirred in DCM (25.0 ml) under atmosphere of nitrogen. DIEA (3.23 ml, 18.6 mmol) followed by tert-butylchlorodimethylsilane (2.0 g, 13.3 mmol) was added and the reaction mixture was stirred at room temperature over night. The reaction mixture was poured into ether/water. The aqueous layer was extracted with ether three times. The combined organic layer was dried over MgSO$_4$ and evaporated and remaining material was dried under high vacuum to afford title compound (1.4 g, yield: 56%). $^1$H-NMR (400 MHz, CDCl$_3$) δ 0.08 (s, 6 H) 0.91 (s, 9 H) 1.93 (br. s., 1 H) 2.48 (s, 3 H) 2.71 (t, 2 H) 3.75 (t, 2 H).

Example—160

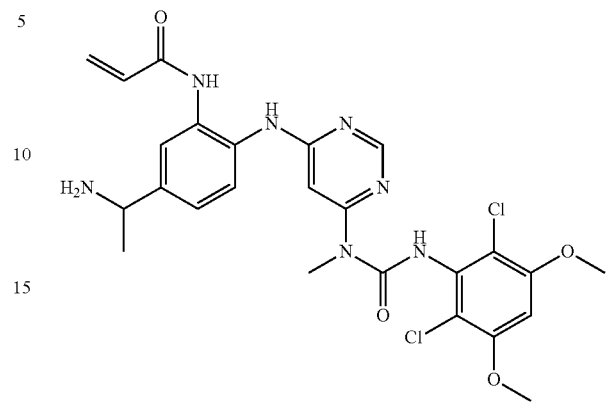

N-(5-(1-aminoethyl)-2-((6-(3-(2,6-dichloro-3,5-di-methoxyphenyl)-1-methylureido)pyrimidin-4-yl)amino)phenyl)acrylamide TFA Salt The compound was synthesized following the approach outlined in Procedure 2G (Example 123) substituting tert-butyl (1-(4-amino-3-nitrophenyl)ethyl)carbamate, Pd(dba)$_2$, Brettphos and sodium tert-butoxide in step (d) to afford the free base which was converted to TFA salt. The free base was dissolved in DCM and 1 equivalent of TFA was added. The mixture was evaporated and trituration with ether afforded the title compound (65 mg, yield: 23% in five steps). $^1$H-NMR (400 MHz, MeOH-d$_4$) δ 1.67 (d, 3 H) 3.33-3.37 (s, 3 H) 3.92-3.97 (s, 6 H) 4.49 (m, 1 H) 5.75-5.83 (m, 1 H) 6.30-6.50 (m, 3 H) 6.81 (s, 1 H) 7.36 (dd, 1 H) 7.69 (d, 1 H) 7.82 (d, 1 H) 8.36-8.43 (m, 1 H); ESI-MS: 560 [M+H].

Preparation of tert-butyl (1-(4-amino-3-nitrophenyl)ethyl)carbamate

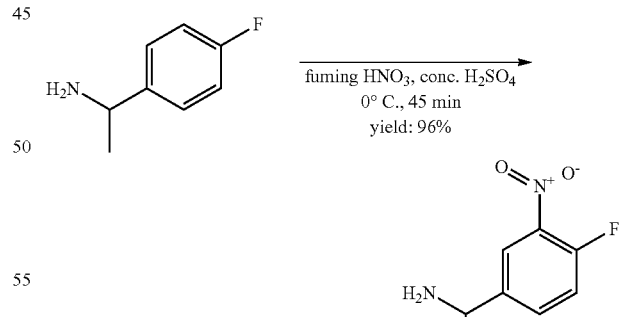

a. 1-(4-fluoro-3-nitrophenyl)ethanamine

Fuming HNO$_3$ (0.48 ml, 10.8 mmol) was added carefully to ice bath cooled concentrated H$_2$SO$_4$ (3.6 ml, 68.2 mmol). To the mixture was added 1-(4-fluorophenyl)ethanamine (1.0 g, 7.2 mmol) dropwise. The reaction mixture was stirred with cooling for 50 minutes. The reaction mixture was poured into ice and basified with 3M NaOH solution (24 ml, 72.00 mmol) to about pH8.0. The alkaline solution was extracted with DCM twice. The combined organic layer was dried over Na$_2$SO$_4$ and evaporated to afford title compound (1.3 g, yield: 96%). $^1$H-NMR (400 MHz, CDCl$_3$) δ 1.41 (d, 6 H) 4.25 (q, 1 H) 7.21-7.26 (m, 1 H) 7.67 (ddd, 1 H) 8.10 (dd, 1 H)

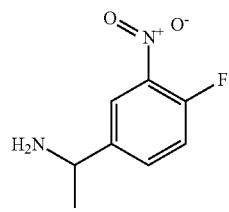

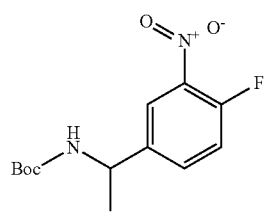

b. tert-butyl (1-(4-fluoro-3-nitrophenyl)ethyl)carbamate

To the suspension of 1-(4-fluoro-3-nitrophenyl)ethanamine (1.3 g, 6.9 mmol) in THF (10.0 ml) was added DIEA (2.4 ml, 13.8 mmol) followed by di-tert-butyl dicarbonate (1.9 ml, 8.3 mmol). The reaction mixture was stirred at room temperature under nitrogen atmosphere for 2 hours. The reaction mixture was poured into EtOAc/water and organic layer was washed with brine, dried over MgSO$_4$ and evaporated. The resulting material was purified by flash chromatography on silica eluting with 10% to 70% EtOAc/Hexane to afford the title compound (1.5 g, yield: 75%). $^1$H-NMR (400 MHz, CDCl$_3$) δ 1.37-1.50 (m, 12 H) 4.81 (br. s., 2 H) 7.23-7.26 (m, 1 H) 7.59 (ddd, 1 H) 8.01 (dd, 1 H).

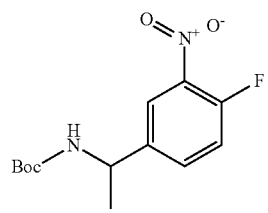

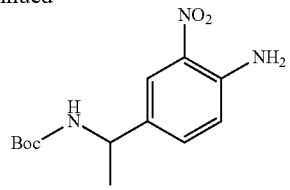

c. tert-butyl (1-(4-amino-3-nitrophenyl)ethylcarbamate

Tert-butyl (1-(4-fluoro-3-nitrophenyl)ethyl)carbamate (500 mg, 1.75 mmol) was stirred in THF (2 ml). NH$_4$OH (0.978 ml, 7.0 mmol) was added and the reaction mixture was heated at 150° C. for 30 minutes using microwave (Biotage Initiator). NH$_4$OH (0.600 ml) was added and then heated at 180° C. After cooling to room temperature, the reaction mixture was poured into EtOAc/water. The organic layer was washed with brine, dried over MgSO$_4$ and evaporated. The resulting material was purified by flash chromatography on silica eluting with 0% to 50% EtOAc/Hexane to afford the title compound (376 mg, yield: 76%) $^1$H-NMR (400 MHz, CDCl$_3$) δ 1.43-1.48 (m, 12 H) 4.71 (br. s., 2 H) 6.79 (d, 1 H) 7.34 (dd, 1 H) 8.05 (d, 1 H).

Example—161

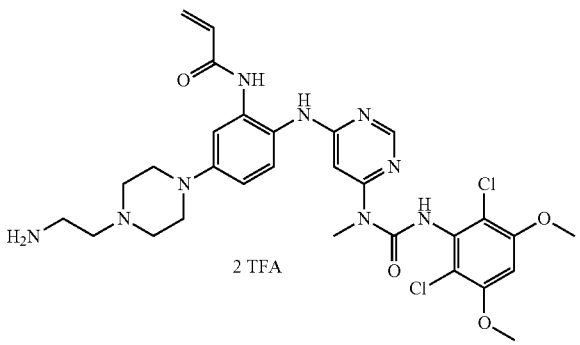 [SMILES: C=CC(=O)Nc1cc(N2CCN(CCN)CC2)ccc1Nc1cc(N(C)C(=O)Nc2c(Cl)c(OC)cc(OC)c2Cl)ncn1]

Preparation of N-(5-(4-(2-aminoethyl)piperazin-1-yl)-2-((6-(3-(2,6-dichloro-3,5-dimethoxyphenyl)-1-methylureido)pyrimidin-4-yl)amino)phenyl)acrylamide 2 TFA Salt

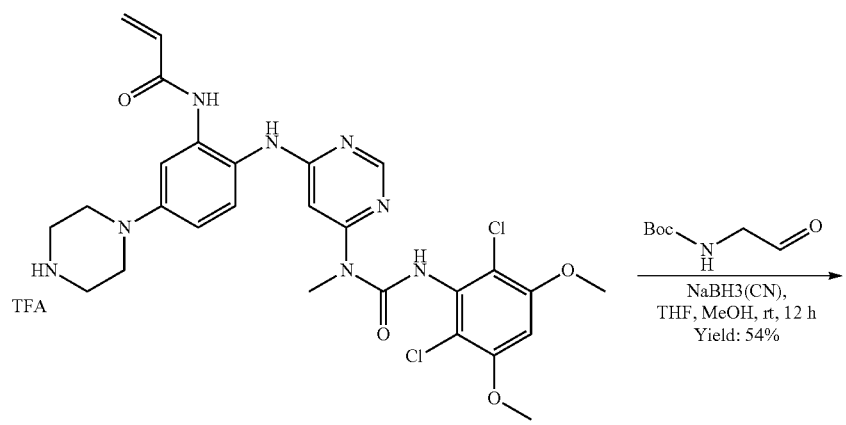

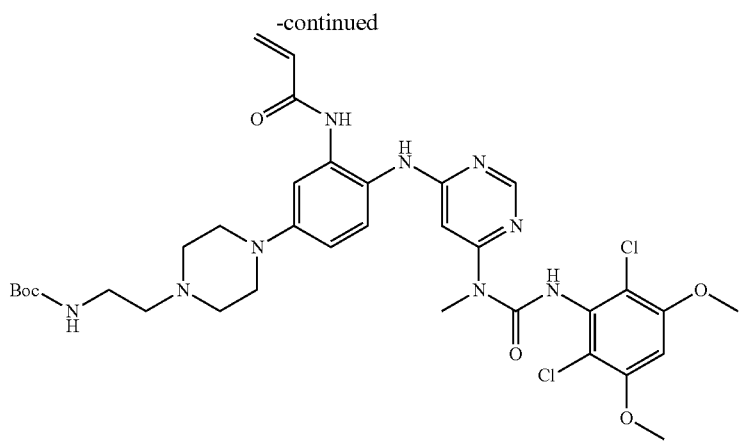

a. tert-butyl (2-(4-(3-acrylamido-4-((6-(3-(2,6-dichloro-3,5-dimethoxyphenyl)-1-methylureido)pyrimidin-4-yl)amino)phenyl)piperazin-1-yl)ethyl)carbamate To the solution of N-(2-((6-(3-(2,6-dichloro-3,5-dimethoxyphenyl)-1-methylureido)pyrimidin-4-yl)amino)-5-(piperazin-1-yl)phenyl)acrylamide 2,2,2-trifluoroacetate (Procedure 2L, Example 157)(30 mg, 0.042 mmol) in THF (1.0 ml) and MeOH (1.0 ml) was added tert-butyl (2-oxoethyl)carbamate (13 mg, 0.08 mmol). The reaction mixture was stirred at room temperature for 10 minutes. Sodium cyanoborohydride (7.0 mg, 0.12 mmol) was added and the reaction mixture was stirred at room temperature over night. Solvent was evaporated and saturated NaHCO₃ solution was added. The mixture was extracted three times with DCM. Combined organic layer was dried over Na₂SO₄ and evaporated. The remaining material was purified by flash chromatography on silica eluting with 0% to 15% MeOH in DCM to afford the title compound (17 mg, yield: 54%) ESI-MS: 744 [M+H]⁺.

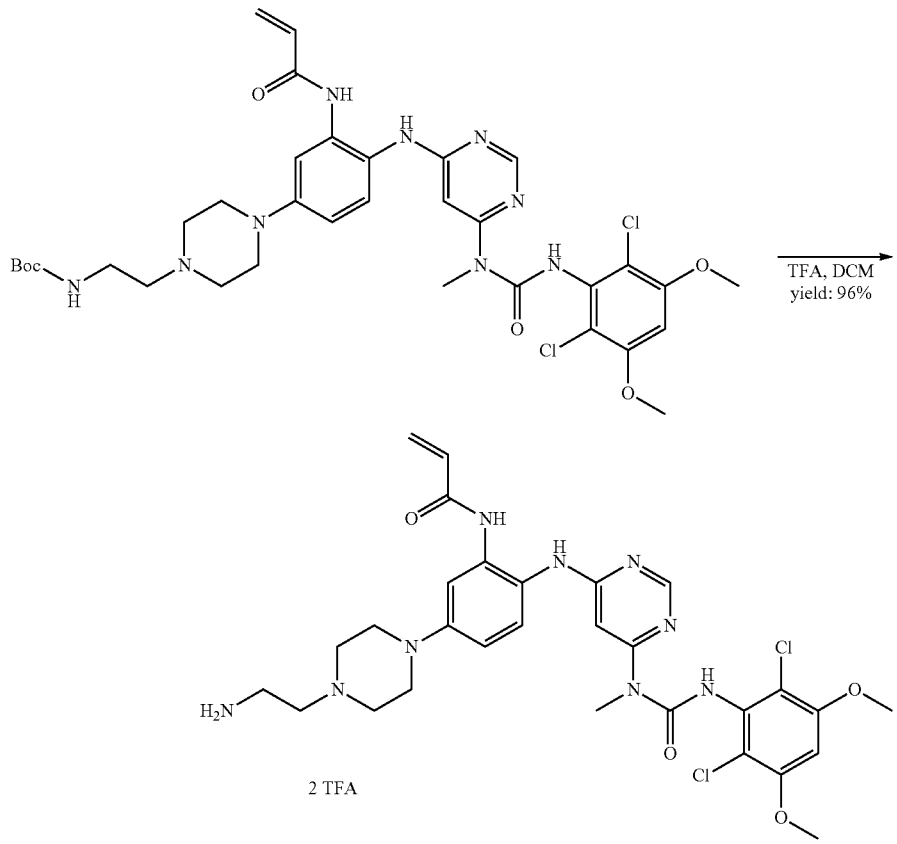

181

N-(5-(4-(2-aminoethyl)piperazin-1-yl)-2-((6-(3-(2,6-dichloro-3,5-dimethoxyphenyl)-1-methylureido)pyrimidin-4-yl)amino)phenyl)acrylamide 2 TFA Salt tert-butyl (2-acrylamido-4-(4-(2-((tert-butoxycarbonyl)amino)ethyl)piperazin-1-yl)phenyl)(6-(3-(2,6-dichloro-3,5-dimethoxyphenyl)-1-methyl-3-((2-(trimethylsilyl)ethoxy)methyl)ureido) pyrimidin-4-yl)carbamate (17 mg, 0.017 mmol) was stirred in DCM (1.0 ml). TFA (200 µl, 2.6 mmol) was added and the mixture was stirred at room temperature for 2 hours. Solvent was evaporated and remaining material was triturated with ether. The resulting solid was collected washed with ether and dried under stream of nitrogen to afford the title compound (15 mg, yield: 96%). $^1$H-NMR (400 MHz, MeOH-$d_4$) δ 2.90 (br. s., 6 H) 3.15-3.22 (m, 2 H) 3.33-3.41 (m, 4 H) 3.94 (s, 6 H) 5.74-5.79 (m, 1 H) 6.17 (s, 1 H) 6.32-6.44 (m, 2 H) 6.81 (s, 1 H) 6.92-6.98 (m, 1 H) 7.35 (d, 2 H) 8.32 (d, 1 H); ESI-MS: 644 [M+H]$^+$.

Example—162

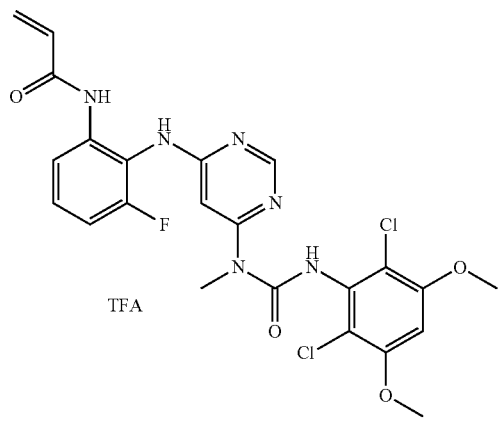 [SMILES: C=CC(=O)Nc1cccc(F)c1Nc1cc(N(C)C(=O)Nc2c(Cl)c(OC)cc(OC)c2Cl)ncn1]

N-(2-((6-(3-(2,6-dichloro-3,5-dimethoxyphenyl)-1-methylureido)pyrimidin-4-yl)amino)-3-fluorophenyl)acrylamide 2,2,2-trifluoroacetate The compound was synthesized following the approach outlined in Procedure 2G (Example 123), substituting 2-fluoro-6-nitroaniline, Pd(dba)$_2$, Brettphos and sodium tert-butoxide in step (d) to afford the free base, which was converted to TFA salt. The free base was dissolved in DCM and 1 equivalent of TFA was added. The mixture was evaporated and trituration with ether afforded the title compound (47 mg, yield: 22% in four steps). $^1$H-NMR (400 MHz, MeOH-$d_4$) δ 3.30 (s, 3 H) 3.93 (s, 6 H) 5.72-5.78 (m, 2 H) 6.21-6.29 (m, 1 H) 6.23 (d, 1 H) 6.27 (d, 1 H) 6.32-6.40 (m, 1 H) 6.56 (dd, 1 H) 6.90 (s, 1 H) 7.10 (t, 1 H) 7.25-7.37 (m, 1 H) 7.76 (d, 1 H) 8.32 (s, 1 H) 8.89 (s, 1 H) 9.66 (s, 1 H) 11.96 (s, 1 H); ESI-MS: 535 [M+H]$^+$

Example—163

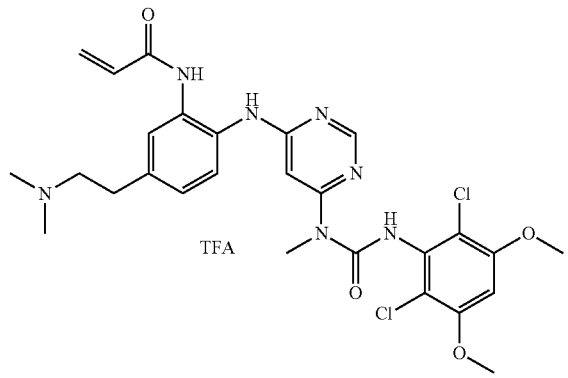

N-(2-((6-(3-(2,6-dichloro-3,5-dimethoxyphenyl)-1-methylureido)pyrimidin-4-yl)amino)-5-(2-(dimethylamino)ethyl)phenyl)acrylamide 2,2,2-trifluoroacetate The compound was synthesized following the approach outlined in Procedure 2G (Example 123), substituting tert-butyl 4-amino-3-nitrophenethylcarbamate (procedure shown below), Pd(dba)$_2$ and Brettphos in step (d) to afford crude TFA salt of the free terminal amine, which was used as-is in the following additional step: To the solution of N-(5-(2-aminoethyl)-2-((6-(3-(2,6-dichloro-3,5-dimethoxyphenyl)-3-(hydroxymethyl)-1-methylureido)pyrimidin-4-yl)amino)phenyl)acrylamide 2,2,2-trifluoroacetate (9.2 mg, 0.014 mmol) in THF (1.0 ml) and MeOH (1.0 ml) was added formaldehyde (5.1 µl, 0.068 mmol). The reaction mixture was stirred at room temperature for 10 minutes. Sodium cyanoborohydride (3.4 mg, 0.055 mmol) was added and the reaction mixture was stirred at room temperature over night. Solvent was evaporated and saturated NaHCO$_3$ solution was added. The mixture was extracted three times with DCM. Combined organic layer was dried over Na$_2$SO$_4$ and evaporated. The remaining material was purified by flash chromatography on silica eluting with 10% to 70% MeOH in DCM to afford free base. To a solution of free base in DCM, TFA (11 µl, 0.014 mmol) was added. The solvent was evaporated and dried under high vacuum to afford the title compound (6.3 mg, yield: 66%). $^1$H-NMR (400 MHz, MeOH-$d_4$) δ 2.97 (s, 6 H) 3.10 (dd, 2 H) 3.34 (s, 3 H) 3.45 (dd, 2 H) 3.94 (s, 6 H) 4.63-4.63 (m, 1 H) 5.76-5.81 (m, 1 H) 6.31-6.48 (m, 3 H) 6.81 (s, 1 H) 7.25 (dd, 1 H) 7.55 (d, 1 H) 7.62-7.72 (m, 1 H) 8.35 (s, 1 H); ESI-MS: 588 [M+H].

Preparation of tert-butyl 4-amino-3-nitrophenethylcarbamate

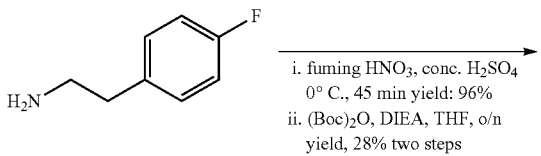

i. fuming HNO$_3$, conc. H$_2$SO$_4$
   0° C., 45 min yield: 96%
ii. (Boc)$_2$O, DIEA, THF, o/n
    yield, 28% two steps

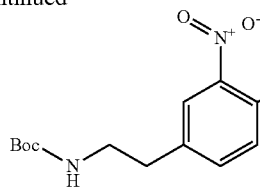

a. tert-butyl 4-fluoro-3-nitrophenethylcarbamate 2-(4-fluorophenyl)ethanamine (1.0 g, 7.2 mmol) was dissolved in concentrated $H_2SO_4$ (4.0 ml, 75 mmol) and cooled over ice bath. Fuming $HNO_3$ (0.48 ml, 10.8 mmol) was added carefully dropwise to the mixture. The reaction mixture was stirred with cooling for 45 minutes and poured into ice. The mixture was basified with 3M NaOH solution (60 ml, 180 mmol) and the alkaline solution was extracted with DCM three times. The combined organic layer was dried over $Na_2SO_4$ and evaporated to afford crude amine. The crude material was dissolved in THF (15.0 ml). Di-tert-butyl dicarbonate (1.7 g, 7.9 mmol) and DIEA (2.5 ml, 14.4 mmol) were added and the reaction mixture was stirred at room temperature for 12 hours. The reaction mixture was poured into water and extracted with EtOAc. The organic layer was washed with brine, dried over $MgSO_4$ and evaporated. The resulting material was purified by flash chromatography on silica eluting with 0% to 20% EtOAc/Hexane to afford title compound (569 mg, yield: 28%). $^1$H-NMR (400 MHz, $CDCl_3$) δ 1.44 (s, 9 H) 2.88 (t, 2 H) 3.40 (d, 2 H) 7.24 (t, 1 H) 7.42-7.54 (m, 1 H) 7.89 (dd, 1 H)

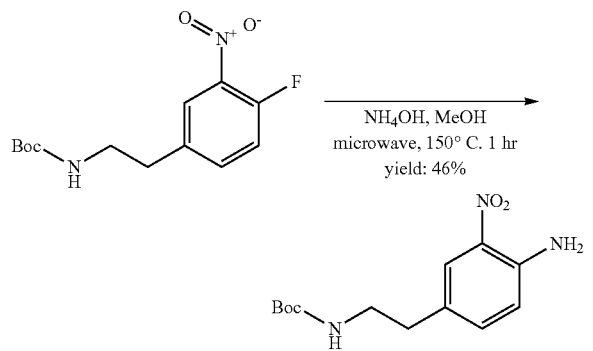

b. tert-butyl 4-amino-3-nitrophenethylcarbamate

Tert-butyl 4-fluoro-3-nitrophenethylcarbamate (569 mg, 2.00 mmol) was stirred in THF (2.64 ml). $NH_4OH$ (2.50 ml, 17.97 mmol) was added and the reaction mixture was heated at 150° C. for 30 minutes using microwave (Biotage Initiator). NH4OH (0.600 ml) was added and then heated at 180° C. After cooling to room temperature, the reaction mixture was poured into EtOAc/water. The organic layer was washed with brine, dried over $MgSO_4$ and evaporated. The resulting material was purified by flash chromatography on silica eluting with 0% to 30% EtOAc/Hexane to afford the title compound (257 mg, yield: 46%) $^1$H-NMR (400 MHz, $CDCl_3$) δ 1.44 (s, 9 H) 2.73 (t, J=7.03 Hz, 2 H) 3.34 (m, 2 H) 4.46-4.62 (m, 1 H) 6.78 (d, J=8.53 Hz, 1 H) 7.24 (dd, J=8.53, 1.76 Hz, 1 H) 7.94 (d, J=1.76 Hz, 1 H).

Example—164

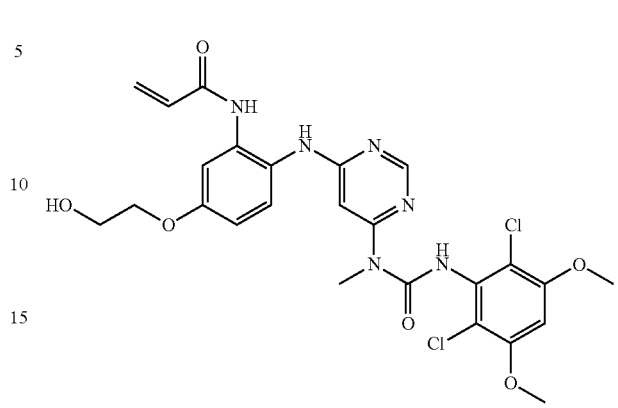

N-(2-((6-(3-(2,6-dichloro-3,5-dimethoxyphenyl)-1-methylureido)pyrimidin-4-yl)amino)-5-(2-(dimethylamino)ethyl)phenyl)acrylamide 2,2,2-trifluoroacetate The compound was synthesized following the approach outlined in Procedure 2L (Example 157), substituting 2-nitro-4-(2-((tetrahydro-2H-pyran-2-yl)oxy)ethoxy)aniline (preparation shown below) and sodium tert-butoxide in step (d) to afford the title compound (7 mg, yield: 2.7% over four steps). $^1$H-NMR (400 MHz, MeOH-$d_4$) δ 3.28 (s, 3 H) 3.88-3.97 (m, 8 H) 4.06-4.14 (m, 2 H) 5.76 (dd, 1 H) 6.12 (s, 1 H) 6.32-6.46 (m, 2 H) 6.79 (s, 1 H) 6.91 (dd, 1 H) 7.34-7.41 (m, 2 H) 8.31 (d, 1 H); ESI-MS: 577 $[M+H]^+$.

Preparation of 2-nitro-4-(2-((tetrahydro-2H-pyran-2-yl)oxy)ethoxy)aniline

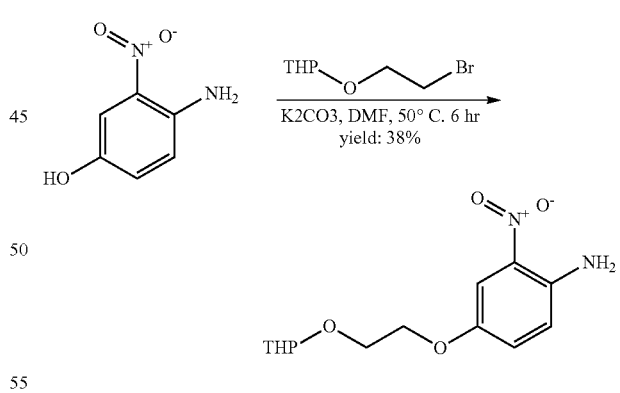

a. 2-nitro-4-(2-((tetrahydro-2H-pyran-2-yl)oxy)ethoxy)aniline 4-amino-3-nitrophenol (2.0 g, 12.977 mmol) was dissolved in DMF (20 ml) and Potassium carbonate (3.59 g, 25.953 mmol) was added. To the mixture was added 2-(2-bromoethoxy)tetrahydro-2H-pyran (2.55 ml, 16.87 mmol) and the reaction mixture was stirred at 50° C. for 6 hours and then for 3 days at room temperature. The reaction mixture was poured into EtOAc/brine. The aqueous layer was extracted twice with EtOAc. The combined organic layer was washed with brine three times, dried over MgSO4 and evaporated. The resulting material was purified by flash chromatography on silica eluting with 5% to 40% EtOAc/Hexane to afford title compound (1.4 g, yield: 38%). ¹H-NMR (400 MHz, CDCl₃) 1.51-1.68 (m, 4 H) 1.71-1.89 (m, 2 H) 3.46-3.61 (m, 1 H) 3.72-3.99 (m, 2 H) 4.03-4.24 (min, 3 H) 4.64-4.79 (m, 1 H) 6.78 (d, 1 H) 7.09-7.17 (m, 1 H) 7.60 (d, 1 H).

Example—165

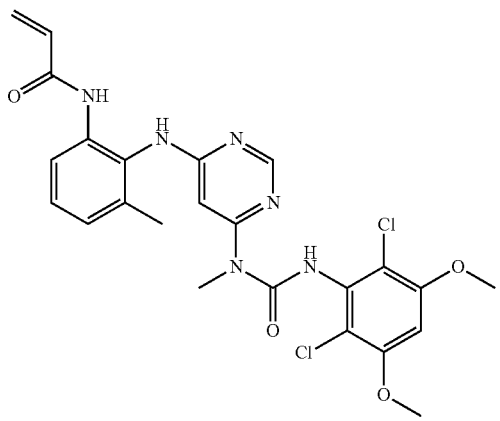 [SMILES: C=CC(=O)Nc1cccc(C)c1Nc1cc(N(C)C(=O)Nc2c(Cl)c(OC)cc(OC)c2Cl)ncn1]

N-(2-((6-(3-(2,6-dichloro-3,5-dimethoxyphenyl)-1-methylureido)pyrimidin-4-yl)amino)-3-methylphenyl)acrylamide The compound was synthesized following the approach outlined in Procedure 2G (Example 123), substituting 2-methyl-6-nitroaniline, Pd(dba)₂, Brettphos and sodium tert-butoxide in step (d) to afford the title compound (3.0 mg, yield: 6% in five steps). ¹H-NMR (400 MHz, MeOH-d₄) δ 3.52 (m, 3 H) 3.95 (m, 6 H) 5.69 (dd, 1 H) 6.21 (dd, 1 H) 6.46 (dd, 1 H) 6.64 (d, 1 H) 6.73 (d, 1 H) 6.82 (s, 1 H) 7.11 (t, 1 H) 8.06 (d, 1 H) 8.55 (d, 1H); ESI-MS: 531 [M+H]⁺

Example—166

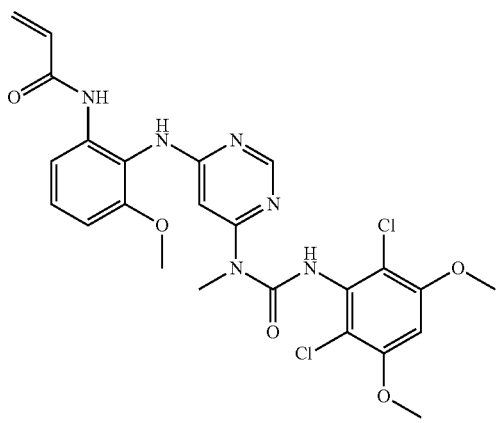 [SMILES: C=CC(=O)Nc1cccc(OC)c1Nc1cc(N(C)C(=O)Nc2c(Cl)c(OC)cc(OC)c2Cl)ncn1]

N-(2-((6-(3-(2,6-dichloro-3,5-dimethoxyphenyl)-1-methylureido)pyrimidin-4-yl)amino)-3-methoxyphenyl)acrylamide The compound was synthesized following the approach outlined in Procedure 2G (Example 123), substituting 2-methoxy-6-nitroaniline, Pd(dba)₂, Brettphos and sodium tert-butoxide in step (d) to afford the title compound (33.0 mg, yield: 6.1% in five steps). ¹H-NMR (400 MHz, MeOH-d₄) δ 3.76 (s, 3 H) 3.93 (s, 6 H) 5.70 (dd, 1 H) 6.23 (d, 1 H) 6.52 (d, 1 H) 6.88-6.95 (m, 2 H) 7.27 (t, 1 H) 7.44-7.56 (m, 1 H) 8.28 (s, 1 H) 8.57 (br. s., 1 H) 9.40-9.57 (m, 1 H) 12.15 (s, 1 H); ESI-MS: 547 [M+H]⁺

Example—167

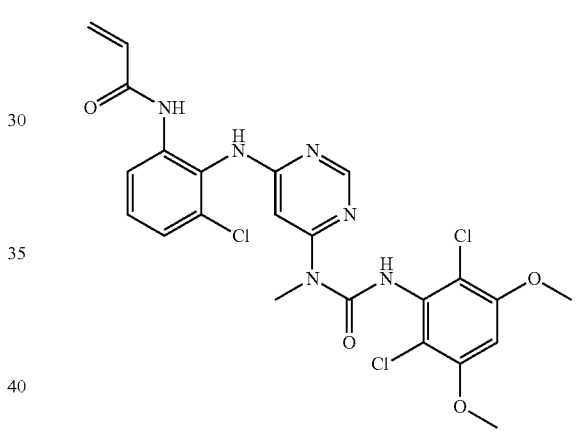

N-(3-chloro-2-((6-(3-(2,6-dichloro-3,5-dimethoxyphenyl)-1-methylureido)pyrimidin-4-yl)amino)phenyl)acrylamide The compound was synthesized following the approach outlined in Procedure 2G (Example 123), substituting 2-chloro-6-nitroaniline, Pd(dba)₂, Brettphos and sodium tert-butoxide in step (d) to afford the title compound (11.0 mg, yield: 5% in five steps). ¹H-NMR (400 MHz, MeOH-d₄) δ 3.29 (s, 3 H) 3.94 (s, 6 H) 5.71-5.75 (m, 1 H) 6.23 (dd, 1 H) 6.56 (dd, 1 H) 6.90 (s, 1 H) 7.31-7.39 (m, 2 H) 7.94 (d, 1 H) 8.30 (s, 1 H) 9.01 (s, 1 H) 9.51-9.70 (m, 1 H) 12.04 (s, 1 H); ESI-MS: 551 [M+H]⁺.

Example—168

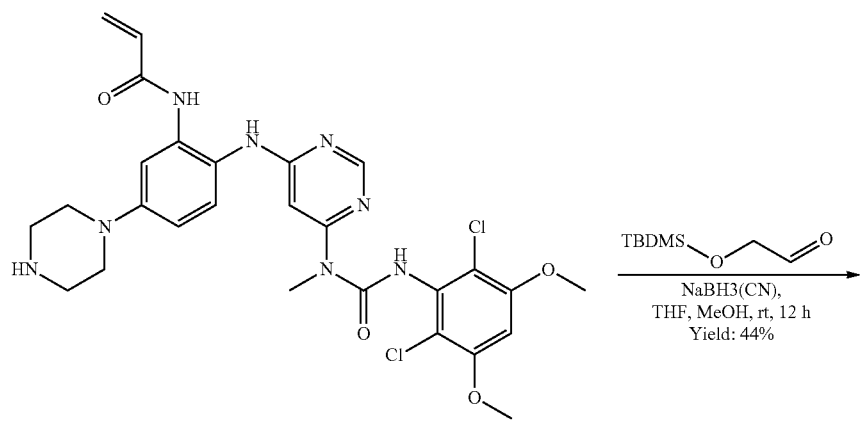

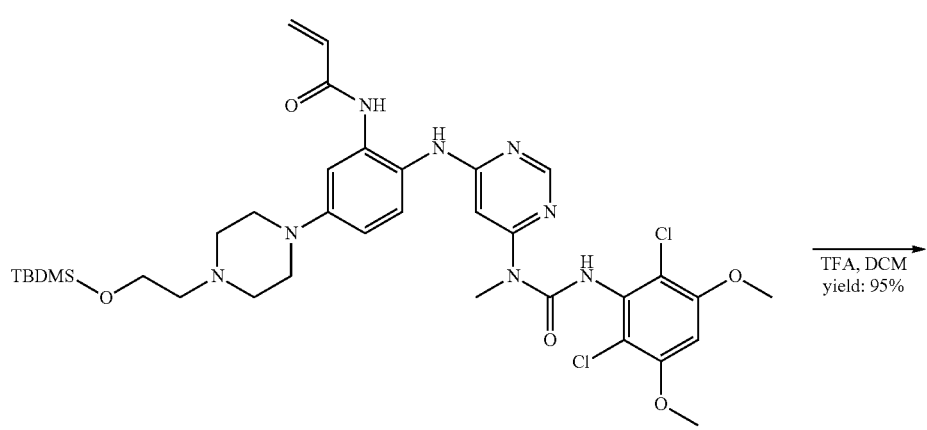

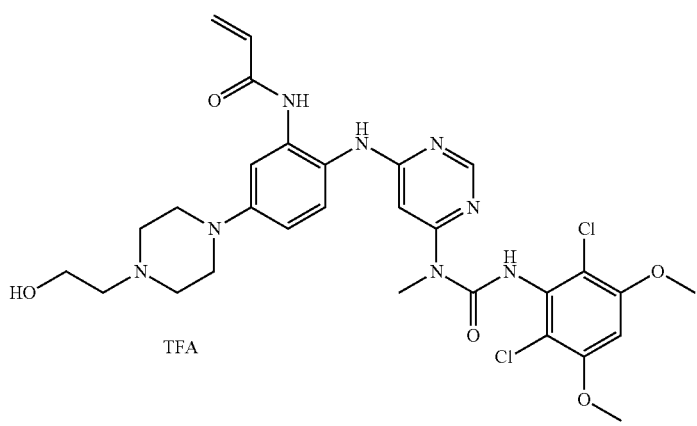

Preparation of N-(2-((6-(3-(2,6-dichloro-3,5-dimethoxyphenyl)-1-methylureido)pyrimidin-4-yl)amino)-5-(4-(2-hydroxyethyl)piperazin-1-yl)phenyl) acrylamide TFA Salt The compound was synthesized following the approach outlined in Example 161, substituting 2-(((tert-butyldimethylsilyl)oxy)acetaldehyde in step (a) to afford the title compound (13 mg, yield: 42% two steps) $^1$H-NMR (400 MHz, MeOH-d$_4$) δ 3.14-3.20 (m 2 H) 3.35-3.37 (m, 2 H) 3.73-3.76 (m, 2 H) 3.84-3.96 (m, 10 H) 5.75-5.79 (m, 1 H) 6.24 (s, 1 H) 6.37-6.47 (m, 2 H) 6.81 (s, 1 H) 6.99 (dd, 1 H) 7.37-7.46 (m, 2 H) 8.34-8.36 (m, 1 H); ESI-MS: 645 [M+H]$^+$.

Example—170

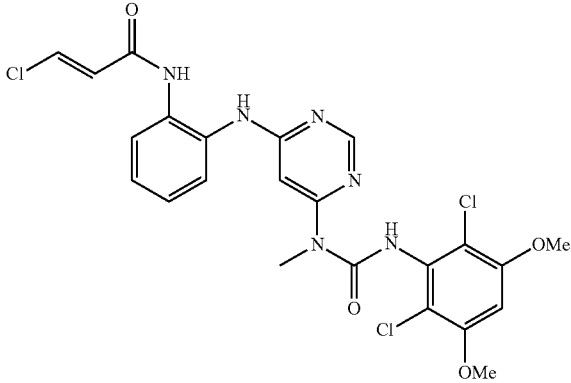 [SMILES: COc1cc(OC)c(Cl)c(NC(=O)N(C)c2cc(Nc3ccccc3NC(=O)/C=C/Cl)ncn2)c1Cl]

(E)-3-chloro-N-(2-((6-(3-(2,6-dichloro-3,5-dimethoxyphenyl)-1-methylureido)pyrimidin-4-yl)amino)phenyl)acrylamide The title compound was synthesized following the approach outlined in Procedure 2A (Example 100), modifying step (i) to the following procedure: To a solution of 1-(6-((2-aminophenyl)amino)pyrimidin-4-yl)-3-(2,6-dichloro-3,5-dimethoxyphenyl)-1-methylurea (10 mg, 0.022 mmol), triethylamine (10.9 mg, 0.11 mmol), and (E)-3-chloroacrylic acid (2.76 mg, 0.026 mmol) in DCM (0.4 ml, 6.22 mmol), cooled to 0° C., was added 2,4,6-tripropyl-1,3,5,2,4,6-trioxatriphosphinane 2,4,6-trioxide (0.023 ml, 0.039 mmol, 50% solution in EtOAc). The resulting mixture was stirred at room temperature for 4h and concentrated. The remaining residue was purified by silica gel flash chromatography to obtain the title compound (7.2 mg, yield: 61%). $^1$HNMR (400 MHz, CDCl3) δ 3.30 (s, 3 H) 3.90 (s, 6 H) 6.02 (s, 1 H) 6.36 (d, J=12.92 Hz, 1 H) 6.49 (s, 1 H) 7.21-7.33 (m, 2 H) 7.36-7.50 (m, 2 H) 7.75 (d, J=6.53 Hz, 1 H) 7.93 (br. s., 1 H) 8.41 (s, 1 H) 12.50 (s, 1 H); MS (ESI): 551.0 [M+H]$^+$

Example—171

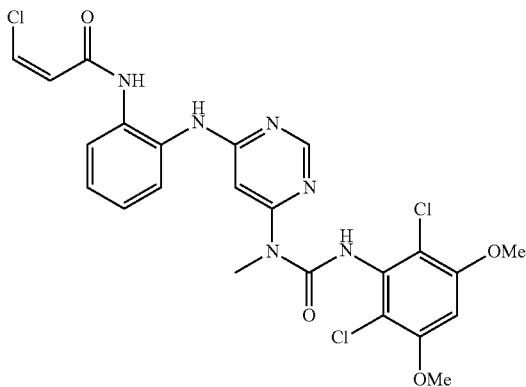 [SMILES: COc1cc(OC)c(Cl)c(NC(=O)N(C)c2cc(Nc3ccccc3NC(=O)/C=C\Cl)ncn2)c1Cl]

(Z)-3-chloro-N-(2-((6-(3-(2,6-dichloro-3,5-dimethoxyphenyl)-1-methylureido)pyrimidin-4-yl)amino)phenyl)acrylamide The title compound was synthesized following the approach outlined in Procedure 2A (Example 100), modifying step (i) to the following procedure: To a solution of 1-(6-((2-aminophenyl)amino)pyrimidin-4-yl)-3-(2,6-dichloro-3,5-dimethoxyphenyl)-1-methylurea (20 mg, 0.043 mmol), triethylamine (21.8 mg, 0.22 mmol), and (Z)-3-chloroacrylic acid (5.5 mg, 0.052 mmol) in DCM (0.86 ml, 13.3 mmol), cooled to 0° C. was added 2,4,6-tripropyl-1,3,5,2,4,6-trioxatriphosphinane 2,4,6-trioxide (49 mg, 0.78 mmmol, 50% solution of EtOAc). The resulting mixture was stirred at room temperature for 2 h and concentrated. The residue was purified by silica gel column chromatography to obtain the title compound (15 mg, yield: 63%). $^1$H NMR (400 MHz, CDCl3) δ X; MS (ESI): 551.0 [M+H]$^+$.

Example—172

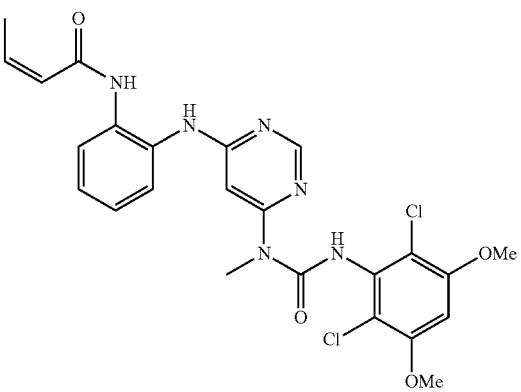 [SMILES: C/C=C\C(=O)Nc1ccccc1Nc1cc(N(C)C(=O)Nc2c(Cl)c(OC)cc(OC)c2Cl)ncn1]

(Z)—N-(2-((6-(3-(2,6-dichloro-3,5-dimethoxyphenyl)-1-methylureido)pyrimidin-4-yl)amino)phenyl)but-2-enamide The title compound was synthesized following the approach outlined in Procedure 2A (Example 100), modifying step (i) to the following procedure: To a solution of 1-(6-((2-aminophenyl)amino)pyrimidin-4-yl)-3-(2,6-dichloro-3,5-dimethoxyphenyl)-1-methylurea (20 mg, 0.043 mmol), triethylamine (21.8 mg, 0.22 mmol), and (Z)-but-2-enoic acid (4.5 mg, 0.052 mmol) in DCM (0.86 ml, 13.3 mmol) was added a solution of 2,4,6-tripropyl-1,3,5,2,4,6-trioxatriphosphinane 2,4,6-trioxide (49.4 mg, 0.78 mmol, 50% solution EtOAc) at 0° C., and the resulting mixture was stirred at room temperature for 2 h. The mixture was concentrated and the residue was purified by silica gel column to obtain the title compound (8.5 mg, yield: 37%). 1H NMR (400 MHz, CDCl3) δ 2.20 (dd, J=7.28, 1.76 Hz, 3 H) 3.30 (s, 3 H) 3.92 (s, 6 H) 5.85 (dd, J=11.42, 1.76 Hz, 1 H) 5.99 (s, 1 H) 6.29 (dd, J=11.36, 7.34 Hz, 1 H) 6.52 (s, 1 H) 7.23-7.34 (m, 2 H) 7.46 (d, J=7.40 Hz, 1 H) 7.55 (br. s., 1 H) 7.78 (d, J=7.53 Hz, 1 H) 8.40 (d, J=0.88 Hz, 1 H) 12.50 (s, 1 H); MS (ESI): 531.3 [M+H]$^+$.

Example—175

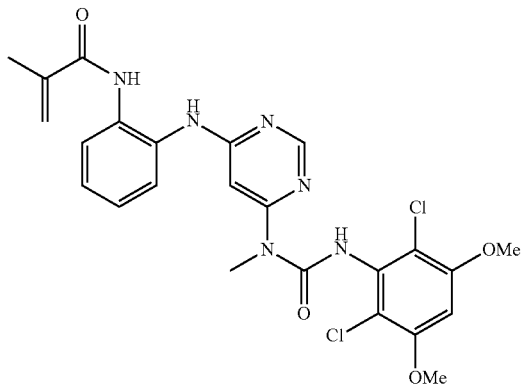 [SMILES: C=C(C)C(=O)Nc1ccccc1Nc1cc(N(C)C(=O)Nc2c(Cl)c(OC)cc(OC)c2Cl)ncn1]

(S,Z)—N-(2-((6-(3-(2,6-dichloro-3,5-dimethoxyphenyl)-1-methylureido)pyrimidin-4-yl)amino)phenyl)-4-hydroxypent-2-enamide The compound was synthesized following the approach outlined in Procedure 2G (Example 123), substituting 2-nitroaniline in step (d) and methacryloyl chloride in step (g) to afford the title compound (13 mg, yield: 72%). 1 H NMR (400 MHz, CDCl3) 2.03 (br. s., 3 H) 3.31 (s, 3 H) 3.92 (s, 6 H) 5.49 (s, 1 H) 5.81 (s, 1 H) 6.00 (s, 1 H) 6.53 (s, 1 H) 7.29 (m, 3 H) 7.44 (d, J=7.91 Hz, 1 H) 7.83 (d, J=7.53 Hz, 1 H) 7.92 (s, 1 H) 8.41 (s, 1 H) 12.34 (s, 1 H). MS (ESI): 531.1 [M+H]$^+$.

Example—181

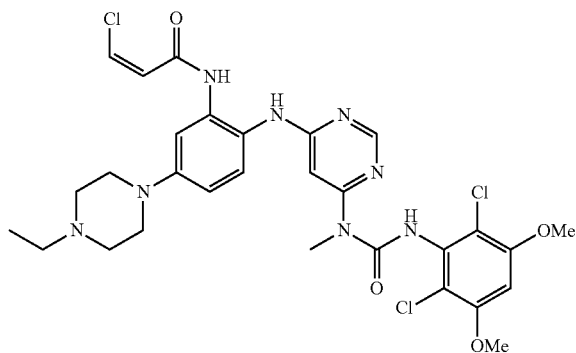 [SMILES: CCN1CCN(c2ccc(Nc3cc(N(C)C(=O)Nc4c(Cl)c(OC)cc(OC)c4Cl)ncn3)c(NC(=O)/C=C\Cl)c2)CC1]

(Z)-3-chloro-N-(2-((6-(3-(2,6-dichloro-3,5-dimethoxyphenyl)-1-methylureido)pyrimidin-4-yl)amino)-5-(4-ethylpiperazin-1-yl)phenyl)acrylamide The title compound was synthesized following the approach outlined in Procedure 2C (Example 108), modifying step (g) to the following procedure: To a solution of 1-(6-((2-amino-4-(4-ethylpiperazin-1-yl)phenyl)amino)pyrimidin-4-yl)-3-(2,6-dichloro-3,5-dimethoxyphenyl)-1-methylurea (11 mg, 0.019 mmol), triethylamine (9.67 mg, 0.096 mmol), and (Z)-3-chloroacrylic acid (2.43 mg, 0.023 mmol) in DCM (0.4 ml, 6.21 mmol) was added a solution of 2,4,6-tripropyl-1,3,5,2,4,6-trioxatriphosphinane 2,4,6-trioxide (21.9 mg, 0.034 mmol) at 0° C., and the resulting mixture was stirred at room temperature for 30 min. The mixture was concentrated and the residue was purified by silica gel column to obtain the title compound (7.5 mg, yield: 59%). $^1$H NMR (400 MHz, CDCl3) δ 1.29 (t, J=8.0 Hz, 3 H) 2.90 (br. s., 4 H) 3.27 (s, 3 H) 3.45 (t, J=4.64 Hz, 4 H) 3.91 (s, 6 H) 5.90 (s, 1 H) 6.32 (d, J=8.41 Hz, 1 H) 6.52 (s, 1 H) 6.59 (d, J=8.41 Hz, 1 H) 6.73 (dd, J=8.78, 2.76 Hz, 1 H) 7.09 (br. s., 1 H) 7.24 (s, 2 H) 7.83 (br. s., 1 H) 8.36 (s, 1 H) 8.69 (br. s., 1 H) 12.52 (s, 1 H); MS (ESI): 663.1 [M+H]$^+$.

Example—185

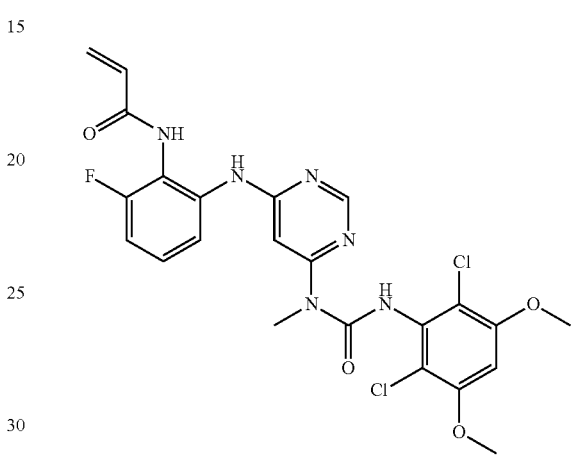

N-(2-((6-(3-(2,6-dichloro-3,5-dimethoxyphenyl)-1-methylureido)pyrimidin-4-yl)amino)-6-fluorophenyl)acrylamide The compound was synthesized following the approach outlined in Procedure 2G (Example 123), substituting 3-fluoro-2-nitroaniline in step (d), omitting step (e), and modifying step (g) to the following procedure: To a solution of 1-(6-((2-amino-3-methylphenyl)amino)pyrimidin-4-yl)-3-(2,6-dichloro-3,5-dimethoxyphenyl)-1-methyl-3-((2-(trimethylsilyl)ethoxy)methyl)urea (31 mg, 0.051 mmol), diisopropyl ethylamine (13.1 mg, 0.103 mmol), and acrylic acid (39.9 mg, 0.055 mmol) in DCM (1 ml, 15.54 mmol) was added a solution of 2,4,6-tripropyl-1,3,5,2,4,6-trioxatriphosphinane 2,4,6-trioxide (48.1 mg, 0.076 mmol, 50% solution EtOAc) at 0° C., and the resulting mixture was stirred at room temperature for 2 h. The mixture was concentrated and the residue was purified by silica gel column to obtain the SEM protected title compound (24 mg, yield: 71% in three steps). Following the final step (g), the title compound was isolated (12 mg, yield: 62%). $^1$H-NMR (400 MHz, CDCl$_3$) δ 3.40 (s, 3 H) 3.93 (m, 6 H) 5.91 (d, 1 H) 6.20 (s, 1 H) 6.30-6.45 (m, 1 H) 6.50-6.58 (m, 2 H) 7.01 (t, 1 H) 7.28-7.35 (m, 1 H) 7.42-7.63 (m, 2 H) 8.41 (s, 1 H) 12.43 (br. s., 1 H); ESI-MS: 535 [M+H]$^+$.

Assays of Biological Activity

Assay of Binding to FGFR4. Purified, recombinant FGFR4 was pre-incubated with 10 μM compound overnight at 4° C., or for 1 hour at room temperature. Following pre-incubation, protein samples were separated using SDS-PAGE and gels were stained with SimplyBlue™ SafeStain (Life Technologies, Grand Island, N.Y.). FGFR bands were cut out and digested using an In-Gel Tryptic Digestion Kit (Thermo Scientific, Waltham, Mass.). Digested samples were run on a Thermo Scientific Q Exactive™ LCMS using reverse phase separation and tandem mass spectrometry to identify modified peptides.

Alternatively, following pre-incubation FGFR4 was concentrated and buffer exchanged on an OPTI-TRAP protein concentrating and desalting C4 column (Optimize Technologies). Protein was eluted in acetonitrile containing 0.1% formic acid and run by direct injection on a Thermo Scientific Q Exactive™ LCMS to identify modified, intact FGFR4.

Results provided below in Table 2 confirm covalent adduct formation of the tested compounds with the peptides by correspondence of the expected mass of the peptide-ligand adduct with the mass observed.

TABLE 2

| Compound # | Expected mass [Da] | Observed mass [Da] |
|---|---|---|
| 100 | 3133.50 | 3134.48 |
| 100 | 35835.9 | 35836.1 |
| 108 | 35948.0 | 35948.1 |

$IC_{50}$ Profiling of Kinase Activity Inhibition. Compounds were profiled for FGFR inhibition activity at Reaction Biology Corporation (Malvern, Pa.) with their Kinase HotSpot$^{SM}$ assay. See, Anastassiadis et al., 2011, Comprehensive assay of kinase catalytic activity reveals features of kinase inhibitor selectivity. Nat Biotechnol 29, 1039-1045.

Recombinant FGFR1 (2.5 nM), FGFR2 (1 nM), FGFR3 (5 nM), or FGFR4 (12 nM) (Invitrogen™) was prepared as a mixture with substrate KKKSPGEYVNIEFG (SEQ ID NO:1) (20 µM, FGFR1 substrate); and Poly [E,Y] 4:1 (0.2 mg/ml, FGFR2,3,4 substrate)] in kinase reaction buffer (20 mM HEPES-HCl, pH 7.5, 10 mM $MgCl_2$, 2 mM $MnCl_2$, 1 mM EGTA, 0.02% Brij35, 0.1 mM $Na_3VO_4$, 0.02 mg/ml BSA, 2 mM DTT, and 1% DMSO). Compound was added to the enzyme/substrate mixture using acoustic technology (Labcyte® Echo 550, Sunnyvale, Calif.)(see, Olechno et al., 2006, Improving $IC_{50}$ results with acoustic droplet ejection. JALA 11, 240-246) and pre-incubated for 0, 15, or 60 minutes at room temperature. After compound pre-incubation, a mixture of ATP (Sigma-Aldrich®) and $^{33}$P-γ-ATP (PerkinElmer) was added to a final concentration of 10 µM to initiate kinase reactions. Reactions were incubated for 120 minutes at room temperature and then spotted onto Whatman™ P81 ion exchange filter paper. Unbound phosphate was removed by extensively washing filters in 0.75% phosphoric acid. See, Anastassiadis et al., 2011, Comprehensive assay of kinase catalytic activity reveals features of kinase inhibitor selectivity. Nat Biotechnol 29, 1039-1045.

Results for FGFR4 and FGFR1 are shown next to individual compounds listed in Table 1 above. The compounds showed selective inhibition of FGFR4, with a higher $IC_{50}$ for FGFR1.

Without wishing to be bound by theory, the $IC_{50}$ activity with respect to FGFR1 is generally representative of the activity with respect to FGFR1, FGFR2, and FGFR3. See also, Dieci et al., 2013, Fibroblast Growth Factor Receptor Inhibitors as a Cancer Treatment: From a Biologic Rationale to Medical Perspectives. Cancer Discovery, F1-F16.

To confirm, some of the compounds were also tested for FGFR2 and FGFR3 inhibition. These results shown below in Table 3 are consistent with the $IC_{50}$ activity of FGFR1 being generally representative of the activity of FGFR1, FGFR2, and FGFR3, and further demonstrates the selectivity of these FGFR4 inhibitors.

TABLE 3

| Compound # | FGFR2 $IC_{50}$ (µM) | FGFR3 $IC_{50}$ (µM) | FGFR1 $IC_{50}$ (µM) | FGFR4 $IC_{50}$ (µM) |
|---|---|---|---|---|
| 100 | 4.18 | 1.98 | >10.1 | <0.001 |
| 108 | 1.98 | 2.00 | 0.173 | <0.001 |

In Vivo Efficacy in Tumor Models. Compound 108 was evaluated for its ability to inhibit tumor growth in nude mice bearing tumor xenografts from three different human hepatocellular carcinoma tumor cell lines. These cell lines are representative of cancers having an altered FGFR4 and/or FGF19 status. See Sawey et al., Cancer Cell 19(3): 347-358 (2011).

Animals: Nude mice, ages 6-8 weeks, and weighing approximately 19-25 g, were purchased from Taconic (Taconic, Hudson, N.Y.). All animal experiments were done in accordance with protocols approved by the Institutional Animal Care and Use Committee.

Tumor Xenografts and Treatment: $7.5 \times 10^6$ HUH7 cells (HSRRB cat. no. JCRB0403), $5 \times 10^6$ Hep3B (ATCC cat. no. HB8064), or $2.5 \times 10^6$ JHH7 cells (HSRRB cat. no. JCRB1031), each in a total volume of 100 µl, 1:1 Matrigel (Corning Inc, Corning, N.Y.), were injected subcutaneously (s.c.) into the right lateral flank. When tumors reached 150-200 mm$^3$, the mice were randomized into treatment groups of 5-10 animals. Dosing was performed twice daily by intraperitoneal injection at the indicated dosages for 15 days using Compound 108, formulated in a vehicle of 5% DMSO (Alfa Aesar, Ward Hill, Mass.), 10% PEG300 (Sigma, St. Louis, Mo.), 8% TWEEN® 80 (Sigma, St. Louis, Mo.), 77% USP Saline at the desired concentration. Tumor volumes were collected twice weekly using the formula Volume=(length*width$^2$)/2. Body weights were collected twice weekly, as well. All animals were observed and cared for in accordance with The Guide for Care and Use of Laboratory Animals, 8th edition (National Academies Press, Washington D.C.).

Statistical Methods: Statistical comparisons were made at the end of the experiment using Repeated Measures Anova with Bonferroni post-test for comparisons of treatment groups, using GraphPad Prism 5. The following criteria were used to determine Progressive Disease, Stable Disease, Partial Regression, and Complete Regression. Progressive Disease is defined as three consecutive measurements increasing from best response or >120% initial tumor volume. Stable Disease is three consecutive measurements <120% and >50% of initial tumor volume, whereas three consecutive measurements <50% initial tumor volume qualifies as a Partial Regression. A Complete Regression is three consecutive measurements <30 mm$^3$. Chi-squared test was used to compare responses between treatment groups (Microsoft Excel).

Figure 2:
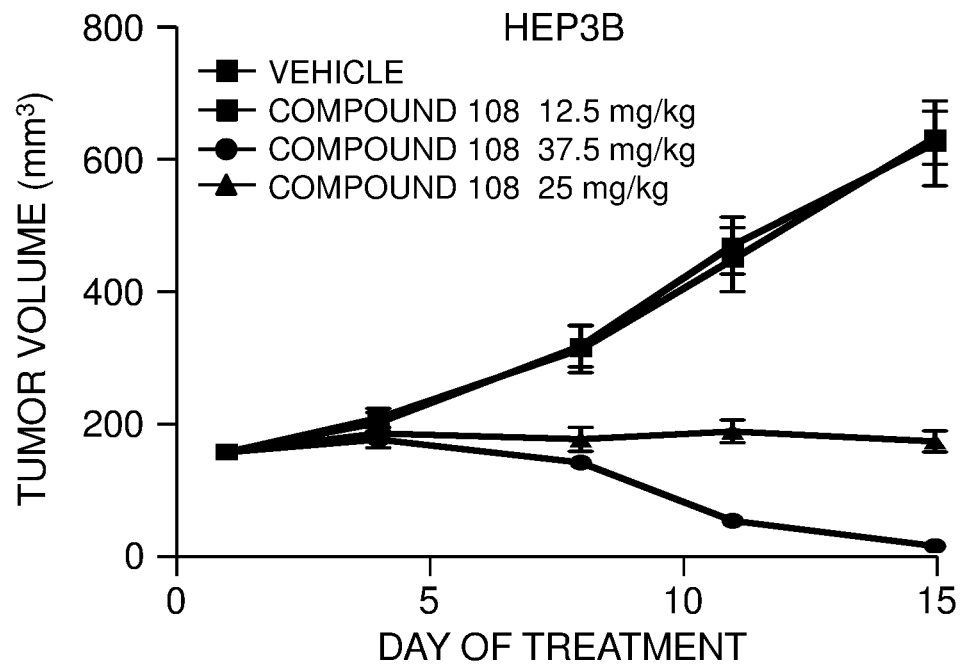
FIG. 2 presents the results of in vivo efficacy testing in hepatocellular carcinoma model using HEP3B cells. Compound 108 (12.5 mg/kg, 25 mg/kg or 37.5 mg/kg) or Vehicle control was administered via intraperitoneal injection, and tumor volume was measured twice weekly over the course of 15 days.
Figure 3:
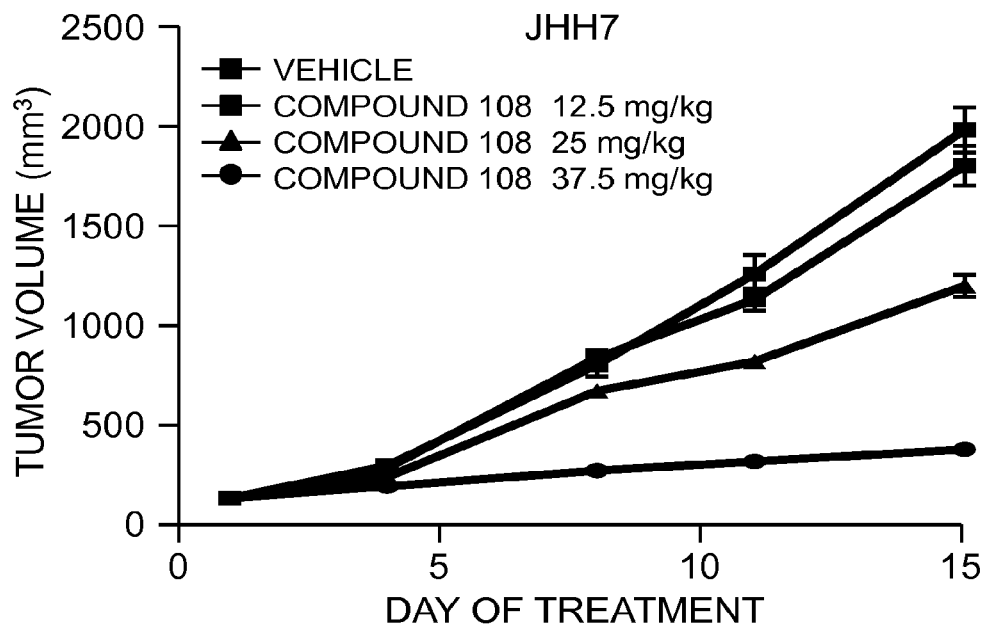
FIG. 3 presents the results of in vivo efficacy testing in hepatocellular carcinoma model using JHH7 cells. Compound 108 (12.5 mg/kg, 25 mg/kg or 37.5 mg/kg) or Vehicle control was administered via intraperitoneal injection, and tumor volume was measured twice weekly over the course of 15 days.

Results from animals bearing tumors from HUH7, HEP3B, and JHH7 cancer cells are shown in FIGS. 1-3, respectively, and are also reflected in Table 4.

TABLE 4

Inhibition of Tumor Growth in FGF19 amplified HCC xenografts

| Dose (mg/kg) | Complete Regression | Partial Regression | Stable Disease | Progressive Disease |
|---|---|---|---|---|
| HUH7 (n = 10 per group) | | | | |
| 25 | 1 | 4 | 3 | 2 |
| 37.5 | 2 | 5 | 3 | 0 |
| HEP3B (n = 5 per group) | | | | |
| 12.5 | 0 | 0 | 0 | 5 |
| 25 | 0 | 1 | 4 | 0 |
| 37.5 | 5 | 0 | 0 | 0 |
| JHH7 (n = 10 per group) | | | | |
| 12.5 | 0 | 0 | 0 | 10 |
| 25 | 0 | 0 | 0 | 10 |
| 37.5 | 0 | 0 | 0 | 10 |

These data demonstrate that compound 108 is efficacious in all models. Among the three models, HEP3B is the most sensitive, JHH7 the least sensitive and HUH7 showing intermediate sensitivity to compound 108. Although a dose response can be seen in FIG. 3 for JHH7, there was Progressive Disease in all dose levels tested.

Comparative Studies of Compound 108 with BGJ398. Comparative studies were done with Compound 108 and the known FGFR inhibitor BJG398.

Biochemical Kinase Assay Protocol to Obtain $IC_{50}$: Recombinant FGFR1 (2.5 nM), or FGFR4 (12 nM) was prepared as a mixture with substrate KKKSPGEYVNIEFG (SEQ ID NO:1)(20 µM, FGFR1 substrate); Poly [E,Y] 4:1 (0.2 mg/ml, FGFR2,3,4 substrate)] in kinase reaction buffer (20 mM HEPES-HCl, pH 7.5, 10 mM $MgCl_2$, 2 mM $MnCl_2$, 1 mM EGTA, 0.02% Brij35, 0.1 mM $Na_3VO_4$, 0.02 mg/ml BSA, 2 mM DTT, and 1% DMSO). Compound was added to the enzyme/substrate mixture using acoustic technology and pre-incubated for 0, 15, or 60 minutes at room temperature. After compound pre-incubation, $^{33}P$-γ-ATP was added at a final concentration of 10 µM to initiate kinase reactions. Reactions were incubated for 120 minutes at room temperature. Substrate phosphorylation was monitored by filter assay, as above. Results are shown in Table 5. The results reported show that compound 108 is a more potent FGFR4 inhibitor, whereas BGJ398 is a more potent FGFR1 inhibitor.

TABLE 5

Comparative Testing of Compound 108 and BGJ398 with Biochemical Kinase assay

| Kinase | Compound 108 $IC_{50}$ (nM) | BGJ398 $IC_{50}$ (nM) |
|---|---|---|
| FGFR4 | <0.2 | 13 |
| FGFR1 | 513 | 1.0 |

Cellular Viability Assay Protocol to Obtain $GI_{50}$: Cells lines were cultured at 37° C., 5% $CO_2$ and 95% humidity. Culture media were purchased from GIBCO®, USA. For viability assay, 2000 cells/well were seeded in 96 well plates, incubated for 24 h before compound treatment. Following compound addition, plates were incubate for 72 h at 37° C. with 5% $CO_2$, and then measured by means of CTG assay (CellTiter-Glo® Luminescent Cell Viability Assay, Cat. No.: G7572, Promega). Results are shown in Table 6. The table shows compound 108 is more potent than BGJ398 in Hep3B cells, an FGF19 amplified line. The potency in HUH7 and JHH7, the other two FGF19 amplified lines, are comparable between compound 108 and BGJ398. HepG2 (ATCC cat. no. HB-8065), SNU398 (ATCC cat. no. CRL-2233) and SNU449 (ATCC cat. no. CRL-2234) are FGF19 non-amplified cell lines that were used as controls.

$GI_{50}$ is the concentration of test drug where 100×(T−T0)/(C−T0)=50. See, e.g., Monks et al., *Feasibility of a High-Flux Anticancer Drug Screen Using a Diverse Panel of Cultured Human Tumor Cell Lines*, J Natl Cancer Inst (1991) 83(11):757-766; Boyd et al., *Data Display and Analysis Strategies for the NCI Disease-oriented In Vitro Antitumor Drug Screen*, in CYTOTOXIC ANTICANCER DRUGS: MODELS AND CONCEPTS FOR DRUG DISCOVERY AND DEVELOPMENT, Valeriote et al., eds. (1990), pp. 11-34. The luminescence of the test well after a 72 h period of exposure to test drug is T, the luminescence at time zero is T0, and the control luminescence is C. The $GI_{50}$ measures the growth inhibitory power of the test agent.

TABLE 6

Comparative Testing of Compound 108 and BGJ398 in Cellular Viability assays

| Cell Line | Compound 108 $GI_{50}$ (nM) | BGJ398 $GI_{50}$ (nM) |
|---|---|---|
| HEP3B | 18 ± 6 nM (n = 27) | 74 ± 23 nM (n = 6) |
| JHH7 | 216 ± 70 nM (n = 4) | 178 ± 30 nM (n = 2) |
| HUH7 | 408 ± 128 nM (n = 4) | 231 ± 100 nM (n = 2) |
| HEPG2 | 6506 ± 1424 nM (n = 27) | 2260 ± 1182 nM (n = 6) |
| SNU398 | >10,000 (n = 2) | not measured |
| SNU449 | >10,000 (n = 2) | not measured |

Figure 4:
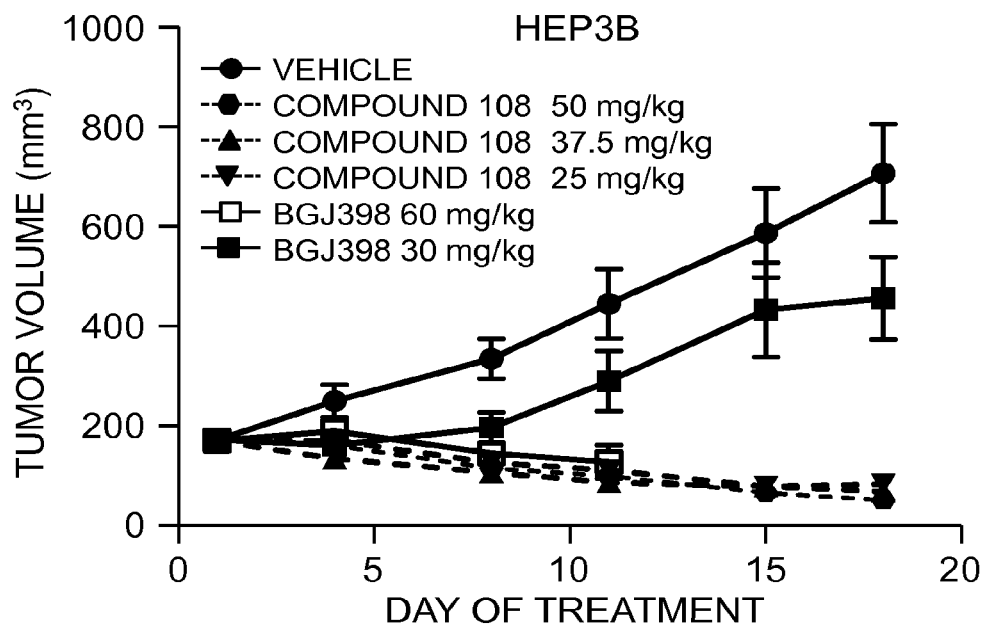
FIG. 4 presents the results of comparative in vivo efficacy testing in hepatocellular carcinoma model using HEP3B cells. Compound 108 (25 mg/kg, 37.5 mg/kg or 50 mg/kg) was administered twice daily via intraperitoneal injection, or BGJ398 (30 mg/kg or 60 mg/kg) was administered orally twice daily.

In Vivo Efficacy Comparison: Nude mice were used for these experiments as above. $5.0 \times 10^6$ Hep3B cells in a total volume of 100 µl, 1:1 Matrigel (Corning Inc, Corning, N.Y.), were injected s.c. into the right lateral flank. When tumors reached 150-200 $mm^3$ the mice were randomized into treatment groups of 5-10 animals. Treatment was then started using Compound 108, formulated in a vehicle of 5% DMSO (Alfa Aesar, Ward Hill, Mass.), 10% PEG300 (Sigma, St. Louis, Mo.), 8% TWEEN® 80 (Sigma, St. Louis, Mo.), 77% USP Saline at the desired concentration. BGJ398, formulated as a suspension in 0.5% Methylcellulose (Sigma)/0.2% TWEEN® 80, was suspended at the desired concentration. Both drugs were dosed for 18 dyas, except for one treatment group (see below). Tumor volumes were collected twice weekly using the formula Volume=(length*$width^2$)/2. Body weights were collected twice weekly as well. All animals were observed and cared for in accordance with The Guide for Care and Use of Laboratory Animals, 8th edition (National Academies Press, Washington D.C.). The results of this comparative in vivo study are shown in FIG. 4.

The data show that compound 108 is more efficacious than BGJ398 at tolerable dosage levels. Although BGJ398 at 60 mg/kg showed efficacy comparable to compound 108, the dosing of this BGJ398 60 mg/kg group had to be terminated on Day 11 due to poor health of animals. This difference in toxicity is not due to routes of administration because the group of animals dosed orally with BGJ398 at 30 mg/kg did not exhibit poor health.

The foregoing is illustrative of the present invention, and is not to be construed as limiting thereof. The invention is defined by the following claims, with equivalents of the claims to be included therein.

We claim:

1. A method of treating cholangiocarcinoma in a subject in need thereof comprising administering to said subject a treatment effective amount of a compound of Formula I:

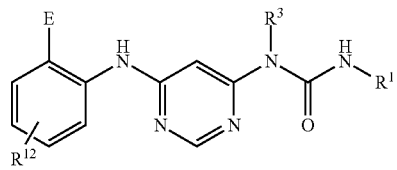

wherein:

$R^3$ is selected from the group consisting of: $C_{1-6}$alkyl, $C_{1-6}$alkoxy$C_{1-6}$alkyl, $NR^{10}R^{11}C_{1-6}$alkyl, $R^{10}$heterocyclyl$C_{1-6}$alkyl, $R^{10}$aryl$C_{1-6}$alkyl, and $R^{10}$heteroaryl$C_{1-6}$alkyl, wherein $R^{10}$ and $R^{11}$ are each independently selected from the group consisting of: hydrogen and $C_{1-6}$alkyl;

E is selected from the group consisting of:
—$NR^{13}C(O)CR^{14}$=$CHR^{15}$, and
—$NR^{13}C(O)C$≡$CR^{14}$,
wherein $R^{13}$ is selected from the group consisting of: hydrogen and methyl, and $R^{14}$ and $R^{15}$ are each independently selected from the group consisting of: hydrogen, methyl, fluoro and chloro;

$R^{12}$ is selected from the group consisting of: hydrogen, halo, $C_{1-6}$alkyl, $C_{1-6}$alkoxy, hydroxy$C_{1-6}$alkyl, hydroxy$C_{1-6}$alkoxy, $C_{1-6}$alkoxy$C_{1-6}$alkoxy, $C_{1-6}$alkoxy$C_{1-6}$alkyl, $R^5R^6$heterocyclyl, —C(O)heterocyclyl$R^5R^6$, $R^5R^6$heterocyclyl$C_{1-6}$alkyl, $NR^5R^6$, $NR^5R^6C_{1-6}$alkyl, —C(O)$NR^5R^6$, and $NR^5R^6C_{1-6}$aloxy, wherein $R^5$ and $R^6$ are each independently selected from the group consisting of hydrogen, $C_{1-6}$alkyl, hydroxy$C_{1-6}$alkyl, amino$C_{1-6}$alkyl, —C(O)$C_{1-6}$alkyl and $C_{1-6}$alkylsulfonyl; and $R^1$ is phenyl, wherein said phenyl is substituted 2, 3, or 4 times with independently selected halo or $C_{1-6}$alkoxy, or a pharmaceutically acceptable salt thereof, wherein said cholangiocarcinoma has an expression or overexpression of FGFR4.

2. The method of claim 1, wherein said compound is selected from the group consisting of:

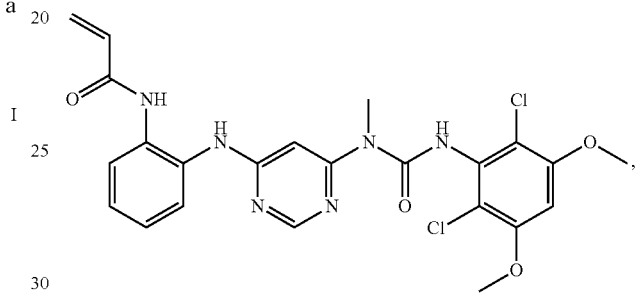

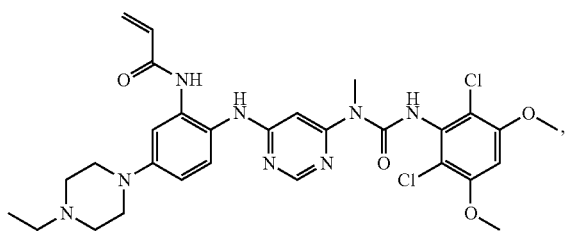

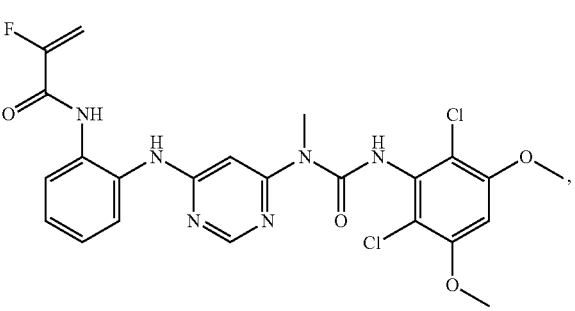

199 200
-continued -continued
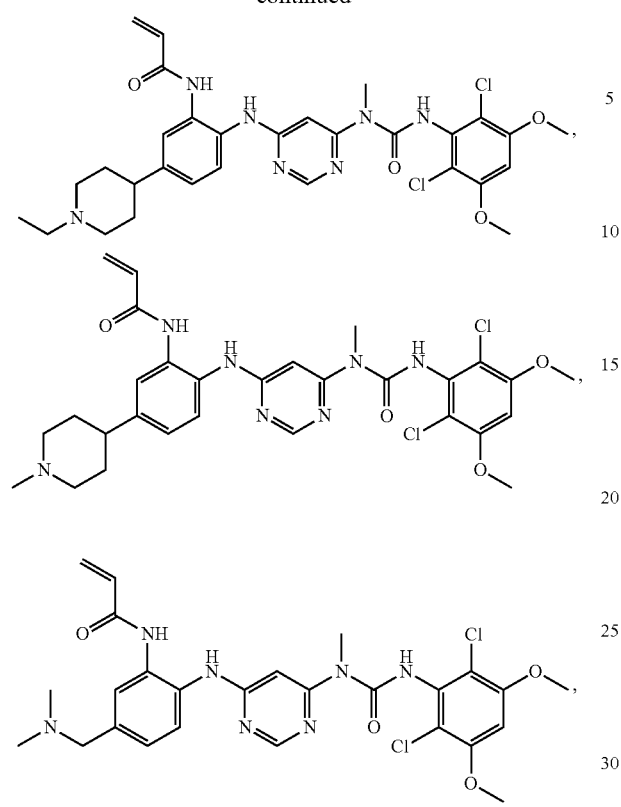
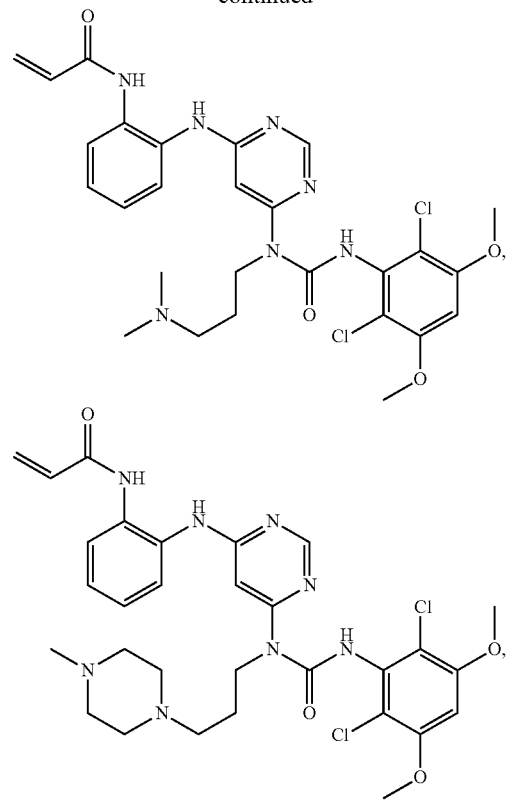

201
-continued
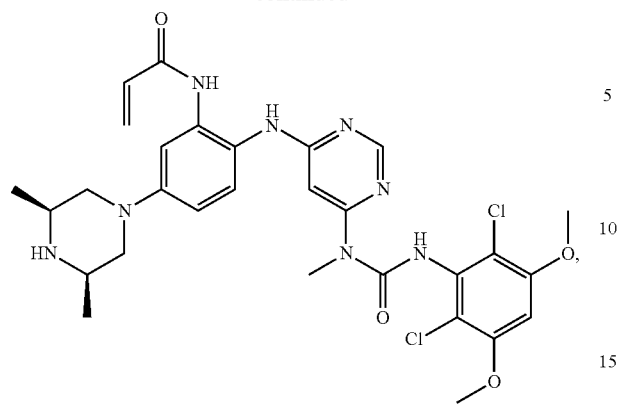
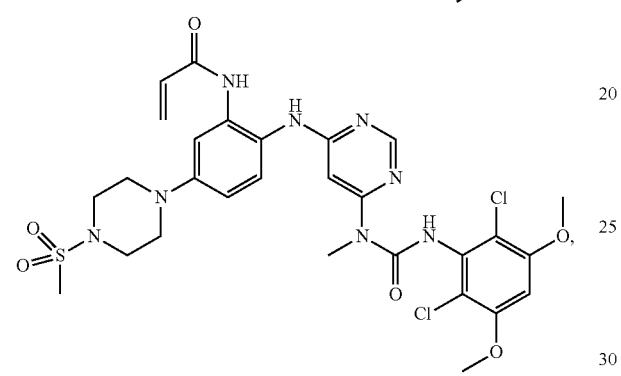
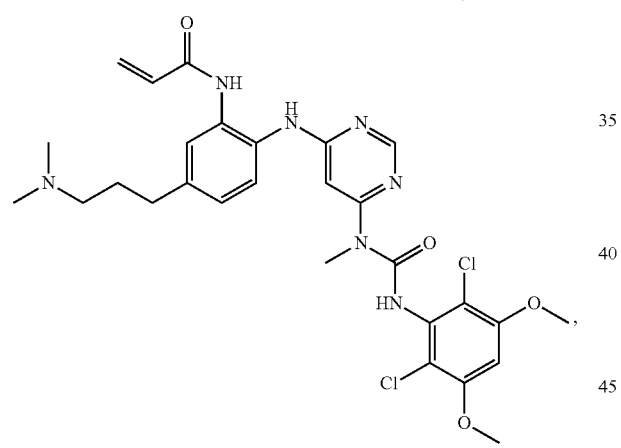
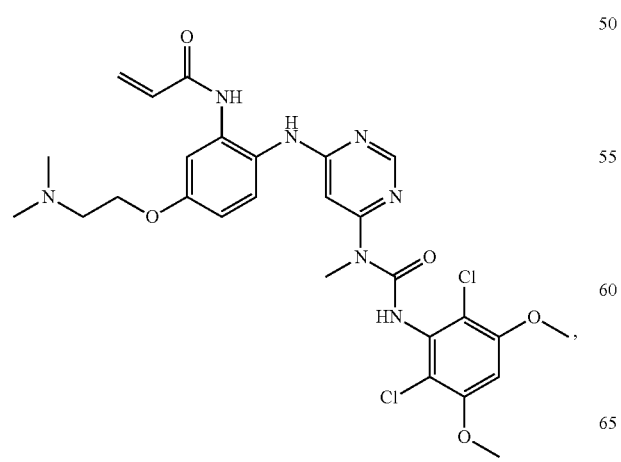
202
-continued
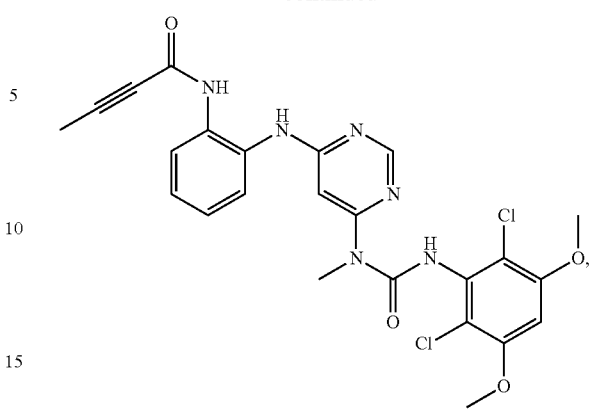
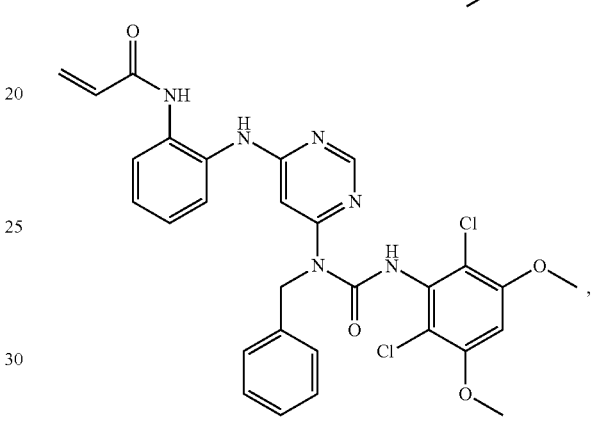
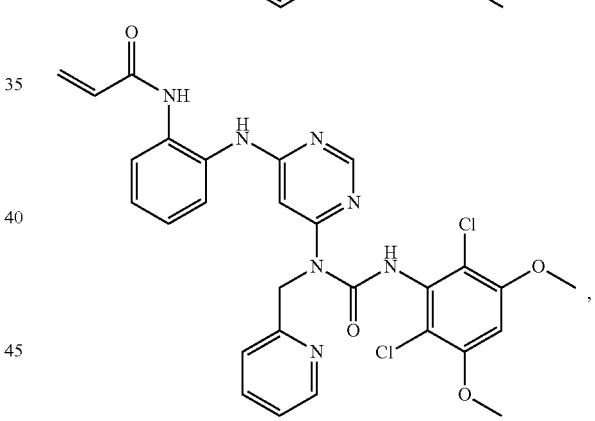
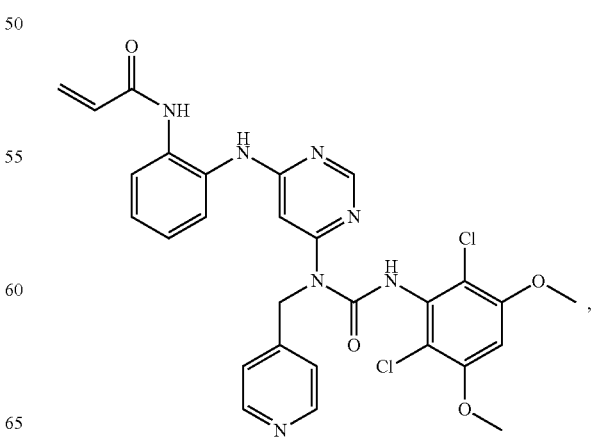

203
-continued
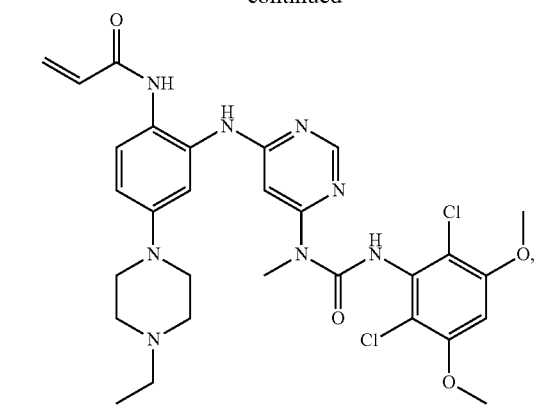
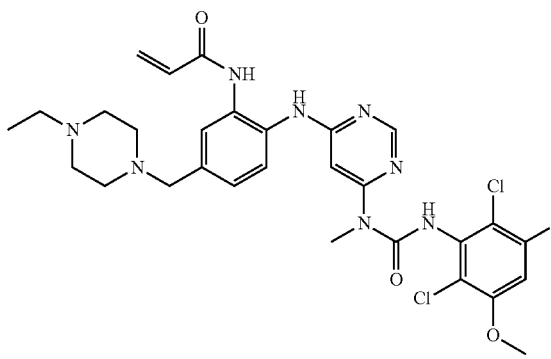
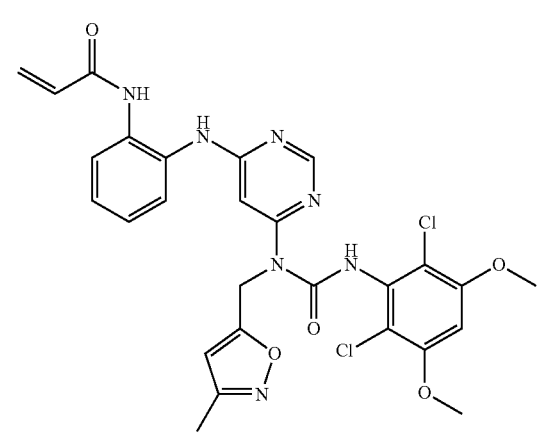
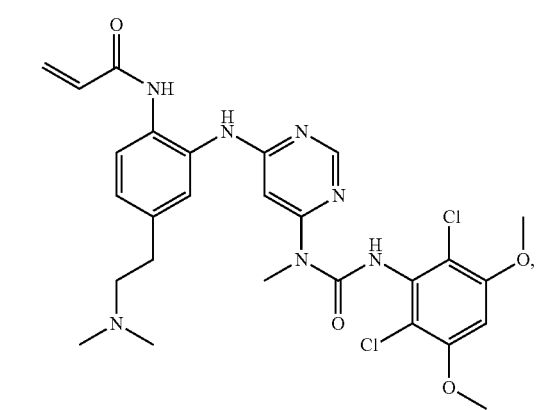
204
-continued
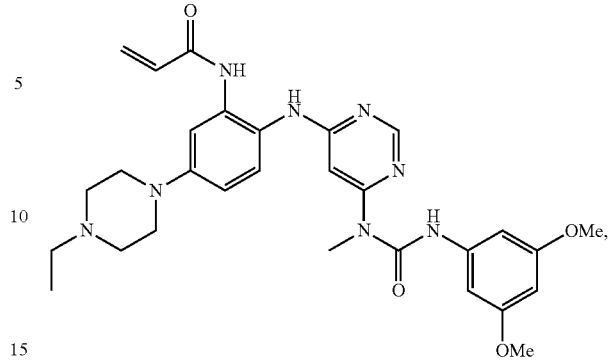
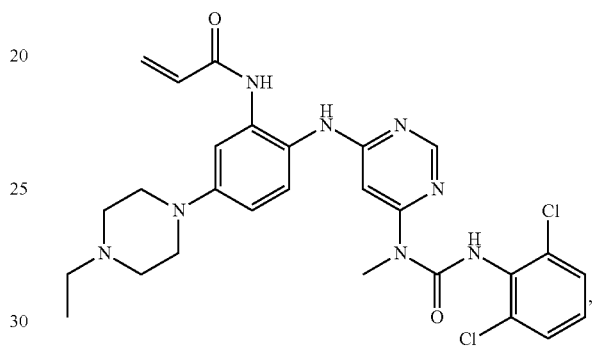
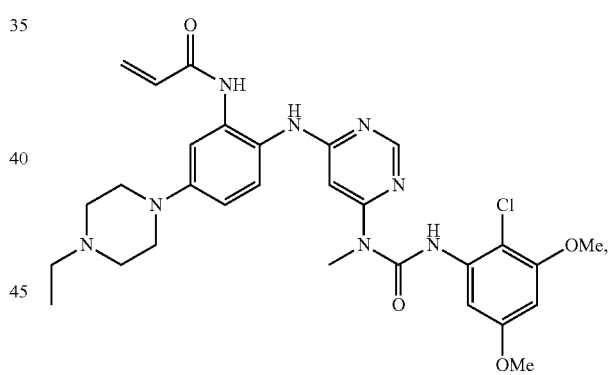
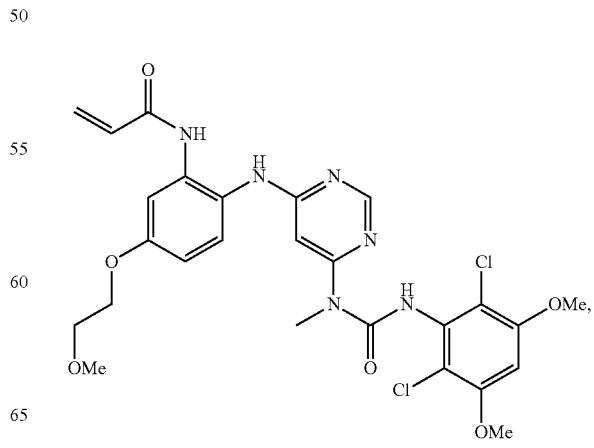

205
-continued
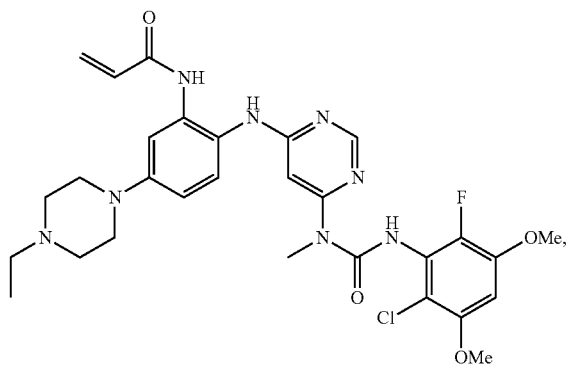 [SMILES: C=CC(=O)Nc1cc(N2CCN(CC)CC2)ccc1Nc1cc(N(C)C(=O)Nc2c(F)c(OC)cc(OC)c2Cl)ncn1]
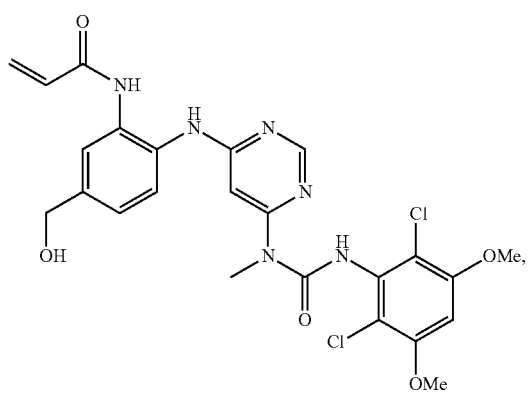
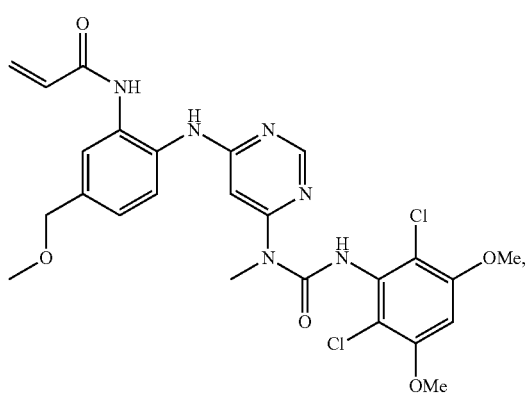
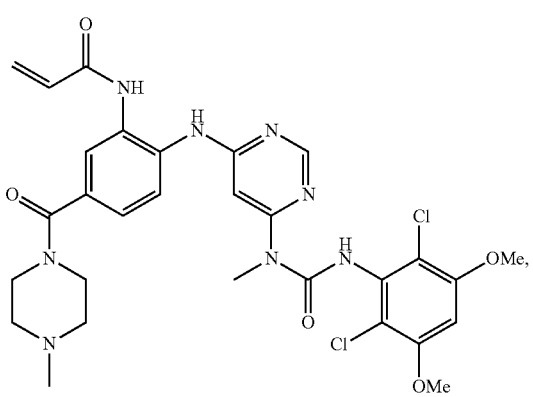
206
-continued
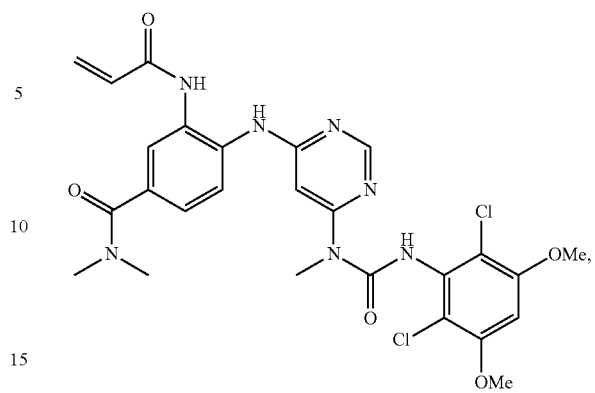
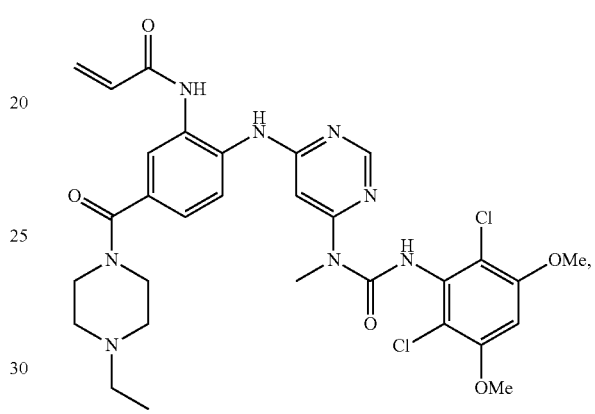
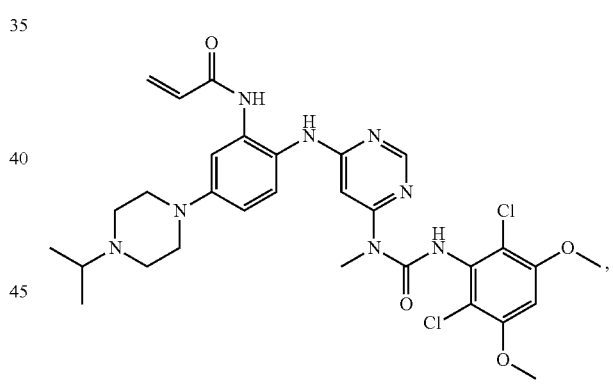
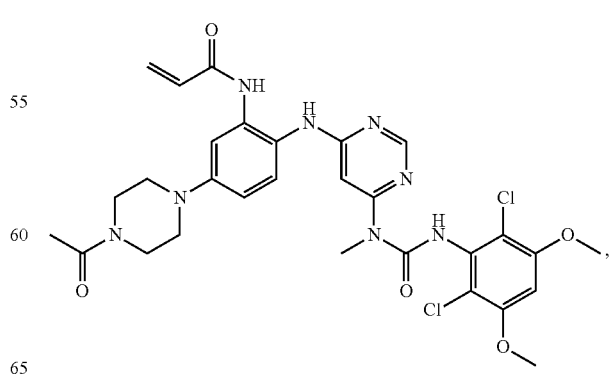

-continued
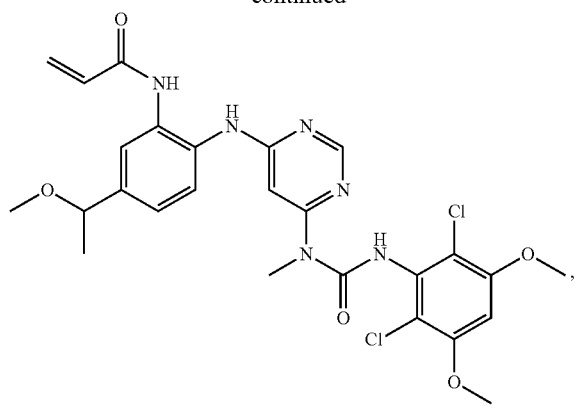
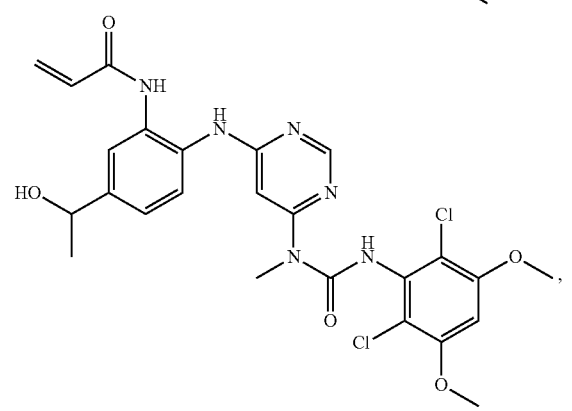
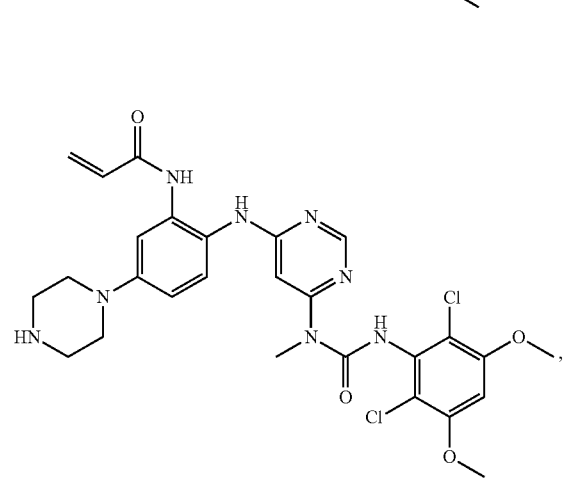
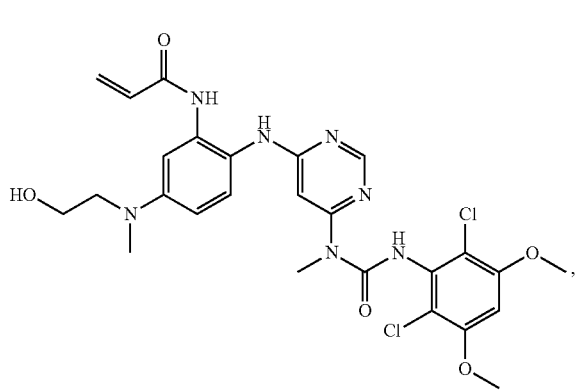
-continued
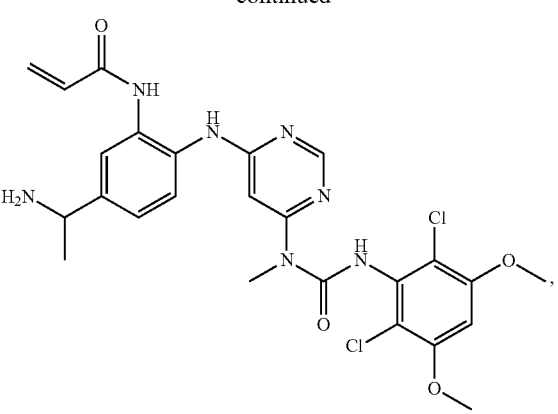
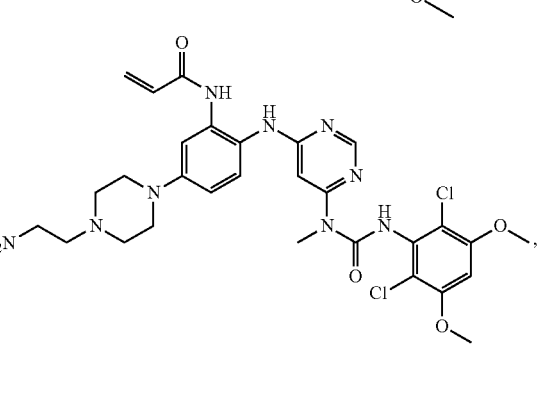
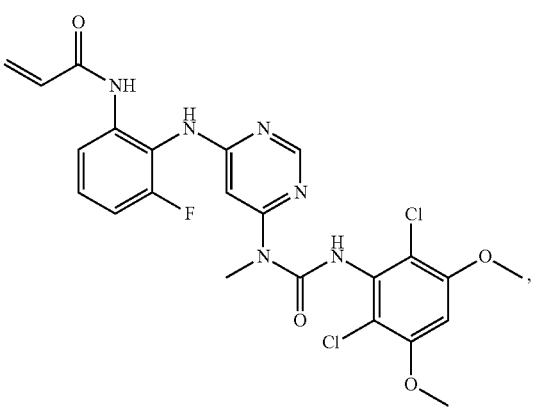
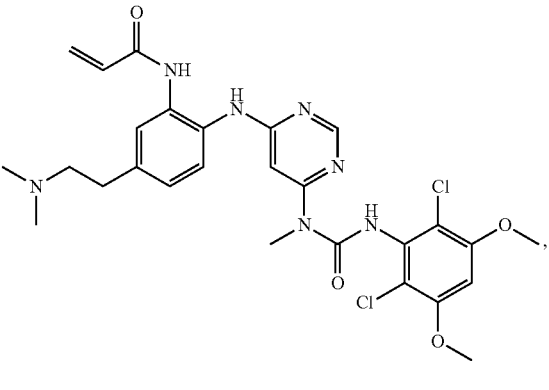

209
-continued
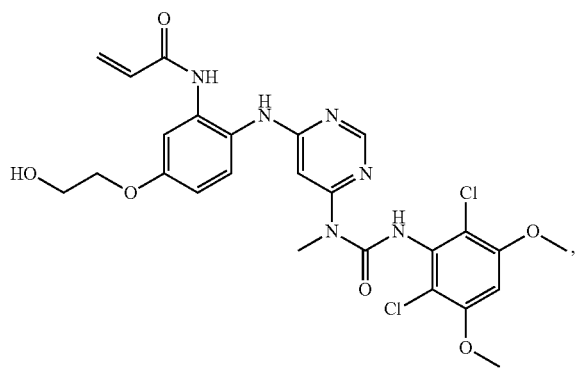
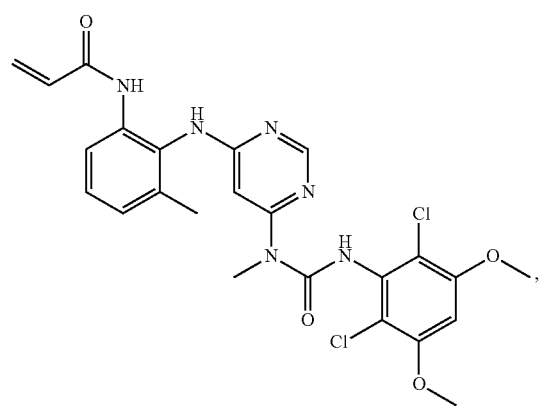
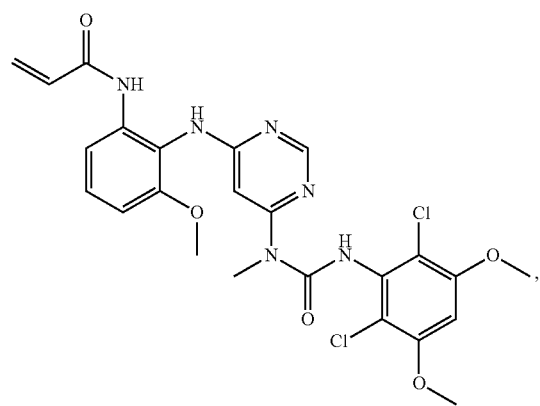
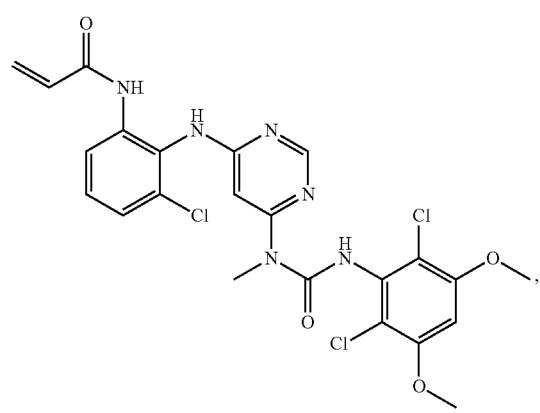
210
-continued
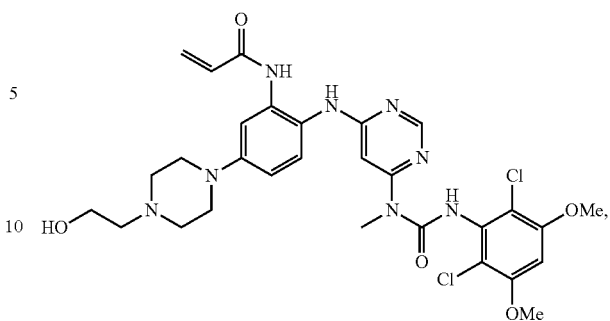
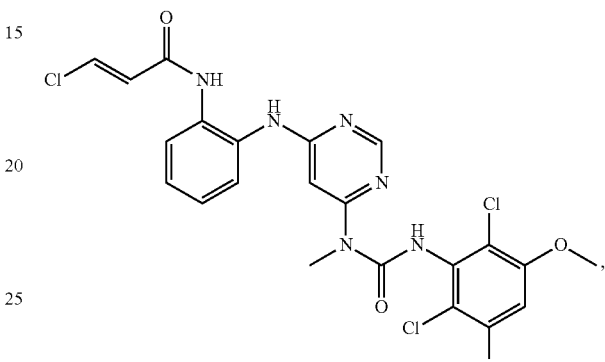
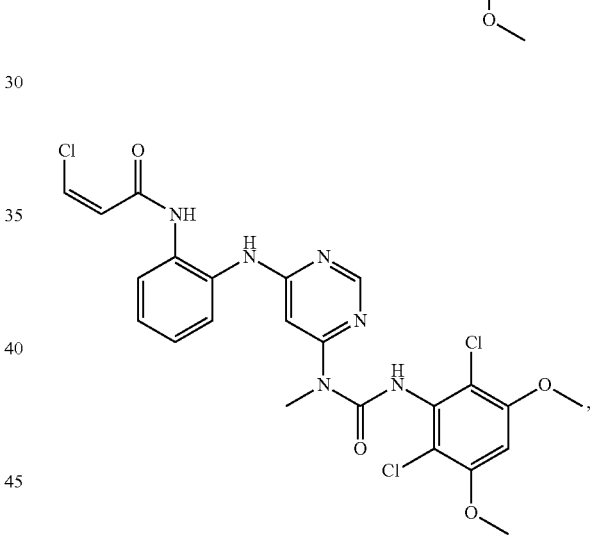
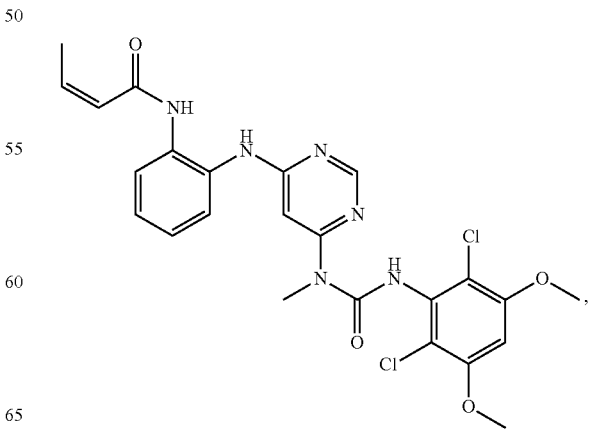

-continued
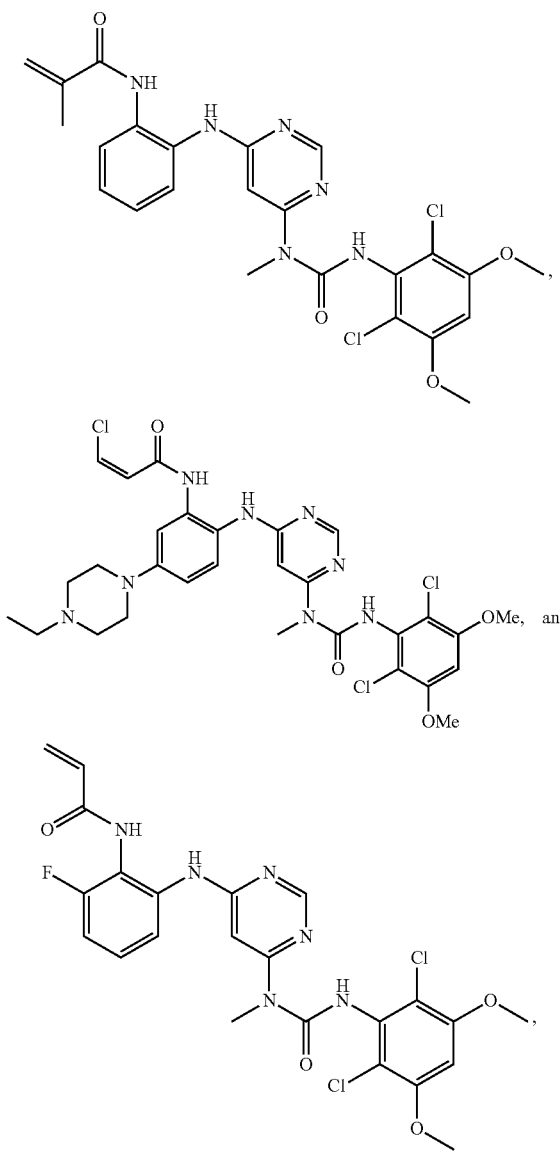
or a pharmaceutically acceptable salt thereof.
3. The method of claim 1, wherein said compound is selected from the group consisting of:
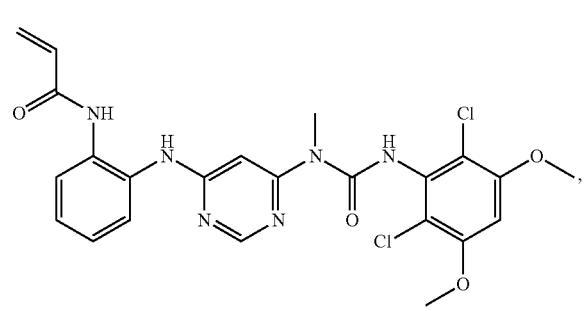
-continued
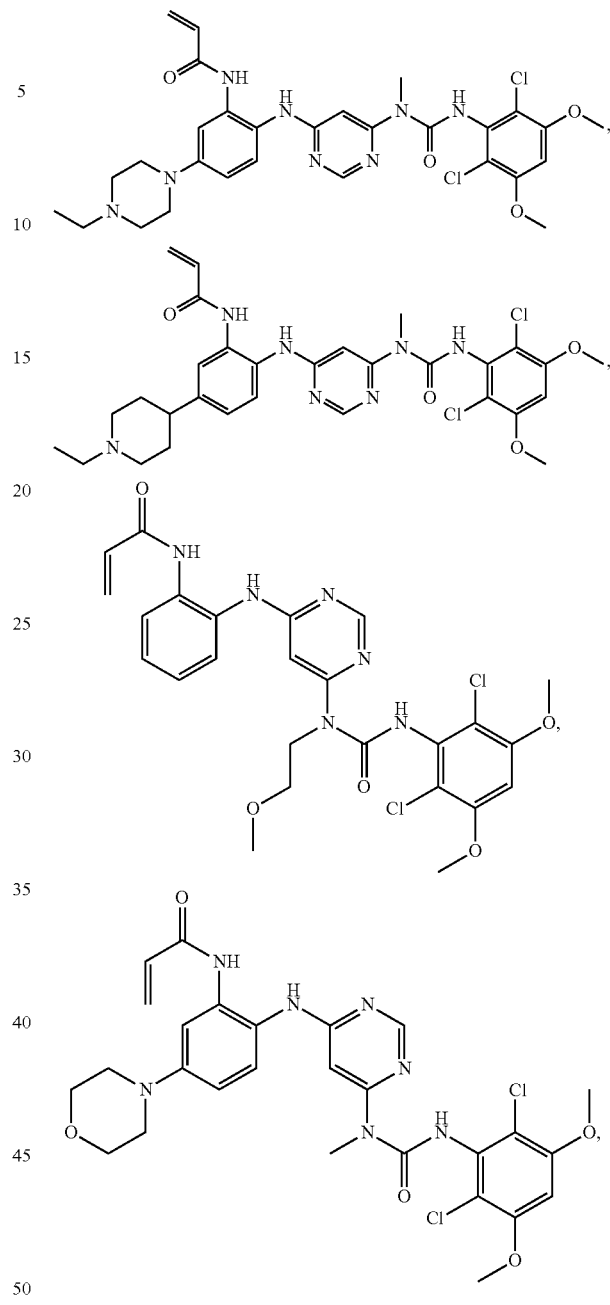
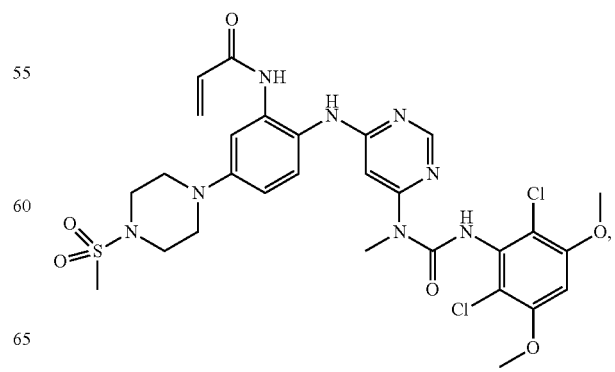

213
-continued
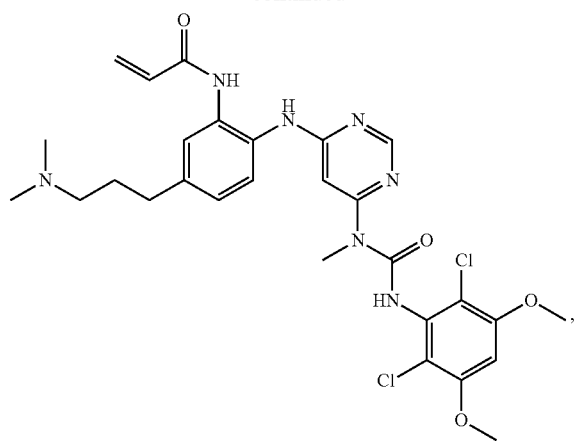
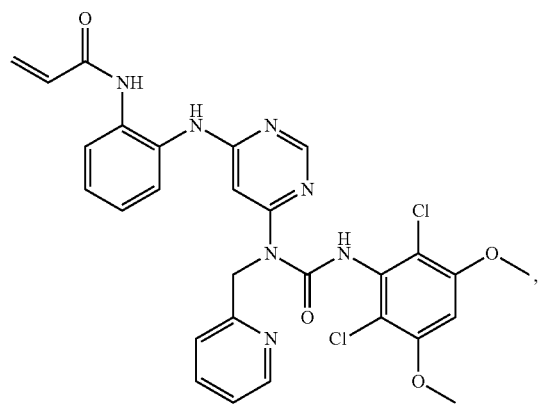
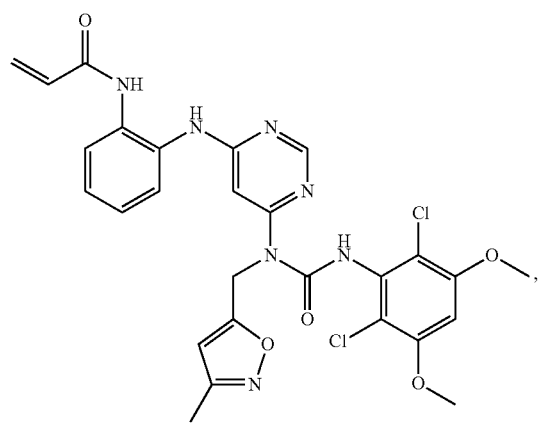
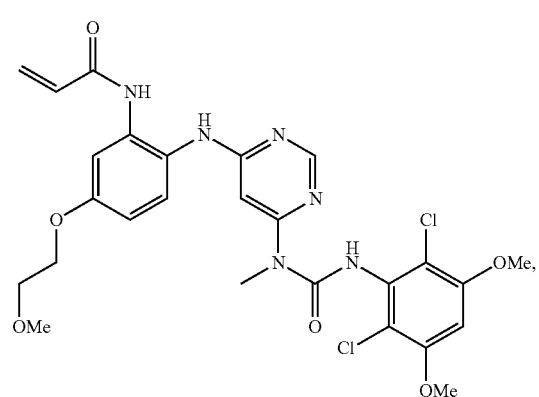
214
-continued
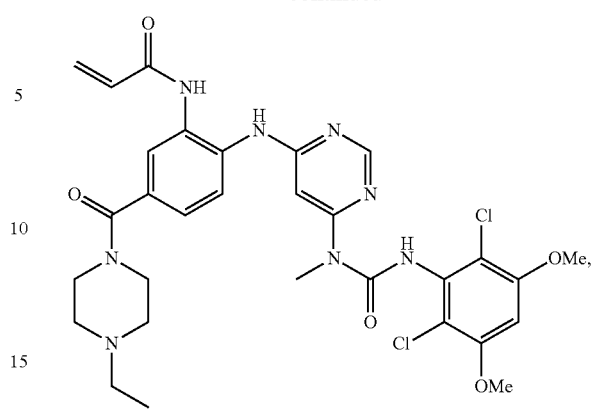
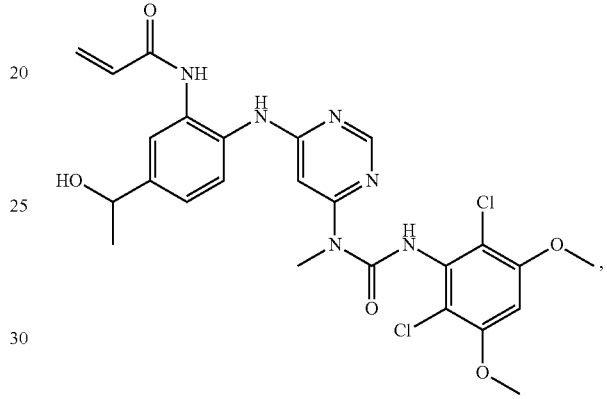
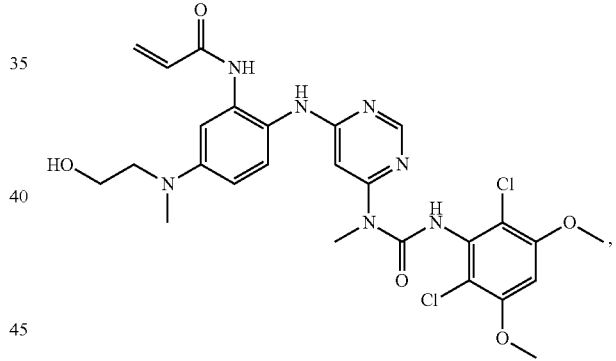
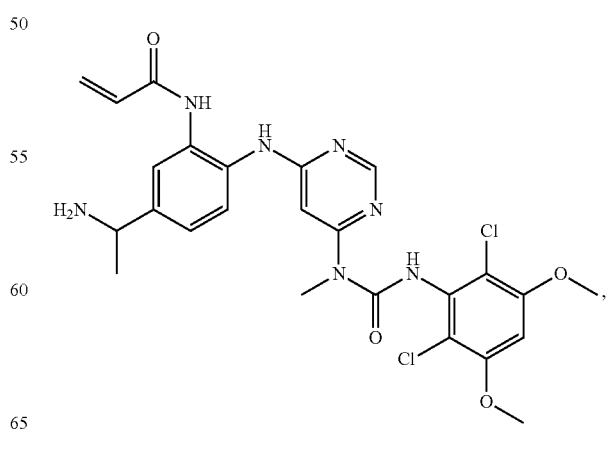

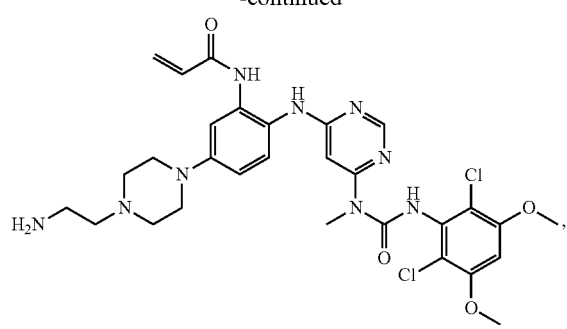
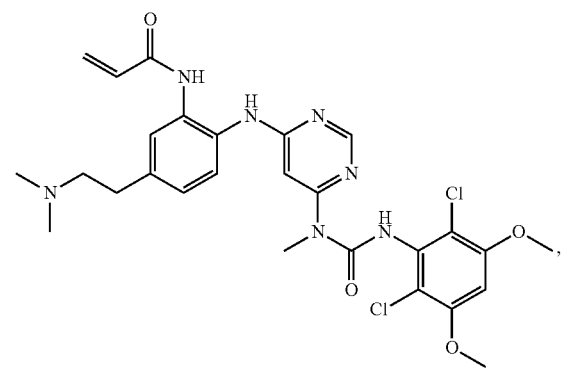
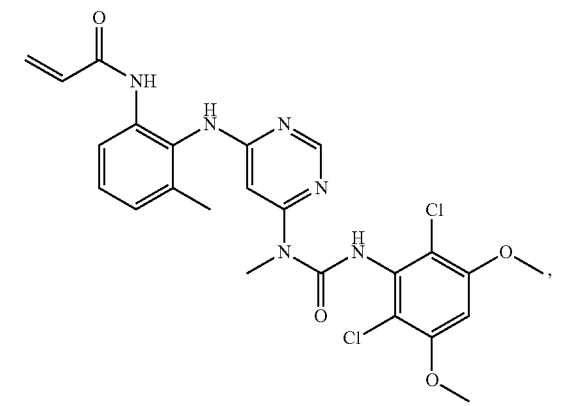
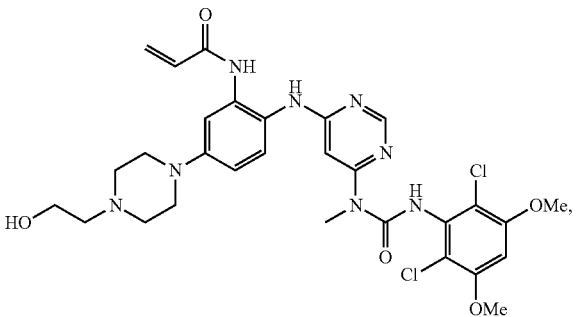
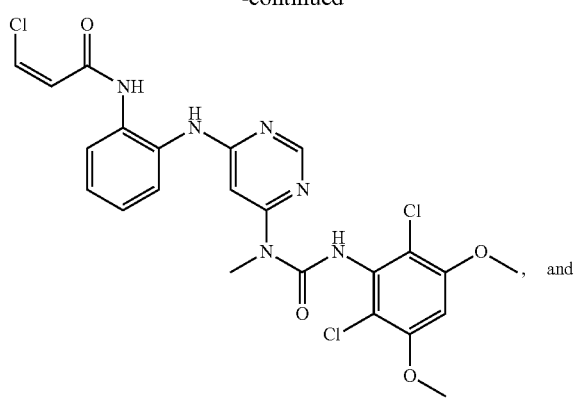
or a pharmaceutically acceptable salt thereof.
4. The method of claim 1, wherein said compound is selected from the group consisting of:
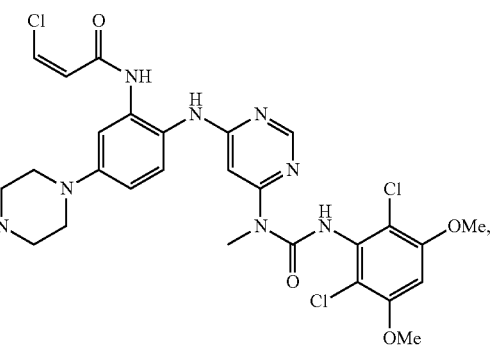

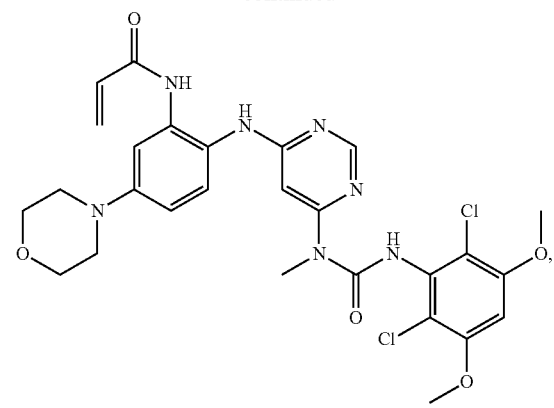

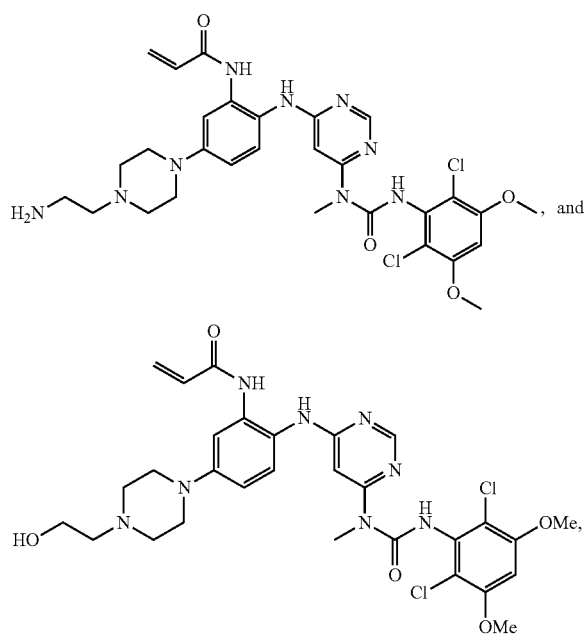

or a pharmaceutically acceptable salt thereof.

5. The method of claim 1, wherein the compound or pharmaceutically acceptable salt thereof is the following compound:

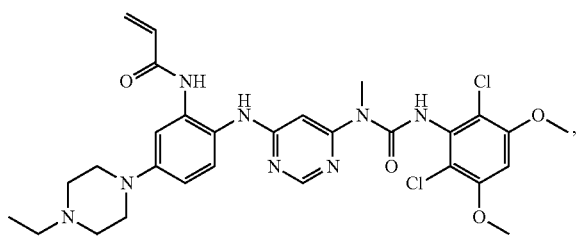 [SMILES: C=CC(=O)Nc1cc(N2CCN(CC)CC2)ccc1Nc1cc(N(C)C(=O)Nc2c(Cl)c(OC)cc(OC)c2Cl)ncn1]

or a pharmaceutically acceptable salt thereof, wherein said cholangiocarcinoma has an expression or overexpression of FGFR4.

6. A method of treating cholangiocarcinoma in a subject in need thereof, comprising:

administering an effective amount of a compound having the formula:

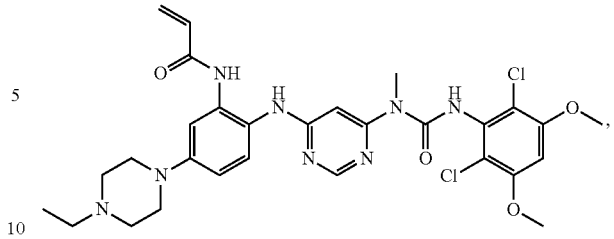

or a pharmaceutically acceptable salt thereof to a patient in which expression or overexpression of FGFR4 has been detected in a biological sample from said patient, said biological sample containing cells of said cholangiocarcinoma.

7. A method of treating hepatocellular carcinoma in a subject in need thereof comprising administering to said subject a treatment effective amount of a compound of Formula I:

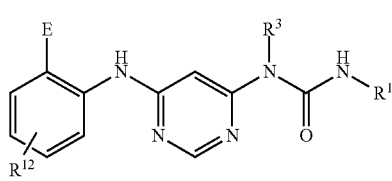

wherein:

$R^3$ is selected from the group consisting of: $C_{1-6}$alkyl, $C_{1-6}$alkoxy$C_{1-6}$alkyl, $NR^{10}R^{11}C_{1-6}$alkyl, $R^{10}$heterocycl$C_{1-6}$alkyl, $R^{10}$aryl$C_{1-6}$alkyl, and $R^{10}$heteroaryl$C_{1-6}$alkyl, wherein $R^{10}$ and $R^{11}$ are each independently selected from the group consisting of: hydrogen and $C_{1-6}$alkyl;

E is selected from the group consisting of:

—$NR^{13}C(O)CR^{14}$=$CHR^{15}$, and

—$NR^{13}C(O)C$≡$CR^{14}$, wherein $R^{13}$ is selected from the group consisting of: hydrogen and methyl, and $R^{14}$ and $R^{15}$ are each independently selected from the group consisting of: hydrogen, methyl, fluoro and chloro;

$R^{12}$ is selected from the group consisting of: hydrogen, halo, $C_{1-6}$alkyl, $C_{1-6}$alkoxy, hydroxy$C_{1-6}$alkyl, hydroxy$C_{1-6}$alkoxy, $C_{1-6}$alkoxy$C_{1-6}$alkoxy, $C_{1-6}$alkoxy$C_{1-6}$alkyl, $R^5R^6$heterocyclyl, —C(O)heterocyclyl$R^5R^6$, $R^5R^6$heterocyclyl$C_{1-6}$alkyl, $NR^5R^6$, $NR^5R^6C_{1-6}$alkyl, —C(O)$NR^5R^6$, and $NR^5R^6C_{1-6}$alkoxy, wherein $R^5$ and $R^6$ are each independently selected from the group consisting of hydrogen, $C_{1-6}$alkyl, hydroxy$C_{1-6}$alkyl, amino$C_{1-6}$alkyl, —C(O)$C_{1-6}$alkyl and $C_{1-6}$alkylsulfonyl; and $R^1$ is phenyl, wherein said phenyl is substituted 2, 3, or 4 times with independently selected halo or $C_{1-6}$alkoxy, or a pharmaceutically acceptable salt thereof, wherein said hepatocellular carcinoma has an increased expression of FGFR4.

8. The method of claim 7, wherein said compound is selected from the group consisting of:

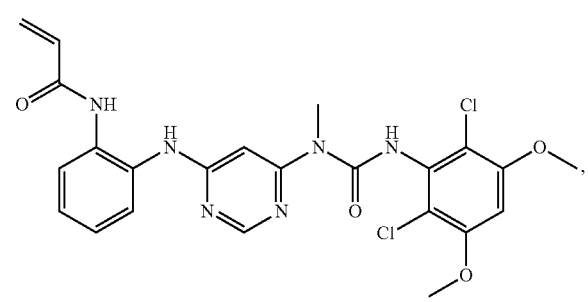
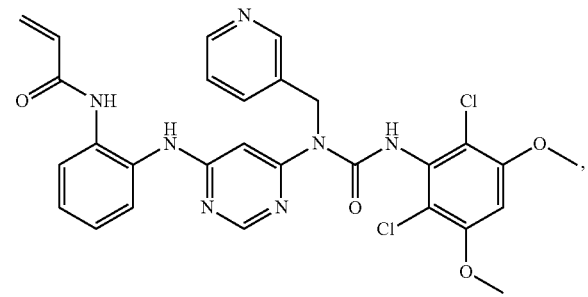
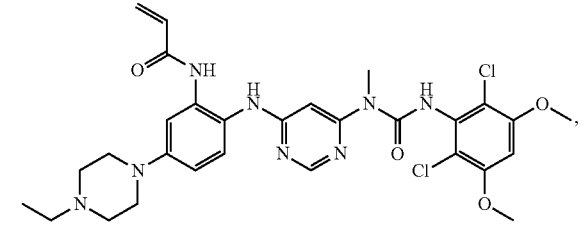 [SMILES: C=CC(=O)Nc1cc(N2CCN(CC)CC2)ccc1Nc1cc(N(C)C(=O)Nc2c(Cl)c(OC)cc(OC)c2Cl)ncn1]
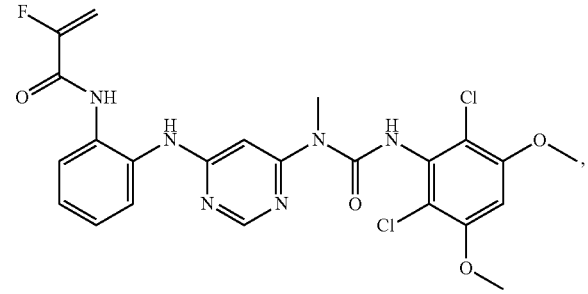
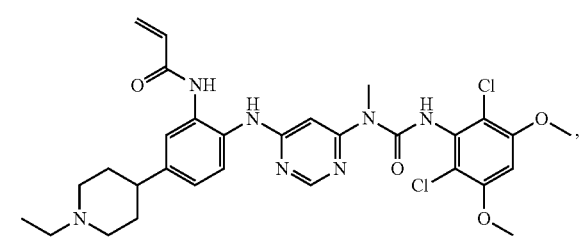
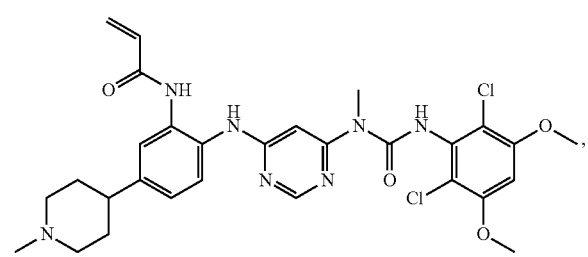
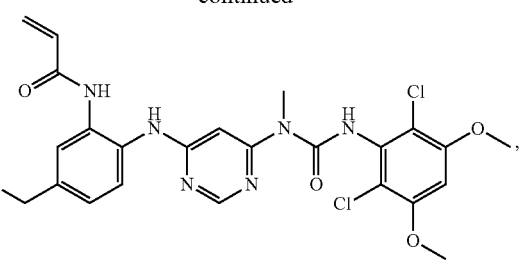
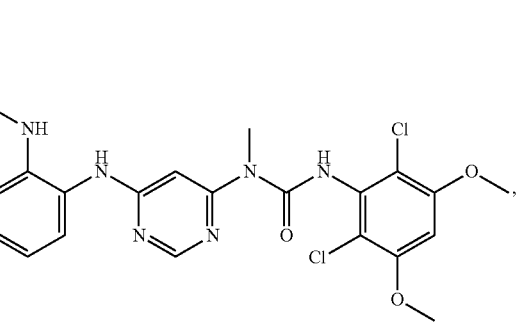
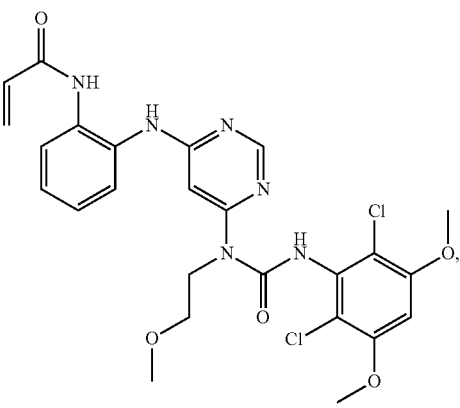
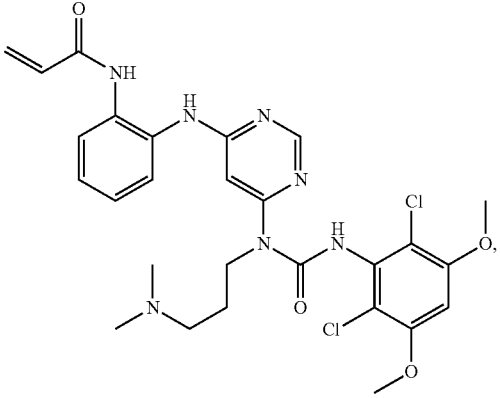

221
-continued
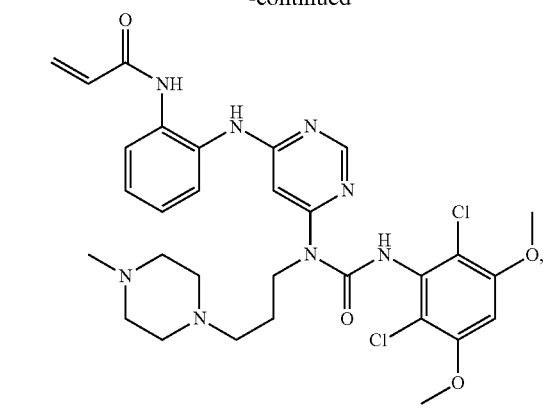
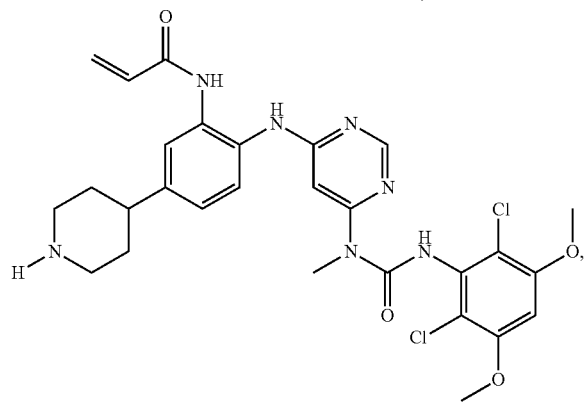
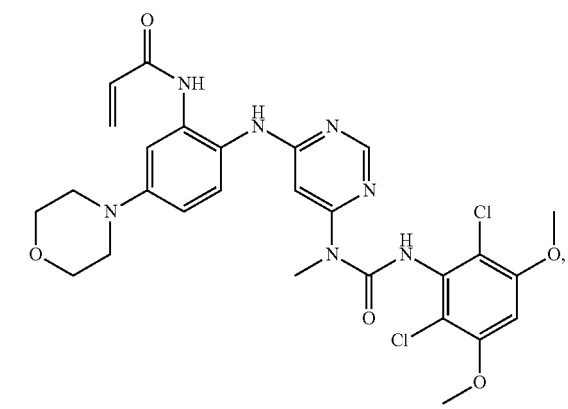
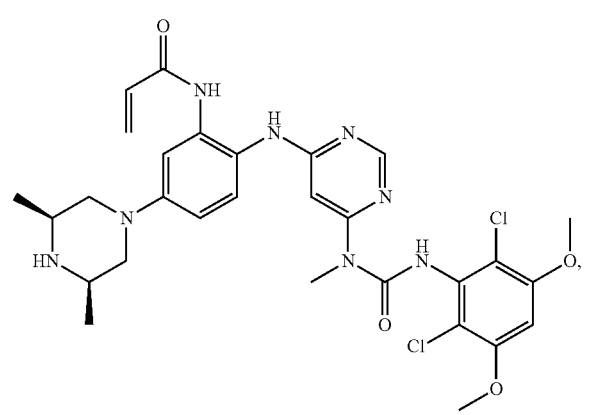
222
-continued
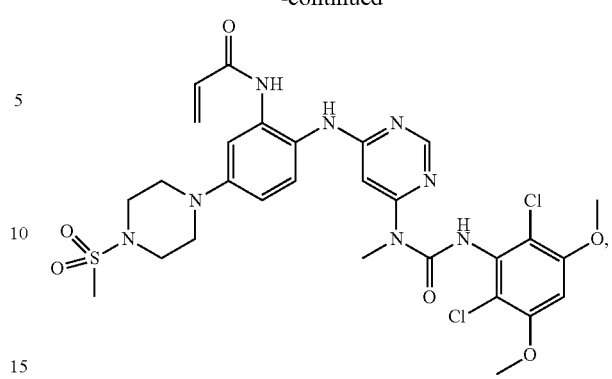
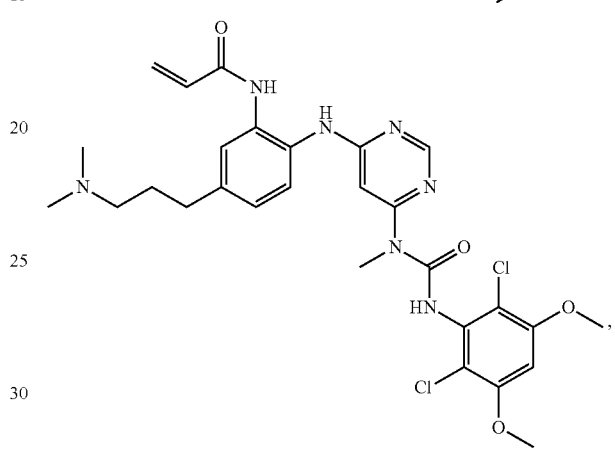
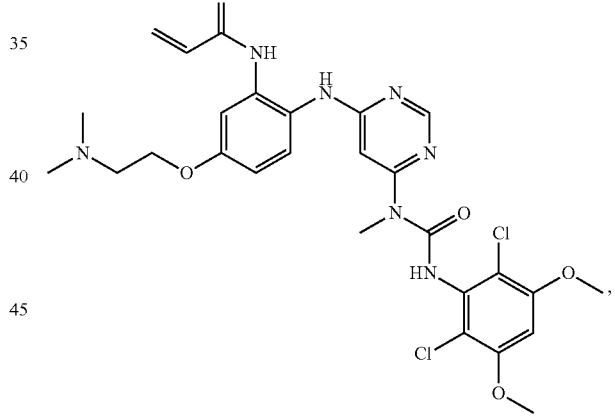
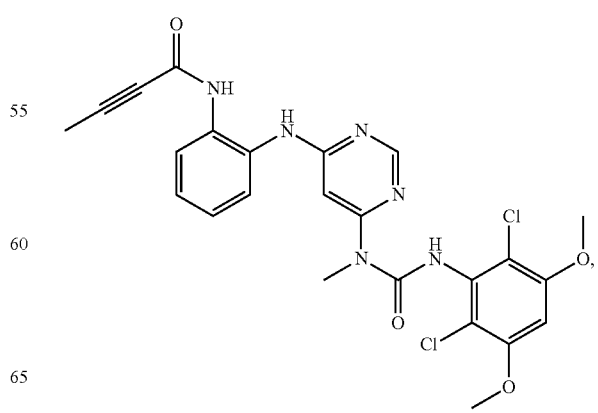

223
-continued
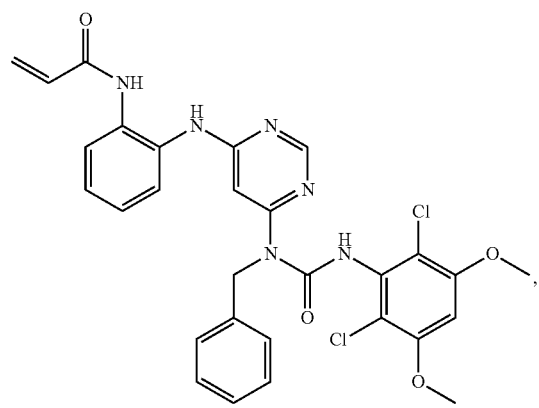
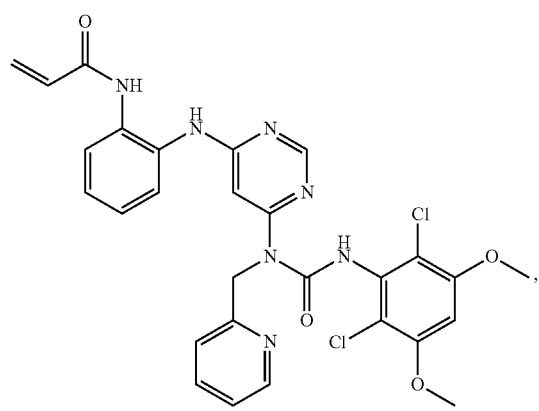
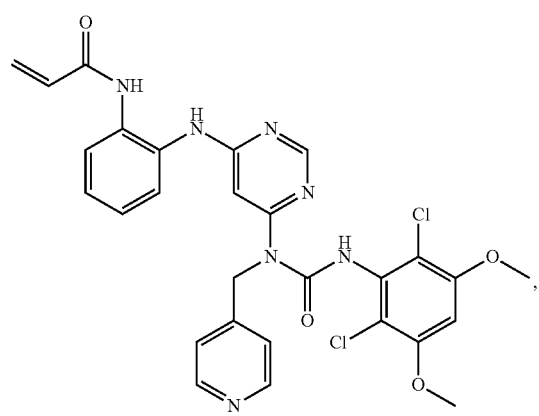
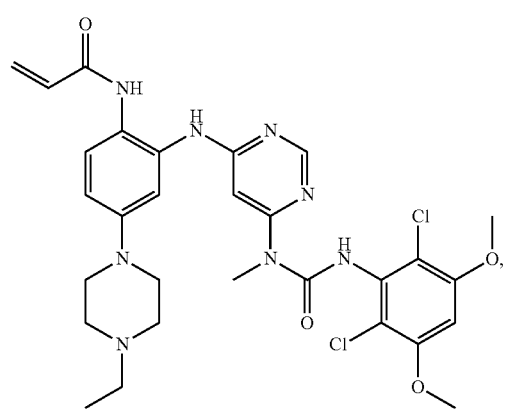
224
-continued
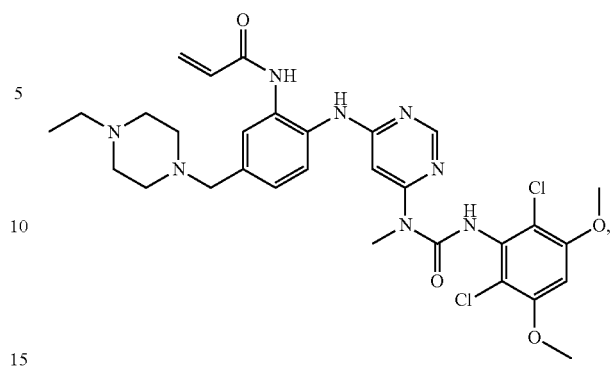
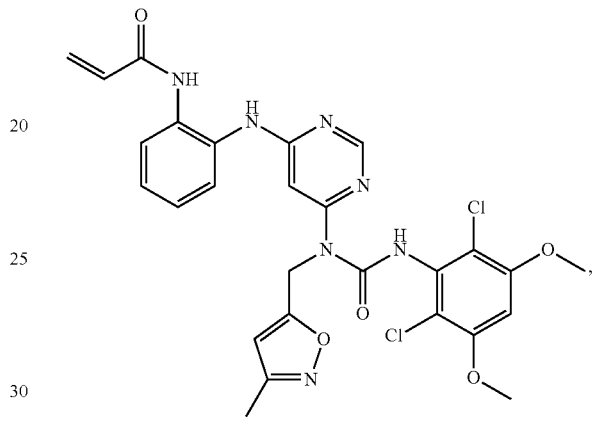
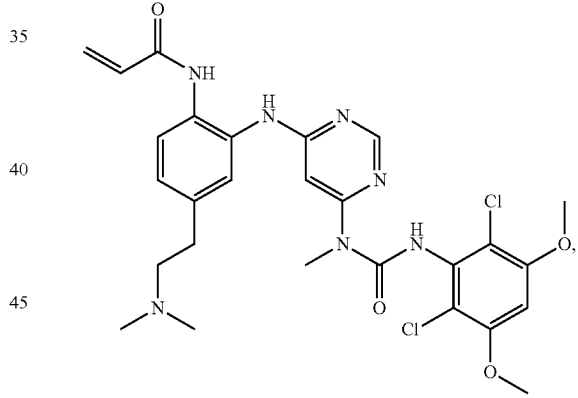
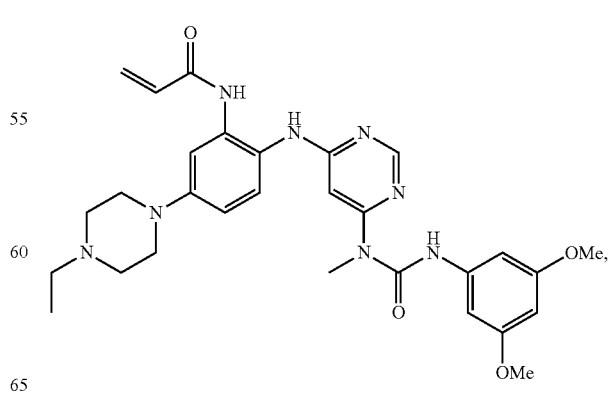

225
-continued
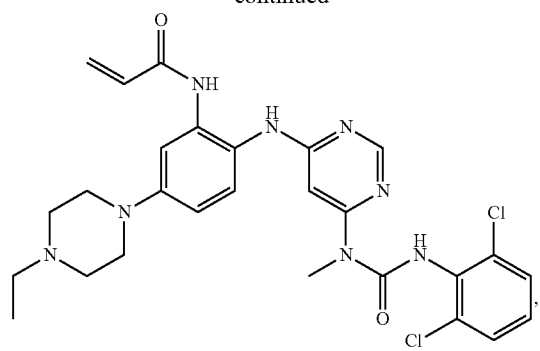
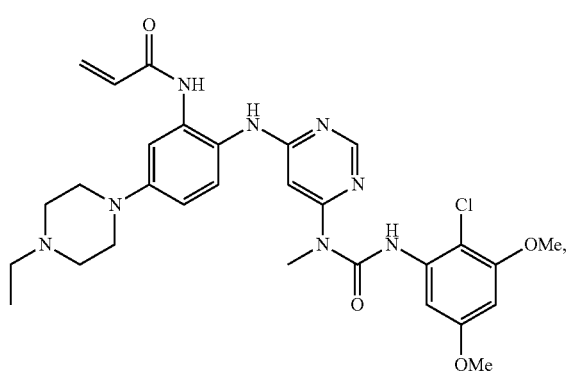
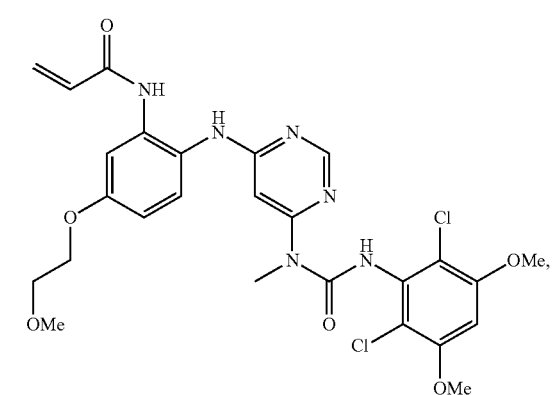
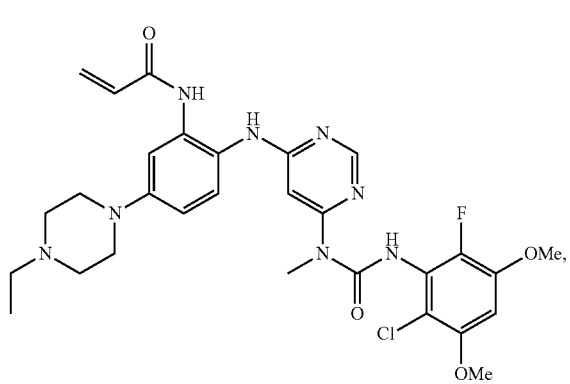 [SMILES: C=CC(=O)Nc1cc(N2CCN(CC)CC2)ccc1Nc1cc(N(C)C(=O)Nc2c(F)c(OC)cc(OC)c2Cl)ncn1]
226
-continued
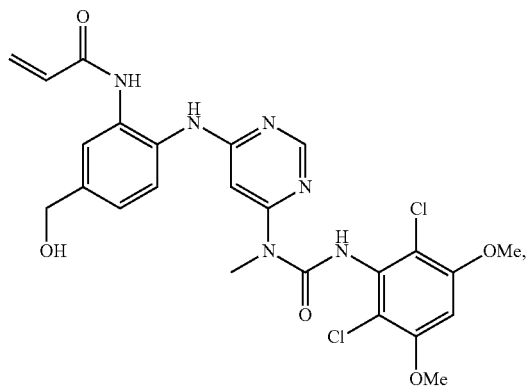
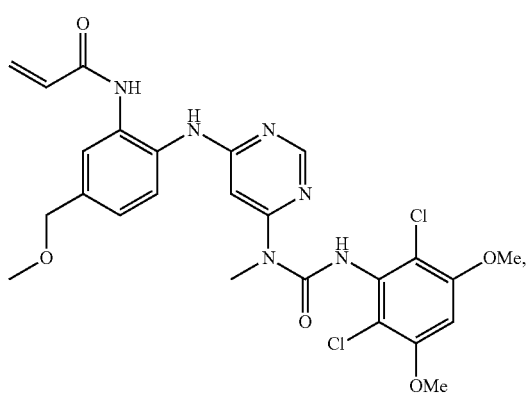
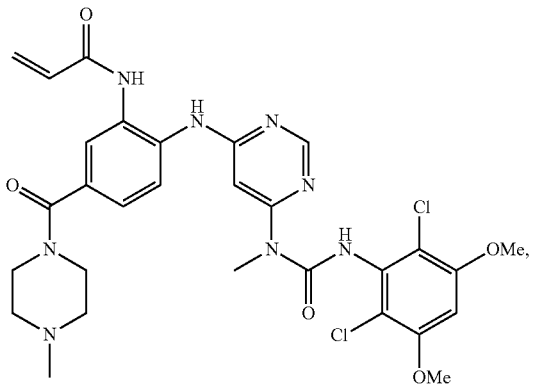
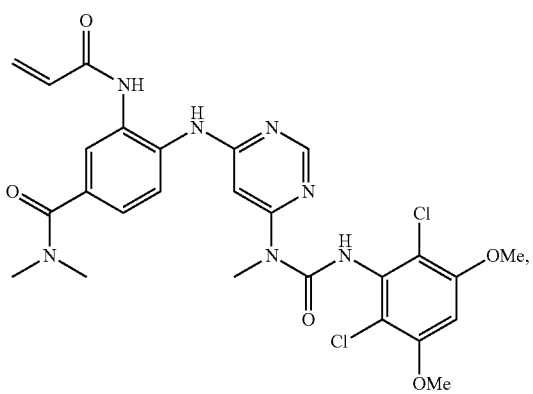

227
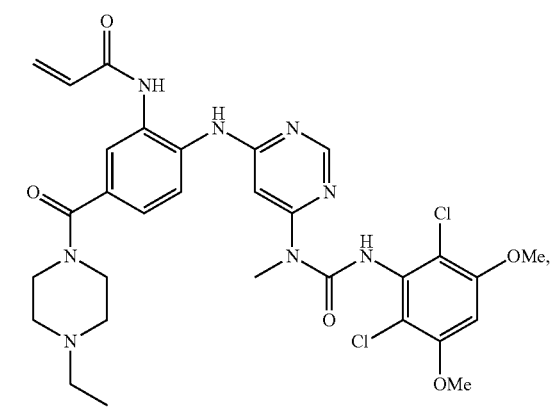
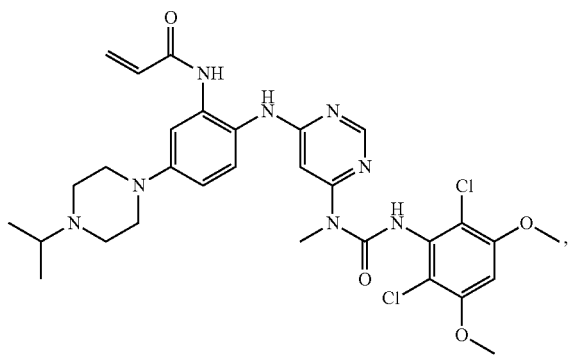
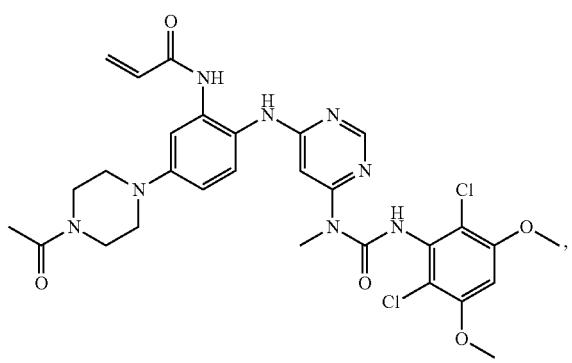
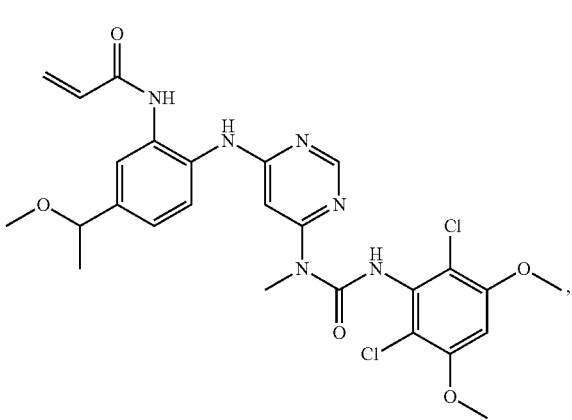
228
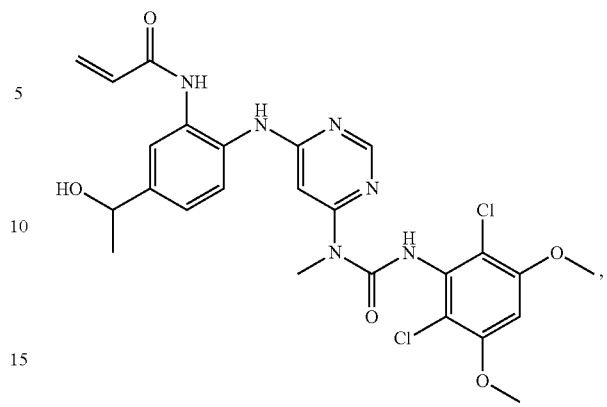
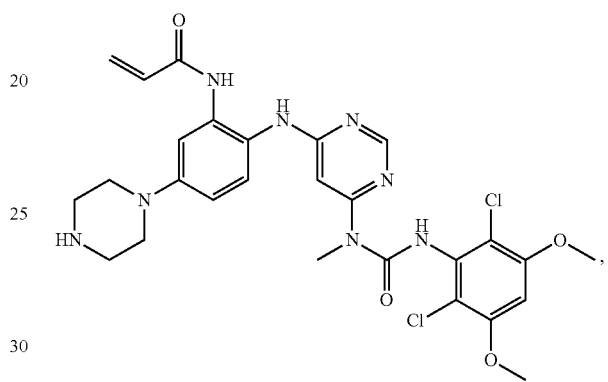
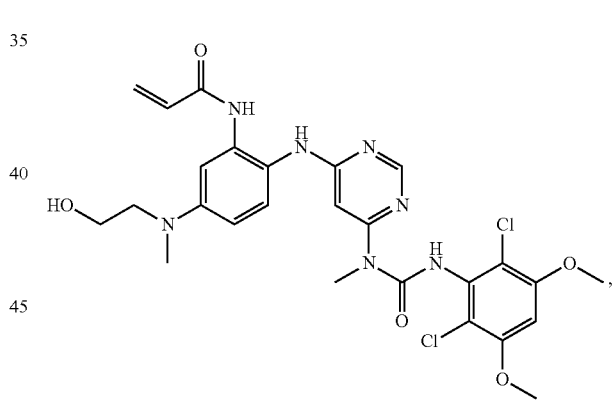
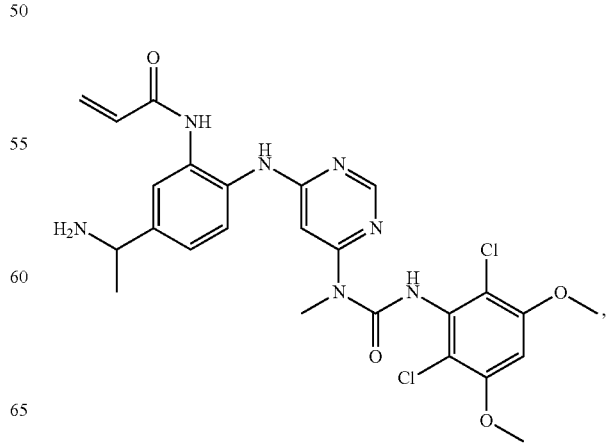

229
-continued
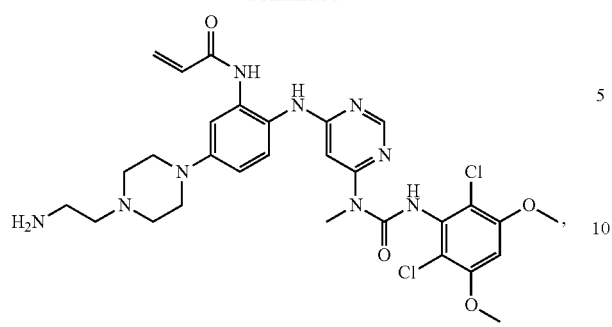
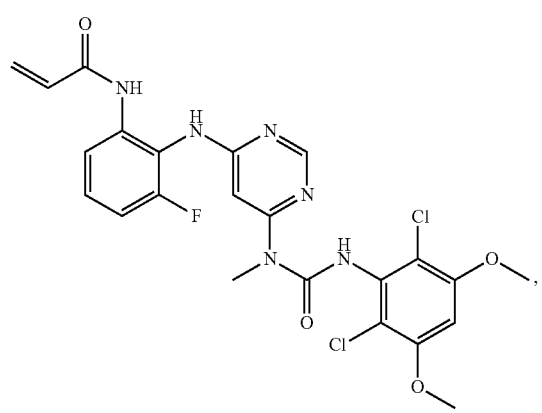
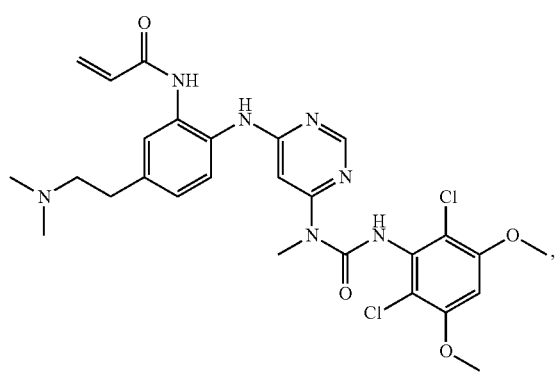
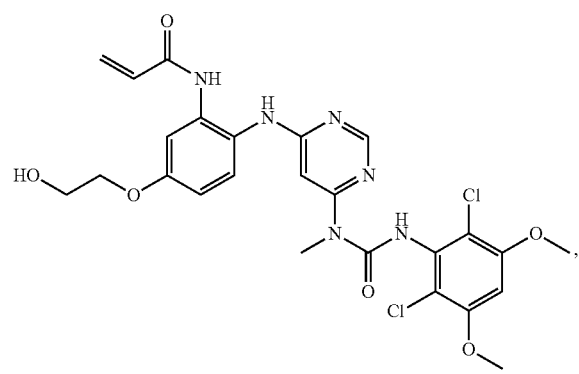
230
-continued
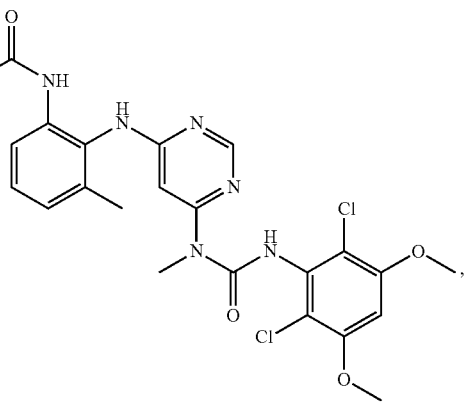
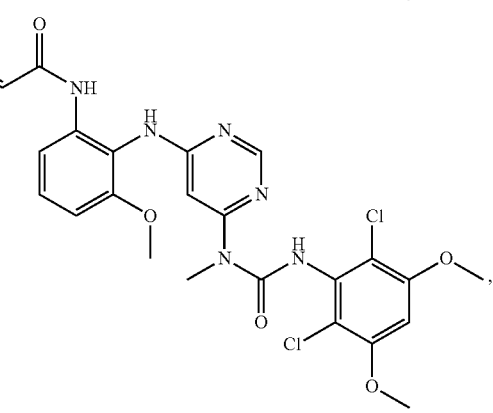
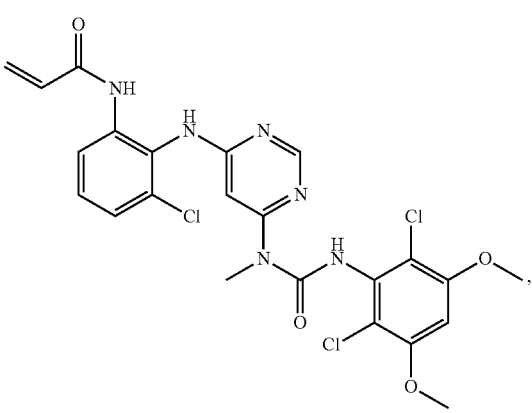
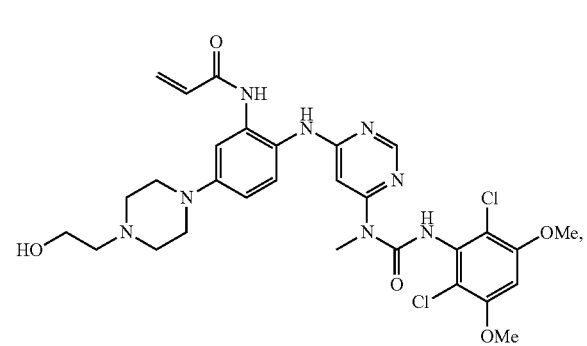

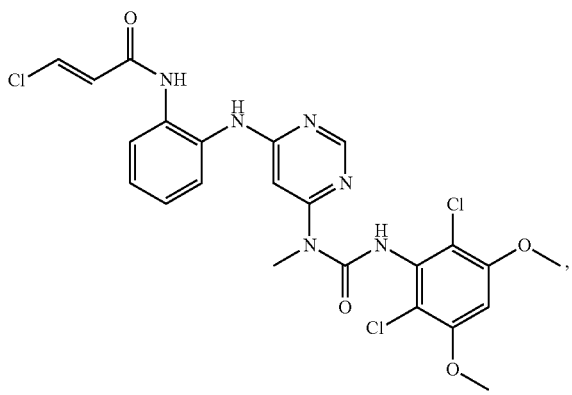
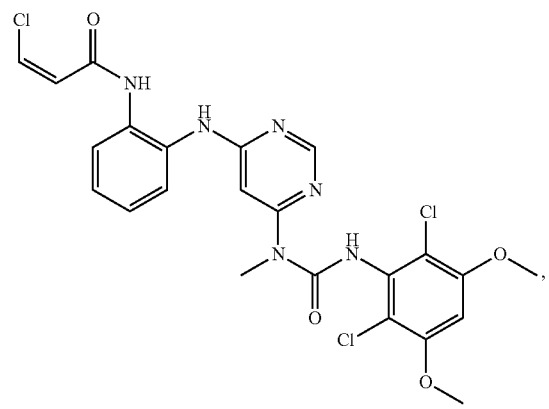
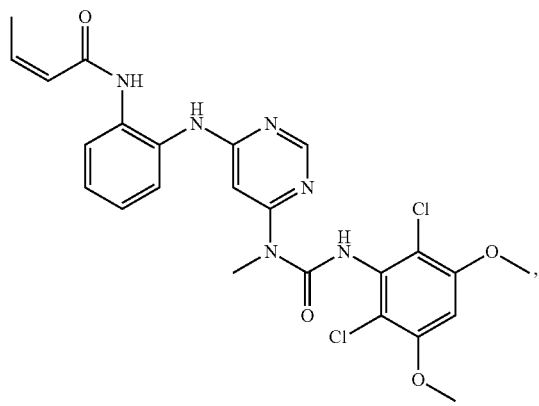
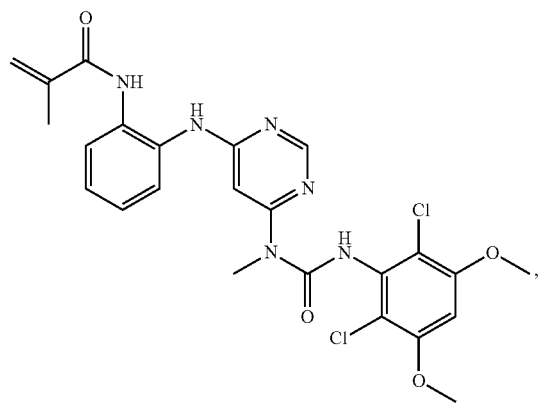
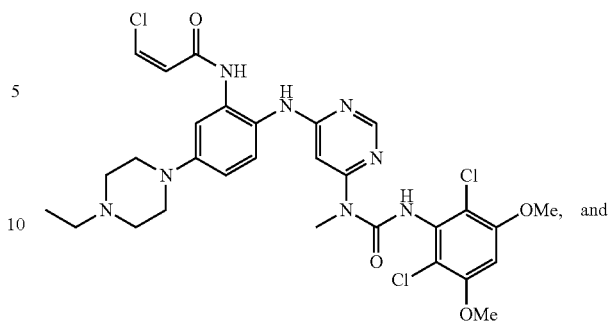
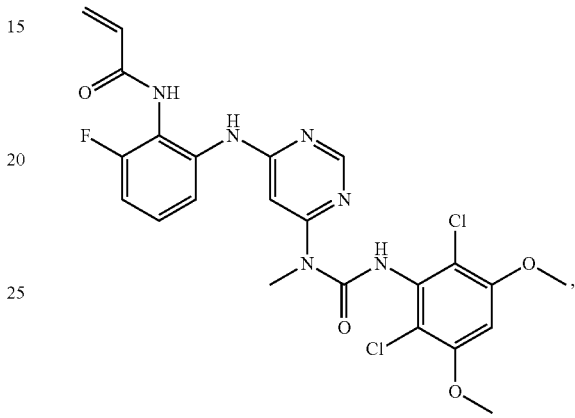
or a pharmaceutically acceptable salt thereof.
9. The method of claim 7, wherein said compound is selected from the group consisting of:
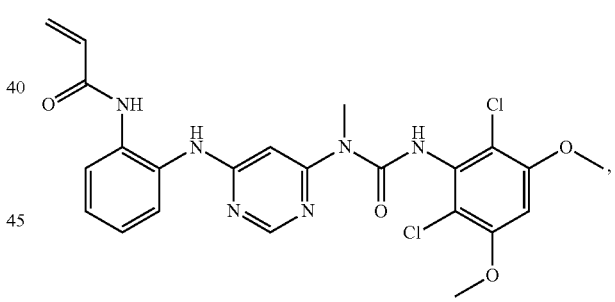
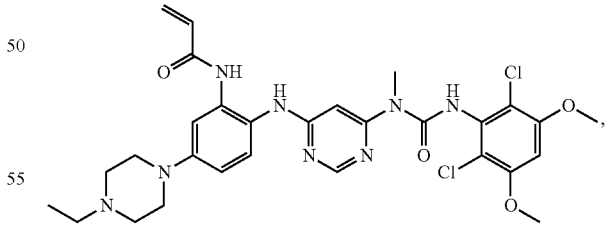
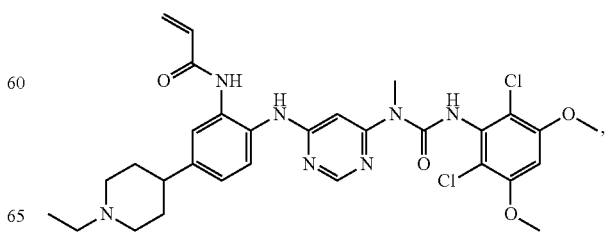

233
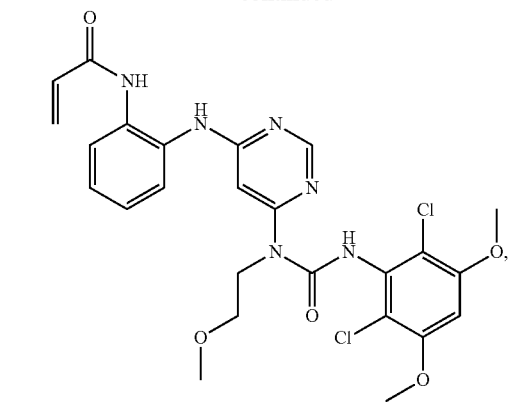
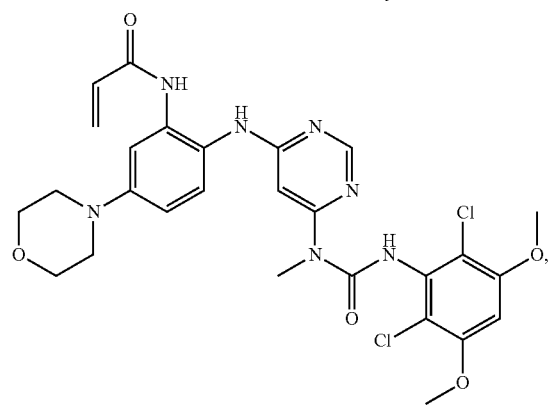
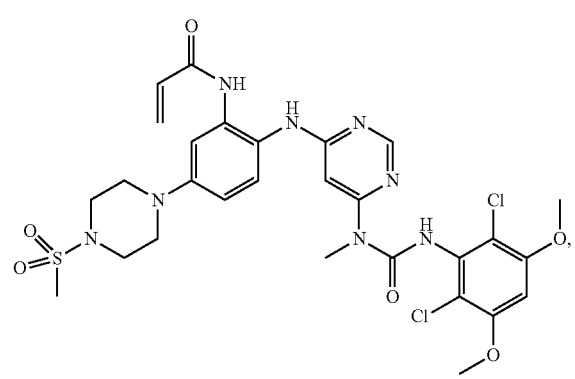
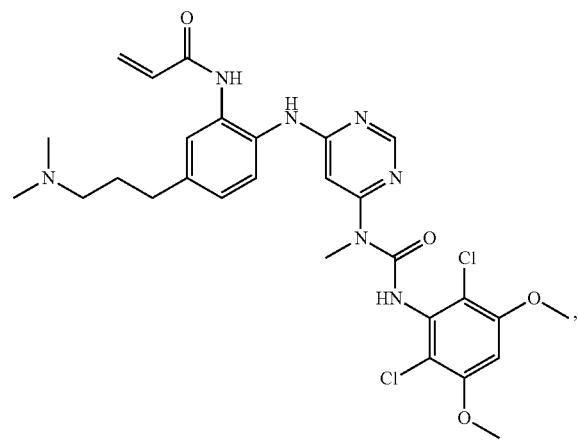
234
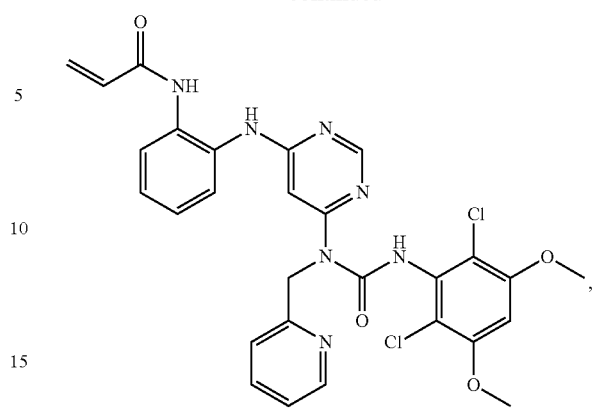
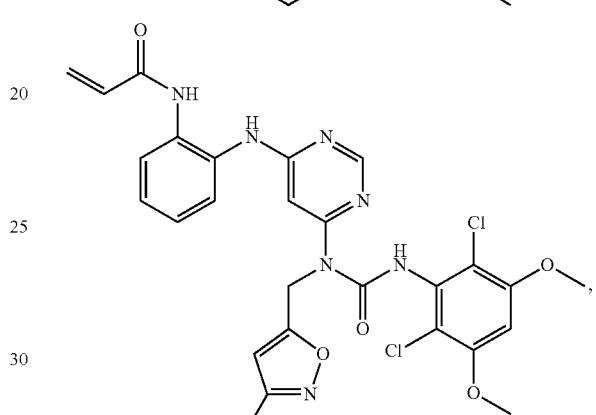
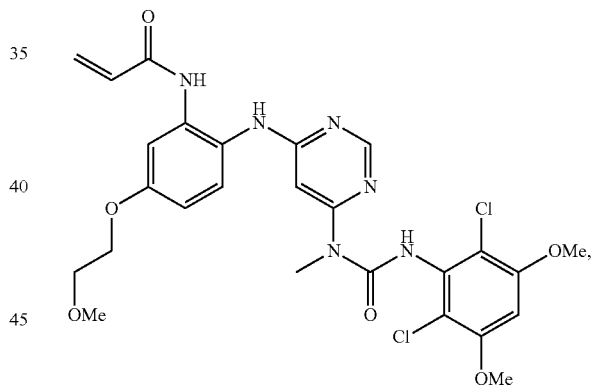
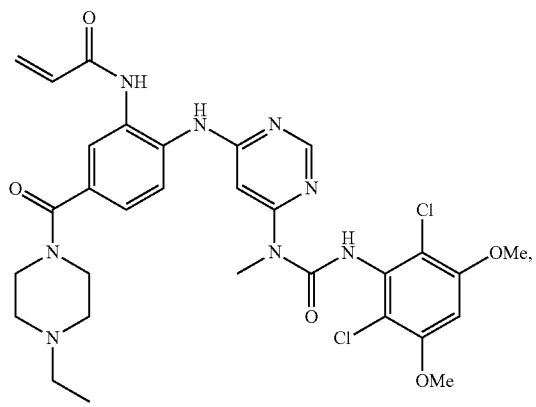

235
-continued
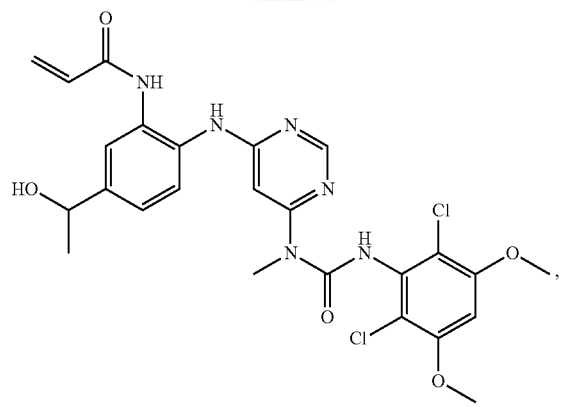
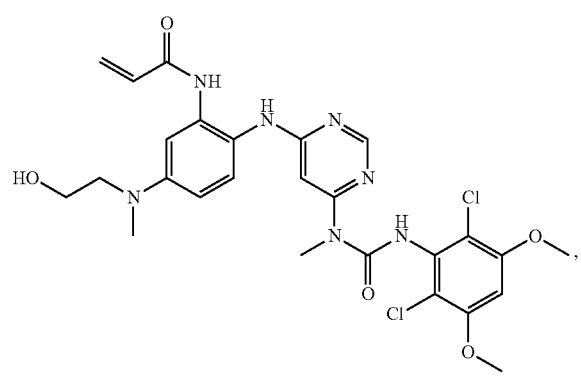
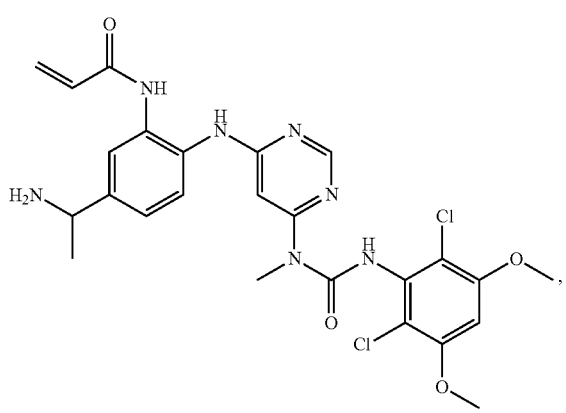
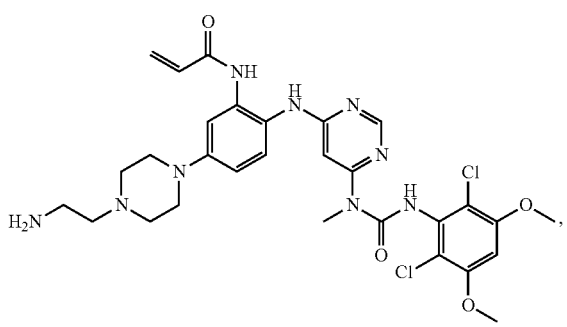
236
-continued
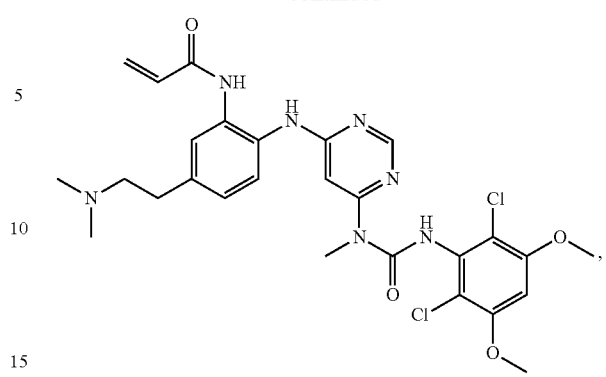
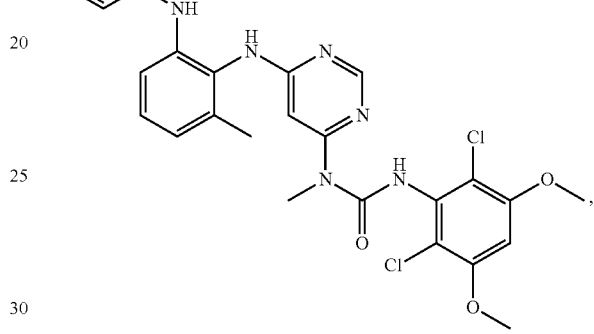
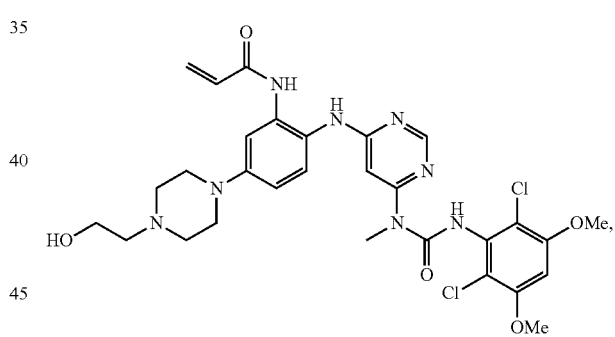
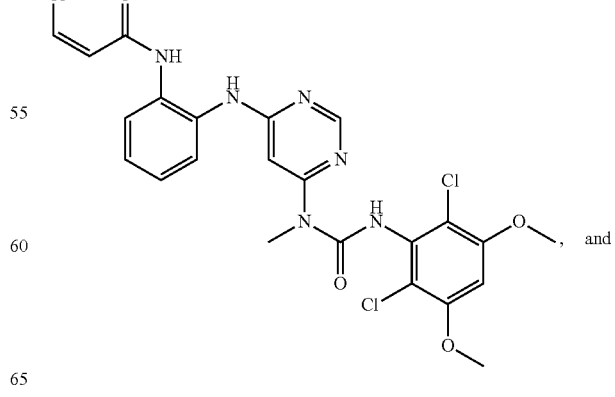
and -continued

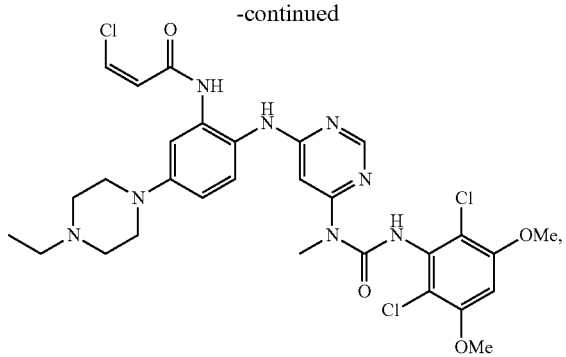

or a pharmaceutically acceptable salt thereof.

10. The method of claim 7, wherein said compound is selected from the group consisting of:

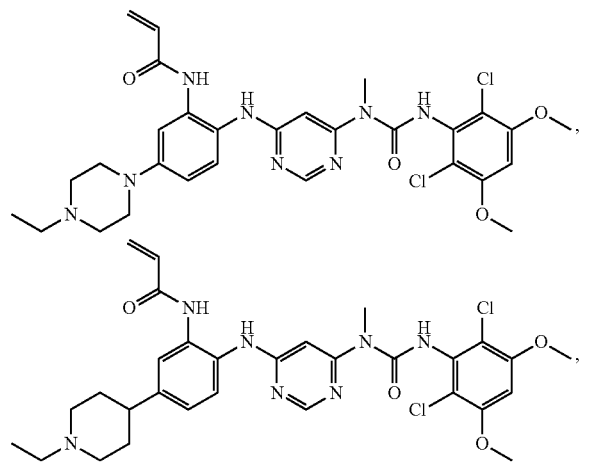

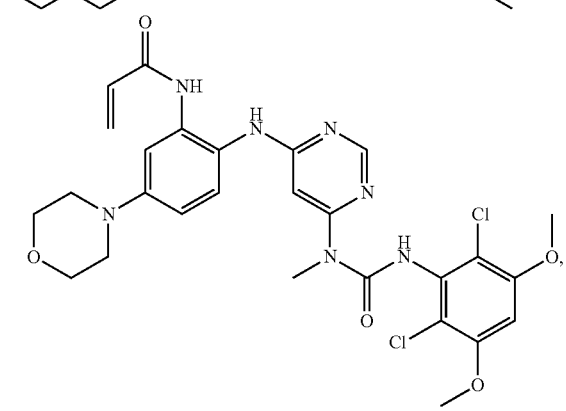

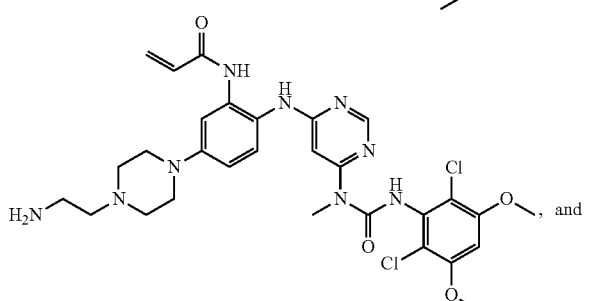

-continued

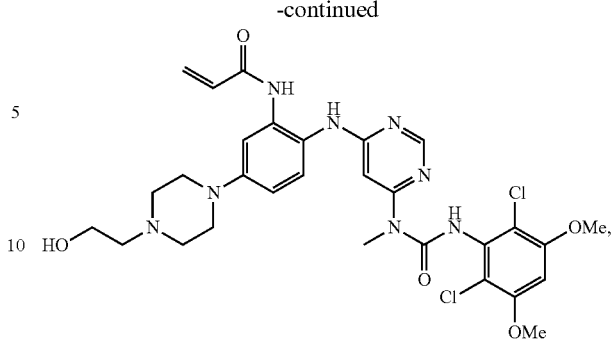

or a pharmaceutically acceptable salt thereof.

11. The method of claim 7, wherein the compound or pharmaceutically acceptable salt thereof is the following compound:

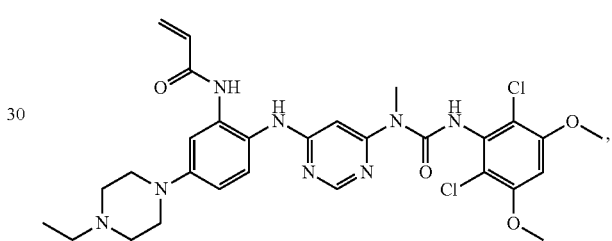

or a pharmaceutically acceptable salt thereof, wherein said hepatocellular carcinoma has an increased expression of FGFR4.

12. A method of treating hepatocellular carcinoma in a subject in need thereof, comprising:

administering an effective amount of a compound having the formula:

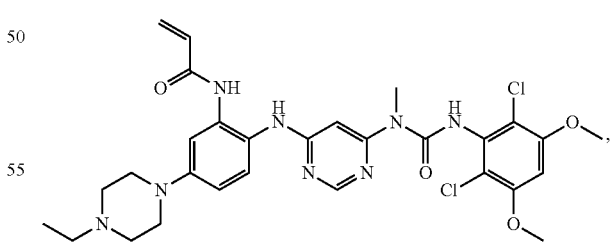

or a pharmaceutically acceptable salt thereof to a patient in which increased expression of FGFR4 has been detected in a biological sample from said patient, said biological sample containing cells of said hepatocellular carcinoma.

* * * * *